United States Patent
Georges et al.

(10) Patent No.: US 11,690,997 B2
(45) Date of Patent: Jul. 4, 2023

(54) MAMMALIAN BODY CONDUIT INTRALUMENAL DEVICE AND LUMEN WALL ANCHOR ASSEMBLY, COMPONENTS THEREOF AND METHODS OF IMPLANTATION AND EXPLANATION THEREOF

(71) Applicant: Puzzle Medical Devices Inc., Montreal (CA)

(72) Inventors: Gabriel Georges, Quebec (CA); Philippe Genereux, New York, NY (US); François Trudeau, Quebec (CA); Yves-Antoine Crête, Montreal (CA)

(73) Assignee: Puzzle Medical Devices Inc., Montreal (CA)

(*) Notice: Subject to any disclaimer, the term of this patent is extended or adjusted under 35 U.S.C. 154(b) by 0 days.

(21) Appl. No.: 17/752,378

(22) Filed: May 24, 2022

(65) Prior Publication Data
US 2022/0323744 A1 Oct. 13, 2022

Related U.S. Application Data

(63) Continuation of application No. PCT/US2021/012083, filed on Jan. 4, 2021, which is
(Continued)

(30) Foreign Application Priority Data

Apr. 6, 2018 (CA) ................................ CA 3000429

(51) Int. Cl.
*A61M 60/865* (2021.01)
*A61M 60/861* (2021.01)
(Continued)

(52) U.S. Cl.
CPC .......... *A61M 60/865* (2021.01); *A61M 60/13* (2021.01); *A61M 60/135* (2021.01);
(Continued)

(58) Field of Classification Search
CPC .............. A61M 60/865; A61M 60/804; A61M 60/135; A61M 60/13; A61M 60/861; A61M 2205/0266
(Continued)

(56) References Cited

U.S. PATENT DOCUMENTS 4,646,719 A 3/1987 Neuman et al.
4,753,221 A 6/1988 Kensey et al.
(Continued)

FOREIGN PATENT DOCUMENTS

CA 2701810 A1 4/2009
CA 3014105 A1 8/2017
(Continued)

OTHER PUBLICATIONS

Rhee and Blackshear, "Left Ventricular Assist Using a Jet Pump," ASAIO Trans., Jul.-Sep. 1990, 36(3):M515-M518.
(Continued)

*Primary Examiner* — Erin M Piateski

(57) ABSTRACT

Transcatheterly implantable mammalian body conduit intralumenal device and lumen wall anchor assembly. Anchor includes: wire network, connector positioning wires having a secured and a released position, and a connector disposed at end of each wire. Anchor has: a compact-secured-configuration, an expanded-secured-configuration, an expanded-released-configuration. When the anchor is in the expanded-secured-configuration, the wire network exerts a force on conduit lumen wall and the connector positioning wires are the in secured position. When the anchor is in the expanded-released-configuration, the con-
(Continued)

nector positioning wires are in the released position, and do not obstruct fluid flow axially through conduit. Device includes an interconnector that allows for the releasable interconnector of the connectors thereto. Device and anchor assembly can be explanted from the conduit. Or, device can be released from the anchor at the implantation site and only the device explanted with the anchor remaining within the conduit.

21 Claims, 44 Drawing Sheets

Related U.S. Application Data a continuation-in-part of application No. PCT/ZA2020/050022, filed on May 4, 2020, said application No. PCT/ZA2020/050022 is a continuation-in-part of application No. PCT/CA2019/050421, filed on Apr. 5, 2019.

(60) Provisional application No. 63/007,899, filed on Apr. 9, 2020, provisional application No. 63/000,439, filed on Mar. 26, 2020, provisional application No. 62/957,115, filed on Jan. 3, 2020, provisional application No. 62/824,101, filed on Mar. 26, 2019.

(51) Int. Cl.
*A61M 60/13* (2021.01)
*A61M 60/135* (2021.01)
*A61M 60/804* (2021.01)

(52) U.S. Cl.
CPC ........ *A61M 60/804* (2021.01); *A61M 60/861* (2021.01); *A61M 2205/0266* (2013.01)

(58) Field of Classification Search
USPC .......................................................... 600/16
See application file for complete search history.

(56) References Cited

U.S. PATENT DOCUMENTS

| | | |
|---|---|---|
| 4,957,504 A | 9/1990 | Chardack |
| 4,964,864 A | 10/1990 | Summers et al. |
| 5,112,349 A | 5/1992 | Summers et al. |
| 5,749,855 A | 5/1998 | Reitan |
| 5,888,241 A | 3/1999 | Jarvik |
| 5,957,672 A | 9/1999 | Aber |
| 6,015,272 A | 1/2000 | Antaki et al. |
| 6,050,987 A | 4/2000 | Rosenbaum |
| 6,210,318 B1 | 4/2001 | Lederman |
| 6,245,007 B1 | 6/2001 | Bedingham et al. |
| 6,527,800 B1 | 3/2003 | McGuckin, Jr. et al. |
| 6,669,624 B2 | 12/2003 | Frazier |
| 6,827,733 B2 | 12/2004 | Boneau |
| 6,942,611 B2 | 9/2005 | Siess |
| 7,027,875 B2 | 4/2006 | Siess et al. |
| 7,144,364 B2 | 12/2006 | Barbut et al. |
| 7,479,102 B2 | 1/2009 | Jarvik |
| 7,762,977 B2 | 7/2010 | Porter et al. |
| 7,909,862 B2 | 3/2011 | Garrison et al. |
| 7,914,436 B1 | 3/2011 | Kung |
| 7,918,880 B2 * | 4/2011 | Austin ...................... A61F 2/95 623/1.11 |
| 7,993,259 B2 | 8/2011 | Kang et al. |
| 7,998,190 B2 | 8/2011 | Gharib et al. |
| 8,012,079 B2 | 9/2011 | Delgado, III |
| 8,075,472 B2 | 12/2011 | Zilbershlag et al. |
| 8,157,758 B2 | 4/2012 | Pecor et al. |
| 8,308,798 B2 | 11/2012 | Pintor et al. |
| 8,333,687 B2 | 12/2012 | Farnan et al. |
| 8,343,029 B2 | 1/2013 | Farnan et al. |
| 8,394,010 B2 | 3/2013 | Farnan |
| 8,439,859 B2 | 5/2013 | Pfeffer et al. |
| 8,449,443 B2 | 5/2013 | Rodefeld et al. |
| 8,489,190 B2 | 7/2013 | Pfeffer et al. |
| 8,579,858 B2 | 11/2013 | Reitan et al. |
| 8,585,572 B2 | 11/2013 | Mehmanesh |
| 8,617,239 B2 | 12/2013 | Reitan |
| 8,690,749 B1 | 4/2014 | Nunez |
| 8,727,959 B2 | 5/2014 | Reitan et al. |
| 8,734,331 B2 | 5/2014 | Evans et al. |
| 8,777,832 B1 | 7/2014 | Wang et al. |
| 8,784,291 B2 | 7/2014 | Farnan et al. |
| 8,821,366 B2 | 9/2014 | Farnan et al. |
| 9,022,916 B2 | 5/2015 | Farnan et al. |
| 9,211,367 B2 | 12/2015 | Farnan et al. |
| 9,314,559 B2 | 4/2016 | Smith et al. |
| 9,328,741 B2 | 5/2016 | Liebing |
| 9,339,597 B2 | 5/2016 | Khanal et al. |
| 9,572,915 B2 | 2/2017 | Heuring et al. |
| 9,616,159 B2 | 4/2017 | Anderson et al. |
| 9,744,281 B2 | 8/2017 | Siegenthaler |
| 9,861,729 B2 | 1/2018 | Morello et al. |
| 9,878,079 B2 | 1/2018 | Pfeffer et al. |
| D811,588 S | 2/2018 | Kaiser et al. |
| 9,889,242 B2 | 2/2018 | Pfeffer et al. |
| D826,401 S | 8/2018 | Epple |
| 10,039,873 B2 | 8/2018 | Siegenthaler |
| 10,137,232 B2 | 11/2018 | Yomtov et al. |
| 10,179,197 B2 | 1/2019 | Kaiser et al. |
| 10,183,104 B2 | 1/2019 | Anderson et al. |
| D855,175 S | 7/2019 | Epple |
| 10,413,648 B2 | 9/2019 | Delgado, III |
| 10,426,880 B2 | 10/2019 | Kushwaha et al. |
| 10,443,738 B2 | 10/2019 | Durst et al. |
| 10,449,276 B2 | 10/2019 | Pfeffer et al. |
| 10,478,539 B2 | 11/2019 | Pfeffer et al. |
| 10,500,323 B2 | 12/2019 | Heuring et al. |
| 10,596,019 B2 | 3/2020 | Melsheimer et al. |
| 10,799,624 B2 | 10/2020 | Pfeffer et al. |
| 10,898,626 B2 | 1/2021 | Siegenthaler |
| 10,980,927 B2 | 4/2021 | Pfeffer et al. |
| 11,103,690 B2 | 8/2021 | Epple |
| 11,123,539 B2 | 9/2021 | Pfeffer et al. |
| 11,129,978 B2 | 9/2021 | Pfeffer et al. |
| 11,154,704 B2 | 10/2021 | Farnan et al. |
| 11,167,124 B2 | 11/2021 | Pfeffer et al. |
| 11,179,557 B2 | 11/2021 | Georges et al. |
| 11,202,902 B2 | 12/2021 | Najar |
| 11,235,137 B2 | 2/2022 | Salys |
| 11,235,138 B2 | 2/2022 | Gross-Hardt et al. |
| 11,241,569 B2 | 2/2022 | Delgado, III |
| 11,318,017 B2 | 5/2022 | Besselink |
| 11,324,940 B2 | 5/2022 | Earles et al. |
| 11,331,465 B2 | 5/2022 | Epple |
| 11,351,359 B2 | 6/2022 | Clifton et al. |
| 11,452,859 B2 | 9/2022 | Earles et al. |
| 11,471,665 B2 | 10/2022 | Clifton et al. |
| 2005/0220636 A1 | 10/2005 | Henein et al. |
| 2007/0156006 A1 | 7/2007 | Smith et al. |
| 2007/0213690 A1 | 9/2007 | Phillips et al. |
| 2008/0132748 A1 | 6/2008 | Shifflette |
| 2009/0112312 A1 | 4/2009 | LaRose et al. |
| 2010/0249489 A1 | 9/2010 | Jarvik |
| 2011/0106120 A1 | 5/2011 | Haselby et al. |
| 2012/0053670 A1 * | 3/2012 | Purdy ...................... A61F 2/07 623/1.11 |
| 2012/0172654 A1 * | 7/2012 | Bates .................... A61M 60/20 600/16 |
| 2012/0203328 A1 | 8/2012 | Yribarren |
| 2012/0253387 A1 | 10/2012 | Teichman et al. |
| 2012/0310036 A1 | 12/2012 | Peters et al. |
| 2013/0138205 A1 | 5/2013 | Kushwaha et al. |
| 2013/0204362 A1 | 8/2013 | Toellner et al. |
| 2014/0031607 A1 | 1/2014 | Zilbershlag et al. |
| 2014/0066979 A1 | 3/2014 | Jonsson |
| 2014/0275726 A1 | 9/2014 | Zeng |
| 2015/0250935 A1 | 9/2015 | Anderson et al. |
| 2015/0306291 A1 | 10/2015 | Bonde et al. |

(56) References Cited

U.S. PATENT DOCUMENTS

| | | |
|---|---|---|
| 2016/0089482 A1* | 3/2016 | Siegenthaler ......... A61M 60/17 600/16 |
| 2016/0206798 A1 | 7/2016 | Williams et al. |
| 2016/0279310 A1 | 9/2016 | Scheckel et al. |
| 2017/0087288 A1 | 3/2017 | Gross-Hardt et al. |
| 2017/0119945 A1 | 5/2017 | Neumann |
| 2017/0173242 A1 | 6/2017 | Anderson et al. |
| 2017/0274128 A1 | 9/2017 | Tamburino et al. |
| 2017/0340789 A1 | 11/2017 | Bonde et al. |
| 2018/0103901 A1 | 4/2018 | Gandhi et al. |
| 2018/0110909 A1 | 4/2018 | LaRose et al. |
| 2018/0193543 A1 | 7/2018 | Sun |
| 2018/0250457 A1 | 9/2018 | Morello et al. |
| 2019/0046703 A1 | 2/2019 | Shambaugh et al. |
| 2019/0358382 A1 | 11/2019 | Delgado, III |
| 2020/0023109 A1 | 1/2020 | Epple |
| 2020/0023158 A1 | 1/2020 | Epple |
| 2020/0054806 A1 | 2/2020 | Sun |
| 2020/0192423 A1 | 6/2020 | Hsu et al. |
| 2020/0316277 A1 | 10/2020 | Delgado, III |
| 2021/0008263 A1 | 1/2021 | Leonhardt |
| 2021/0077687 A1 | 3/2021 | Leonhardt |
| 2021/0106808 A1 | 4/2021 | Siegenthaler |
| 2021/0260360 A1 | 8/2021 | Georges et al. |
| 2022/0080183 A1 | 3/2022 | Earles et al. |
| 2022/0080184 A1 | 3/2022 | Clifton et al. |
| 2022/0134082 A1 | 5/2022 | Pfeffer et al. |
| 2022/0226634 A1 | 7/2022 | Gross-Hardt et al. |
| 2022/0257920 A1 | 8/2022 | Earles et al. |
| 2022/0296852 A1 | 9/2022 | Georges |
| 2022/0296880 A1 | 9/2022 | Clifton et al. |
| 2022/0331576 A1 | 10/2022 | Leonhardt |

FOREIGN PATENT DOCUMENTS

| | | | |
|---|---|---|---|
| CA | 3054771 A1 | 9/2018 | |
| CN | 106456857 B | 11/2018 | |
| CN | 110049792 B | 1/2022 | |
| DE | 19613565 C1 | 7/1997 | |
| DE | 102004054714 A1 | 5/2006 | |
| EP | 2860849 A1 | 4/2015 | |
| EP | 3539584 A1 | 9/2019 | |
| EP | 2745805 B2 * | 5/2022 | ............. A61F 2/013 |
| WO | WO-0227225 A1 | 4/2002 | |
| WO | WO-2008017289 A2 | 2/2008 | |
| WO | WO-2008027366 A2 | 3/2008 | |
| WO | WO-2017217946 A1 | 12/2017 | |
| WO | WO-2018096531 A1 | 5/2018 | |
| WO | WO-2018158635 A1 | 9/2018 | |
| WO | WO-2019083989 A1 | 5/2019 | |
| WO | WO-2019152875 A1 | 8/2019 | |
| WO | WO-2019191851 A1 | 10/2019 | |
| WO | WO-2020036886 A1 | 2/2020 | |
| WO | WO-2020198765 A2 | 10/2020 | |

OTHER PUBLICATIONS

International Preliminary Report on Patentability issued in PCT/CA2019/050421, dated Oct. 6, 2020, 9 pages.
International Preliminary Report on Patentability issued in PCT/CA2020/051673, dated Mar. 12, 2021, 7 pages.
International Preliminary Report on Patentability issued in PCT/CA2020/051677, dated Mar. 12, 2021, 7 pages.
International Preliminary Report on Patentability issued in PCT/ZA2020/050022, dated Sep. 28, 2021, 5 pages.
International Search Report and Written Opinion for PCT/ZA2020/050022, dated Sep. 24, 2020, 6 pages.
International Search Report and Written Opinion issued in PCT/CA2019/050421 dated Jul. 8, 2019, 12 pages.
International Search Report and Written Opinion issued in PCT/CA2020/051673 dated Mar. 26, 2021, 12 pages.
International Search Report and Written Opinion issued in PCT/CA2020/051677, dated Mar. 15, 2021, 11 pages.
International Search Report and Written Opinion issued in PCT/CA2021/050469 dated Jul. 28, 2021, 10 pages.
International Search Report and Written Opinion issued in PCT/IB2020/061913 dated Mar. 19, 2021, 11 pages.
International Search Report and Written Opinion issued in PCT/IB2021/052925 dated Jul. 28, 2021, 14 pages.
International Search Report and Written Opinion issued in PCT/IB2021/054395 dated Aug. 12, 2021, 9 pages.
International Search Report and Written Opinion issued in PCT/US2021/012083 dated Mar. 31, 2021, 7 pages.
International Search Report and Written Opinion issued in PCT/US2021/043341 dated Nov. 10, 2021, 9 pages.
Notice of Allowance issued in U.S. Appl. No. 17/047,598 dated May 3, 2021, 7 pages.
Supplemental International Search Report issued in PCT/ZA2020/050022, dated Jul. 13, 2021, 8 pages.

* cited by examiner

MAMMALIAN BODY CONDUIT INTRALUMENAL DEVICE AND LUMEN WALL ANCHOR ASSEMBLY, COMPONENTS THEREOF AND METHODS OF IMPLANTATION AND EXPLANATION THEREOF

CROSS-REFERENCE

The present application is a continuation of International Patent Application No. PCT/US2021/012083, filed Jan. 4, 2021, which claims priority to and the benefit of U.S. Provisional Patent Application No. 62/957,115, filed Jan. 3, 2020, and is a continuation-in-part of International Patent Application No. PCT/ZA2020/050022, filed May 4, 2020, (hereinafter referred to as the "'022 PCT").

The '022 PCT claims priority to and the benefit of U.S. Provisional Patent Application No. 62/824,101, filed Mar. 26, 2019; U.S. Provisional Patent Application No. 63/000,439, filed Mar. 26, 2020; and U.S. Provisional Patent Application No. 63/007,899, filed Apr. 9, 2020. The '022 PCT is also a continuation-in-part of International Patent Application Serial No. PCT/CA2019/050421, filed Apr. 5, 2019 (hereinafter referred to as the "'421 PCT"). The '421 PCT claims priority to and the benefit of U.S. Provisional Patent Application No. 62/824,101, filed Mar. 26, 2019; and CA Application Serial No. 3,000,429, filed Apr. 6, 2018. The contents of each of the foregoing applications are incorporated herein by reference in their entirety for all purposes.

FIELD

The present technology relates to mammalian body conduit intralumenal device and lumen wall anchor assemblies, components, methods of implantation and explantation thereof.

BACKGROUND

Medical devices may be implanted within the lumen of various fluid carrying conduits in a patient. Examples of such fluid carrying conduits include arteries and veins, lymphatic vessels, bile ducts, esophagi, trachea, ureters and other fluid conduits near the heart, liver, lungs, stomach, bladder or kidneys. Some such intraluminal medical devices are "acutely" implanted (i.e., for a few hours to a few weeks), others are "chronically" implanted (i.e., multiple weeks to years) before being retrieved from the patient's body, if they are to be retrieved at all.

Over the device's period of implantation, there may be varying levels of tissue growth over the portions of the device in contact with the wall of the body fluid carrying conduit. Device retrieval may be difficult due to this tissue overgrowth. Additionally, retrieving the device, regardless of the level of tissue growth may tear and cause damage to the wall tissue in contact with the device. This is especially true in the case of endovascular devices, where there may be intimal overgrowth over the device. Tearing the intima when retrieving such a device may lead to catastrophic scenarios such as intimal tear and/or vessel dissection. Should vessel dissection occur, depending on the site thereof, the patient may suffer from multi-organ failure, cardiogenic shock or death.

This reality is especially true as regards large endovascular devices, such as endovascular micro-axial blood pumps (examples of which are described in the WO '765 Publication, including in its background section). These pumps are required to be solidly anchored to the vessel wall during the time that they are implanted in the patient; however, they also may be required to be removed from the patient, e.g., in the event of pump malfunction, once the patient has recovered, etc.

Methods for anchoring intralumenal medical devices, including endovascular micro-axial blood pumps, include struts extending from the device and anchored directly into an arterial or venous wall, as well as radially expanding structures holding the device in place by strong outwardly biased radial forces. Either of these structures may be combined with anchoring pins that engage the vessel wall. Such anchoring systems have been referred to in the prior art in descriptions of devices or systems that are required to be anchored to and centered within the lumen of a vessel or other conduit.

One such example of a simple anchor structure is disclosed in United States Patent Application Publication No. 2016/0022890 A1 (Schwammenthal et al.), entitled "Renal-Pump" and assigned to Magenta Medical Ltd. Schwammenthal et al. discloses: "As shown in FIG. 19B [reproduced herein as FIG. 1] generally-cylindrical central portion 220 of cage 154, becomes anchored to the blood vessel, such that the longitudinal axis of the cage is aligned with the longitudinal axis of the blood vessel. Since the longitudinal axes of the impeller and the cage are aligned with one another, the generally-cylindrical central portion of the cage causes the impeller to be disposed within the blood vessel such that the longitudinal axis of the impeller is aligned with the longitudinal axis of the blood vessel" (para. [0666]).

In this application by Schwammenthal et al., the pumping apparatus of the device is anchored and centered within the blood vessel by an expandable cage exerting pressure on the vessel walls. The device can be delivered via a catheter (e.g., a delivery sheath) and the cage expands when it exits the sheath (in a similar fashion to a conventional self-expanding stent). The device can be retrieved by re-sheathing the cage in a catheter (e.g., a retrieval sheath), causing the cage to revert to a compressed and retrievable configuration.

A second similar example of a simple anchor structure is the Second Heart Assist™, described in International Patent Application Publication No. WO 2019/183247 A1, entitled "Circulatory Assist Pump", assigned to Second Heart Assist, Inc. This publication describes a transcatheter blood pump that is currently in development and that has a similar anchoring system to that described in Schwammenthal el al. (See, for example, FIG. 16 of Second Heart Assist, Inc., reproduced herein as FIG. 2)

In a system such as those described in Schwammenthal el al. and Second Heart Assist, Inc., if the device needed to be retrieved after having been used chronically (i.e., for multiple weeks to years), the interventionist would run the risk of harming the patient by damaging the vessel wall when retrieving the device. This is the case as the portions of the device (in this instance, the cage) will have been incorporated, to a varying extent, into the vessel wall as described hereinabove.

One approach to solving this problem is to not anchor the device inside the vessel at all. This is the approach taken with the Impella™ family of micro-pump devices from Abiomed™. An Impella device consists of a micro-axial pump (e.g., having an impeller) with a canula (e.g., a small tube-like structure) and is implanted within the left ventricle (in the case of an LVAD) or right ventricle (in the case of an RVAD) of the heart so as to cross the aortic valve (in the case of an LVAD) or the tricuspid and pulmonary valve (in the case of an RVAD). An Impella device is unanchored. An example is shown in FIG. 1 of U.S. Pat. No. 7,022,1000 B1 (Aboul-Hosn et al., issued Apr. 4, 2006, entitled "Guidable Intravascular Blood Pump and RelatedMethods"), reproduced herein as FIG. 3. As can be seen in FIG. 3, the inlet of the pump is within the ventricle (although it could be within the vessels that discharge fluid into the ventricle) and the outlet of the pump is outside of the heart, in the aorta (as an LVAD is shown in FIG. 3). (The outlet would have been in the pulmonary trunk in the case of an RVAD.)

As can also be seen in FIG. 3, Impella™ pumps are centered inside the lumen of the vessel by the heart valve it crosses. However, since the device is not anchored, movement of the pump or pump displacement is not prohibited. If pump displacement occurs, the pump may not offer optimal patient cardiac support and may even damage surrounding structures, such as the heart valves. In order to prevent pump displacement, the patient is meant to stay bedridden with very limited movement (amongst other things) until the pump is removed.

Although this might be acceptable in an acute support scenario (e.g., for hours to days), the quality of life of such patients would be extremely limited if such limitations (e.g., being bedridden with very limited movement) were applied in the context of chronic support. For this reason, avoiding vessel wall damage at the time of retrieval of the device by completely eliminating the anchoring element of the device would be unwise in devices with a potential for chronic implantation.

A very recently theoretical alternative to risking vessel wall damage during device retrieval (while still having an anchored device) is the use of a two-component system. In such a system, the anchor and the medical device itself are two separate components and may be physically interconnected or disconnected at different points in time. The device may be connected to the anchor when the device is in use to securely position it inside the vessel. The device may be disconnected from the anchor at the time of the device's retrieval. And, after its disconnection and separation from the anchor, the device may be retrieved while the anchor is left in place in the patient's vasculature. Since the anchor is not retrieved, it remains in contact with the vessel wall and potential tears in or damage to the vessel wall through the retrieval process may be avoided.

In such an assembly, over time, the anchor remaining in the vessel will progressively become fully incorporated into the vessel wall in the same way as currently is the case with conventional coronary or peripheral vascular stents that are routinely used in cardiovascular disease patient care. In the case of such conventional stents, as long as the scaffold of the stent is completely applied against the wall of the vessel in which it is implanted and there are no elements thereof protruding towards the inside or center of the vessel lumen, the risks associated with permanently leaving the stent structure in place are limited and generally accepted by the medical community. (Such risks include in-stent thrombosis, which mostly occurs in medium to small vessels, such as the coronary arteries, but very rarely occurs in larger vessels, such as the aorta or its main branches (renal arteries, common iliacs, femoral arteries). Also, rarely, the stent may become infected and require antibiotic treatment or surgical removal.)

To the knowledge of developers of the present technology, two such two-component pump assemblies (i.e., with a separate anchor and pumping device) have been described in the patent literature to date.

A first description of such a two-component system occurs in U.S. Patent Application Publication No. 2006/0036157 (Delgado, III), published Feb. 16, 2006, entitled "Method and Apparatus for Long-Term Assisting a Left Ventricle to Pump Blood", assigned to Procyrion, Inc. (now U.S. Pat. No. 8,012,079 B2). Delgado, III discloses " . . . at least one transluminally deliverable pump and a transluminally deliverable support structure which secures the at least one pump within the aorta for long-term use" (abstract). FIGS. 3 and 4 of Delgado, III are reproduced herein as FIGS. 4 and 5 (respectively). In discussing those figures, Delgado, III provides: "With reference to FIGS. 3 and 4, preferably, the outer end 122 of at least one strut 121, and preferably each of the outer ends of the support members, or struts, 121 are provided with an anchor element, such as a small hook 123, or similar structure, which serves to anchor each of the struts 121 at the desired location within descending aorta 98. If desired, a plurality of anchor elements may be used. Preferably, the left ventricle assist device 80 of the present invention is initially sheathed in a sheath 130 of approximately 22 to 23 French size in diameter in its undeployed configuration, as show in FIG. 3. If the struts 121 are of a spring-type design, the sheath 130 retains the support members 121 in the desired configuration illustrated in FIG. 3. Housing 114 preferably has a diameter of approximately 20 French. The strut system, or struts, 121, may also be deployed as a separate unit from the pump and initially deployed, and thereafter the pump 110 can then be deployed into the center of the strut system utilizing a locking mechanism, so that the pump may be removed and replaced at a later date so as to allow the ability to replace the pump if it should fail . . . " [para. 0038, emphasis added.]

In Delgado, III, other than that set forth above, no information is provided as to exactly how the pump and "separate unit" strut system or struts interact with each other. No specific designs incorporating these elements are described in the reference. There are no drawings of such mechanisms or apparatuses and there is no description of any method relating to a particular sequence of events enabling such system.

Further, there are no details about "the locking mechanism" provided at all. At best, one skilled in the art might imagine that the locking mechanism would engage once the pre-implanted struts or strut system come into contact with the pump. However, as there are no details or illustrations to explicitly describe the mechanisms and explain how the system would work, it is unclear how such a system would be constructed or operated.

Further still, there is no description as to how this locking mechanism may be "unlocked" to allow retrieval of the pump without removing the locked struts or strut system (which is simply stated to occur). Whatever this system is, it needs to be operated transcatheter, from a remote peripheral access site of the vasculature, and using conventional two-dimensional fluoroscopy.

Finally, in a situation where the pump has been "unlocked" from the strut system or struts and the pump has been retrieved, Delgado, III provides no information as to the shape of the struts or strut system that remain in the vessel. If elements of the struts or strut system protrude towards the center of the lumen, this may lead to thrombosis of the struts (which may lead in turn to embolic strokes or visceral organ embolization) or even complete lumen obstruction (if thrombi extend through the holes destined to accept the pumping units), most likely leading to the death of the patient.

In summary, Delgado, III merely only makes a passing reference to such a two-component assembly or system, but does not enable such an assembly (system) at all.

A second description of such a two-component assembly (system) occurs in U.S. Patent Application Publication No. 2015/0250935 A1 (Anderson et al.), published Sep. 10, 2015, entitled "Modular Implantable Ventricular Assist Device", assigned to Medtronic Vascular Galaway (now U.S. Pat. No. 9,616,159 B2). Anderson et al. discloses " . . . modular implantable ventricular assist devices configured to be, at least in part, assembled within a patient. The devices generally include a pump assembly and an expandable frame. The frame is configured to engage tissue of a patient when implanted. The pump assembly is configured to be operably coupled to the frame when the frame is implanted and in the expanded configuration" (Abstract.)

Referring to FIG. 5D of Anderson et al. (which is reproduced herein as FIG. 6), in one embodiment Anderson et al. teaches that an expandable frame be anchored to a vessel wall, followed by attachment of a scaffold to the frame. Alternatively, in other embodiments, the expandable frame and scaffold are single structure, which is itself expandable. In either case, the scaffold has multiple openings therein that are meant to receive and retain individual pumping units (modules). The patent teaches that once the scaffold is in place the individual pumping units are then advanced through the patient's vasculature by the surgeon and then pushed into the scaffold openings. One serious concern with this design is exactly how the surgeon will be able to guide the individual pumping units into the exact precise position that will be required to insert them into the scaffold openings. This is essentially a task (that will need to be repeated multiple times) which will require the surgeon to manipulate a guide wire or an individual pumping unit to reach the correct positioning and orientation in three dimensions, while being guided only via standard conventional two-dimensional fluoroscopy. Assuming this is even possible, the amount of time required for the intervention will be prohibitive.

Further, there is no teaching in Anderson et al. as to how such a device may be removed from a patient's vasculature in the context of a pumping unit failure (be it mechanical, thrombus-related, otherwise) or should the patient recuperate and need to be weaned-off the device. It may be while that the individual pumping units may be able to be pulled out of the scaffold, the frame and scaffold themselves appear to be non-retrievable by transcatheter techniques and would thus require being left in place permanently or to be removed via open surgical intervention.

As mentioned previously, generally the risks associated with leaving a stent structure permanently in place inside a vessel are generally quite low and accepted by the medical community. However, in this particular patent publication, the device component that is anchored to the vessel wall consists of a scaffold and a frame (which may be separate entities or a single entity). In such a device, it is clearly described that the scaffold or scaffold element of the frame is absolutely required to at least partially transversely obstruct the lumen of the vessel in order to provide a structure to which the pumping units may be connected.

In the event where it would be possible to only retrieve the pumping units of the system and to leave the frame and scaffold in place, having a scaffold transversely obstructing the vessel lumen may lead to thrombosis of the scaffold (which may lead in turn to embolic strokes or visceral organ embolization) or even complete lumen obstruction (if thrombi extend through the holes destined to accept the pumping units) most likely leading to the death of the patient.

Therefore, in summary, it is believed that both of the anchor and pump assemblies described in Delgado et al. and Anderson et al. (both those assembles described herein and others described in those references), are not viable solutions to the difficulties described hereinabove with respect to the prior art. Further, no product is currently available that embodies the technology described in those patents, which means that, to the developer of the present technology's knowledge, no product employing any type of anchor and pump assembly allowing atraumatic system retrieval following chronic device use is currently available for use at all.

Notwithstanding the fact that the designs for pump and anchor assembly structure in Delgado et al. and Anderson et al. have not reached a stage of development where they are appropriate for use in patients, given their potential in overcoming some of the drawbacks of other types of VADs, VADs employing separate pump and anchor assembly structures are believed to be an area in which further development is desirable. However, neither the structure described in Delgado et al. nor that of Anderson et al. is believed to be an appropriate starting point from which to continue such development. A new system (and related methods) that enable atraumatic retrieval of an intraluminal device using transcatheter techniques (whether the device has been used in an acute or a chronic setting) "starting from scratch" is believed to be required.

SUMMARY

It is an object of the present technology to ameliorate at least some of the inconveniences present in the prior art.

In summary, the present technology is based (at least in part) on the developers' observations and findings that certain devices such as micro-axial blood pumps may be implanted for long periods of time in a patient's vasculature and may serve as a scaffold for tissue overgrowth and may become incorporated into the vessel wall. Removal of such an incorporated device may prove to be dangerous for the patient or require open surgical intervention. Further, the developers of the present technology have noted that none of the prior art references provide a teaching of an assembly, system, device, etc. the ameliorates such situations.

The present technology attempts to provide the patient with an intraluminal device and anchor assembly that presents medically acceptable risks (and, if possible, but not required, would be completely atraumatic) to the lumen wall at the time of the implant and at the time of explant (i.e., retrieval), be it after acute or chronic assembly use. This goal is achieved through a modular assembly in which the anchor can be released from the device/anchor assembly while inside the patient at the time of explant (if so contemplated by the interventionist). Thus, the device may be explanted while leaving the anchor in place at the lumen wall; the anchor left in place having reduced medical risks to the patient (as compared with the prior art described hereinabove).

At a very high level, the present technology includes an anchor that is expandable when implanted, to anchor itself and a connected medical device within a body conduit. Should the medical interventionist so decide, only the device itself may be retrieved from the body, leaving the anchor in place, at the time of explant. In such cases, an interconnector connecting the device to the anchor is released, disconnecting the device from the anchor, allowing only the device to be retrieved. Further, the anchor, once disconnected, changes its configuration (e.g., shape and disposition of its components) so that it reduces the medical risk associated with leaving that structure inside the body presents to the patient.

Aspect 1.0—Clauses 1-34

Thus, in one aspect, the present technology provides: A mammalian body conduit intralumenal device and lumen wall anchor assembly.

The mammalian body conduit device (hereinafter generally referred to simply as the "device") is shaped and dimensioned to be deliverable to a delivery site within a lumen of a mammalian body conduit via a catheter. The device has a first interconnector structured to releasably connect the device with a lumen wall anchor for use in maintaining the device in place within the mammalian body conduit.

The lumen wall anchor (hereinafter generally referred to simply as the "anchor"), the lumen wall anchor has: (i) a 3D-shaped wire network having a central longitudinal axis; (ii) a plurality of first connector positioning wires extending from the wire network, each wire of the plurality of first connector positioning wires being moveable between a secured position and a released position and being overcomeably biased towards the released position; and (iii) at least one first connector disposed at an end of at least one wire of the plurality of first connector positioning wires.

The lumen wall anchor also has a compact-secured-configuration, an expanded-secured-configuration, and an expanded-released-configuration.

When the lumen wall anchor is in the compact-secured-configuration, the lumen wall anchor is shaped and dimensioned to be deliverable to the delivery site within the lumen of the mammalian body conduit via the catheter (the wire network is "compact"); and each wire of the first plurality of connector positioning wires is in the secured position. The secured position is the end of that wire of the first plurality of connector positioning wires being positioned in proximity to the first interconnector of the device such that the at least one first connector disposed at the end of that wire is positioned to be releasably connectable to the first interconnector of the device. In the compact-secured-position (of this aspect of the technology) each of the at least one first connector are releasably connected to the first interconnector of the device.

When the lumen wall anchor is in the expanded-secured-configuration, the wire network is dimensioned and shaped to exert a force on a wall of the lumen of the conduit (the wire network has "expanded" from being compact). The exerted force is sufficient to anchor the mammalian body conduit intralumenal device and lumen wall anchor assembly in place at an implantation site; and each wire of the first plurality of connector positioning wires is in the secured position (described in the previous paragraph). In the expanded-secured-position (of this aspect of the technology) each of the at least one first connector are releasably connected to the first interconnector of the device.

When the lumen wall anchor is in the expanded-released-configuration, the wire network is dimensioned and shaped to exert a force on the wall of the lumen of the mammalian body conduit intralumenal device and lumen wall anchor assembly in place at the implantation site; and each wire of the plurality of first connector positioning wires is in the released position. The released position is each of the at least one first connector being released from and unconnected to the first interconnector of the device. In the expanded-released-position (of this aspect of the technology) the plurality of first connector positioning wires and all of the at least one first connector (when considered together) do not obstruct fluid flow axially through the mammalian body conduit while the lumen wall anchor is anchored in place at the implantation site.

While most embodiments of the present technology are for use in humans, the "mammalian" body conduit devices described herein are in the context of humans. It should be understood however that veterinary uses of the present technology are also possible, and that, although no embodiments particularly structured for a particular veterinary use are described herein, as the skilled addressee would understand, such uses are within the scope of the present technology. "Mammalian" in the present disclosure thus includes non-human animals. The dimensions of the device will differ in embodiments depending on the particular mammal and the conduit thereof in which the device is to be implanted and operate.

The devices of the embodiments particularly described hereinbelow are shaped and dimensioned to be deliverable to a delivery site within a lumen of the vasculature (e.g., an aorta), being one of any number of various types, sizes, etc. over a range of human bodies, via a catheter. It is thus foreseen that various device embodiments of the present technology may be one of "one-size-fits-all", "one-size-fits-most", or particularly tailored for a particular applications or applications. The devices described in the embodiments hereinbelow are all fluid pumps of the type described in the WO '765 Publication. However, this has been done only for ease of description and understanding of the present technology. As the skilled addressee would understand, devices of the present technology are not limited to fluid pumps in general, nor to fluid pumps as described in the WO '765 Publication specifically. Nor is the implantation site (or delivery site) limited to the aorta or to any other particular blood vessel or even the vasculature of the body. The present technology may be used in any conduit within that is appropriate for the device and anchor being implanted, such as the urinary, biliary, gastrointestinal, respiratory tract or any of the heart chambers In many embodiments, the "catheter" referred to hereinabove is a "delivery sheath", however, any type of appropriate catheter is within the scope of the present technology.

In the embodiments particularly described hereinbelow, the first interconnector (and second interconnector, where present) are components of the device that are incorporated into the body of the device or into one of the modular units thereof. It should be understood that this is not required to be the case however, and in some embodiments the interconnector may be a separate component of the device not incorporated into the body of the device or one of the modular units thereof.

As was described hereinabove, the lumen wall anchor has a compact-secured-configuration, an expanded-secured-configuration, and an expanded-released-configuration. Depending the embodiment of the anchor, these three configurations may be the only configurations of an anchor embodiment, or an anchor embodiment may have other configurations in addition to these three. Both categories of embodiments are within the scope of the present technology.

As will be described in further detail hereinbelow: The compact-secured-configuration is typically the configuration the anchor is in during transcatheter implantation and explantation of the device and anchor assembly. The expanded-secured-configuration is typically the configuration that the anchor is in during operation of the device (e.g., the anchor is anchoring the device in place while the device is operable.) In some embodiments, the device and anchor assembly is structured to allow for the explantation of both the device and the anchor while the two remain connected together, should the medical interventionist decide to do so. In such embodiments, the retrieval process of the while assembly begins with the anchor in the expanded-secured-configuration, as is described in further detail hereinbelow. It should be understood, however, this is not necessarily the case in every embodiment of the present technology. In some embodiments, the device and anchor assembly may not be structured to allow for the explantation of the assembly as a whole at all. In such embodiments, only explantation of the device may be possible. The expanded-released-configuration is typically the configuration that the anchor is in once the releasable connection between the anchor and the device has been released. This configuration is typically used when the device will be explanted but the anchor will not; the anchor will remain in place anchored to the wall of the conduit into which it was implanted. Thus, the device may be explanted with little or no effect on the lumen wall (in view of any tissue growth over the anchor or otherwise), materially reducing the risks described hereinabove.

Further, as was described hereinabove, when the anchor is in the expanded-released-configuration, amongst other things, the end of each wire of the first plurality of connector positioning wires is proximate the wall of the lumen of the conduit. Thus, the first connector positioning wires and the first connectors disposed thereon do not obstruct fluid flow axially through the conduit while the anchor is anchored in place at the implantation site. These aspects of the expanded-released-configuration contribute materially to the reduction of the risks of leaving the anchor in place at the implantation site after explant of the device described above. For example, these aspects, contribute to the reduced risk of the anchor resulting in thrombus formation or material or complete obstruction of the conduit lumen. Thus, in the context of the present disclosure while it is believed that the skilled addressee would understand the meaning of the expressions "proximate" and "do not obstruct" as used herein in this context and that no further definitional detail need be given. However, if such is not the case, the expression " . . . the end of each wire . . . is proximate the wall of the lumen of the conduit . . . " shall be taken to mean that the shortest distance between the end of each wire (of the first or second) plurality of connector positioning wires (as the case may be) to the wall of the conduit is not more than 20% of the smallest cross-sectional diameter of the conduit taken through the wire network of the anchor when the anchor is anchored in place. Similarly, however, if such is not the case, the expression " . . . and do not obstruct fluid flow axially through the mammalian body conduit while the lumen wall anchor is anchored in place at the implantation site . . . " shall be taken to mean that the maximum amount of the smallest cross-sectional area of the conduit taken through the wire network of the anchor when the anchor is anchored in place that is blocked off by the first connector positioning wires and/or first connectors (as the case may be) is not more than 20%.

In some embodiments, when in the anchor is in the expanded-secured-configuration and/or in the expanded-released-configuration, the wire network is dimensioned and shaped to exert a force on the wall of the lumen of the conduit indirectly by exerting a force directly on the wall of a stent having been previously implanted within the conduit. Thus, some embodiments of the present technology are compatible with and may be used in conjunction with stents, should it be so decided to do so.

In some embodiments, the device has a proximal end and a distal end (which are designated consistently with the device's implantation orientation).

In some embodiments, the device has an elongate body having a central longitudinal axis and an exterior surface. The first interconnector is disposed, at least in part, on the exterior surface of the device. In the context of the present disclosure an interconnector is " . . . disposed, at least in part on the exterior surface of the device . . . " includes embodiments where, at a minimum, the interconnector is accessible from the exterior surface of the device.

In some embodiments, the at least one first connector disposed at the end of at least one wire of the plurality of first connector positioning wires is a plurality of first connectors. In some such embodiments, a single one of the plurality of first connectors is disposed at the end of each wire of the plurality of first connector positioning wires. In other such embodiments, ends of some of the plurality of first connector positioning wires are joined together in multiples, a single one of plurality of first connectors being disposed at the joined ends of each of the multiples.

In some embodiments, the first interconnector includes two openings in the exterior surface of the device and an interconnector wire. The interconnector wire traverses from an interior of the device to an exterior of the device through a first one of the two openings, extends extending outside the exterior of the device, and then traverses from the exterior of the device to the interior of the device through a second one of the two openings. In some such embodiments, the device has a first cavity extending within the body. The first cavity has a first portion extending from the exterior of the device to the first opening and a second portion extending from the second opening within the interior of the device. The interconnector wire further extends from the exterior of the device within the first portion of the first cavity to the first opening and from the second opening within the second portion of the first cavity.

In some embodiments, the first interconnector has multiple sub-first-interconnectors. In the context of the present technology, the expression "sub-first-interconnectors" is a reference to individual interconnector components that connect to separate first connectors of the anchor. This expression is not intended to mean that there exists any particular hierarchy between the individual interconnector components. The sub-first-interconnectors are (typically tangentially) spaced apart from one another. Each sub-first-interconnector includes two openings in the exterior surface of the device and a sub-first-interconnector wire. Each sub-first-interconnector wire traverses from an interior of the device to an exterior of the device through a first one of the two openings of its sub-first-interconnector, extends outside the exterior of the device, and then traverses from the exterior of the device to the interior of the device through a second one of the two openings of its sub-first-interconnector.

In some such embodiments, the device has a first cavity extending within the body the first cavity having a first portion extending within the interior of the device to the first opening of each sub-first-interconnector and a second portion extending from the second opening of each sub-first-interconnector within the interior of the device. The sub-first-interconnector wire of each sub-first-interconnector extends within at least part of the first portion of the first cavity to the first opening of that sub-first-interconnector and from the second opening of that sub-first-interconnector within at least part of the second portion of the first cavity. In some such embodiments, a majority of the first cavity extends within the body of the device generally parallel to the central longitudinal axis of the body of the device.

In some other such embodiments, the device further has multiple first cavities extending within the body. Each first cavity is associated with a one of the sub-first-interconnectors. Each first cavity has a first portion extending within the interior of the device to the first opening of the sub-first-interconnector associated with that first cavity and a second portion extending from the second opening of the sub-first-interconnector associated with that first cavity within the interior of the device. The sub-first-interconnector wire of each sub-first-interconnector further extends from the exterior of the device within the first portion of the first cavity associated with that sub-first-interconnector to the first opening associated with its sub-first-interconnector and from the second opening associated with its sub-first-interconnector within the second portion of the first cavity associated with that sub-first-interconnector.

A cavity in the context of the present technology is an absence of material within the body of the device that defines a pathway in the interior of the device. The interconnector wires and sub-interconnector wires generally extend along pathways formed by the cavities. Further, a cavity defining a pathway may be physically formed in an embodiment of the present technology from more than one physical structure, e.g., by more than one channel within the body. Thus, for example, a cavity of the present technology include two (or more) channels. And the reverse is also true, channels may be parts of multiple cavities. Thus, in the context of the present technology, one, some or all of the multiple first cavities may overlap in part. Overlapping cavities means that the pathways thereof are formed by the same physical structure (e.g., a primary channel, a branch channel, etc.) but that there are parts of the pathway thereof that are formed by different distinct physical structures (e.g., a primary channel, a branch channel, etc.). Thus, two (or more) of multiple first cavities can overlap in part.

In those embodiments having multiple first cavities, in such of such embodiments, a majority of each first cavity extends within the body of the device generally parallel to the central longitudinal axis of the body of the device.

In some embodiments, the sub-first-interconnectors are equally tangentially spaced apart along the exterior surface of the device in a plane perpendicular to the central longitudinal axis of the body of the device.

In some embodiments, a number of the plurality of first connectors is equal to a number of the sub-first-interconnectors, and each one of the plurality of first connectors is associated with a single one of the multiple sub-first-interconnectors.

In some embodiments, each one of the plurality of first connectors includes an element having a hole therein. The hole is shaped and dimensioned to allow the sub-first-interconnector wire of the sub-first-interconnector associated with that one of the first connectors to pass therethrough.

In some embodiments, each one of the plurality of first connectors includes an element having two holes therein. The holes are shaped and dimensioned, and positioned on the element with respect to each other, to allow the sub-first-interconnector wire of the sub-first-interconnector associated with that one of the first connectors to pass therethrough.

In some embodiments, each element is positioned, shaped and dimensioned such that, when the first connector positioning wire on which the one of the plurality of first connectors of which that element is included is disposed is in its securing position, each of the two holes in that element is disposed between a first plane perpendicular to the central longitudinal axis of the body of the device that includes at least a part of the first opening of the sub-first-interconnector associated with the one of the plurality of first connectors of which that element is included and a second plane perpendicular to the central longitudinal axis of the body of the device that includes at least part of the second opening of that sub-first-interconnector.

In some embodiments, each element is positioned, shaped and dimensioned such that, when the first connector positioning wire on which the one of the plurality of first connectors of which that element is disposed is in its securing position, a first hole of the two holes in that element is positioned adjacent the first opening of the sub-first-interconnector associated with the one of the plurality of first connectors of which that element is included, and a second hole of the two holes in that element is positioned adjacent the second opening of that sub-first-interconnector.

In some embodiments, each element is shaped to mate with a portion of the exterior surface of the device between the first opening of the sub-first interconnector associated with the one of the plurality of first connectors of which that element is included and the second opening of that sub-first interconnector.

In some embodiments, wherein when the lumen wall anchor is in the expanded-secured configuration, for each sub-first-interconnector, the sub-first-interconnector wire of that sub-first-interconnector: (i) Extends from within the interior of the device within at least part of the first portion of the first cavity for a first length towards the first opening of that sub-first-interconnector. (ii) Traverses to the exterior of the device through the first opening of that sub-first-interconnector. (iii) Passes through the first hole of the two holes of the element of the one of the plurality of first connectors associated with that sub-first-interconnector. (iv) Extends outside the exterior of the device to the second hole of the two holes of that element; (v) Passes through the second hole of the two holes of that element. (vi) Traverses through the second opening of that sub-first-interconnector (vii) extends within at least part of the second portion of the first cavity for a second length.

In some embodiments, for each sub-first-interconnector: An exterior surface of the sub-first-interconnector wire of that sub-first-interconnector frictionally engages an interior surface of the first cavity. A force generated by the bias towards the released position of the first connector positioning wire on which the one of the plurality of first connectors associated with that sub-first-interconnector is disposed exerts a force on the sub-first-interconnector wire of that sub-first-interconnector. That force exerted on the sub-first-interconnector wire of that sub-first-interconnector being insufficient to overcome a force generated by frictional engagement of the exterior surface of that sub-first-interconnector wire with the interior surface of the first cavity and with exterior surfaces of other wires within the first cavity. Whereby, the bias of that first connector positioning wire toward the released position is overcome and that first connector positioning wire remains in the secured position.

In some embodiments, for each sub-first-interconnector: The sub-first-interconnector wire of that sub-first-interconnector is at least indirectly pullable from the exterior of the device with a sufficient amount of force to overcome the force generated by frictional engagement of the exterior surface of the sub-first-interconnector wire of that sub-first-interconnector with the interior surface of the first cavity and with exterior surfaces of the other wires within the first cavity, to remove the sub-first-interconnector wire of that sub-first-interconnector from passing through the two holes of the element of the one of the plurality of first connectors associated with that sub-first-interconnector, thereby disconnecting that one of the plurality of first connectors from that sub-first-interconnector and allowing the first connector positioning wire on which that one of the plurality of first connectors is disposed to move to the released position. In the context of the present disclosure, "wire . . . is at least directly pullable . . . " should be understood to mean that the wire may be directly pullable by pulling on the wire, or may indirectly pullable by pulling on something eventually attached to the wire. An example of the latter is a handle attached to an actuation wire attached to the wire in question. The wire in question should be understood to be at least indirectly pullable by the handle.

In some embodiments, when the lumen wall anchor is in the expanded-secured configuration, for each sub-first-interconnector, the sub-first-interconnector wire of that sub-first-interconnector: (i) Extends within at least in a part of the first portion of the first cavity associated with that sub-first-interconnector for a first length towards the first opening of that sub-first-interconnector. (ii) Traverses to the exterior of the device through the first opening of that sub-first-interconnector. (iii) Passes through the first hole of the two holes of the element of the one of the plurality of first connectors associated with that sub-first-interconnector. (iv) Extends outside the exterior of the device to the second hole of the two holes of that element. (v) Passes through the second hole of the two holes of that element. (vi) traverses through the second opening of that sub-first-interconnector. (vii) Extends within at least a part of the second portion of the first cavity associated with that sub-first-interconnector for a second length.

In some embodiments, for each sub-first-interconnector: An exterior surface of the sub-interconnector-wire of that sub-first-interconnector frictionally engages an interior surface of the first cavity associated with that sub-first-interconnector. A force generated by the bias towards the released position of the first connector positioning wire on which the one of the plurality of first connectors associated with that sub-first-interconnector is disposed exerts a force on the sub-first-interconnector wire of that sub-first-interconnector. That force exerted on the sub-first-interconnector wire of that sub-first-interconnector is insufficient to overcome a force generated by frictional engagement of the exterior surface of that sub-first-interconnector wire with the interior surface of the first cavity associated with that sub-first-interconnector. Whereby, the bias of that first connector positioning wire toward the released position is overcome and that first connector positioning wire remains in the secured position.

In some embodiments, for each sub-first-interconnector: The sub-first-interconnector wire of that sub-first-interconnector is at least indirectly pullable from the exterior of the device with a sufficient amount of force to overcome the force generated by frictional engagement of the exterior surface of the sub-first-interconnector wire of that sub-first-interconnector with the interior surface of the first cavity associated with that sub-first-interconnector to remove the sub-first-interconnector wire of that sub-first-interconnector from passing through the two holes of the element of the one of the plurality of first connectors associated with that sub-first-interconnector. Thereby disconnecting that one of the plurality of first connectors from that sub-first-interconnector and allowing the first connector positioning wire on which that one of the plurality of first connectors is disposed to move to the released position.

In some embodiments, the sub-first-interconnector wires of all of the sub-first-interconnectors of the first interconnector are simultaneously at least indirectly pullable from the exterior of the device. In some such embodiments, the sub-first-interconnector wires of all of the sub-first-interconnectors of the first interconnector are at least indirectly connected to single first connector actuation wire at least indirectly pullable from the exterior of the device.

In some embodiments, the device is disconnected from the lumen wall anchor when all of the sub-first-interconnectors of the first interconnector are disconnected from each one of the plurality of first connectors associated with each sub-first-interconnector.

In some embodiments, the sub-first-interconnector wires of each of the sub-first-interconnectors of the first connector extend proximally away from the proximal end of the device.

In some embodiments, the single first connector actuation wire extends proximally away from the proximal end of the device.

In some embodiments, the lumen wall anchor, when in the expanded-secured-configuration, extends from the first interconnector toward the distal end of the device In some embodiments, each of the first connector positioning wires in the secured position forms a proximally-facing sloped surface such that a retrieval sheath being manoeuvered from the proximal end of the device towards the distal end of the device, via contact with the sloped surfaces of the first connector positioning wires, causes, at least in part, the lumen wall anchor to adopt the compact-secured-configuration as it enters a lumen of the retrieval sheath.

Aspect 1.1—Clauses 35 to 55

In a first sub-aspect of the first aspect, embodiments of the device further have a second interconnector spaced-apart from and distal to the first interconnector, the second interconnector being structured to releasably connect the device with the lumen wall anchor for use in maintaining the device in place within the mammalian body conduit.

The lumen wall anchor further includes: (i) A plurality of second connector positioning wires extending from the wire network, each wire of the plurality of second connector positioning wires being moveable between a secured position and a released position and being overcomeably biased towards the released position. (ii) A plurality of second connectors, a single one of the plurality of second connectors being disposed at an end of each wire of the plurality of second connector positioning wires.

When the lumen wall anchor is in the expanded-secured-configuration: (i) Each wire of the plurality of second connector positioning wires is in the secured position, the secured position being the end of that wire of the second plurality of connector wires being positioned in proximity to the second interconnector of the device such that each of the plurality of second connectors is positioned to be releasably connectable to the second interconnector of the device. (ii) Each of the plurality of second connectors is releasably connected to the second interconnector of the device.

When the lumen wall anchor is in the expanded-released-configuration: (i) Each wire of the plurality of second connector positioning wires is in the released position, the released position being the end of that wire of the plurality of second connector positioning wires being proximate the wall of the lumen of the conduit. (ii) The plurality of second connector positioning wires and the plurality of second connectors do not obstruct fluid flow axially through the wire network while the lumen wall anchor is anchored in place.

In some embodiments, each wire of the plurality of second connector positioning wires extends from a point intermediate between each end of the wire network.

In some embodiments, the plurality of first connector positioning wires and the plurality of second connector positioning wires extend from opposite ends of the wire network.

In some embodiments, the plurality of second connector positioning wires extend from the wire network at points more distal than points from which the plurality of first connector positioning wires extend.

In some embodiments, when the lumen wall anchor is in the expanded-released-configuration, each of the second connectors is generally aligned with a periphery of the wire network.

In some embodiments, the second interconnector has multiple sub-second-interconnectors. The sub-second-interconnectors are spaced-apart from one another. Each sub-second-interconnector includes two openings in the exterior surface of the device and a sub-second-interconnector wire; the sub-second-interconnector wire: traverses from the interior of the device to the exterior of the device through a first one of the two openings, extends outside the exterior of the device, and then traverses from the exterior of the device to the interior of the device through a second one of the two openings.

In some embodiments: (i) The second portion of the first cavity extends to the first opening of each sub-second-interconnector and a third portion extends from the second opening of each sub-second-interconnector within the interior of the device. (ii) The sub-second-interconnector wire of each sub-second-interconnector extends within the interior of the device within at least part of the first portion of the first cavity and the second portion of the first cavity to the first opening of that sub-second-interconnector and from the second opening of that sub-second-interconnector within at least part of the third portion of the first cavity.

In some embodiments: (i) The device has multiple second cavities extending within the body. The second cavities are distinct from the first cavities. Each second cavity is associated with one of the sub-second-interconnectors. Each second cavity has a first portion extending within the interior of the device to the first opening of the sub-second-interconnector associated with that cavity and a second portion extending from the second opening of that sub-second-interconnector within the interior of the device. (ii) The sub-second-interconnector wire of each sub-second-interconnector further extends from within the interior of the device within at least a part of the first portion of the cavity associated with that sub-second-interconnector to the first opening associated with that sub-second-interconnector and from the second opening associated with that sub-second-interconnector within at least a part of the second portion of the cavity associated with that sub-second-interconnector.

In some embodiments, a majority of each second cavity extends within the body generally parallel to the central longitudinal axis of the body of the device.

In some embodiments: (i) The sub-second-interconnectors are equally tangentially spaced-apart along the exterior surface of the device in a plane perpendicular to the central longitudinal axis of the body of the device. (ii) Each of the sub-second-interconnectors is tangentially aligned with a one of the sub-first-interconnectors along a line parallel to the central longitudinal axis of the body of the device.

In some embodiments, a number of the plurality of second connectors is equal to a number of the sub-second-interconnectors, and each one of the plurality of second connectors is associated with a single one of the multiple sub-second-interconnectors.

In some embodiments: (i) Each one of the second connectors includes an element having two holes therein. The holes are shaped and dimensioned, and positioned on the element with respect to each other, to allow the sub-second-interconnector wire of the sub-second-interconnector associated with that one of the second connectors to pass therethrough. (ii) Each element is positioned, shaped and dimensioned such that, when the second connector positioning wire on which the one of the plurality of second connectors of which that element is included is disposed in its securing position, a first hole of the two holes in that element is positioned adjacent the first opening of the sub-second-interconnector associated with that one of the plurality of second connectors and a second hole of the two holes in the element is positioned adjacent the second opening of that one of the plurality of sub-second-interconnectors.

In some embodiments when the lumen wall anchor is in the expanded-secured configuration: (i) For each sub-first-interconnector, the sub-first-interconnector wire of that sub-first-interconnector: (a) Extends within the interior of the device within at least part of the first portion of the first cavity for a first length towards the first opening of that sub-first-interconnector. (b) Traverses to the exterior of the device through the first opening of that sub-first-interconnector. (c) Passes through the first hole of the two holes of the element of the one of the plurality of first connectors associated with that sub-first-interconnector. (d) Extends outside the exterior of the device to the second hole of the two holes of that element. (e) Passes through the second hole of the two holes of that element. (f) Traverses through the second opening of that sub-first-interconnector. (g) Extends within at least part of the second portion of the first cavity for a second length. (ii) For each sub-second-interconnector, the sub-second-interconnector wire of that sub-second-interconnector: (a) Extends within the interior of the device within at least part of the first portion of the first cavity and the second portion of the first cavity for a first length towards the first opening of that sub-second-interconnector. (b) Traverses to the exterior of the device through the first opening of that sub-second-interconnector. (c) Passes through the first hole of the two holes of the element of the one of the plurality of second connectors associated with that sub-second-interconnector. (d) Extends outside the exterior of the device to the second hole of the two holes of that element. (e) Passes through the second hole of the two holes of that element. (f) Traverses through the second opening of that sub-second-interconnector. (g) Extends within at least a part of the third portion of the first cavity for a second length.

In some embodiments: (i) For each sub-first-interconnector: (a) An exterior surface of the sub-first-interconnector wire of that sub-first-interconnector frictionally engages an interior surface of the first cavity. (b) A force generated by the bias towards the released position of the first connector positioning wire on which the one of the plurality of first connectors associated with that sub-first-interconnector is disposed exerts a force on the sub-first-interconnector wire of that sub-first-interconnector, that force exerted on the sub-first-interconnector wire of that sub-first-interconnector being insufficient to overcome a force generated by frictional engagement of the exterior surface of that sub-first-interconnector wire with the interior surface of the first cavity and with exterior surfaces of other interconnector wires within the first cavity; whereby, the bias of that first connector positioning wire toward the released position is overcome and that first connector positioning wire remains in the secured position. (ii) For each sub-second-interconnector: (a) An exterior surface of the sub-second interconnector wire of that sub-second-interconnector frictionally engages an interior surface of the first cavity. (b) A force generated by the bias towards the released position of the second connector positioning wire on which the one of the plurality of second connectors associated with that sub-second-interconnector is disposed exerts a force on the sub-second-interconnector wire of that sub-second-interconnector. That force exerted on the sub-second-interconnector wire of that sub-second-interconnector is insufficient to overcome a force generated by frictional engagement of the exterior surface of that sub-second-interconnector wire with the interior surface of the first cavity and with exterior surfaces of other interconnector wires within the first cavity; whereby, the bias of that second connector positioning wire toward the released position is overcome and that second connector positioning wire remains in the secured position.

In some embodiments: (i) For each sub-first-interconnector, the sub-first-interconnector wire of that sub-first-interconnector is at least indirectly pullable from the exterior of the device with a sufficient amount of force to overcome the force generated by frictional engagement of the exterior surface of the sub-first-interconnector wire of that sub-first-interconnector with the interior surface of the first cavity and with exterior surfaces of the other interconnector wires within the first cavity, to remove the sub-first-interconnector wire of that sub-first-interconnector from passing through the two holes of the element of the one of the plurality of first connectors associated with that sub-first-interconnector, thereby disconnecting that one of the plurality of first connectors from that sub-first-interconnector and allowing the first connector positioning wire on which that one of the plurality of first connectors is disposed to move to the released position. (ii) For each sub-second-interconnector, the sub-second-interconnector wire of that sub-second-interconnector is at least indirectly pullable from the exterior of the device with a sufficient amount of force to overcome the force generated by frictional engagement of the exterior surface of the sub-second-interconnector wire of that sub-second-interconnector with the interior surface of the first cavity and with exterior surfaces of the other interconnector wires within the first cavity, to remove the sub-second-interconnector wire of that sub-second-interconnector from passing through the two holes of the element of the one of the plurality of second connectors associated with that sub-second-interconnector, thereby disconnecting that one of the plurality of second connectors from that sub-second-interconnector and allowing the second connector positioning wire on which that one of the plurality of second connectors is disposed to move to the released position.

In some embodiments, when the lumen wall anchor is in the expanded-secured configuration: (i) For each sub-first-interconnector, the sub-first-interconnector wire of that sub-first-interconnector: (a) Extends within the interior of the device within at least a part of the first portion of the first cavity associated with that sub-first-interconnector for a first length towards the first opening of that sub-first-interconnector. (b) Traverses to the exterior of the device through the first opening of that sub-first-interconnector. (c) Passes through the first hole of the two holes of the element of the one of the plurality of first connectors associated with that sub-first-interconnector. (d) Extends outside the exterior of the device to the second hole of the two holes of that element. (e) Passes through the second hole of the two holes of that element. (f) Traverses through the second opening of that sub-first-interconnector. (g) Extends within at least a part of the second portion of the first cavity associated with that sub-first-interconnector for a second length. (ii) For each sub-second-interconnector, the sub-second-interconnector wire of that sub-second-interconnector: (a) Extends within the interior of the device within at least a part of the first portion of the second cavity associated with that sub-second-interconnector for a first length to the first opening of that sub-second-interconnector. (b) Traverses to the exterior of the device through the first opening of that sub-second-interconnector. (c) Passes through the first hole of the two holes of the element of the one of the plurality of second connectors associated with that sub-second-interconnector. (d) Extends outside the exterior of the device to the second hole of the two holes of that element. (e) Passes through the second hole of the two holes of that element. (f) Traverses through the second opening of that sub-second-interconnector. (g) Extends within at least a part of the second portion of the first cavity associated with that sub-second-interconnector for a second length.

In some embodiments: (i) For each sub-first-interconnector: (a) An exterior surface of the sub-first-interconnector wire of that sub-first-interconnector frictionally engages an interior surface of the first cavity associated with that sub-first-interconnector. (b) A force generated by the bias towards the released position of the first connector positioning wire on which the one of the plurality of first connectors associated with that sub-first-interconnector is disposed exerts a force on the sub-first-interconnector wire of that sub-first-interconnector. That force exerted on the sub-first-interconnector wire of that sub-first-interconnector is insufficient to overcome a force generated by frictional engagement of the exterior surface of that sub-first-interconnector wire with the interior surface of the first cavity associated with that sub-first-interconnector; whereby, the bias of that first connector positioning wire toward the released position is overcome and that first connector positioning wire remains in the secured position. (ii) For each sub-second-interconnector: (a) An exterior surface of the sub-second-interconnector wire of that sub-second-interconnector frictionally engages an interior surface of the second cavity associated with that sub-second-interconnector. (b) A force generated by the bias towards the released position of the second connector positioning wire on which the one of the plurality of second connectors associated with that sub-second-interconnector is disposed exerts a force on the sub-second-interconnector wire of that sub-second-interconnector. That force exerted on the sub-second-interconnector wire of that sub-second-interconnector being insufficient to overcome a force generated by frictional engagement of the exterior surface of the sub-second-interconnector wire of that sub-second-interconnector with the interior surface of the first cavity associated with that sub-second-interconnector; whereby, the bias of that wire of the second connector positioning wires toward the released position is overcome and that second connector positioning wire remains in the secured position.

In some embodiments: (i) For each sub-first-interconnector, the sub-first-interconnector wire of that sub-first-interconnector is at least indirectly pullable from the exterior of the device with a sufficient amount of force to overcome the force generated by frictional engagement of the exterior surface of the sub-first-interconnector wire of that sub-first-interconnector with the interior surface of the first cavity associated with that sub-first-interconnector to remove the sub-first-interconnector wire of that sub-first-interconnector from passing through the two holes of the element of the one of the plurality of first connectors associated with that sub-first-interconnector, thereby disconnecting that one of the plurality of first connectors from that sub-first-interconnector and allowing the first connector positioning wire on which that one of the plurality of first connectors is disposed to move to the released position. (ii) For each sub-second-interconnector, the sub-second-interconnector wire of that sub-second-interconnector is at least indirectly pullable from the exterior of the device with a sufficient amount of force to overcome the force generated by frictional engagement of the exterior surface of the sub-second-interconnector wire of that sub-second-interconnector with the interior surface of the second cavity associated with that sub-second-interconnector, to remove that sub-second-interconnector wire from passing through the two holes of the element of the one of the plurality of second connectors associated with that sub-second-interconnector, thereby disconnecting that one of the plurality of second connectors from that sub-second-interconnector and allowing the one of the plurality of second connector wires on which that one of the second connectors is disposed to move to the released position.

In some embodiments, the sub-second-interconnector wires of all of the sub-second interconnectors of the second interconnector are simultaneously at least indirectly pullable from the exterior of the device.

In some embodiments, the device is disconnected from the lumen wall anchor when: Each of the sub-first-interconnectors of the first interconnector is disconnected from the one of the plurality of first connectors associated with that sub-first-interconnector. Each of the sub-second-interconnectors of the second interconnector is disconnected from the one of the plurality of second connectors associated with that sub-second-interconnector.

In some embodiments, the sub-second-interconnector wires of the each of the plurality of sub-second-interconnectors of the second connector exteriorly extend away from the proximal end of the device.

Aspect 1.2—Clauses 56 to 64

In a second sub-aspect of this first aspect, in some embodiments: (i) The second interconnector has multiple sub-second-interconnectors. The sub-second-interconnectors are tangentially spaced-apart from one another, and axially spaced-apart from the sub-first-connectors. (ii) Each of the second-sub-connectors is tangentially aligned in a one-to-one relationship a single one of the sub-first-connectors. (iii) Each sub-second-interconnector includes two openings in the exterior surface of the device.

In some embodiments, the second portion of the first cavity extends from the second opening of each sub-first-interconnector to the first opening of each sub-second-interconnector, and the first cavity has a third portion extending from the second opening of each sub-second-interconnectors within the interior of the device.

In some embodiments, each first cavity is further associated with the one of the sub-second-interconnectors that is in a one-to-one relationship with the one of the sub-first interconnectors that that first cavity is associated with. The second portion of each first cavity extends from the second opening of its associated sub-first-interconnector to the first opening of its associated sub-second-interconnector. Each first cavity has a third portion extending from the second opening of its associated sub-second-interconnector within the interior of the device.

In some embodiments: (i) A number of the plurality of second connectors is equal to a number of the sub-second-interconnectors, and each one of the plurality of second connectors is associated with a single one of the sub-second-interconnectors. (ii) Each one of the plurality of second connectors includes an element having two holes therein. The holes are shaped and dimensioned, and positioned on the element with respect to each other, to allow the sub-first-interconnector wire of the sub-first-interconnector associated with the sub-second-interconnector associated with that one of the plurality of second connectors to pass therethrough. (iii) Each element is positioned, shaped and dimensioned such that, when the second connector positioning wire on which the one of the plurality of second connectors of which that element is included is disposed is in its securing position, a first hole of the two holes in that element is positioned adjacent the first opening of the sub-second-interconnector associated with the one of the plurality of second connectors of which that element is included, and a second hole of the two holes in that element is positioned adjacent the second opening of that sub-second-interconnector.

In some embodiments, when the lumen wall anchor is in the expanded-secured-configuration, for each sub-first interconnector and its associated sub-second-interconnector, the sub-first-interconnector wire of that sub-first-interconnector: (i) Extends within the interior of the device within at least part of the first portion of the first cavity for a first length towards the first opening of that sub-first-interconnector. (ii) Traverses to the exterior of the device through the first opening of that sub-first-interconnector. (iii) Passes through the first hole of the two holes of the element of the one of the plurality of first connectors associated with that sub-first-interconnector. (iv) Extends outside the exterior of the device to the second hole of the two holes of that element. (v) Passes through the second hole of the two holes of that element. (vi) Traverses through the second opening of that sub-first-interconnector. (vii) Extends with the second portion of the first cavity for a second length to the first opening of the sub-second-connector associated with that sub-first interconnector. (viii) Traverses to the exterior of the device through the first opening of that sub-second-interconnector. (ix) Passes through the first hole of the two holes of the element of the one of the plurality of second connectors associated with that sub-second-interconnector. (x) Extends outside the exterior of the device to the second hole of the two holes of that element. (xi) Passes through the second hole of the two holes of that element (xii) Traverses through the second opening of that sub-second-interconnector. (xiii) Extends within at least part of the third portion of the first cavity for a third length.

In some embodiments: (i) For each sub-first-interconnector: (a) an exterior surface of the sub-first-interconnector wire of that sub-first-interconnector frictionally engages an interior surface of the first cavity. (b) a force generated by the bias towards the released position of the first connector positioning wire on which the one of the plurality of first connectors associated with that sub-first-interconnector is disposed exerts a force on the sub-first-interconnector wire of that sub-first-interconnector. That force exerted on the sub-first-interconnector wire of that sub-first-interconnector is insufficient to overcome a force generated by frictional engagement of the exterior surface of that sub-first-interconnector wire with the interior surface of the first cavity and with exterior surfaces of other interconnector wires within the first cavity; whereby, the bias of that first connector positioning wire toward the released position is overcome and that first connector positioning wire remains in the secured position. (ii) For each sub-second-interconnector: (a) a force generated by the bias towards the released position of the second connector positioning wire on which the one of the plurality of second connectors associated with that sub-second-interconnector is disposed exerts a force on the sub-first-interconnector wire of the sub-first-interconnector wire associated with that sub-second-interconnector. That force exerted on that sub-first-interconnector wire is insufficient to overcome the force generated by frictional engagement of the exterior surface of that sub-first-interconnector wire with the interior surface of the first cavity; whereby, the bias of that wire of the second connector positioning wires toward the released position is overcome and that second connector positioning wire remains in the secured position.

In some embodiments, when the lumen wall anchor is in the expanded-secured configuration, for each sub-first-interconnector and its associated sub-second-interconnector, the sub-first-interconnector wire of that sub-first-interconnector: (i) Extends within the interior of the device within at least part of the first portion of the first cavity associated with that sub-first-interconnector for a first length towards the first opening of that sub-first-interconnector. (ii) Traverses to the exterior of the device through the first opening of that sub-first-interconnector. (iii) Passes through the first hole of the two holes of the element of the one of the plurality of first connectors associated with that sub-first-interconnector. (iv) Extends outside the exterior of the device to the second hole of the two holes of that element. (v) Passes through the second hole of the two holes of that element. (vi) Traverses through the second opening of that sub-first-interconnector. (vii) Extends with the second portion of the first cavity associated with that sub-first-interconnector for a second length to the first opening of the sub-second-connector associated with that sub-first interconnector. (viii) Traverses to the exterior of the device through the first opening of that sub-second-interconnector. (ix) Passes through the first hole of the two holes of the element of the one of the plurality of second connectors associated with that sub-second-interconnector. (x) Extends outside the exterior of the device to the second hole of the two holes of that element. (xi) Passes through the second hole of the two holes of that element. (xii) Traverses through the second opening of that sub-second-interconnector. (xiii) Extends within at least part of the third portion of the first cavity associated with that sub-second-interconnector for a third length.

In some embodiments: (i) For each sub-first-interconnector: (a) An exterior surface of the sub-first-interconnector wire of that sub-first-interconnector frictionally engages an interior surface of the first cavity associated with that sub-first-interconnector. (b) A force generated by the bias towards the released position of the first connector positioning wire on which the one of the plurality of first connectors associated with that sub-first-interconnector is disposed exerts a force on the sub-first-interconnector wire of that sub-first-interconnector. That force exerted on the sub-first-interconnector wire of that sub-first-interconnector is insufficient to overcome a force generated by frictional engagement of the exterior surface of that sub-first-interconnector wire with the interior surface of the first cavity associated with that sub-first-interconnector; whereby, the bias of that first connector positioning wire toward the released position is overcome and that first connector positioning wire remains in the secured position; (ii) for each sub-second-interconnector: (a) A force generated by the bias towards the released position of the second connector positioning wire on which the one of the plurality of second connectors associated with that sub-second-interconnector is disposed exerts a force on the sub-first-interconnector wire of the sub-first-interconnector wire associated with that sub-second-interconnector. That force exerted on that sub-first-interconnector wire is insufficient to overcome the force generated by frictional engagement of the exterior surface of that sub-first-interconnector wire with the interior surface of the first cavity associated with that sub-second-interconnector; whereby, the bias of that wire of the second connector positioning wires toward the released position is overcome and that second connector positioning wire remains in the secured position.

In some embodiments: (i) For each sub-second-interconnector, the sub-first-interconnector wire of the sub-first-interconnector associated with that sub-second-interconnector is at least indirectly pullable from the exterior of the device by a first length to remove that sub-first-interconnector wire from passing through the two holes of the element of the one of the plurality of second connectors associated with that sub-second-interconnector, thereby disconnecting the one of the plurality of second connectors associated with that sub-second-interconnector from that sub-second-interconnector and allowing the one of the second connector wires on which the one of the plurality of second connectors associated with that sub-second-interconnector is disposed to move to the released position, the first length being insufficient to remove that sub-first-interconnector wire from passing through the two holes of the element of the one of the plurality of first connectors associated the sub-first-interconnector associated with that sub-second-interconnector. (ii) For each sub-first-interconnector, that sub-first-interconnector wire is thereafter at least indirectly pullable from the exterior of the device by a second length to remove that interconnector wire from passing through the two holes of the element of the one of the plurality of first connectors associated with that sub-first-interconnector, thereby disconnecting the one of the plurality of first connectors associated with that sub-first-interconnector from that sub-first-interconnector and allowing the one of the first connector positioning wires on which the one of the plurality of first connectors associated with that sub-first-interconnector is disposed to move to the released position.

In some embodiments: (i) Each of the sub-first-interconnectors of the first interconnector is disconnected from the one of the plurality of first connectors associated with that sub-first-interconnector. (ii) Each of the sub-second-interconnectors of the second interconnector is disconnected from the one of the second connectors associated with that sub-second-interconnector.

Aspect 1.3—Clauses 66 to 72

In a third sub-aspect of the first aspect, in some embodiments: (i) a number of the plurality of second connectors is equal to a number of the sub-second-interconnectors, and each one of the plurality of second connectors is associated with a single one of the sub-second-interconnectors. (ii) Each one of the plurality of second connectors includes an element having two holes therein. The holes are shaped and dimensioned, and positioned on the element with respect to each other, to allow the sub-second-interconnector wire of the sub-second-interconnector associated with that one of the plurality of second connectors to pass therethrough. Each element is positioned, shaped and dimensioned such that, when the second connector positioning wire on which the one of the plurality of second connectors of which that element is included is disposed is in its securing position, a first hole of the two holes in that element is positioned adjacent the first opening of the sub-second-interconnector associated with the one of the plurality of second connectors of which that element is included, and a second hole of the two holes in that element is positioned adjacent the second opening of that sub-second-interconnector.

In some embodiments: (i) The sub-first-interconnector wire of each of the sub-first-interconnectors has a hollow core. (ii) The sub-second-interconnector wire of each of the sub-second-interconnectors is disposed within the hollow core of the sub-first-interconnector wire of the one of the sub-first-interconnectors associated with that sub-second-interconnector.

In some embodiments: (i) The second portion of the first cavity extends to the first opening of each sub-second-interconnector and a third portion extends from the second opening of each sub-second-interconnector within the interior of the device. (ii) When the lumen wall anchor is in the expanded-secured configuration, for each sub-first-interconnector and its associated sub-second-interconnector: (a) the sub-first-interconnector wire of that sub-first-interconnector, has a proximal end, and has a distal end that extends within the second portion of the first cavity for a second length and ends before reaching the first opening of the sub-second-connector associated with that sub-first interconnector. (b) The sub-second-interconnector wire of that sub-second-connector, has a proximal end that extends proximally beyond the proximal end of the sub-first-interconnector wire of the sub-first-interconnector associated with that sub-second-interconnector, and has a distal end that: (I) Exits the hollow core of the sub-first-interconnector wire of that sub-first-connector within the second portion of the first cavity. (II) Extends within the second portion of the first cavity to the first opening of that sub-second-interconnector. (III) Traverses to the exterior of the device through the first opening of that sub-second-interconnector. (IV) Passes through the first hole of the two holes of the element of the one of the plurality second connectors associated with that sub-second-interconnector. (V) Extends outside the exterior of the device to the second hole of the two holes of that element. (VI) Passes through the second hole of the two holes of that element. (VII) Traverses through the second opening of that sub-second-interconnector. (VIII) Extends within at least part of the third portion of the first cavity for a third length. (c) An exterior surface of the sub-second-interconnector wire of that sub-second-interconnector frictionally engages an interior surface of the hollow core of the sub-first-interconnector wire of the sub-first-interconnector within which that sub-second-interconnector wire is disposed prior to exiting the hollow core of that sub-first-interconnector wire. (d) The exterior surface of the sub-second-interconnector wire of that sub-second-interconnector further frictionally engages an interior surface of the first cavity after exiting the hollow core of the sub-first-interconnector wire of that sub-first-connector associated with that sub-second-connector. (e) A force generated by the bias towards the released position of the second connector positioning wire on which the one of the plurality of second connectors associated with that sub-second-interconnector is disposed exerts a force on the sub-second-interconnector wire of that sub-second-interconnector. That force exerted on that sub-second-interconnector wire being insufficient to overcome a force generated by frictional engagement of the exterior surface of that sub-second-interconnector wire with the interior surface of the first cavity and of the exterior surface of that sub-second-interconnector wire with the interior surface of the hollow core of the sub-first-interconnector wire of the sub-first-interconnector within which that sub-second-interconnector wire is disposed; whereby, the bias of that wire of the second connector positioning wire towards the released position is overcome and that second connector positioning wire remains in the secured position.

In some embodiments: (i) For each sub-second-interconnector, the sub-second-interconnector wire of that sub-second-interconnector is at least indirectly pullable from the exterior of the device with a sufficient amount of force to overcome the force generated by frictional engagement of the exterior surface of that sub-second-interconnector wire with the interior surface of the first cavity and of the exterior surface of that sub-second-interconnector wire and the interior surface of the hollow core of the sub-first-interconnector wire of the sub-first-interconnector within which that sub-second-interconnector wire is disposed, to remove that sub-second-interconnector wire from passing through the two holes of the element of the one of the plurality of second connectors associated with that sub-second-interconnector, thereby disconnecting the one of the plurality of second connectors associated with that sub-second-interconnector from that sub-second-interconnector and allowing the one of the second connector positioning wires on which the one of the plurality of second connectors associated with that sub-second-interconnector is disposed to move to the released position, while leaving that sub-first-interconnector wire in place. (ii) For each sub-first-interconnector, the sub-first-interconnector wire of that sub-first-interconnector is thereafter at least indirectly pullable from the exterior of the device with a sufficient amount of force to overcome the force generated by frictional engagement of the exterior surface of the sub-first-interconnector wire of that sub-first-interconnector with the interior surface of the first cavity and with exterior surfaces of the other interconnector wires within the first cavity, to remove the sub-first-interconnector wire of that sub-first-interconnector from passing through the two holes of the element of the one of the plurality of first connectors associated with that sub-first-interconnector, thereby disconnecting that one of the plurality of first connectors from that sub-first-interconnector and allowing the first connector positioning wire on which that one of the plurality of first connectors is disposed to move to the released position.

For some embodiments: (i) each first cavity is further associated with the one of the sub-second-interconnectors that is in a one-to-one relationship with the one of the sub-first interconnectors that that first cavity is associated with. The second portion of each first cavity extends from the second opening of its associated sub-first-interconnector to the first opening of its associated sub-second-interconnector. Each first cavity has a third portion extending from the second opening of its associated sub-second-interconnector within the interior of the device. (ii) when the lumen wall anchor is in the expanded-secured configuration, for each sub-first-interconnector and its associated sub-second-interconnector: (a) The sub-first-interconnector wire of that sub-first-interconnector has a proximal end, and has a distal end that extends within the second portion of the first cavity associated with that sub-first-interconnector for a second length and ends before reaching the first opening of the sub-second-connector associated with that sub-first interconnector. (b) The sub-second-interconnector wire of that sub-second-connector, has a proximal end that extends proximally beyond the proximal end of the interconnector wire of the sub-first-interconnector associated with that sub-second-interconnector; and has a distal end that: (I)

Exits the hollow core of the interconnector wire of that sub-first-connector within the second portion of the first cavity associated with that sub-second-connector. (II) Extends within the second portion of the first cavity to the first opening of that sub-second-interconnector associated with that sub-second-connector. (III) Traverses to the exterior of the device through the first opening of that sub-second-interconnector. (IV) Passes through the first hole of the two holes of the element of the one of the plurality second connectors associated with that sub-second-interconnector. (V) Extends outside the exterior of the device to the second hole of the two holes of that element. (VI) Passes through the second hole of the two holes of that element. (VII) Traverses through the second opening of that sub-second-interconnector. (VIII) Extends within at least part of the third portion of the first cavity associated with that sub-second-interconnector for a third length. (c) An exterior surface of the sub-second-interconnector wire of that sub-second-interconnector frictionally engages an interior surface of the hollow core of the sub-first-interconnector wire of the sub-first-interconnector within which that sub-second-interconnector wire is disposed prior to exiting the hollow core of that sub-first-interconnector wire. (d) The exterior surface of the sub-second-interconnector wire of that sub-second-interconnector further frictionally engages an interior surface of the first cavity within which that sub-second-interconnector wire is disposed after exiting the hollow core of the sub-first-interconnector wire of that sub-first-connector associated with that sub-second-connector. (e) a force generated by the bias towards the released position of the second connector positioning wire on which the one of the plurality of second connectors associated with that sub-second-interconnector is disposed exerts a force on the sub-second-interconnector wire of that sub-second-interconnector. That force exerted on that sub-second-interconnector wire is insufficient to overcome a force generated by frictional engagement of the exterior surface of that sub-second-interconnector wire with the interior surface of the first cavity associated with that sub-second-interconnector and of the exterior surface of that sub-second-interconnector with the interior surface of the hollow core of the sub-first-interconnector wire of the sub-first-interconnector within which that sub-second-interconnector wire is disposed; whereby, the bias of that wire of the second connector positioning wire towards the released position is overcome and that second connector positioning wire remains in the secured position.

In some embodiments: (i) For each sub-second-interconnector, the sub-second-interconnector wire of that sub-second-interconnector is at least indirectly pullable from the exterior of the device with a sufficient amount of force to overcome the force generated by frictional engagement of the exterior surface of that sub-second-interconnector wire with the interior surface of the first cavity associated with that sub-second-interconnector and of the exterior surface of that sub-second-interconnector and the interior surface of the hollow core of the sub-first-interconnector wire of the sub-first-interconnector within which that sub-second-interconnector wire is disposed, to remove that sub-second-interconnector wire from passing through the two holes of the element of the one of the plurality of second connectors associated with that sub-second-interconnector, thereby disconnecting the one of the plurality of second connectors associated with that sub-second-interconnector and allowing the one of the second connector positioning wires on which the one of the plurality of second connectors associated with that sub-second-interconnector is disposed to move to the released position, while leaving that sub-first-interconnector wire in place. (ii) For each sub-first-interconnector, the sub-first-interconnector wire of that sub-first-interconnector is thereafter at least indirectly pullable from the exterior of the device with a sufficient amount of force to overcome the force generated by frictional engagement of the exterior surface of that sub-first-interconnector wire and the interior surface of the first cavity associated with that sub-first-interconnector, to remove that sub-first-interconnector wire from passing through the two holes of the element of the one of the plurality of first connectors associated with that sub-first-interconnector, thereby disconnecting the one of the plurality of first connectors associated with that sub-first-interconnector from that sub-first-interconnector and allowing the one of the first connector positioning wires on which the one of the first connectors associated with that sub-first-interconnector is disposed to move to the released position.

In some embodiments, the device is disconnected from the lumen wall anchor when: (i) Each of the sub-first-interconnectors of the first interconnector is disconnected from the one of the plurality of first connectors associated with that sub-first-interconnector. Each of the sub-second-interconnectors of the second interconnector is disconnected from the one of the second connectors associated with that sub-second-interconnector.

Aspect 1.4—Clauses 73 to 85

In a fourth sub-aspect of the first aspect, in some embodiments: (i) The device further has a second interconnector spaced-apart from and distal to the first interconnector. The second interconnector is structured to releasably connect the device with the lumen wall anchor for use in maintaining the lumen anchor in the compact-secured-configuration. (ii) The lumen wall anchor further includes a plurality of second connectors disposed on the wire network. (iii) When the lumen wall anchor is in the compact-secured-position, each of the plurality of second connectors is connected to the second interconnector. (iv) When the lumen wall anchor is in the expanded-secured-configuration, each of the second connectors is disconnected from the second interconnector. (v) When the lumen wall anchor is in the expanded-released-configuration, each of the second connectors is disconnected from the second interconnector and does not obstruct fluid flow axially through the wire network while the lumen wall anchor is anchored in place.

In some embodiments, the second connectors are disposed distally of the first connectors.

In some embodiments, the second interconnector has multiple sub-second-interconnectors. The sub-second-interconnectors are spaced-apart from one another. Each sub-second-interconnector including two openings in the exterior surface of the device and a sub-second-interconnector wire, the sub-second-interconnector wire: (i) Traversing from the interior of the device to the exterior of the device through a first one of the two openings. (ii) Extending outside the exterior of the device. (iii) Traversing from the exterior of the device to the interior of the device through a second one of the two openings.

In some embodiments: (i) The second portion of the first cavity extends to the first opening of each sub-second-interconnector and a third portion extends from the second opening of each sub-second-interconnector within the interior of the device. (ii) The sub-second-interconnector wire of each sub-second-interconnector extends within the interior of the device within at least part of the first portion of the first cavity and the second portion of the first cavity to the first opening of that sub-second-interconnector and from the second opening of that sub-second-interconnector within at least part of the third portion of the first cavity.

In some embodiments: (i) The device has multiple second cavities extending within the body. The second cavities are distinct from the first cavities. Each second cavity is associated with one of the sub-second-interconnectors. Each second cavity has a first portion extending within the interior of the device to the first opening of the sub-second-interconnector associated with that cavity and a second portion extending from the second opening of that sub-second-interconnector within the interior of the device. (ii) The sub-second-interconnector wire of each sub-second-interconnector further extends from within the interior of the device within at least part of the first portion of the cavity associated with that sub-second-interconnector to the first opening associated with that sub-second-interconnector and from the second opening associated with that sub-second-interconnector within at least part of the second portion of the cavity associated with that sub-second-interconnector.

In some embodiments: (i) The sub-second-interconnectors are equally tangentially spaced-apart along the exterior surface of the device in a plane perpendicular to the central longitudinal axis of the body of the device. (ii) Each of the sub-second-interconnectors is tangentially is aligned with a one of the sub-first-interconnectors along a line parallel to the central longitudinal axis of the body of the device.

In some embodiments, a number of the plurality of second connectors is equal to a number of the sub-second-interconnectors, and each one of the plurality of second connectors is associated with a single one of the multiple sub-second-interconnectors.

In some embodiments: (i) Each one of the second connectors includes an element having two holes therein. The holes are shaped and dimensioned, and positioned on the element with respect to each other, to allow the sub-second-interconnector wire of the sub-second-interconnector associated with that one of the second connectors to pass therethrough. (ii) Each element is positioned, shaped and dimensioned such that, when the lumen wall anchor is in the compact-secured-configuration, a first hole of the two holes in that element is positioned adjacent the first opening of the sub-second-interconnector associated with the one of the second connectors of which that element is included, and a second hole of the two holes in the element is positioned adjacent the second opening of the sub-second-interconnector associated with the one of the second connectors of which that element is included.

In some embodiments, when the lumen wall anchor is in the compact-secured configuration: (i) For each sub-first-interconnector, the sub-first-interconnector wire of that sub-first-interconnector: (a) Extends within the interior of the device within at least part of the first portion of the first cavity for a first length towards the first opening of that sub-first-interconnector. (b) Traverses to the exterior of the device through the first opening of that sub-first-interconnector. (c) Passes through the first hole of the two holes of the element of the one of the plurality of first connectors associated with that sub-first-interconnector. (d) Extends outside the exterior of the device to the second hole of the two holes of that element. (e) Passes through the second hole of the two holes of that element. (f) Traverses through the second opening of that sub-first-interconnector. (g). Extends within at least part of the second portion of the first cavity for a second length. (ii) For each sub-second-interconnector, the sub-second-interconnector wire of that sub-second-interconnector: (a) Extends within the interior of the device within at least part of the first portion of the first cavity and the second portion of the first cavity for a first length towards the first opening of that sub-second-interconnector. (b) Traverses to the exterior of the device through the first opening of that sub-second-interconnector. (i) Passes through the first hole of the two holes of the element of the one of the plurality of second connectors associated with that sub-second-interconnector. (ii) Extends outside the exterior of the device to the second hole of the two holes of that element. (iii) Passes through the second hole of the two holes of that element. (iv) Traverses through the second opening of that sub-second-interconnector. (v) Extends within at least part of the third portion of the first cavity for a second length.

In some embodiments: (i) For each sub-first-interconnector: (a) An exterior surface of the sub-first-interconnector wire of that sub-first-interconnector frictionally engages an interior surface of the first cavity. (b) A force generated by the bias towards the released position of the first connector positioning wire on which the one of the plurality of first connectors associated with that sub-first-interconnector is disposed exerts a force on the sub-first-interconnector wire of that sub-first-interconnector. That force exerted on the sub-first-interconnector wire of that sub-first-interconnector is insufficient to overcome a force generated by frictional engagement of the exterior surface of that sub-first-interconnector wire with the interior surface of the first cavity and with exterior surfaces of other interconnector wires within the first cavity; whereby, the bias of that first connector positioning wire toward the released position is overcome and that first connector positioning wire remains in the secured position. (ii) For each sub-second-interconnector: (a) An exterior surface of the sub-second-interconnector wire of that sub-second-interconnector frictionally engages an interior surface of the first cavity. (b) A force generated by a bias of the lumen wall anchor away from its compact-secured-configuration exerts a force on the sub-second-interconnector wire of that sub-second-interconnector. That force exerted on the sub-second-interconnector wire of that sub-second-interconnector is insufficient to overcome a force generated by frictional engagement of the exterior surface of that sub-second-interconnector wire with the interior surface of the first cavity and with exterior surfaces of other interconnector wires within the first cavity; whereby, the bias of the lumen wall anchor away from its compact-secured-configuration is overcome, and the lumen wall anchor remains in the compact-secured-configuration.

In some embodiments: (i) For each sub-first-interconnector, the sub-first-interconnector wire of that sub-first-interconnector is at least indirectly pullable from the exterior of the device with a sufficient amount of force to overcome the force generated by frictional engagement of the exterior surface of the sub-first-interconnector wire of that sub-first-interconnector with the interior surface of the first cavity and with exterior surfaces of the other interconnector wires within the first cavity, to remove the sub-first-interconnector wire of that sub-first-interconnector from passing through the two holes of the element of the one of the plurality of first connectors associated with that sub-first-interconnector, thereby disconnecting that one of the plurality of first connectors from that sub-first-interconnector and allowing the first connector positioning wire on which that one of the plurality of first connectors is disposed to move to the released position. (ii) For each sub-second-interconnector, the sub-second-interconnector wire of that sub-second-interconnector is at least indirectly pullable from the exterior of the device with a sufficient amount of force to overcome the force generated by frictional engagement of the exterior surface of the sub-second-interconnector wire of that sub-second-interconnector with the interior surface of the first cavity and with exterior surfaces of the other interconnector wires within the first cavity, to remove the sub-second-interconnector wire of that sub-second-interconnector from passing through the two holes of the element of the one of the plurality of second connectors associated with that sub-second-interconnector, thereby disconnecting that one of the plurality of second connectors from that sub-second-interconnector and allowing the lumen wall anchor to adopt, at least in part, the expanded-secured-configuration.

In some embodiments, when the lumen wall anchor is in the compact-secured configuration: (i) For each sub-second-interconnector: (a) The sub-second-interconnector wire of that sub-second-interconnector. (b) Extends within the interior of the device within at least part of the first portion of the second cavity associated with that sub-second-interconnector for a first length to the first opening of that sub-second-interconnector. (c) Traverses to the exterior of the device through the first opening of that sub-second-interconnector. (d) Passes through the first hole of the two holes of the element of the one of the plurality of second connectors associated with that sub-second-interconnector. (e) Extends outside the exterior of the device to the second hole of the two holes of the element of the one of the plurality of second connectors associated with that sub-second-interconnector. (f) Passes through the second hole of the two holes of that element. (g) Traverses through the second opening of that sub-second-interconnector. (h) Extends with at least a part of the second portion of the first cavity associated with that sub-second-interconnector for a second length. (i) An exterior surface of the sub-second-interconnector wire of that sub-second-interconnector frictionally engages an interior surface of the second cavity associated with that sub-second-interconnector. (j) A force generated by a bias of the lumen wall anchor away from its compact-secured-configuration exerts a force on the sub-second-interconnector wire of that sub-second-interconnector. The force exerted on the sub-second-interconnector wire of that sub-second-interconnector is insufficient to overcome a force generated by frictional engagement of the exterior surface of the sub-second-interconnector wire of that sub-second-interconnector with the interior surface of the first cavity associated with that sub-second-interconnector; whereby, the bias of the lumen wall anchor away from its compact-secured-configuration is overcome, and the lumen wall anchor remains in the compact-secured-configuration.

In some embodiments, for each sub-second-interconnector, the sub-second-interconnector wire of that sub-second-interconnector is at least indirectly pullable from the exterior of the device with a sufficient amount of force to overcome the force generated by frictional engagement of the exterior surface of the sub-second-interconnector wire of that sub-second-interconnector with the interior surface of the second cavity associated with that sub-second-interconnector, to remove that sub-section-interconnector wire from passing through the two holes of the element of the one of the plurality of second connectors associated with that sub-second-interconnector, thereby disconnecting that one of the plurality of second connectors associated from that sub-second-interconnector and allowing the lumen wall anchor to adopt, at least in part, the expanded-secured-configuration.

Aspect 1.5—Clauses 86 to 93

In a fifth sub-aspect of the first aspect, in some embodiments: (i) The second interconnector has multiple sub-second-interconnectors. The sub-second-interconnectors being tangentially spaced-apart from one another, and axially spaced-apart from the sub-first-connectors. (ii) Each of the second-sub-connectors is tangentially aligned in a one-to-one relationship a single one of the sub-first-connectors. (iii) Each sub-second-interconnector includes two openings in the exterior surface of the device.

In some embodiments, the second portion of the first cavity extends from the second opening of each sub-first-interconnector to the first opening of each sub-second-interconnector, and the first cavity has a third portion extending from the second opening of each sub-second-interconnectors within the interior of the device.

In some embodiments, each first cavity is further associated with one of the sub-second-interconnectors that is in a one-to-one relationship with the one of the sub-first interconnector that that first cavity is associated with. The second portion of each first cavity extends from the second opening of its associated sub-first-interconnector to a first opening of its associated sub-second-interconnector. Each first cavity having a third portion extending from a second opening of its associated sub-second-interconnector within the interior of the device.

In some embodiments: (a) A number of the plurality of second connectors is equal to a number of the sub-second-interconnectors, and each one of the plurality of second connectors is associated with a single one of the sub-second-interconnectors. (b) Each one of the plurality of second connectors includes an element having two holes therein. The holes are shaped and dimensioned, and positioned on the element with respect to each other, to allow the sub-first-interconnector wire of the sub-first-interconnector associated with the sub-second-interconnector associated with that one of the second connectors to pass therethrough. (c) Each element is positioned, shaped and dimensioned such that, when the lumen wall anchor is in the compact-securing-configuration, a first hole of the two holes in that element is positioned adjacent the first opening of the sub-second-interconnector associated with the one of the plurality of second connectors of which that element is included, and a second hole of the two holes in that element is positioned adjacent the second opening of that sub-second-interconnector.

In some embodiments, when the lumen wall anchor is in the compact-secured-configuration, for each sub-first interconnector and its associated sub-second-interconnector, the sub-first-interconnector wire of that sub-first-interconnector: (i) Extends within the interior of the device within at least part of the first portion of the first cavity for a first length towards the first opening of that sub-first-interconnector. (ii) Traverses to the exterior of the device through the first opening of that sub-first-interconnector. (iii) Passes through the first hole of the two holes of the element of the one of the plurality of first connectors associated with that sub-first-interconnector. (iv) Extends outside the exterior of the device to the second hole of the two holes of that element. (v) Passes through the second hole of the two holes of that element. (vi) Traverses through the second opening of that sub-first-interconnector. (vii) Extends with the second portion of the first cavity for a second length to the first opening of the sub-second-connector associated with that sub-first interconnector. (viii) Traverses to the exterior of the device through the first opening of that sub-second-interconnector. (ix) Passes through the first hole of the two holes of the element of the one of the plurality of second connectors associated with that sub-second-interconnector. (x) Extends outside the exterior of the device to the second hole of the two holes of that element. (xi) Passes through the second hole of the two holes of that element (xii) Traverses through the second opening of that sub-second-interconnector. (xii) Extends within at least part of the third portion of the first cavity for a third length.

In some embodiments: (i) For each sub-first-interconnector: (a) An exterior surface of the sub-first-interconnector wire of that sub-first-interconnector frictionally engages an interior surface of the first cavity. (b) A force generated by the bias towards the released position of the first connector positioning wire on which the one of the plurality of first connectors associated with that sub-first-interconnector is disposed exerts a force on the sub-first-interconnector wire of that sub-first-interconnector. That force exerted on the sub-first-interconnector wire of that sub-first-interconnector being insufficient to overcome a force generated by frictional engagement of the exterior surface of that sub-first-interconnector wire with the interior surface of the first cavity and with exterior surfaces of other interconnector wires within the first cavity; whereby, the bias of that first connector positioning wire toward the released position is overcome and that first connector positioning wire remains in the secured position. (ii) for each sub-second-interconnector: An exterior surface of the sub-first-interconnector wire of the sub-first-interconnector associated with that sub-second-interconnector frictionally engages an interior surface of the first cavity. A force generated by a bias of the lumen wall anchor away from its compact-secured-configuration exerts a force on the sub-first-interconnector wire of the sub-first-interconnector wire associated with that sub-second-interconnector. That force exerted on that sub-first-interconnector wire is insufficient to overcome the force generated by frictional engagement of the exterior surface of that sub-first-interconnector wire with the interior surface of the first cavity; whereby, the bias of the lumen wall anchor away from its compact-secured-configuration is overcome, and the lumen wall anchor remains in the compact-secured-configuration.

In some embodiments, when the lumen wall anchor is in the compact-secured configuration, for each sub-first-interconnector and its associated sub-second-interconnector: (i) The sub-first-interconnector wire of that sub-first-interconnector: (a) Extends within the second portion of the first cavity associated with that sub-first-interconnector for a second length to the first opening of the sub-second-connector associated with that sub-first interconnector. (b) Traverses to the exterior of the device through the first opening of that sub-second-interconnector. (c) Passes through the first hole of the two holes of the element of the one of the plurality of second connectors associated with that sub-second-interconnector. (d) Extends outside the exterior of the device to the second hole of the two holes of that element. (e) Passes through the second hole of the two holes of that element. (f) Traverses through the second opening of that sub-second-interconnector. (g) Extends within at least a part of the third portion of the first cavity associated with that sub-second-interconnector for a third length. (ii) A force generated by a bias of the lumen wall anchor away from its compact-secured-configuration exerts a force on the sub-first-interconnector wire of the sub-first-interconnector associated with that sub-second-interconnector. That force exerted on that sub-first-interconnector wire is insufficient to overcome the force generated by frictional engagement of the exterior surface of that sub-first-interconnector wire and the interior surface of the first cavity associated with that sub-second-interconnector; whereby, the bias of the lumen wall anchor towards its expanded-secured-configuration is overcome, and the lumen wall anchor remains in the compact-secured-configuration.

In some embodiments: (i) For each sub-second-interconnector, the sub-first-interconnector wire of the sub-first-interconnector associated with that sub-second-interconnector is at least indirectly pullable from the exterior of the device by a first length to remove that sub-first-interconnector wire from passing through the two holes of the element of the one of the plurality of second connectors associated with that sub-second-interconnector, thereby disconnecting the one of the plurality of second connectors associated with that sub-second-interconnector from that sub-second-interconnector and allowing the lumen wall anchor to adopt, at least in part, the expanded-secured-configuration, the first length being insufficient to remove that sub-first-interconnector wire from passing through the two holes of the element of the one of the plurality of first connectors associated the sub-first-interconnector associated with that sub-second-interconnector. (ii) For each sub-first-interconnector, that sub-first-interconnector wire is thereafter at least indirectly pullable from the exterior of the device by a second length to remove that sub-first-interconnector wire from passing through the two holes of the element of the one of the plurality of first connectors associated with that sub-first-interconnector, thereby disconnecting the one of the plurality of first connectors associated with that sub-first-interconnector from that sub-first-interconnector and allowing the one of the first connector wires on which the one of the plurality of first connectors associated with that sub-first-interconnector is disposed to move to the released position.

Aspect 1.6—Clauses 94 to 99

In a sixth sub-aspect of the first aspect, in some embodiments: (i) A number of the plurality of second connectors is equal to a number of the sub-second-interconnectors. Each one of the plurality of second connectors is associated with a single one of the sub-second-interconnectors. (ii) Each one of the plurality of second connectors includes an element having two holes therein. The holes are shaped and dimensioned, and positioned on the element with respect to each other, to allow the sub-second-interconnector wire of the sub-second-interconnector associated with that one of the plurality of second connectors to pass therethrough. (iii) Each element is positioned, shaped and dimensioned such that, when the lumen wall anchor is in the compact-securing-configuration, a first hole of the two holes in that element is positioned adjacent the first opening of the sub-second-interconnector associated with the one of the plurality of second connectors of which that element is included, and a second hole of the two holes in that element is positioned adjacent the second opening of that sub-second.

In some embodiments: (i) The sub-first-interconnector wire of each of the sub-first-interconnectors has a hollow core. (ii) The sub-second-interconnector wire of each of the sub-second-interconnectors is disposed within the hollow core of the sub-first-interconnector wire of the one of the sub-first-interconnectors associated with that sub-second-interconnector.

In some embodiments: (i) The second portion of the first cavity extends to the first opening of each sub-second-interconnector and a third portion extends from the second opening of each sub-second-interconnector within the interior of the device. (ii) When the lumen wall anchor is in the compact-secured configuration, for each sub-first-interconnector and its associated sub-second-interconnector: (a) The sub-first-interconnector wire of that sub-first-interconnector, has a proximal end and has a distal end that extends within the second portion of the first cavity for a second length and ends before reaching the first opening of the sub-second-connector associated with that sub-first interconnector. (b) The sub-second-interconnector wire of that sub-second-connector, has a proximal end that extends proximally beyond the proximal end of the sub-first-interconnector wire of the sub-first-interconnector associated with that sub-second-interconnector; and has a distal end that: (I) Exits the hollow core of the sub-first-interconnector wire of that sub-first-connector within the second portion of the first cavity. (II) Extends within the second portion of the first cavity to the first opening of that sub-second-interconnector. (III) Traverses to the exterior of the device through the first opening of that sub-second-interconnector. (IV) Passes through the first hole of the two holes of the element of the one of the plurality second connectors associated with that sub-second-interconnector. (V) Extends outside the exterior of the device to the second hole of the two holes of that element. (VI) Passes through the second hole of the two holes of that element. (VII) Traverses through the second opening of that sub-second-interconnector. (VII) Extends at least in part with the third portion associated with that sub-second-interconnector for a third length. (c) An exterior surface of the sub-second-interconnector wire of that sub-second-interconnector frictionally engages an interior surface of the hollow core of the sub-first-interconnector wire of the sub-first-interconnector within which that sub-second-interconnector wire is disposed prior to exiting the hollow core of that sub-first-interconnector wire. (d) The exterior surface of the sub-second-interconnector wire of that sub-second-interconnector further frictionally engages an interior surface of the first cavity after exiting the hollow core of the sub-first-interconnector wire of that sub-first-connector associated with that sub-second-connector. (e) A force generated by a bias of the lumen wall anchor away from its compact-secured-configuration exerts a force on the sub-second-interconnector wire of that sub-second-interconnector. That force exerted on that sub-second-interconnector wire IS insufficient to overcome a force generated by frictional engagement of the exterior surface of that sub-second-interconnector wire with the interior surface of the first cavity and of the exterior surface of that sub-second-interconnector with the interior surface of the hollow core of the sub-first-interconnector wire of the sub-first-interconnector within which that second-sub-interconnector wire is disposed; whereby, the bias of the lumen wall anchor away from its compact-secured-configuration is overcome, and the lumen wall anchor remains in the compact-secured-configuration.

In some embodiments: (i) For each sub-second-interconnector, the sub-second-interconnector wire of that sub-second-interconnector is at least indirectly pullable from the exterior of the device with a sufficient amount of force to overcome the force generated by frictional engagement of the exterior surface of that sub-second-interconnector wire with the interior surface of the first cavity and of the exterior surface of that sub-second-interconnector and the interior surface of the hollow core of the sub-first-interconnector wire of the sub-first-interconnector within which that sub-second-interconnector wire is disposed, to remove that sub-second-interconnector wire from passing through the two holes of the element of the one of the plurality of second connectors associated with that sub-second-interconnector, thereby disconnecting the one of the plurality of second connectors associated with that sub-second-interconnector from that sub-second-interconnector and allowing the lumen wall anchor to adopt, at least in part, the expanded-secured-configuration. (ii) For each sub-first-interconnector, the sub-first-interconnector wire of that sub-first-interconnector is thereafter at least indirectly pullable from the exterior of the device with a sufficient amount of force to overcome the force generated by frictional engagement of the exterior surface of the sub-first-interconnector wire of that sub-first-interconnector with the interior surface of the first cavity and with exterior surfaces of the other interconnector wires within the first cavity, to remove the sub-first-interconnector wire of that sub-first-interconnector from passing through the two holes of the element of the one of the plurality of first connectors associated with that sub-first-interconnector, thereby disconnecting that one of the plurality of first connectors from that sub-first-interconnector and allowing the first connector positioning wire on which that one of the plurality of first connectors is disposed to move to the released position.

In some embodiments, (i) Each first cavity is further associated with the one of the sub-second-interconnectors that is in a one-to-one relationship with the one of the sub-first interconnectors that that first cavity is associated with. The second portion of each first cavity extending from the second opening of its associated sub-first-interconnector to the first opening of its associated sub-second-interconnector. Each first cavity has a third portion extending from the second opening of its associated sub-second-interconnector within the interior of the device. (ii) Wherein when the lumen wall anchor is in the compact-secured-configuration, for each sub-first-interconnector and its associated sub-second-interconnector: (a) The sub-first-interconnector wire of that sub-first-interconnector, has a proximal end, and has a distal end that extends within the second portion of the first cavity associated with that sub-first-interconnector for a second length and ends before reaching the first opening of the sub-second-connector associated with that sub-first interconnector. (b) The sub-second-interconnector wire of that sub-second-connector, has a proximal end that extends proximally beyond the proximal end of the interconnector wire of the sub-first-interconnector associated with that sub-second-interconnector; and has a distal end that: (I) Exits the hollow core of the sub-first-interconnector wire of that sub-first-connector within the second portion of the first cavity associated with that sub-second-connector. (II) Extends within the second portion of the first cavity to the first opening of that sub-second-interconnector. (III) Traverses to the exterior of the device through the first opening of that sub-second-interconnector. (IV) Passes through the first hole of the two holes of the element of the one of the second connectors associated with that sub-second-interconnector. (V) Extends outside the exterior of the device to the second hole of the two holes of that element. (VI) Passes through the second hole of the two holes of that element. (VII) Traverses through the second opening of that sub-second-interconnector. (VIII) Extends with at least in part the third portion of the first cavity associated with that sub-second-interconnector for a third length. (c) An exterior surface of the sub-second-interconnector wire of that sub-second-interconnector frictionally engages an interior surface of the hollow core of the sub-first-interconnector wire of the sub-first-interconnector within which that sub-second-interconnector wire is disposed prior to exiting the hollow core of that sub-first-interconnector wire. (d) The exterior surface of the sub-second-interconnector wire of that sub-second-interconnector further frictionally engages an interior surface of the first cavity within which that sub-second-interconnector wire is disposed after exiting the hollow core of the sub-first-interconnector wire of that sub-first-connector associated with that sub-second-connector. (e) a force generated by a bias of the lumen wall anchor away from its compact-secured-configuration exerts a force on the sub-second-interconnector wire of that sub-second-interconnector. That force exerted on that sub-second-interconnector wire is insufficient to overcome a force generated by frictional engagement of the exterior surface of that sub-second-interconnector wire with the interior surface of the first cavity associated with that sub-second-interconnector and of the exterior surface of that sub-second-interconnector wire with the interior surface of the hollow core of the sub-first-interconnector wire of the sub-first-interconnector within which that sub-second-interconnector wire is disposed; whereby, the bias of the lumen wall anchor away from its compact-secured-configuration is overcome and the lumen wall anchor remains in the compact-secured-configuration.

In some embodiments: (i) For each sub-second-interconnector, the sub-second-interconnector wire of that sub-second-interconnector is at least indirectly pullable from the exterior of the device with a sufficient amount of force to overcome the force generated by frictional engagement of the exterior surface of that sub-second-interconnector wire with the interior surface of the first cavity associated with that sub-second-interconnector and of the exterior surface of that sub-second-interconnector with the interior surface of the hollow core of the sub-first-interconnector wire of the sub-first-interconnector within which that sub-second interconnector wire is disposed, to remove that sub-second-interconnector wire from passing through the two holes of the element of the one of the plurality of second connectors associated with that sub-second-interconnector, thereby disconnecting the one of the plurality of second connectors associated with that sub-second-interconnector from that sub-second-interconnector and allowing the lumen wall anchor to adopt, at least in part, the expanded-secured-configuration. (ii) For each sub-first-interconnector, that sub-first-interconnector wire is thereafter at least indirectly pullable from the exterior of the device with a sufficient amount of force to overcome the force generated by frictional engagement of the exterior surface of that sub-first-interconnector wire and the interior surface of the first cavity associated with that sub-first-interconnector, to remove that sub-first-interconnector wire from passing through the two holes of the element of the one of the plurality of first connectors associated with that sub-first-interconnector, thereby disconnecting the one of the plurality of first connectors associated with that sub-first-interconnector from that sub-first-interconnector and allowing the one of the first connector positioning wires on which the one of the first connectors associated with that sub-first-interconnector is disposed to move to the released position.

Aspect 1.7—Clauses 100 to 107

In a seventh sub-aspect of the first aspect, in some embodiments, the device is a modular fluid flow influencing device having a central docking unit and a plurality of functional units. The docking unit is non-expandable and is the elongate body of the device. The docking unit has: A plurality of concave receiving surfaces for receiving the functional units, the receiving surfaces extending parallel to the central longitudinal axis of the docking units and being positioned equidistantly radially along the exterior surface thereof. And, a plurality of inter-receiving-surface portions, an inter-receiving-surface portion extending longitudinally, parallel to the central longitudinal axis of the docking unit, between each two adjacent receiving surfaces.

In some embodiments, each of the sub-first-interconnectors is located on a one of the inter-receiving-surface portions. In some embodiments, each of the sub-first-interconnectors includes a first concavity of the one of the inter-receiving surface portions on which that sub-first interconnector is located, with the two openings of that sub-first-interconnector being disposed through a surface of that first concavity. In some embodiments, the element of each one of the plurality of first connectors is convex and confirms to a curvature of the first concavity of the sub-first-interconnector associated with the one of the plurality of first connectors of which that element is included.

In some embodiments, each of the sub-second-interconnectors is located on a one of the inter-receiving-surface portions. In some embodiments, each of the sub-second-interconnectors includes a second concavity of the one of the inter-receiving-surface portions on which that sub-second-interconnector is located, with the two openings of that sub-second-interconnector being disposed through a surface of that second concavity. In some embodiments, the element of each one of the second connectors is convex and confirms to a curvature of the second concavity of the sub-second-interconnector associated with the one of the second connectors of which that element is included. In some embodiments, the element of each one of the second connectors is convex and confirms to a curvature of the second concavity of the sub-second-interconnector.

Aspect 1.8—Clauses 108 to 123

In an eighth sub-aspect of the first aspect, in some embodiments, each of the plurality of first connectors is located at the joined ends of pairs of the plurality of first connector positioning wires. In some embodiments, the pairs of the plurality of first connector positioning wires are unitarily formed as a single structure.

In some embodiments, each of the plurality of first connectors is a loop formed at the joined ends of the pairs of the plurality of first connector positioning wires. In some embodiments, each loop is formed, at least in part, by a clasp. In some embodiments, the first interconnector includes a plurality of hooks positioned, dimensioned and shaped to hook the loops of the lumen wall anchor when the first connector positioning wires on which the loops located are in the secured position. In some embodiments, the first interconnector includes a secured configuration in which the hooked loops are held captive by the first interconnector and a released configuration in which the loops are allowed to be become unhooked from the hooks of the first interconnector.

In some embodiments, the first interconnector of the device includes a distal end portion of the body of the device longitudinally movable along the central longitudinal axis of the body of the device. In some embodiments, the end portion is moveable between a secured position and a released position with respect to a body of the device. In some embodiments, the end portion is an end cap that registers with the body of the device. In some embodiments, the end cap registers with the body of the device when in the end cap is in the secured position. In some embodiments, the end cap is longitudinally spaced apart from the body when of the device when the end cap is in the released position. In some embodiments, the end cap is disposed on rod moveably disposed within a channel within the body of the device, the channel extending along the central longitudinal axis of the body of the device. In some embodiments, actuation of the rod moves the end cap from the secured position to the released position. In some embodiments, the rod is attachable to an interconnector actuation wire for actuating the rod.

In some embodiments: (i) When the end portion is in the secured position the first interconnector is in the secured configuration, whereby the hooked loops are held captive. (ii) When the end portion is in the released position the first interconnector is in the released configuration, whereby the hooked loops are allowed to become unhooked from the hooks of the first interconnector.

In some embodiments: (i) When the end portion is in the secured position: (a) The first interconnector is in the secured configuration, whereby the hooked loops are held captive. (b) A bias of the first connector positioning wires on which the hooked loops are located towards the released position is overcome. (c) The first connector positioning wires on which the hooked loops are located are maintained in the secured position; whereby the first interconnector releasably connects the lumen wall anchor to the device. (ii) When the end portion is in the released position: (a) The first interconnector is in the released configuration, whereby the hooked loops are allowed to become unhooked from the hooks of the first interconnector. (b) The first connector positioning wires on which the hooked loops are located move towards the released position as a result of the bias, unhooking the hooked loops; whereby the first interconnector disconnects the lumen wall anchor from the device.

Aspect 1.9—Clauses 124 to 138

In a ninth sub-aspect of the first aspect, in some embodiments, each first connector is a hook. In some embodiments, the first interconnector includes a plurality of loops positioned, dimensioned and shaped to loop the hooks of the lumen wall anchor when the first connector positioning wires on which the hooks are located are in the secured position. In some embodiments, the first interconnector includes a secured configuration in which the looped hooks are held captive by the first interconnector and a released configuration in which the hooks are allowed to be become unlooped from the loops of the first interconnector. In some embodiments, the body of the device has a channel extending along the central longitudinal axis thereof. In some embodiments, the loops extend through the channel of the body of the device. In some embodiments, the loops are moveable within the channel parallel to the central longitudinal axis of the body of the device. In some embodiments, the loops are moveable between a secured position and a released position with respect to the body of the device. In some embodiments, the loops are within the channel of the body of the device when in the secured position. In some embodiments, the loops are outside of the body of the device when in the released position. In some embodiments, the loops are disposed at an end of a rod disposed within the channel and moveable along one of the central longitudinal axis of the device and a line parallel to the central longitudinal axis of the body of the device. In some embodiments, at least portion of the rod is hollow, and the loops are secured within the hollow portion of the rod. In some embodiments, actuation of the rod moves the loops from the secured position to the released position. In some embodiments, the rod is attached to an actuation wire for actuating the rod.

In some embodiments, the loops, the hooks, the ends of each of the first connector positioning wires on which the hooks are located, and the channel of the body of the device, are all positioned, dimensioned and shaped, each with respect to the others, such that: (i) When the hooks are looped by the loops, and the loops are in the secured position, the first interconnector is in the secured configuration, whereby the looped hooks are held captive within the channel of the body of the device. (ii) When the hooks are looped by the loops, and the loops are in the released position, the first interconnector is in the released configuration, whereby the looped hooks are allowed to become unlooped from the loops of the first interconnector.

In some embodiments, the loops, the hooks, the ends of each of the first connector positioning wires on which the hooks are located, and the channel of the body of the device, are all positioned, dimensioned and shaped, each with respect to the others, such that: (i) When the hooks are looped by the loops, and the loops are in the secured position: (a) The first interconnector is in the secured configuration, whereby the looped hooks are held captive within the channel of the body of the device. (b) A bias of the first connector positioning wires on which the looped hooks towards the released position is overcome; the first connector positioning wires on which the looped hooks are located are maintained in the secured position, whereby the first interconnector releasably connects the lumen wall anchor to the device. (ii) When the hooks are looped by the loops, and the loops are in the released position: (a) The first interconnector is in the secured configuration, whereby the looped hooks are allowed to become unlooped from the loops. (b) The first connector positioning wires on which the looped hooks are located move towards the released position as a result of the bias, unlooping the looped hooks; whereby the first interconnector disconnects the lumen wall anchor from the device.

Aspect 1.10—Clauses 139 to 162

In a tenth sub-aspect of the first aspect, in some embodiments, each wire of the plurality of first connector positioning wires extends from a proximal end of the wire network.

In some embodiments, when in the lumen wall anchor is in at least one of the expanded-secured-configuration and the expanded-released-configuration, the wire network is generally cylindrical in peripheral shape.

In some embodiments, when in the lumen wall anchor is in at least one of the expanded-securing-configuration and the expanded-released-configuration, the wire network is generally a truncated cone in peripheral shape.

In some embodiments, when the lumen wall anchor is in the expanded-released-configuration, each of the plurality of first connectors is generally in line with a periphery of the wire network.

In some embodiments, at least some of the wires of the wire network are one of square and rectangular in cross-section.

In some embodiments, the lumen wall anchor is overcomably biased toward the expanded-released-configuration. In some embodiments, the bias is overcomable, at least in part, via insertion of the lumen wall anchor into the catheter. In some embodiments, the lumen wall anchor consists essentially of a shape-memory alloy. In some embodiments, the wire network consists essentially of nitinol.

In some embodiments, the lumen wall anchor consists essentially of resorbable material. In some embodiments, the lumen wall anchor consists essentially of at least one from a group consisting of poly(L-lactide), poly(D,L-lactide) and platinum.

In some embodiments, the lumen wall anchor is not self-expandable. In some embodiments, the lumen wall anchor is structured to be expanded from the compact-secured-configuration to the expanded-secured-configuration via inflation of a balloon within the wire network.

In some embodiments, the mammalian body conduit is a human body conduit. In some embodiments, the human body conduit is a vascular system conduit. In some embodiments, the vascular system conduit is one of an aorta and an inferior vena cava. In some embodiments, the intralumenal device is a ventricular assist device and the vascular system conduit of one of a group consisting of an aorta, a left ventricle, a vena cava, a pulmonary artery, and a right ventricle.

In some embodiments, the wire network has a plurality of tangentially-spaced-apart projections connected to a distal end thereof. In some embodiments, the tangentially-spaced-apart projections are anchor elements.

In some embodiments, at least a portion of the wire network is covered with at least one sheet of material. In some embodiments, the material is at least one of knitted polyester, expanded polytetrafluoroethylene and polyurethane. In some embodiments, the wire network is open and uncovered.

In some embodiments, the catheter is a delivery sheath.

In some embodiments, the present technology also provides a loader connectable to the delivery sheath, the loader having a cavity in which the mammalian body conduit intralumenal device and lumen wall anchor assembly are disposed in the compact-secured configuration.

Aspect 1.11—Clauses to 163-181

In an eleventh sub-aspect of the first aspect, in some embodiments, the wire network of the lumen wall anchor includes: a first plurality of nodes, a second plurality of nodes, and a plurality of internodal wires (being structural elements)r, each node of the second plurality of nodes being interconnected with at least one node of the first plurality of nodes by at least one internodal wire. In some embodiments, the first plurality of nodes is located at an axial end of the wire network. In some embodiments, the second plurality of nodes is axially spaced-apart from the first plurality of nodes. In some embodiments, nodes of the first plurality of nodes and nodes of the second plurality of nodes tangentially alternate. In some embodiments, each node of the first plurality of nodes is connected to two internodal wires. In some embodiments, each one of the first plurality of nodes is connected to a first internodal wire and a second internodal wire, the first internodal wire interconnecting the that one of the first plurality of nodes with a first one of the second plurality of nodes tangentially adjacent to that one of the first plurality of nodes in a first tangential direction, the second internal wire interconnecting that one of the first plurality of nodes with a second one of the second plurality of nodes tangentially adjacent to that one of the first plurality of nodes in a second tangential direction opposite to the first tangential direction. In some embodiments, when the lumen wall anchor is in the expanded-securing-configuration, each internodal wire is curved in an axial direction. In some embodiments, each one of the second plurality of nodes is connected to a first internodal wire and a second internodal wire, the first internodal wire interconnecting the that one of the second plurality of nodes with a first one of the first plurality of nodes tangentially adjacent to that one of the second plurality of nodes in a first tangential direction, the second internal wire interconnecting that one of the second plurality of nodes with a second one of the first plurality of nodes tangentially adjacent to that one of the second plurality of nodes in a second tangential direction opposite to the first tangential direction.

In some embodiments, each wire of the plurality of first connector positioning wires extends from a node of the second plurality of nodes. In some embodiments, the ends of at least two of the plurality of first connector positioning wires are joined together to form at least one third node, the at least one first connector being connected to the third node. In some embodiments, the ends of the plurality of first connector positioning wires are joined together in multiples to form a plurality of third nodes, a one of the at least one first connector being disposed on each node of the plurality of third nodes. In some embodiments, wherein the ends of the plurality of first connector positioning wires are joined together in twos to form a plurality of third nodes, a one of the at least one first connector being disposed on each node of the plurality of third nodes. In some embodiments, the ends of the plurality of first connector positioning wires are joined together in threes to form a plurality of third nodes, a one of the at least one first connector being disposed on each node of the plurality of third nodes. In some embodiments, the plurality of first connector positioning wires includes unpaired connector positioning wires and paired connector positioning wires. In some embodiments, the plurality of first connector positioning wires includes unpaired first connector positioning wires and paired first connector positioning wires extending from tangentially alternating nodes of the plurality of second nodes. In some embodiments, the wires of each pair of the paired first connector positioning wires are tangentially spaced apart from one another. In some embodiments, each wire of the paired first connector positioning wires has a portion that is shaped to relieve stress when the wire is in the securing position. In some embodiments, each wire of the paired first connector positioning wires has a chevron-shaped portion for relieving stress when the wire is in the securing position. In some embodiments, joined together in threes to form each third node are: a one of the unpaired first connector positioning wires; a one of the wires of the paired first connector positioning wires that is immediately tangentially adjacent to the one of the unpaired first connector positioning wires in a first tangential direction; and a one of the wires of the paired first connector positioning wires that is immediately tangentially adjacent to the one of the unpaired first connector positioning wires in a second tangential direction opposite to the first tangential direction.

Aspect 2.0—Clauses 201 to 203

In a second another aspect, embodiments of the present technology provide: a lumen wall anchor for use in maintaining an intralumenal device in place within a mammalian body conduit, the lumen wall anchor comprising: (i) A 3D-shaped wire network, the wire network having a central longitudinal axis. (ii) A plurality of first connector positioning wires extending from the wire network, each wire of the plurality of first connector positioning wires being moveable between a secured position and a released position and being overcomeably biased towards the released position. (iii) At least one first connector disposed at an end of at least one wire of the plurality of first connector positioning wires.

The lumen wall anchor has distal end, a proximal end, a compact-secured-configuration, an expanded-secured-configuration, and an expanded-released-configuration.

When the lumen wall anchor is in the compact-secured-configuration: (i) The lumen wall anchor is shaped and dimensioned to be deliverable to the delivery site within the lumen of the mammalian body conduit via the catheter. (ii) Each wire of the first plurality of connector positioning wires is in the secured position, the secured position being the end of that wire of the first plurality of connector positioning wires being positioned in proximity to the central longitudinal axis.

When the lumen wall anchor is in the expanded-secured-configuration: (i) The wire network is dimensioned and shaped to exert a force on a wall of the lumen of the conduit, the force being sufficient to anchor the lumen wall anchor assembly in place. (ii) Each wire of the first plurality of connector positioning wires is in the secured position. When the lumen wall anchor is in the expanded-released-configuration: (i) The wire network is dimensioned and shaped to exert a force on a wall of the lumen of the conduit, the force being sufficient to anchor the lumen wall anchor assembly in place. (ii) Each wire of the plurality of first connector positioning wires is in the released position, the released position being the end of each wire of the first plurality of connector positioning wires being generally in line with the periphery of the wire network. (iii) The plurality of first connector positioning wires and all of the at least one first connector do not obstruct fluid flow axially through the wire network while the lumen wall anchor is anchored in place.

In some embodiments, when in the expanded-secured-configuration and in the expanded-released-configuration, the wire network is dimensioned and shaped to exert a force on the wall of the lumen of the conduit indirectly by exerting a force directly on the wall of a stent having been implanted within the conduit.

In some embodiments, the at least one first connector disposed at the end of at least one wire of the plurality of first connector positioning wires is a plurality of first connectors.

Aspect 2.1—Clause 204

In a first sub-aspect of the second aspect, in some embodiments, a single one of the plurality of first connectors is disposed at the end each of wire of the plurality of first connector positioning wires.

Aspect 2.2—Clause 205

In a second sub-aspect of the second aspect, in some embodiments, the ends of the plurality of first connector positioning wires are joined together in multiples, a single one of plurality of first connectors being disposed at the joined ends of each of the multiples.

Aspect 2.3—Clauses 206 to 209

In a third sub-aspect of the second aspect, in some embodiments, each one of the plurality of first connectors includes an element having a hole therein. In some embodiments, each one of the plurality of first connectors includes an element having two holes therein. In some embodiments, each element is convex. In some embodiments, each of the first connector positioning wires when in the secured position, forms a proximally-facing sloped surface such that a retrieval sheath being manoeuvered from the proximal end of the lumen wall anchor towards the distal end of the lumen wall anchor, via contact with the sloped surfaces of the first connector positioning wires, causes, at least in part, the lumen wall anchor to adopt the compact-secured-configuration as it enters a lumen of the retrieval sheath.

Aspect 2.4—Clauses 210 to 216

In a fourth sub-aspect of the present aspect, in some embodiments: (i) The lumen wall anchor further comprises: (a) A plurality of second connector positioning wires extending from the wire network, each wire of the plurality of second connector positioning wires being moveable between a secured position and a released position and being overcomeably biased towards the released position. (b) A plurality of second connectors, a single one of the plurality of second connectors being disposed at an end of each wire of the plurality of second connector positioning wires. (ii) When the lumen wall anchor is in the expanded-securing-configuration, each wire of the plurality of second connector positioning wires is in the secured position. (iii) When the lumen wall anchor is in the expanded-released-configuration: (a) Each wire of the plurality of second connector positioning wires is in the released position, the released position being the end of that wire of the plurality of second connector positioning wires being generally in line with the periphery of wire network. (b) The plurality of second connector positioning wires and the plurality of second connectors do not obstruct fluid flow axially through the wire network while the lumen wall anchor is anchored in place.

In some embodiments, each wire of the plurality of second connector positioning wires extends from a point intermediate ends of the wire network. In some embodiments, when the lumen wall anchor is in the expanded-released-configuration, each of the second connectors is generally aligned with a periphery of the wire network. In some embodiments, each one of the plurality of second connectors includes an element having a hole therein. In some embodiments, each one of the plurality of second connectors includes an element having two holes therein. In some embodiments, each element of the plurality of second connectors is convex. In some embodiments, each of the second connector positioning wires when in the secured position, forms a proximally-facing sloped surface such that a retrieval sheath being manoeuvered from the proximal end of the lumen wall anchor towards the distal end of the lumen wall anchor, via contact with the sloped surfaces of the second connector positioning wires, causes, at least in part, the lumen wall anchor to adopt the compact-secured-configuration as it enters a lumen of the retrieval sheath.

Aspect 2.5—Clauses 217 to 222

In a fifth sub-aspect of the second aspect, in some embodiments: (i) The lumen wall anchor further includes a plurality of second connectors disposed on the wire network. (ii) When the lumen wall anchor is the compact-secured-position each of the plurality of second connectors is in a secured position. (iii) When the lumen wall anchor is in a one of the expanded-secured-configuration and the expanded-released-configuration, each of the plurality of second connectors is in a released position being proximate the wall of the lumen of the conduit such that the plurality of second connectors do not obstruct fluid flow axially through the wire network while the lumen wall anchor is anchored in place.

In some embodiments, the second connectors are disposed distally of the first connectors. In some embodiments, when the lumen wall anchor is in the one of the expanded-secured-configuration and the expanded-released-configuration, each of the second connectors is generally aligned with a periphery of the wire network. In some embodiments, each one of the plurality of second connectors includes an element having a hole therein. In some embodiments, each one of the plurality of second connectors includes an element having two holes therein. In some embodiments, each element of the second plurality of connectors is convex.

Aspect 2.6—Clauses 223 to 226

In a sixth sub-aspect of the second aspect, in some embodiments, each of the plurality of first connectors is located at the joined ends of pairs of the plurality of first connector positioning wires. In some embodiments, the pairs of the plurality of first connector positioning wires are unitarily formed as a single structure. In some embodiments, each of the plurality of first connectors is a loop formed at the joined ends of the pairs of the plurality of first connector positioning wires. In some embodiments, each loop is formed, at least in part, by a clasp.

Aspect 2.7—Clause 227

In a seventh sub-aspect of the second aspect, in some embodiments, each first connector is a hook.

Aspect 2.8—Clauses 228 to 247

In an eighth sub-aspect of the second aspect, in some embodiments, each wire of the plurality of first connector positioning wires extends from a proximal end of the wire network. In some embodiments, when in the lumen wall anchor is in at least one of the expanded-secured-configuration and the expanded-released-configuration, the wire network is generally cylindrical in peripheral shape. In some embodiments, when in the lumen wall anchor is in at least one of the expanded-securing-configuration and the expanded-released-configuration, the wire network is generally a truncated cone in peripheral shape. In some embodiments, when the lumen wall anchor is in the expanded-released-configuration, each of the plurality of first connectors is generally aligned with a periphery of the wire network. In some embodiments, at least some of the wires of the wire network are one of square and rectangular in cross-section.

In some embodiments, the lumen wall anchor is overcomably biased toward the expanded-released-configuration. In some embodiments, the bias is overcomable, at least in part, via insertion of the lumen wall anchor into the catheter. In some embodiments, the lumen wall anchor consists essentially of a shape-memory alloy. In some embodiments, the wire network consists essentially of nitinol.

In some embodiments, the lumen wall anchor consists essentially of resorbable material. In some embodiments, the lumen wall anchor consists essentially of at least one from a group consisting of poly(L-lactide), poly(D,L-lactide) and platinum.

In some embodiments, the lumen wall anchor is not self-expandable. In some embodiments, the lumen wall anchor is structured to be expanded from the compact-secured-configuration to the expanded-secured-configuration via inflation of a balloon within the wire network.

In some embodiments, the mammalian body conduit is a human body conduit. In some embodiments, the human body conduit is a vascular system conduit. In some embodiments, the vascular system conduit is one of an aorta a left ventricle, a vena cava, a pulmonary artery, and a right ventricle.

In some embodiments, the wire network has a plurality of tangentially-spaced-apart projections connected to a distal end thereof. In some embodiments, the tangentially-spaced-apart projections are anchor elements.

In some embodiments, at least a portion of the wire network is covered with at least one sheet of material. In some embodiments, the wire network is open and uncovered.

In some embodiments, the catheter is a delivery sheath.

Aspect 3.0—Clauses 301 to 314

In a third aspect, embodiments of the present technology provide a mammalian body conduit intralumenal device. The device is shaped and dimensioned to be deliverable to a delivery site within a lumen of a mammalian body conduit via a catheter. The device has: (i) A first interconnector for releasably connecting the device with a lumen wall anchor for maintaining the device in place within the mammalian body conduit. (ii) An elongate body having a central longitudinal axis. (iii) A proximal end and a distal end. (iv) An exterior surface.

In some embodiments, the first interconnector includes two openings in the exterior surface of the device. In some embodiments, the first interconnector further includes an interconnector wire, the interconnector wire: (i) Traverses from an interior of the device to an exterior of the device through a first one of the two openings. (ii) Extends outside the exterior of the device. (iii) Traverses from the exterior of the device to the interior of the device through a second one of the two openings.

In some embodiments: (i) The device has a first cavity extending within the body. The first cavity has a first portion extending from the exterior of the device to the first opening and a second portion extending from the second opening within the interior of the device. (ii) The interconnector wire further extends from the exterior of the device within the first portion of the first cavity to the first opening and from the second opening within the second portion of the first cavity.

In some embodiments, the first interconnector has multiple sub-first-interconnectors, the sub-first-interconnectors being spaced apart from one another, each sub-first-interconnector including two openings in the exterior surface of the device. In some embodiments, each sub-first-interconnector further includes a sub-first-interconnector wire, the sub-first-interconnector wire: (i) Traverses from an interior of the device to an exterior of the device through a first one of the two openings of that sub-first-interconnector. (ii) Extends outside the exterior of the device. (iii) Traverses from the exterior of the device to the interior of the device through a second one of the two openings of that sub-first-interconnector.

In some embodiments: (i) The device has a first cavity extending within the body, the first cavity having a first portion extending within the interior of the device to the first opening of each sub-first-interconnector and a second portion extending from the second opening of each sub-first interconnector within the interior of the device. (ii) The sub-first-interconnector wire of each sub-first-interconnector extends within at least a part of the first portion of the first cavity to the first opening of that sub-first-interconnector and from the second opening of that sub-first-interconnector within at least a part of the second portion of the first cavity. In some embodiments, a majority of the first cavity extends within the body of the device generally parallel to the central longitudinal axis of the body of the device.

In some embodiments: (i) The device further has multiple first cavities extending within the body, each first cavity being associated with a one of the sub-first-interconnectors, each first cavity having a first portion extending within the interior of the device to the first opening of the sub-first-interconnector associated with that first cavity and a second portion extending from the second opening of the sub-first-interconnector associated with that first cavity within the interior of the device. (ii) The sub-first-interconnector wire of each sub-first-interconnector further extends at least in part of within the first portion of the first cavity associated with that sub-first-interconnector to the first opening associated with that sub-first-interconnector and from the second opening associated with that sub-first-interconnector within at least a part of the second portion of the first cavity associated with that sub-first-interconnector. In some embodiments, a majority of each first cavity extends within the body of the device generally parallel to the central longitudinal axis of the body of the device.

In some embodiments, the sub-first-interconnectors are equally tangentially spaced apart along the exterior surface of the device in a plane perpendicular to the central longitudinal axis of the body of the device.

In some embodiments, for each sub-first-interconnector, the sub-first-interconnector wire of that sub-first-interconnector is at least indirectly pullable from the exterior of the device. In some embodiments, the interconnector wires of all of the sub-first interconnectors of the first interconnector are simultaneously at least indirectly pullable from the exterior of the device.

In some embodiments, the interconnector wires of each of the sub-first-interconnectors of the first connector exteriorly extend away from the proximal end of the device.
Aspect 3.1—Clauses 315 to 326

In a first sub-aspect of the third aspect, in some embodiments, the device further has a second interconnector spaced-apart from and distal to the first interconnector, the second interconnector for releasably connecting the device with the lumen wall anchor for maintaining the device in place within the mammalian body conduit.

In some embodiments, the device further has a second interconnector spaced-apart from and distal to the first interconnector, the second interconnector for releasably connecting the device with the lumen wall anchor for maintaining the lumen anchor in the compact-secured-configuration.

In some embodiments, the second interconnector has multiple sub-second-interconnectors, the sub-second-interconnectors being spaced-apart from one another, each sub-second-interconnector including two openings in the exterior surface of the device.

In some embodiments, each sub-second-connector further includes a sub-second-interconnector wire, the sub-second-interconnector wire: Traversing from the interior of the device to the exterior of the device through a first one of the two openings. Extends outside the exterior of the device. And then, traverses from the exterior of the device to the interior of the device through a second one of the two openings.

In some embodiments: (i) The second portion of the first cavity extends to the first opening of each sub-second-interconnector and a third portion extends from the second opening of each sub-second-interconnector within the interior of the device. (ii) The sub-second-interconnector wire of each sub-second-interconnector extends within at least a part of the first portion of the first cavity and at least a part of the second portion of the first cavity to the first opening of that sub-second-interconnector and from the second opening of that sub-second-interconnector within at least in part the third portion of the first cavity.

In some embodiments: (i) The device has a second cavity extending within the body, the second cavity having a first portion extending within the interior of the device to the first opening of each sub-second-interconnector and a second portion extending from the second opening of each sub-second interconnector within the interior of the device. (ii) The sub-second-interconnector wire of each sub-second-interconnector extends from the within at least a part of the first portion of the second cavity to the first opening of that sub-second-interconnector and from the second opening of that sub-second-interconnector within at least a part of the second portion of the second cavity.

In some embodiments: (i) The device has multiple second cavities extending within the body, the second cavities being distinct from the first cavities, each second cavity being associated with one of the sub-second-interconnectors, each second cavity having a first portion extending within the interior of the device to the first opening of the sub-second-interconnector associated with that cavity and a second portion extending from the second opening of that sub-second-interconnector within the interior of the device. (ii) The sub-second-interconnector wire of each sub-second-interconnector further extends from within the interior of the device within at least a part of the first portion of the cavity associated with that sub-second-interconnector to the first opening associated with that sub-second-interconnector and from the second opening associated with that sub-second-interconnector within at least a part of the second portion of the cavity associated with that sub-second-interconnector. In some embodiments, a majority of each second cavity extends within the body generally parallel to the central longitudinal axis of the body of the device.

In some embodiments: (i) The sub-second-interconnectors are equally tangentially spaced-apart along the exterior surface of the device in a plane perpendicular to the central longitudinal axis of the body of the device. (ii) Each of the sub-second-interconnectors is tangentially is aligned with a one of the sub-first-interconnectors along a line parallel to the central longitudinal axis of the body of the device.

In some embodiments, for each sub-second-interconnector, the sub-second-interconnector wire of that sub-second-interconnector is at least indirectly pullable from the exterior of the device. In some embodiments, the sub-second-interconnector wires of all of the sub-second interconnectors of the second interconnector are simultaneously at least indirectly pullable from the exterior of the device.

In some embodiments, the sub-second-interconnector wires of the each of the plurality of sub-second-interconnectors of the second connector exteriorly extend away from the proximal end of the device.
Aspect 3.2—Clauses 327 to 331

In a second sub-aspect of the third aspect, in some embodiments: (i) The second interconnector has multiple sub-second-interconnectors, the sub-second-interconnectors being tangentially spaced-apart from one another, and axially spaced-apart from the sub-first-connectors. (ii) Each of the second-sub-connectors is tangentially aligned in a one-to-one relationship a single one of the sub-first-connectors. (iii) Each sub-second-interconnector includes two openings in the exterior surface of the device.

In some embodiments: (i) The second portion of the first cavity extends to the first opening of each sub-second-interconnector and a third portion extending from the second opening of each sub-second-interconnector within the interior of the device. (ii) The sub-second-interconnector wire of each sub-first-interconnector further extends within the second portion of the first cavity to the first opening of the sub-second-interconnector associated with that sub-first interconnector and from the second opening of that sub-second-interconnector within at least a part of the third portion of the first cavity.

In some embodiments, each first cavity is further associated with the one of the sub-second-interconnectors that is in a one-to-one relationship with the one of the sub-first interconnectors that that first cavity is associated with, the second portion of each first cavity extending from the second opening of its associated sub-first-interconnector to a first opening of its associated sub-second-interconnector, and each first cavity having a third portion extending from a second opening of its associated sub-second-interconnector within the interior of the device.

In some embodiments, each one of the plurality of second connectors includes an element having two holes therein, the holes being shaped and dimensioned, and positioned on the element with respect to each other, to allow the interconnector wire of the sub-first-interconnector associated with the sub-second-interconnector associated with that one of the plurality of second connectors to pass therethrough.

In some embodiments, for each sub-second-interconnector, the interconnector wire of the sub-first-interconnector associated with that sub-second-interconnector is at least indirectly pullable from the exterior of the device.
Aspect 3.3—Clauses 332 to 333

In a third sub-aspect of the third aspect, in some embodiments, the first portion and a first part of the second portion of the first cavity have a first cross-sectional diameter, and a second part of the second portion and the third portion of the first cavity have a second cross-sectional diameter, the second cross-sectional diameter being less than the first cross-sectional diameter. In some embodiments, for each first cavity, the first portion and a first part of the second portion of that first cavity have a first cross-sectional diameter, and a second part of the second portion and the third portion of that first cavity have a second cross-sectional diameter, the second cross-sectional diameter being less than the first cross-sectional diameter.

Aspect 3.4—Clauses 334 to 338

In a fourth sub-aspect of the third aspect, in some embodiments, the device is a modular fluid flow influencing device having a central docking unit and a plurality of functional units. The docking unit is non-expandable and being the elongate body of the device. The docking units has: (i) A plurality of concave receiving surfaces for receiving the functional units, the receiving surfaces extending parallel to the central longitudinal axis of the docking units and being positioned equidistantly radially along the exterior surface thereof. (ii) A plurality of inter-receiving-surface portions, an inter-receiving-surface portion extending longitudinally, parallel to the central longitudinal axis of the docking unit, between each two adjacent receiving surfaces.

In some embodiments, each of the sub-first-interconnectors is located on a one of the inter-receiving surface portions. In some embodiments, each of the sub-first-interconnectors includes a first concavity of the one of the inter-receiving surface portions on which that sub-first interconnector is located, with the two openings of that sub-first-interconnector being disposed through a surface of that first concavity.

In some embodiments, each of the sub-second-interconnectors is located on a one of the inter-receiving surface portions. In some embodiments, each of the sub-second-includes a second concavity of the one of the inter-receiving surface portions on which that sub-second interconnector is located, with the two openings of that sub-second-interconnector being disposed through a surface of that second concavity.

Aspect 3.5—Clauses 339 to 349

In a fifth sub-aspect of the third aspect, in some embodiments, the first interconnector includes a plurality of hooks for hooking loops of a lumen wall anchor. In some embodiments, the first interconnector includes a secured configuration in which hooked loops of the lumen wall anchor are held captive by the first interconnector and a released configuration in which the hooks of the first interconnector are allowed to become unhooked by the loops of the lumen wall anchor.

In some embodiments, the first interconnector of the device includes a distal end portion of the body of the device longitudinally movable along the central longitudinal axis of the body of the device. In some embodiments, the end portion is moveable between a secured position and a released position with respect to the body of the device. In some embodiments, the end portion is an end cap that registers with the body of the device. In some embodiments, the end cap registers with the body of the device when in the end cap is in the secured position. In some embodiments, the end cap is longitudinally spaced apart from the body when of the device when the end cap in the released position. In some embodiments, the end cap is disposed on rod moveably disposed within a channel within the body of the device, the channel extending along the central longitudinal axis of the body of the device. In some embodiments, actuation of the rod moves the end cap from the secured position to the released position. In some embodiments, the rod is attachable to an interconnector actuation wire for actuating the rod.

In some embodiments: (i) when the end portion is in the secured position the first interconnector is in the secured configuration, whereby the hooked loops are held captive. (ii) When the end portion is in the released position the first interconnector is in the released configuration, whereby the hooked loops are allowed to become unhooked from the hooks of the first interconnector.

Aspect 3.6—Clauses 350 to 362

In a sixth sub-aspect of the third aspect, in some embodiments, the first interconnector includes a plurality of loops for looping hooks of a lumen wall anchor. In some embodiments, the first interconnector includes a secured configuration in which looped hooks are held captive by the first interconnector and a released configuration in which the loops of the first interconnector are allowed to become unlooped from the hooks of the lumen wall anchor.

In some embodiments, the body of the device has a channel extending along the central longitudinal axis thereof. In some embodiments, the loops extend through the channel of the body of the device. In some embodiments, the loops are moveable within the channel parallel to the central longitudinal axis of the body of the device. In some embodiments, the loops are moveable between a secured position and a released position with respect to the body of the device. In some embodiments, the loops are within the channel of the body of the device when in the secured position. In some embodiments, the loops are outside of the body of the device when in the released position.

In some embodiments, the loops are disposed at an end of a rod disposed within a channel and moveable along one of the central longitudinal axis of the device and a line parallel to the central longitudinal axis of the body of the device. In some embodiments, at least portion of the rod is hollow, and the loops are secured within the hollow portion of the rod. In some embodiments, actuation of the rod moves the loops from the secured position to the released position. In some embodiments, the rod is attached to an actuation wire for actuating the rod.

In some embodiments: (i) When the hooks are looped by the loops, and the loops are in the secured position, the first interconnector is in the secured configuration, whereby the looped hooks are held captive within the channel of the body of the device. (ii) When the hooks are looped by the loops, and the loops are in the released position, the first interconnector is in the released configuration, whereby the looped hooks are allowed to become unlooped from the loops of the first interconnector.

Aspect 3.7—Clauses 363 to 367

In seventh sub-aspect, in some embodiments, wherein the mammalian body conduit is a human body conduit. In some embodiments, the human body conduit is a vascular system conduit. In some embodiments, the vascular system conduit is one of an aorta and an inferior vena cava. In some embodiments, the intralumenal device is a ventricular assist device and the vascular system conduit of one of a group consisting of an aorta, a left ventricle, a vena cava, a pulmonary artery, and a right ventricle. In some embodiments, the catheter is a delivery sheath.

Aspect 4.1—Clauses 401-405

In a first sub-aspect of a fourth aspect, implementations of the present technology provide a method of implanting a mammalian body conduit intralumenal device and lumen wall anchor assembly into a mammalian body, the assembly having,
- a mammalian body conduit intralumenal device, the device being shaped and dimensioned to be deliverable to an implantation site within a lumen of a mammalian body conduit via a delivery sheath, the device having an elongate body, a central longitudinal axis, and a first interconnector structured to releasably connect the device with a lumen wall anchor for use in maintaining the device in place within the mammalian body conduit, the first interconnector having multiple sub-first-interconnectors, and
- the lumen wall anchor, the lumen wall anchor including,
  - a 3D-shaped wire network, the wire network having a central longitudinal axis,
  - a plurality of first connector positioning wires extending from the wire network, each wire of the plurality of first connector positioning wires being moveable between a secured position and a released position and being overcomeably biased towards the released position,
  - a plurality of first connectors, a single one of the plurality of first connectors being disposed at an end of each of wire of the plurality of first connector positioning wires, a number of the plurality of first connectors being equal to a number of the sub-first-interconnectors, and each one of the plurality of first connectors being associated with a single one of the multiple sub-first-interconnectors,
  - the lumen wall anchor having a compact-secured-configuration, an expanded-secured-configuration, and an expanded-released-configuration,
  - when the lumen wall anchor is in the compact-secured-configuration,
    - the lumen wall anchor is shaped and dimensioned to be deliverable to the delivery site within the lumen of the mammalian body conduit via the delivery sheath, and
    - each wire of the first plurality of connector positioning wires is in the secured position, the secured position being the end of that wire of the first plurality of connector positioning wires being positioned in proximity to the first interconnector of the device such that each of the plurality of first connectors is positioned to be releasably connectable to its associated sub-first interconnector of the first interconnector of the device, and
    - each of the first connectors is releasably connected to its associated sub-first-interconnector;
  - when the lumen wall anchor is in the expanded-secured-configuration,
    - the wire network is dimensioned and shaped to exert a force on a wall of the lumen of the conduit, the force being sufficient to anchor the mammalian body conduit intralumenal device and lumen wall anchor assembly in place at the implantation site, and
    - each wire of the first plurality of connector positioning wires is in the secured position, and
    - each of the first connectors is releasably connected to its associated sub-first-interconnector; and
  - when the lumen wall anchor is in the expanded-released-configuration,
    - the wire network is dimensioned and shaped to exert a force on the wall of the lumen of the conduit, the force being sufficient to anchor the lumen wall anchor assembly in place at the implantation site, and
    - each wire of the plurality of first connector positioning wires is in the released position, the released position being each of the plurality of first connectors being released from and unconnected to its associated sub-first interconnector, and the end of each wire of the first plurality of connector positioning wires being proximate the wall of the lumen of the conduit, and
    - the plurality of first connector positioning wires and the plurality of first connectors do not obstruct fluid flow axially through the wire network while the lumen wall anchor is anchored in place at the implantation site,
  - the lumen wall anchor being overcomeably biased away from its compact-secured-configuration, the assembly having a distal end and a proximal end,
the method comprising:
a) obtaining access to the conduit system of the mammalian body;
b) guiding a delivery sheath through the conduit system to the implantation site;
c) inserting the mammalian body conduit intralumenal device and lumen wall anchor assembly distal end first into the delivery sheath, with the lumen wall anchor being in the compact-secured-configuration;
d) guiding the assembly within the delivery sheath to the implantation site;
e) promoting exit of the assembly from the delivery sheath at the implantation site;
f) allowing the bias of the lumen wall anchor to cause the lumen wall anchor to adopt the expanded-secured-configuration and exert a force on the wall of the lumen of the conduit at the implantation site, anchoring the assembly in place; and
g) withdrawing the delivery sheath from the body.

In some implementations,
the device further has a second interconnector spaced-apart from and distal to the first interconnector, the second interconnector being structured to releasably connect the device with the lumen wall anchor for use in maintaining the device in place within the mammalian body conduit, the second interconnector having multiple sub-second-interconnectors,
the lumen wall anchor further includes
- a plurality of second connector positioning wires extending from the wire network, each wire of the plurality of second connector positioning wires being moveable between a secured position and a released position and being overcomeably biased towards the released position;
- a plurality of second connectors, a single one of the plurality of second connectors being disposed at an end of each wire of the plurality of second connector positioning wires, a number of the plurality of second connectors being equal to a number of the sub-second-interconnectors, and each one of the plurality of second connectors being associated with a single one of the multiple sub-second-interconnectors;

when the lumen wall anchor is in the expanded-secured-configuration,
- each wire of the plurality of second connector positioning wires is in the secured position, the secured position being the end of that wire of the second plurality of connector positioning wires being positioned in proximity to the second interconnector of the device such that each of the plurality of second connectors is positioned to be releasably connectable to its associated sub-second-interconnector, and each of the second connectors is releasably connected to its associated sub-second-interconnector of the device;

when the lumen wall anchor is in the expanded-released-configuration, each wire of the plurality of second connector positioning wires is in the released position, the released position being the end of that wire of the plurality of second connector positioning wires being proximate the wall of the lumen of the conduit, and the plurality of second connector positioning wires and the plurality of second connectors do not obstruct fluid flow axially through the wire network while the lumen wall anchor is anchored in place at the implantation site.

In some implementations, the device further having a control cable attached thereto, an outer diameter of the control cable being sized to be able to pass through the delivery sheath to the implantation site, wherein guiding the assembly within the delivery sheath to the implantation site includes pushing the control cable attached to the device.

In some implementations, promoting exit of the assembly at the implantation site includes pushing the control cable attached to the device.

In some implementations, the device is a modular fluid flow influencing device having a central docking unit and a plurality of functional units, the docking unit being non-expandable and being the elongate body of the device, the docking unit having:

a plurality of concave receiving surfaces for receiving the functional units, the receiving surfaces extending parallel to the central longitudinal axis of the docking units and being positioned equidistantly radially along the exterior surface thereof, a plurality of inter-receiving-surface portions, an inter-receiving-surface portion extending longitudinally, parallel to the central longitudinal axis of the docking unit, between each two adjacent receiving surfaces, promoting exit of the assembly at the implantation site includes, promoting exit of the plurality of functional units of the device from the delivery sheath at the implantation site and then promoting exit of the central docking unit from the delivery sheath at the implantation site; and the method further comprises, after f), pulling a control wire of each of the functional units to guide each functional unit into being received by one of the receiving surfaces of the docking unit.

Aspect 4.2—Clause 406 to 410

In a second sub-aspect of the fourth aspect, implementations of the present technology provide a method of explanting a mammalian body conduit intralumenal device and lumen wall anchor assembly having been implanted into a mammalian body and anchored at an implantation site, the assembly having, a mammalian body conduit intralumenal device, the device being shaped and dimensioned to be deliverable to a delivery site within a lumen of a mammalian body conduit via a delivery sheath, the device having an elongate body, a central longitudinal axis, and a first interconnector structured to releasably connect the device with a lumen wall anchor for use in maintaining the device in place within the mammalian body conduit, the first interconnector having multiple sub-first-interconnectors, and the lumen wall anchor, the lumen wall anchor including, a 3D-shaped wire network, the wire network having a central longitudinal axis, a plurality of first connector positioning wires extending from the wire network, each wire of the plurality of first connector positioning wires being moveable between a secured position and a released position and being overcomeably biased towards the released position, a plurality of first connectors, a single one of the plurality of first connectors being disposed at an end of each of wire of the plurality of first connector positioning wires, a number of the plurality of first connectors being equal to a number of the sub-first-interconnectors, and each one of the plurality of first connectors being associated with a single one of the multiple sub-first-interconnectors, the lumen wall anchor having a compact-secured-configuration, an expanded-secured-configuration, and an expanded-released-configuration, when the lumen wall anchor is in the compact-secured-configuration, the lumen wall anchor is shaped and dimensioned to be deliverable to the delivery site within the lumen of the mammalian body conduit via the catheter, and each wire of the first plurality of connector positioning wires is in the secured position, the secured position being the end of that wire of the first plurality of connector positioning wires being positioned in proximity to the first interconnector of the device such that each of the plurality of first connectors is positioned to be releasably connectable to its associated sub-first interconnector of the first interconnector of the device, and each of the first connectors is releasably connected to its associated sub-first-interconnector;

when the lumen wall anchor is in the expanded-secured-configuration, the wire network is dimensioned and shaped to exert a force on a wall of the lumen of the conduit, the force being sufficient to anchor the mammalian body conduit intralumenal device and lumen wall anchor assembly in place at the implantation site, and each wire of the first plurality of connector positioning wires is in the secured position, and each of the first connectors is releasably connected to its associated sub-first-interconnector; and when the lumen wall anchor is in the expanded-released-configuration, the wire network is dimensioned and shaped to exert a force on the wall of the lumen of the conduit, the force being sufficient to anchor the lumen wall anchor assembly in place at the implantation site, and each wire of the plurality of first connector positioning wires is in the released position, the released position being each of the plurality of first connectors being released from and unconnected to its associated sub-first interconnector, and the end of each wire of the first plurality of connector positioning wires being proximate the wall of the lumen of the conduit, and the plurality of first connector positioning wires and the plurality of first connectors do not obstruct fluid flow axially through the wire network while the lumen wall anchor is anchored in place at the implantation site, the lumen wall anchor being overcomeably biased away from its compact-secured-configuration, the assembly having a distal end and a proximal end, the method comprising:

a) obtaining access to the conduit system of the mammalian body;
b) guiding a retrieval sheath to the implantation site;
c) promoting entry of the assembly into the retrieval sheath proximal end first at the implantation site;
d) overcoming the bias of the lumen wall anchor via contact of the retrieval sheath with the proximally-facing sloped surfaces of the first connector positioning wires, causing the lumen wall anchor to adopt the compact-secured-configuration, unanchoring the assembly;
e) completing entry of the assembly into the retrieval sheath at the implantation site; and
f) withdrawing the retrieval sheath and the assembly from the body.

In some implementations:

the device further has a second interconnector spaced-apart from and distal to the first interconnector, the second interconnector being structured to releasably connect the device with the lumen wall anchor for use in maintaining the device in place within the mammalian body conduit, the second interconnector having multiple sub-second-interconnectors, the lumen wall anchor further includes a plurality of second connector positioning wires extending from the wire network, each wire of the plurality of second connector positioning wires being moveable between a secured position and a released position and being overcomeably biased towards the released position;

a plurality of second connectors, a single one of the plurality of second connectors being disposed at an end of each wire of the plurality of second connector positioning wires, a number of the plurality of second connectors being equal to a number of the sub-second-interconnectors, and each one of the plurality of second connectors being associated with a single one of the multiple sub-second-interconnectors;

when the lumen wall anchor is in the expanded-secured-configuration, each wire of the plurality of second connector positioning wires is in the secured position, the secured position being the end of that wire of the second plurality of connector wires being positioned in proximity to the second interconnector of the device such that each of the plurality of second connectors is positioned to be releasably connectable to its associated sub-second-interconnector, and each of the second connectors is releasably connected to its associated sub-second-interconnector of the device;

when the lumen wall anchor is in the expanded-released-configuration, each wire of the plurality of second connector positioning wires is in the released position, the released position being the end of that wire of the plurality of second connector positioning wires being proximate the wall of the lumen of the conduit, and the plurality of second connector positioning wires and the plurality of second connectors do not obstruct fluid flow axially through the wire network while the lumen wall anchor is anchored in place at the implantation site.

In some implementations, the device further has a control cable attached thereto passing from the implantation site through the conduit system of the body, wherein withdrawing the retrieval sheath and the assembly from the body includes pulling the control cable attached to the device In some implementations, promoting entry of the assembly into the retrieval sheath proximal end first at the implantation site includes pulling the control cable attached to the device.

In some implementations, the device being a modular fluid flow influencing device having a central docking unit and a plurality of functional units, the docking unit being non-expandable and being the elongate body of the device, the docking unit having:

a plurality of concave receiving surfaces for receiving the functional units, the receiving surfaces extending parallel to the central longitudinal axis of the docking units and being positioned equidistantly radially along the exterior surface thereof, a plurality of inter-receiving-surface portions, an inter-receiving-surface portion extending longitudinally, parallel to the central longitudinal axis of the docking unit, between each two adjacent receiving surfaces, each of the plurality of functional units having been received by one of the receiving surfaces of the docking unit, the method further comprising, prior to c) pushing a control wire of each of the functional units to guide each functional unit from being received by one of the receiving surfaces of the docking unit, and wherein promoting entry of the assembly into the retrieval sheath includes, promoting entry of the central docking unit into the retrieval sheath and then promoting entry of the functional units into the retrieval sheath.

Aspect 4.3—Clauses 411-416

In a third sub-aspect of the fourth aspect, implementations of the present technology provide a method of explanting a modular fluid flow influencing intralumenal device being part of assembly including a lumen wall anchor, the assembly having been implanted into a mammalian body and an anchored at an implantation site, the assembly having, a mammalian body conduit intralumenal device, the device being shaped and dimensioned to be deliverable to a delivery site within a lumen of a mammalian body conduit via a catheter, the device having an elongate body, a central longitudinal axis, and a first interconnector structured to releasably connect the device with a lumen wall anchor for use in maintaining the device in place within the mammalian body conduit, the first interconnector having multiple sub-first-interconnectors, and the lumen wall anchor, the lumen wall anchor including, a 3D-shaped wire network, the wire network having a central longitudinal axis, a plurality of first connector positioning wires extending from the wire network, each wire of the plurality of first connector positioning wires being moveable between a secured position and a released position and being overcomeably biased towards the released position, a plurality of first connectors, a single one of the plurality of first connectors being disposed at an end of each of wire of the plurality of first connector positioning wires, a number of the plurality of first connectors being equal to a number of the sub-first-interconnectors, and each one of the plurality of first connectors being associated with a single one of the multiple sub-first-interconnectors, the lumen wall anchor having a compact-secured-configuration, an expanded-secured-configuration, and an expanded-released-configuration, when the lumen wall anchor is in the compact-secured-configuration,
   the lumen wall anchor is shaped and dimensioned to be deliverable to the delivery site within the lumen of the mammalian body conduit via the catheter, and
   each wire of the first plurality of connector positioning wires is in the secured position, the secured position being the end of that wire of the first plurality of connector positioning wires being positioned in proximity to the first interconnector of the device such that each of the plurality of first connectors is positioned to be releasably connectable to its associated sub-first interconnector of the first interconnector of the device, and
   each of the first connectors is releasably connected to its associated sub-first-interconnector;

when the lumen wall anchor is in the expanded-secured-configuration,
   the wire network is dimensioned and shaped to exert a force on a wall of the lumen of the conduit, the force being sufficient to anchor the mammalian body conduit intralumenal device and lumen wall anchor assembly in place at the implantation site, and
   each wire of the first plurality of connector positioning wires is in the secured position, and
   each of the first connectors is releasably connected to its associated sub-first-interconnector; and when the lumen wall anchor is in the expanded-released-configuration,
   the wire network is dimensioned and shaped to exert a force on the wall of the lumen of the conduit, the force being sufficient to anchor the lumen wall anchor assembly in place at the implantation site, and
   each wire of the plurality of first connector positioning wires is in the released position, the released position being each of the plurality of first connectors being released from and unconnected to its associated sub-first interconnector, and the end of each wire of the first plurality of connector positioning wires being proximate the wall of the lumen of the conduit, and
   the plurality of first connector positioning wires and the plurality of first connectors do not obstruct fluid flow axially through the wire network while the lumen wall anchor is anchored in place at the implantation site,
   the lumen wall anchor being biased away from its compact-secured-configuration, the assembly having a distal end and a proximal end, the method comprising:
a) obtaining access to the conduit system of the mammalian body;
b) guiding a retrieval sheath to the implantation site;
c) pulling at least one wire operationally connected to the sub-first-interconnectors, causing the release of each of the first connectors from its connection to its associated first-sub-interconnector, disconnecting the lumen wall anchor from the device and allowing the first connector positioning wires to move to the released position;
d) promoting entry of the device into the retrieval sheath proximal end first at the implantation site;
e) withdrawing the retrieval sheath and the device from the body.

In some implementations,
the device further has a second interconnector spaced-apart from and distal to the first interconnector, the second interconnector being structured to releasably connect the device with the lumen wall anchor for use in maintaining the device in place within the mammalian body conduit, the second interconnector having multiple sub-second-interconnectors, the lumen wall anchor further includes
   a plurality of second connector positioning wires extending from the wire network, each wire of the plurality of second connector positioning wires being moveable between a secured position and a released position and being overcomeably biased towards the released position;
   a plurality of second connectors, a single one of the plurality of second connectors being disposed at an end of each wire of the plurality of second connector positioning wires, a number of the plurality of second connectors being equal to a number of the sub-second-interconnectors, and each one of the plurality of second connectors being associated with a single one of the multiple sub-second-interconnectors;

when the lumen wall anchor is in the expanded-secured-configuration,
   each wire of the plurality of second connector positioning wires is in the secured position, the secured position being the end of that wire of the second plurality of connector wires being positioned in proximity to the second interconnector of the device such that each of the plurality of second connectors is positioned to be releasably connectable to its associated sub-second-interconnector, and
      each of the second connectors is releasably connected to its associated sub-second-interconnector of the device;

when the lumen wall anchor is in the expanded-released-configuration,
   each wire of the plurality of second connector positioning wires is in the released position, the released position being the end of that wire of the plurality of second connector positioning wires being proximate the wall of the lumen of the conduit, and
   the plurality of second connector positioning wires and the plurality of second connectors do not obstruct fluid flow axially through the wire network while the lumen wall anchor is anchored in place at the implantation site;

the method further comprising, after b) and prior to c), pulling at least one wire operationally connected to the sub-second-interconnectors, causing the release of each of the second connectors from its connection to its associated sub-second-interconnector, and allowing the second connector positioning wires to move to the released position.

In some implementations, the device further has a control cable attached thereto passing from the implantation site through the conduit system to outside the conduit system of the body, wherein guiding the retrieval sheath to the implantation site includes railing the retrieval sheath over the control cable.

In some implementations, promoting entry of the device into the retrieval sheath proximal end first at the implantation site includes pulling the control cable attached to the device.

In some implementations, withdrawing the retrieval sheath and the device from the body includes pulling the control cable attached to the device.

In some implementations,
the device is a modular fluid flow influencing device having a central docking unit and a plurality of functional units,
the docking unit being non-expandable and being the elongate body of the device,
the docking unit having:
a plurality of concave receiving surfaces for receiving the functional units, the receiving surfaces extending parallel to the central longitudinal axis of the docking units and being positioned equidistantly radially along the exterior surface thereof,
a plurality of inter-receiving-surface portions, an inter-receiving-surface portion extending longitudinally, parallel to the central longitudinal axis of the docking unit, between each two adjacent receiving surfaces,
each of the plurality of functional units has been received by one of the receiving surfaces of the docking unit,
the method further comprises, prior to c) pushing a control wire of each of the functional units to guide each unit from being received by one of the receiving surfaces of the docking unit, and
promoting entry of the assembly into the retrieval sheath includes, promoting entry of the central docking unit into the retrieval sheath and then promoting entry of the functional units into the retrieval sheath.

Aspect 4.5—Clauses 417-418

In a fourth sub-aspect of the fourth aspect, implementations of the present technology provide a method of implanting a modular fluid flow influencing intralumenal device and lumen wall anchor assembly into a mammalian body, the assembly having,
a mammalian body conduit intralumenal device, the device being shaped and dimensioned to be deliverable to a delivery site within a lumen of a mammalian body conduit via a catheter, the device having an elongate body, a central longitudinal axis, a first interconnector structured to releasably connect the device with a lumen wall anchor for use in maintaining the device in place within the mammalian body conduit, the first interconnector having multiple sub-first-interconnectors, and a second interconnector spaced-apart from and distal to the first interconnector, the second interconnector being structured to releasably connect the device with the lumen wall anchor for use in maintaining the lumen anchor in a compact-secured-configuration, the second interconnector having multiple sub-second-interconnectors, and the lumen wall anchor, the lumen wall anchor including,
a 3D-shaped wire network, the wire network having a central longitudinal axis,
a plurality of first connector positioning wires extending from the wire network, each wire of the plurality of first connector positioning wires being moveable between a secured position and a released position and being overcomeably biased towards the released position,
a plurality of first connectors, a single one of the plurality of first connectors being disposed at an end of each of wire of the plurality of first connector positioning wires, a number of the plurality of first connectors being equal to a number of the sub-first-interconnectors, and each one of the plurality of first connectors being associated with a single one of the multiple sub-first-interconnectors,
a plurality of second connectors disposed on the wire network, a number of the plurality of second connectors being equal to a number of the sub-second-interconnectors, and each one of the plurality of second connectors being associated with a single one of the multiple sub-second-interconnectors,
the lumen wall anchor having the compact-secured-configuration, an expanded-secured-configuration, and an expanded-released-configuration,
when the lumen wall anchor is in the compact-secured-configuration,
the lumen wall anchor is shaped and dimensioned to be deliverable to the delivery site within the lumen of the mammalian body conduit via the catheter, and
each wire of the first plurality of connector positioning wires is in the secured position, the secured position being the end of that wire of the first plurality of connector positioning wires being positioned in proximity to the first interconnector of the device such that each of the plurality of first connectors is positioned to be releasably connectable to its associated sub-first interconnector of the first interconnector of the device, and
each of the first connectors is releasably connected to its associated sub-first-interconnector;
each of the second connectors is releasably connected to its associated sub-second-interconnector;
when the lumen wall anchor is in the expanded-secured-configuration,
the wire network is dimensioned and shaped to exert a force on a wall of the lumen of the conduit, the force being sufficient to anchor the mammalian body conduit intralumenal device and lumen wall anchor assembly in place at an implantation site, and
each wire of the first plurality of connector positioning wires is in the secured position, and
each of the first connectors is releasably connected to its associated sub-first-interconnector,
each of the second connectors is released from and unconnected to its associated sub-second-interconnector, and
when the lumen wall anchor is in the expanded-released-configuration, the wire network is dimensioned and shaped to exert a force on the wall of the lumen of the conduit, the force being sufficient to anchor the lumen wall anchor assembly in place at the implantation site, and each wire of the plurality of first connector positioning wires is in the released position, the released position being each of the plurality of first connectors being released from and unconnected to its associated sub-first interconnector, and the end of each wire of the first plurality of connector positioning wires being proximate the wall of the lumen of the conduit, and the plurality of first connector positioning wires, the plurality of first connectors, and the plurality of second connectors do not obstruct fluid flow axially through the wire network while the lumen wall anchor is anchored in place at the implantation site, the lumen wall anchor being biased away from its compact-secured-configuration, the assembly having a distal end and a proximal end, the method comprising:
a) obtaining access to the conduit system of the mammalian body;
b) guiding a delivery sheath through the conduit system to a delivery site in advance of the implantation site;
c) inserting the assembly with the lumen wall anchor in its compact-secured-configuration into the delivery sheath;
d) guiding the assembly within the delivery sheath to the delivery site;
e) promoting exit of the assembly from the delivery sheath at the delivery site;
f) advancing the assembly to the implantation site;
g) pulling at least one wire operationally connected to the sub-second-interconnectors, causing the release of each of the second connectors from its connection to its associated sub-second-interconnector, thereby allowing the bias of the lumen wall anchor to cause the lumen wall anchor to adopt the expanded-secured-configuration and exert a force on the wall of the lumen of the conduit at the implantation site, anchoring the assembly in place at the implantation site; and
h) withdrawing the delivery sheath from the body.

In some implementations, the device being a modular fluid flow influencing device having a central docking unit and a plurality of functional units, the docking unit being non-expandable and being the elongate body of the device, the docking unit having:
a plurality of concave receiving surfaces for receiving the functional units, the receiving surfaces extending parallel to the central longitudinal axis of the docking units and being positioned equidistantly radially along the exterior surface thereof, a plurality of inter-receiving-surface portions, an inter-receiving-surface portion extending longitudinally, parallel to the central longitudinal axis of the docking unit, between each two adjacent receiving surfaces, wherein:
inserting the assembly with the lumen wall anchor in its compact-secured-configuration into the delivery sheath includes first inserting the plurality of functional units one-after-another into the delivery sheath and then inserting the docking units into the delivery sheath;

promoting exit of the assembly from the delivery sheath at the delivery site includes promoting exit of the functional units, one-by-one, from the delivery sheath at the at the delivery site and after promoting exit of the docking unit and the lumen wall anchor, with the lumen wall anchor remaining in the compact-secured-configuration;

the method further comprises, after e) and prior to f), bringing the device into a configuration with the functional units side-by-side with each other and proximate the distal end of the docking unit;

wherein advancing the assembly to the implantation site is advancing the assembly to the implantation site with the device in the configuration; and the method further comprises, after g), pulling a control wire of each of the functional units to guide each functional unit into being received by one of the receiving surfaces of the docking unit.

Aspect 4.6—Clauses 419-420

In a sixth sub-aspect of the fourth aspect, implementations of the present technology provide a method of explanting a modular fluid flow influencing intralumenal device being part of assembly including a lumen wall anchor, the assembly having been implanted into a mammalian body and an anchored at an implantation site, the assembly having, a mammalian body conduit intralumenal device, the device being shaped and dimensioned to be deliverable to a delivery site within a lumen of a mammalian body conduit via a catheter, the device having an elongate body, a central longitudinal axis, a first interconnector structured to releasably connect the device with a lumen wall anchor for use in maintaining the device in place within the mammalian body conduit, the first interconnector having multiple sub-first-interconnectors, and a second interconnector spaced-apart from and distal to the first interconnector, the second interconnector being structured to releasably connect the device with the lumen wall anchor for use in maintaining the lumen anchor in a compact-secured-configuration, the second interconnector having multiple sub-second-interconnectors, and the lumen wall anchor, the lumen wall anchor including,
a 3D-shaped wire network, the wire network having a central longitudinal axis, a plurality of first connector positioning wires extending from the wire network, each wire of the plurality of first connector positioning wires being moveable between a secured position and a released position and being overcomeably biased towards the released position, a plurality of first connectors, a single one of the plurality of first connectors being disposed at an end of each of wire of the plurality of first connector positioning wires, a number of the plurality of first connectors being equal to a number of the sub-first-interconnectors, and each one of the plurality of first connectors being associated with a single one of the multiple sub-first-interconnectors, a plurality of second connectors disposed on the wire network, a number of the plurality of second connectors being equal to a number of the sub-second-interconnectors, and each one of the plurality of second connectors being associated with a single one of the multiple sub-second-interconnectors, the lumen wall anchor having the compact-secured-configuration, an expanded-secured-configuration, and an expanded-released-configuration,
  when the lumen wall anchor is in the compact-secured-configuration,
    the lumen wall anchor is shaped and dimensioned to be deliverable to the delivery site within the lumen of the mammalian body conduit via the catheter, and
    each wire of the first plurality of connector positioning wires is in the secured position, the secured position being the end of that wire of the first plurality of connector positioning wires being positioned in proximity to the first interconnector of the device such that each of the plurality of first connectors is positioned to be releasably connectable to its associated sub-first interconnector of the first interconnector of the device, and
    each of the first connectors is releasably connected to its associated sub-first-interconnector;
    each of the second connectors is releasably connected to its associated sub-second-interconnector;
  when the lumen wall anchor is in the expanded-secured-configuration,
    the wire network is dimensioned and shaped to exert a force on a wall of the lumen of the conduit, the force being sufficient to anchor the mammalian body conduit intralumenal device and lumen wall anchor assembly in place at an implantation site, and
    each wire of the first plurality of connector positioning wires is in the secured position, and
    each of the first connectors is releasably connected to its associated sub-first-interconnector,
    each of the second connectors is released from and unconnected to its associated sub-second-interconnector, and
  when the lumen wall anchor is in the expanded-released-configuration,
    the wire network is dimensioned and shaped to exert a force on the wall of the lumen of the conduit, the force being sufficient to anchor the lumen wall anchor assembly in place at the implantation site, and
    each wire of the plurality of first connector positioning wires is in the released position, the released position being each of the plurality of first connectors being released from and unconnected to its associated sub-first interconnector, and the end of each wire of the first plurality of connector positioning wires being proximate the wall of the lumen of the conduit, and
    the plurality of first connector positioning wires, the plurality of first connectors, and the plurality of second connectors do not obstruct fluid flow axially through the wire network while the lumen wall anchor is anchored in place at the implantation site,
  the lumen wall anchor being biased away from its compact-secured-configuration,
the assembly having a distal end and a proximal end,
the method comprising:
  a) obtaining access to the conduit system of the mammalian body;
  b) guiding a retrieval sheath through the conduit system to a retrieval site in advance of the implantation site;
  c) pulling at least one wire operationally connected to the sub-first-interconnectors, causing the release of each of the first connectors from its connection to its associated first-sub-interconnector, disconnecting the lumen wall anchor from the device and allowing the first connector positioning wires to move to the released position:
  d) withdrawing the assembly from the implantation site to the retrieval site;
  e) promoting entry of the device into the retrieval sheath at the retrieval site;
  f) withdrawing the retrieval sheath and the device from the body.
In some implementations,
  the device is a modular fluid flow influencing device having a central docking unit and a plurality of functional units,
    the docking unit being non-expandable and being the elongate body of the device,
    the docking unit having:
      a plurality of concave receiving surfaces for receiving the functional units, the receiving surfaces extending parallel to the central longitudinal axis of the docking units and being positioned equidistantly radially along the exterior surface thereof,
      a plurality of inter-receiving-surface portions, an inter-receiving-surface portion extending longitudinally, parallel to the central longitudinal axis of the docking unit, between each two adjacent receiving surfaces,
    each of the plurality of functional units has been received by one of the receiving surfaces of the docking unit,
  wherein:
    the method further comprises, prior to e), pushing a control wire of each of the functional units to guide each functional unit from being received by one of the receiving surfaces of the docking unit;
    promoting entry of the device into the retrieval sheath at the delivery site includes promoting entry of the docking unit into the retrieval sheath and after promoting entry of the functional units, one-by-one, into the retrieval sheath.

While the above described methods of implantation and explanation have been described with respect to particular embodiments of the present technology (for the sake of brevity), as a skilled addressee would understand, these methods can be appropriately modified for use with other embodiments of the present technology.

General

In the context of the present specification, the words "first", "second", "third", etc. have been used as adjectives only for the purpose of allowing for distinction between the nouns that they modify from one another, and not for the purpose of describing any particular relationship between those nouns. Thus, for example, it should be understood that, the use of the terms "first unit" and "third unit" is not intended to imply any particular type, hierarchy or ranking (for example) of/between the units. Nor is their use (by itself) intended imply that any "second unit" must necessarily exist in any given situation.

In the context of the present specification, the word "embodiment(s)" is generally used when referring to physical realizations of the present technology and the word "implementations" is generally used when referring to methods that are encompassed within the present technology (which generally involve also physical realizations of the present technology). The use of these different terms is not intended to be limiting of or definitive of the scope of the present technology. These different terms have simply been used to allow the reader to better situate themselves when reading the present lengthy specification.

Embodiments and implementations of the present technology each have at least one of the above-mentioned objects and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments and/or implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description, which is to be used in conjunction with the accompanying drawings, where.

DETAILED DESCRIPTION OF SOME EMBODIMENTS AND IMPLEMENTATIONS

Introduction

Figure 10:
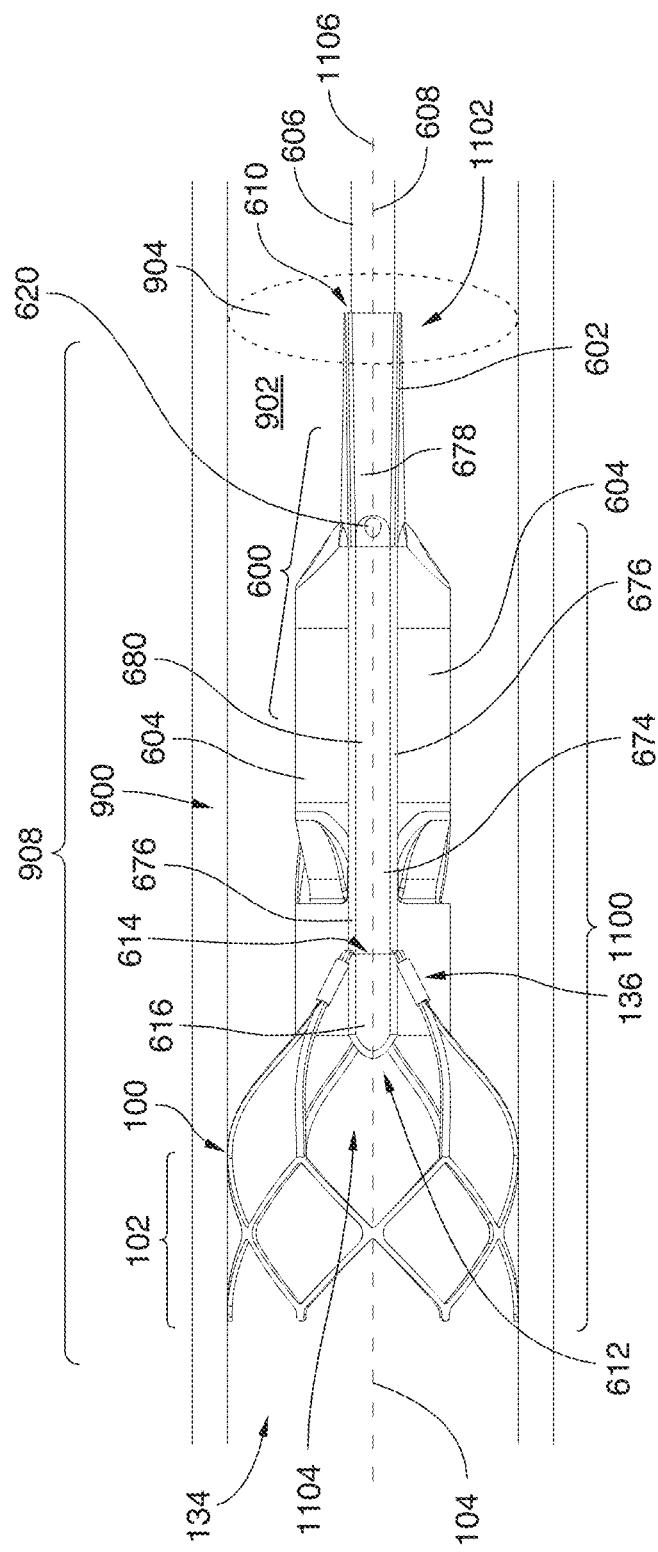
FIG. 10 shows a side view of an intraluminal device and anchor assembly being a first embodiment of the present technology being anchored within the lumen of a body conduit. The assembly includes a first embodiment of a device of the present technology and a first embodiment of an anchor of the present technology. The device is shown with only two of the three pumping units having been received in their receiving surfaces of the docking unit. The anchor is shown in its expanded-secured-configuration.

Referring to FIG. 10, there is shown a mammalian body conduit intralumenal device and lumen wall anchor assembly 1100, which is one embodiment of the present technology. It is to be expressly understood that the assembly 1100 is merely one embodiment, amongst many, of the present technology. Other embodiments are also described hereinbelow. Thus, the description thereof that follows is intended to be only a description of illustrative examples of the present technology. This description is not intended to define the scope or set forth the bounds of the present technology. In some cases, what are believed to be helpful examples of modifications to assembly 1100 and/or other embodiments may also be set forth hereinbelow. This is done merely as an aid to understanding, and, again, not to define the scope or set forth the bounds of the present technology. These modifications are not an exhaustive list, and, as a skilled addressee would understand, other modifications are likely possible. Further, where this has not been done (i.e., where no examples of modifications have been set forth), it should not be interpreted that no modifications are possible and/or that what is described is the sole manner of implementing that element or feature of the present technology. As a skilled addressee would understand, this is likely not the case. In addition, it is to be understood that the assembly 1100 may provide in certain instances a simple embodiment of the present technology, and that where such is the case it has been presented in this manner as an aid to understanding. As a skilled addressee would understand, various embodiments of the present technology are of a greater complexity.

In the description that follows, where multiples of the same element are present, in instances where it is not necessary to distinguish between the multiples, a single (and the same) reference number (e.g., 777) is used to reference each one of the multiples. In instances where it is necessary to distinguish between the multiples, that single reference number is used with a different letter from "a" to "e" and "g" (but not "f") for each one of the multiples (e.g., 777a, 777b, 777c, 777d, 777e, 777g). This convention is generally used throughout this description. Thus, in different instances the same element may be referred to, continuing with the previous example, as 777 or 777a, as the case may be, depending on the circumstance. Further, when used in the description that follows, when used with a reference number, the letter "f" refers to a "first" element and the letter "s" refers to a "second" element (e.g., 777f, 777s), for ease of understanding. In some instances, both lettering systems are used together (e.g., 777as, 777bf, etc.) Finally, an attempt has been made such that for each of the embodiments of the same apparatus (e.g., assembly, device, anchor), similar numbers have been used throughout the description for like components of the various embodiments. For example, the wire network of the anchor 100 is referenced by the number 102, the wire network of the anchor 200 is referenced by the number 202, the wire network of the anchor 300 is referenced by the number 302, and the wire network of the anchor 400 is referenced by the number 402. Similarly, in another example, the docking unit of the device 500 is referenced by the number 502, the docking unit of the device 600 is referenced by the number 602, the docking unit of the device 700 is referenced by the number 702, and the docking unit of the device 800 is referenced by the number 802. For ease of understanding, this numbering convention is generally adhered to in the description that follows, but it may have been departed from in some instances.

Assembly First Embodiment—Introduction

Referring to FIG. 10, there is shown a mammalian body conduit intralumenal device and lumen wall anchor assembly 1100 being a first embodiment of an assembly of the present technology. The assembly 1100 has a proximal end 1102 and a distal end 1104 defined consistently with the orientation in which the assembly 1100 is implanted. The assembly 1100 has a central longitudinal axis 1106. The assembly 1100 includes a mammalian body conduit intralumenal device 600 and a lumen wall anchor 100, each of which will be discussed in turn hereinbelow.

Assembly First Embodiment—Device First Embodiment

The mammalian body conduit intralumenal device 600 is a first embodiment of a device of the present technology. In this embodiment, the device 600 is a modular fluid pump as described in the WO '765 Publication. Thus, the device 600 has a docking unit 602 and three pumping units 604 (only two of which are shown in FIG. 10). The device 600 is shown in FIG. 10 in its assembled configuration with the pumping units 604 having been received in the receiving surfaces 674 (FIG. 35) of the docking unit 600. The device 600, when in its assembled configuration, has a proximal end 610 and a distal end 612. The proximal end 610 and the distal end 612 are defined consistently with the orientation in which the device 600 is implanted. Thus, the proximal end 610 and distal end 612 of the device 600 are defined consistently with the proximal end 1102 and distal end 1104 of the assembly 1100, respectively. The device 600 has a central longitudinal axis 608 which, in this embodiment, is colinear with the central longitudinal axis 1106 of the assembly 1100. A cable housing 606 extends proximally from the proximal end 610 of the device 600. Within the cable housing 606 are the various control wires and electrical wires (not shown) of the pumping units 604 and the docking unit 602 (e.g., the first interconnector actuation wire 630) of the device 600. (The WO '765 Publication provides a detailed description of some of such control wires and electrical wires; that description is not repeated herein for the sake of brevity.)

In this embodiment, the docking unit 602 of the device 600 has three receiving surfaces 674 (FIG. 35), each of which has received therein (in FIG. 10) one of the three pumping units 604 of the device 600. (In this embodiment, the device 600 has three pumping units 604 in total. At the proximal end of each receiving surface 674 is an opening 620 through which control wires, etc. of a pumping unit 604 can pass through the docking unit 602 into the cable housing 606.) In between each of the receiving surfaces 674 of the docking unit 602 is a raised portion 676 of the exterior surface 678 of the docking unit 602. A first interconnector 614 having three sub-first-interconnectors 615 (FIG. 34) located within the docking unit 602 and accessible via the three raised portions 676 thereof (FIG. 33), is present in the device 600. The three sub-first interconnectors 615 are equally tangentially spaced apart (e.g., there is 120° between the centers of each them when angles are measured from the central longitudinal axis 608 of the device 600). As will be described hereinbelow, the first interconnector 614 with its sub-first-interconnectors 615 connects the lumen wall anchor 100 to the device 600.

Assembly First Embodiment—Anchor First Embodiment—General Structure

Still referring to FIG. 10, the lumen wall anchor 100 is first embodiment of an anchor of the present technology. In this embodiment, the anchor 100 has a 3D-shaped wire network 102, which itself has a central longitudinal axis 104. In this embodiment, the central longitudinal axis 104 of the wire network 102 is colinear with the central longitudinal axis 1106 of the assembly 1100 and with the central longitudinal axis 608 of the device 600. In other embodiments this need not be the case.

Figure 32:
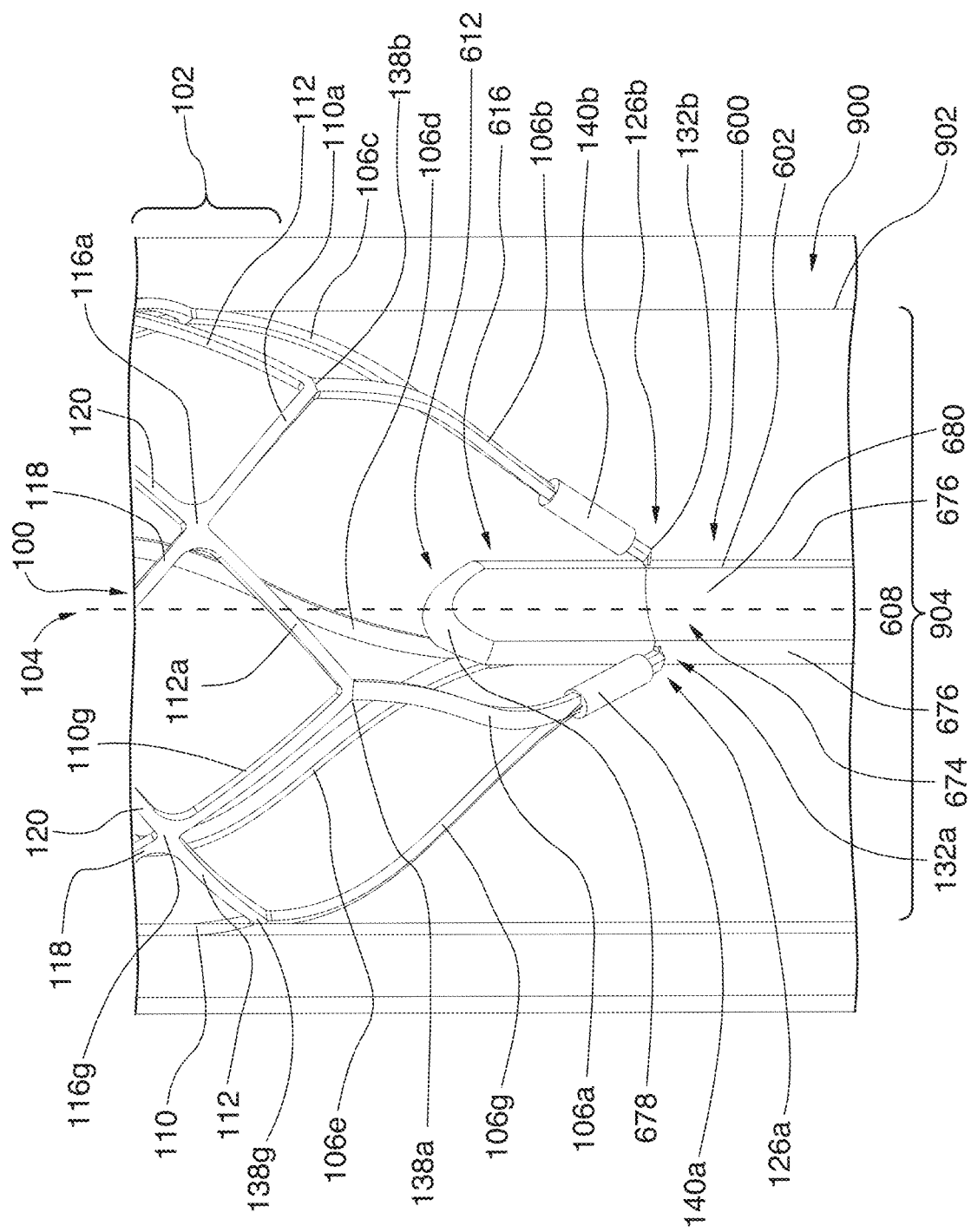
FIG. 32 shows a close-up view of the assembly of FIG. 10 within a body conduit, focusing on the distal end of the docking unit of the device and the proximal end of the anchor. The pumping units of the device are not shown. The anchor is shown in the expanded-secured-configuration.
Figure 33:
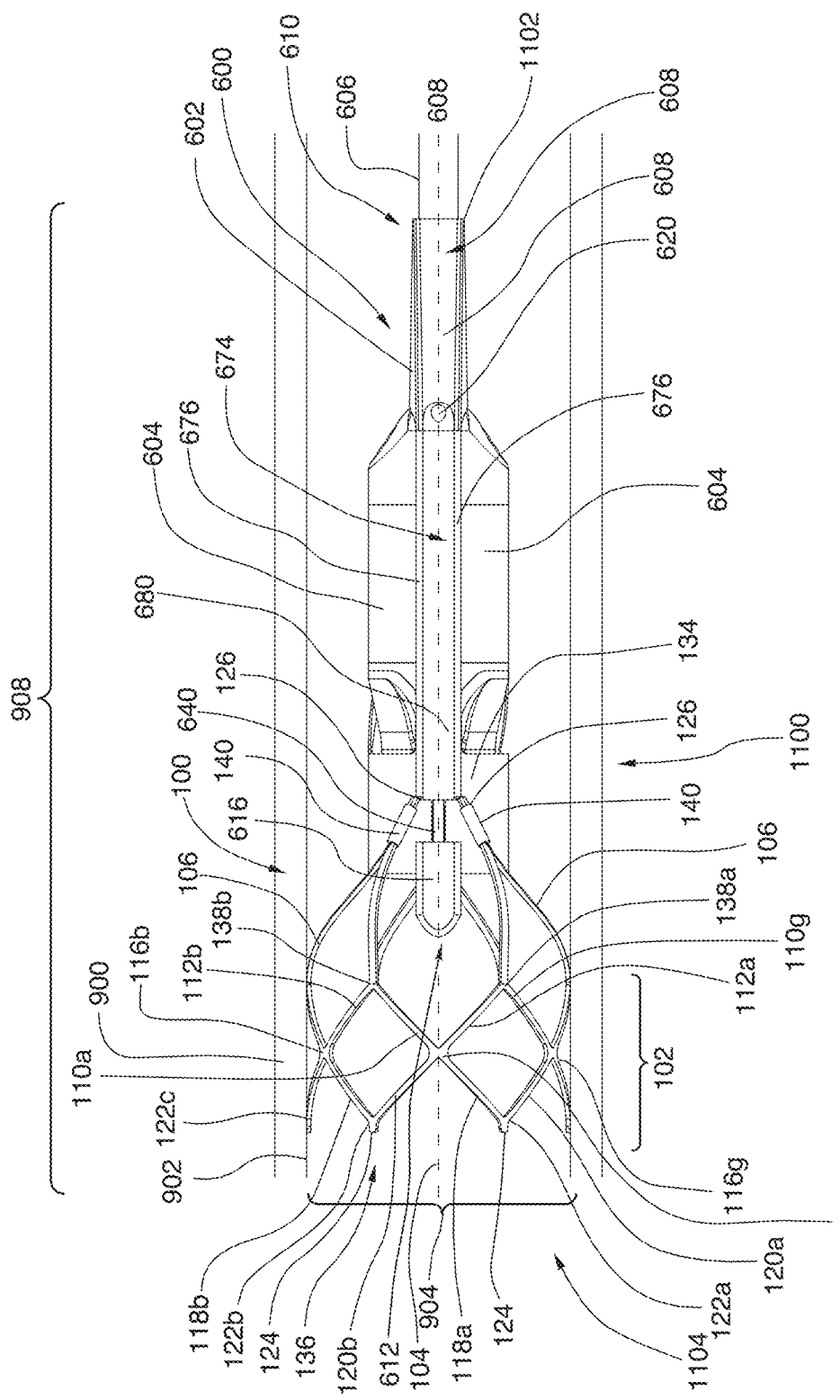
FIG. 33 shows a side view of the assembly of FIG. 10, and is similar to FIG. 10, with the exception that the end cap at the distal end of the docking unit of the device is in its released configuration.

Referring now to FIGS. 32 and 33, the various structures of the anchor 100 are shown. In this embodiment, the wire network 102 of the anchor 100 has various structural members (110, 112, 118, 120) that are joined together at various nodes (116, 122, 138). In this embodiment there are six first nodes 122; with each first node 122 being located at the distal end 136 of the anchor 100. (The anchor 100 has a distal end 136 and a proximal end 134, that are defined consistently with the implantation orientation of the anchor 100, and thus consistently with the distal end 1104 and proximal end 1102 of the assembly.)

Extending from each first node 122 is a first structural member 118 and a second structural member 120. The first structural member 118 and the second structural member 120 of each first node 122 are defined orientationally consistently for each first node 122. The first structural member 118 (e.g., 118*a*—see FIGS. 32-35 for reference numbers with letters) of each first node 122 (e.g., 122*a*) extends proximally to a one of the second nodes 116 (e.g., 116*a*) tangentially in between that first node 122*a* and a tangentially adjacent first node 122 (e.g., 122*b*). The second structural member 120 (e.g., 120*b*) of that adjacent first node 122*b* extends proximally to that one of the second nodes 116a as well. In this embodiment, this configuration is consistent for each of the first nodes 122, the second nodes 116, the first structural members 118, and the second structural members 120. In this embodiment there are six first nodes 122 and six second nodes 116.

Extending from each second node 116 (e.g., 116a) is a third structural member 110 (e.g., 110a) and a fourth structural member 112 (e.g., 112a). The third structural member 110 and the fourth structural member 112 of each second node 116 are defined orientationally consistently for each second node 116. The fourth structural member 112 (e.g., 112a) of each second node 116 (e.g., 116a) extends proximally to a one of the third nodes 138 (e.g., 138a) tangentially in between that second node 116a and a tangentially adjacent second node 116 (e.g., 116g). The third structural member 110 (e.g., 110g) of that adjacent second node 116 (e.g., 116g) extends proximally to that one of the third nodes 138a as well. In this embodiment, this configuration is consistent for each of the second nodes 116, the third nodes 138, the third structural members 110, and the fourth structural members 112. In this embodiment there are six third nodes 138, with each one of the third nodes 138 being axially aligned with a one of the first nodes 122. (For example, third node 138a and first node 122a are axially aligned with one another.)

Figure 34:
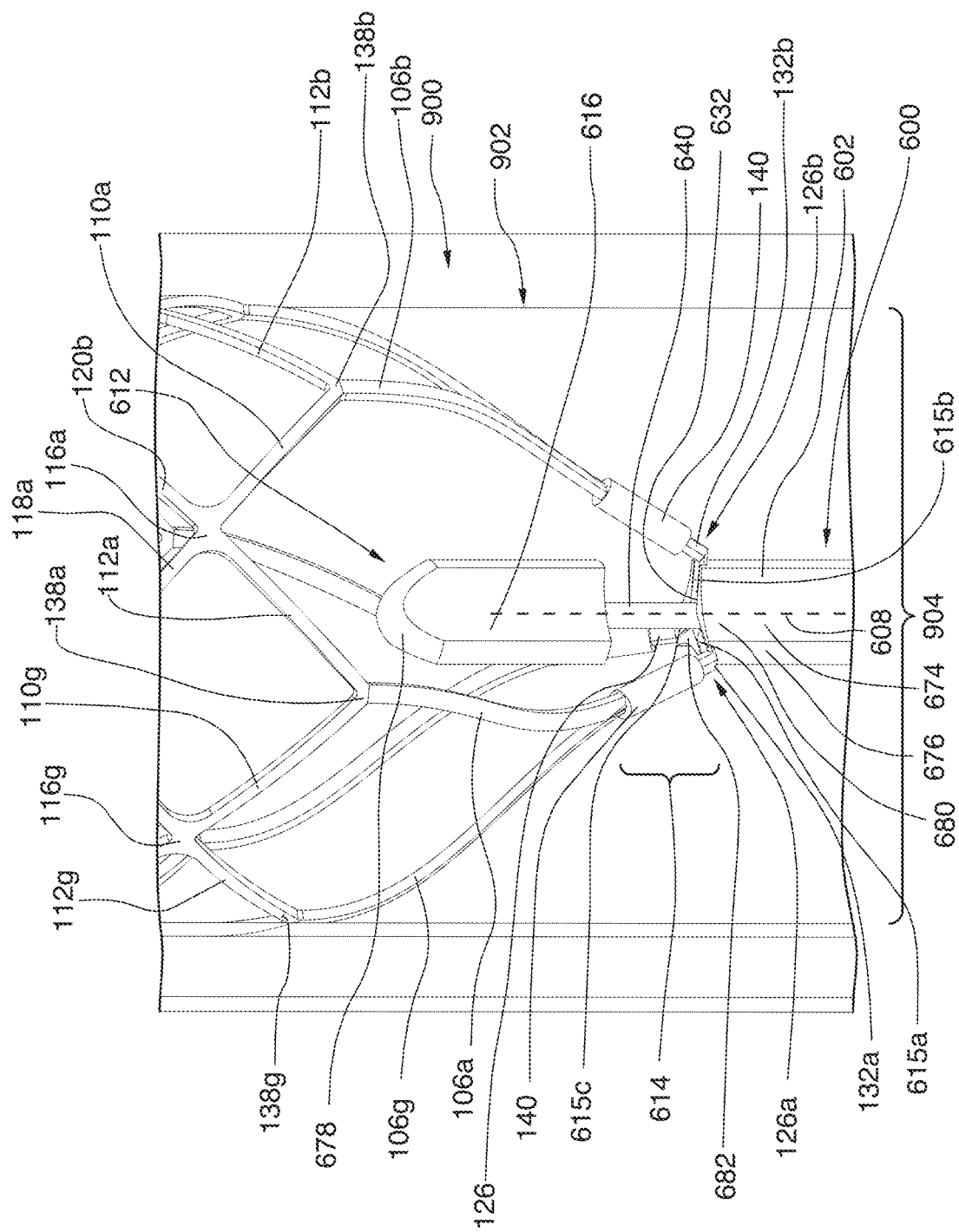
FIG. 34 shows a close-up view of the assembly of FIG. 10 within a body conduit, and is similar to FIG. 32 with the exception that the end cap at the distal end of the docking unit of the device is in its released configuration.

Extending proximally from each of the third nodes 138 are first connector positioning wires 106, one first connector positioning wire 106 (e.g., 106a) per third node 138 (e.g., 138a). The ends of two adjacent first connector positioning wires (e.g., 106a and 106g, 106b and 106c, 106d and 106e) are joined together (in this embodiment via an element 140) at which is located a first connector 126 (e.g., 126a which, in this embodiment, includes loop 132a (FIG. 34, shown schematically in the Figs.)). There are thus three first connectors 126 in total in this embodiment. As will be described in further detail hereinbelow, each first connector 126 is structured to be connectable to one of the sub-first-interconnectors 615 (FIG. 34, shown schematically) of first interconnector 614 of the device 600.

Figure 35:
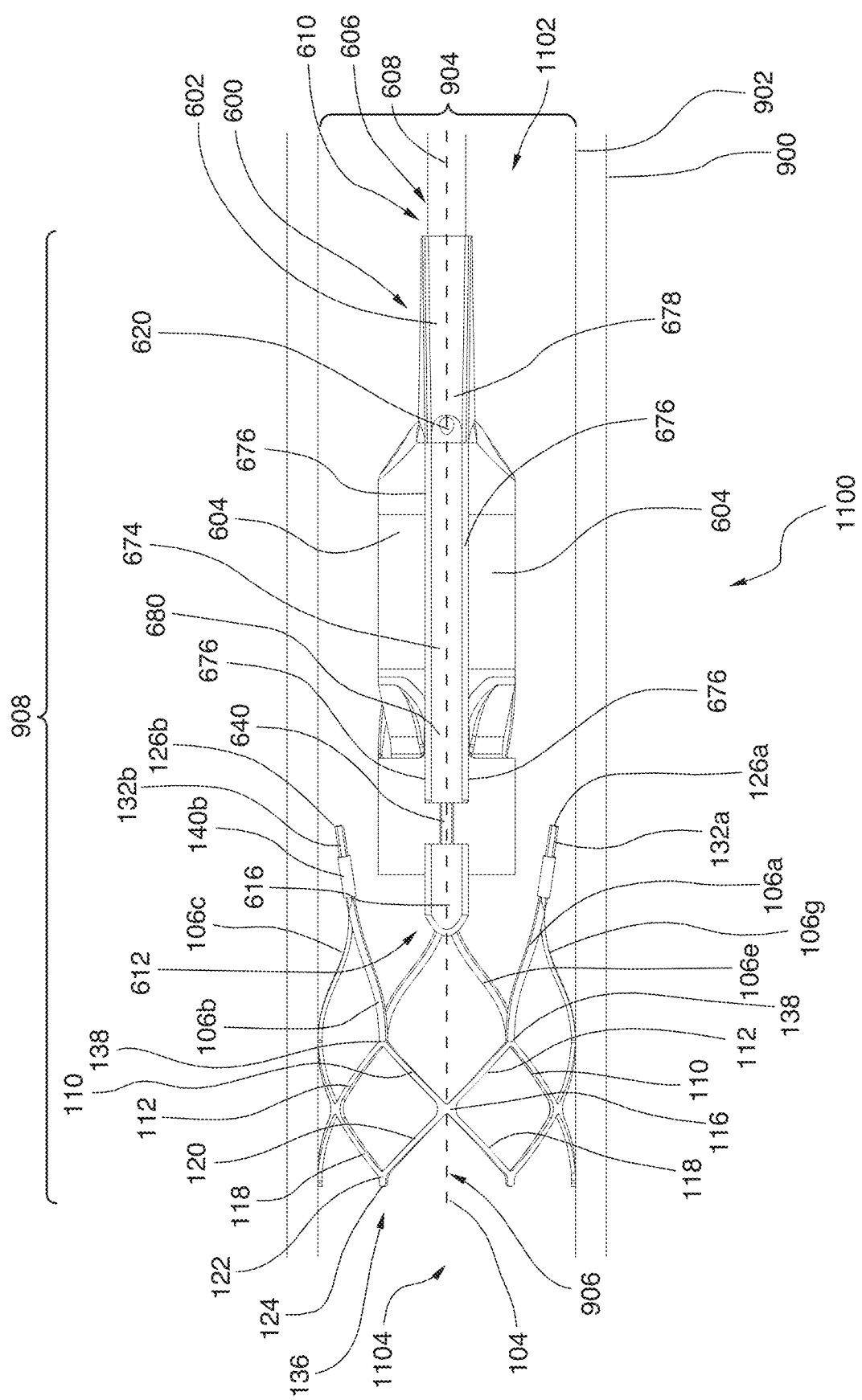
FIG. 35 shows a side of the assembly of FIG. 10, and is similar to FIG. 33, with the exception that the anchor is in the expanded-released-configuration.

Each of the first connector positioning wires 106 is moveable between a secured position (that which is shown in FIG. 10) and a released position (that which is shown in FIG. 35). In the secured position the first connector positioning wires 106 are positioned in proximity to the central longitudinal axis 104 of the anchor 100), such that the first connector 126 (e.g., 126a) which is disposed on that first connector position wire 106 (e.g., 106a) is positioned with respect to a one of the sub-first-interconnectors 615 (e.g., 615a, FIG. 34) to be releasably connectable thereto. In the released position, the first connector positioning wires 106 are away from the central longitudinal axis 104 of the anchor 100. The first connector wires 106 are overcomably biased towards the released position. The first connector wires 106 can be maintained in the secured position by releasable connection of the first connectors 126 (e.g., 126a) to the sub-first-interconnectors 615 (e.g., 615a) of the first connector 614.

Assembly First Embodiment—Anchor First Embodiment—Configurations

The lumen wall anchor 100 has a compact-secured-configuration, an expanded-secured-configuration, and an expanded-released configuration.

Figure 15:
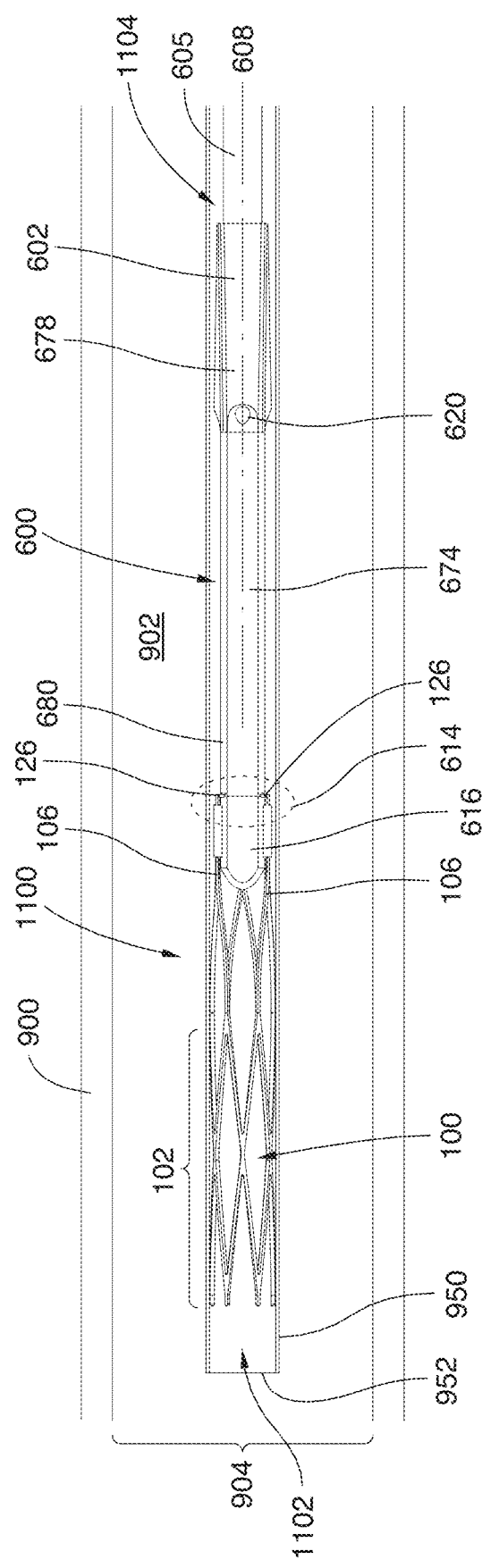
FIG. 15 shows a side view of the assembly of FIG. 10. The device is shown in its unassembled (delivery) configuration and only the docking unit of the device is shown. The pumping units of the device are not shown. The anchor is shown in its compact-secured-configuration. The assembly is shown within a delivery sheath within a body conduit.

Referring to FIG. 15, when the lumen wall anchor 100 is in a compact-secured-configuration, the lumen wall anchor 100 is shaped and dimensioned to be deliverable to a delivery site within a lumen 904 of a body conduit 900 via a catheter (e.g., delivery sheath 950 in FIG. 15). Thus, when the lumen wall anchor 100 is in the compact-secured-configuration, the first connector positioning wires 106 are in their secured position (and are shown in FIG. 15 with the first connectors 126 being releasably connected to first interconnector 614—although the first connectors 126 are not visible in FIG. 15). Further, the wire network 102 is in a compact form within the delivery sheath 950. In FIG. 15, the assembly 1100 (within the delivery sheath 950) is shown within the body conduit 900 prior to being delivered at the delivery site. (See, for example, the WO '765 Publication for a detailed description of a transcatheter implantation technique.) When the lumen wall anchor 100 is in the compact-secured-configuration, it has a diameter of 22 French.

Referring to FIG. 10, when the lumen wall anchor 100 is in an expanded-secured-configuration, the wire network 102 is dimensioned and shaped to exert a force on the wall 902 of the lumen 904 of the conduit 900. This force is sufficient to anchor the assembly 1100 in place at the implantation site 908 (including during operation of the device 600). Further, as can be seen in FIG. 10, when the anchor 100 is in the expanded-secured-configuration, the first connectors positioning wires 106 are in their secured position (and are shown in FIG. 10 with the first connectors 126 being releasably connected to first interconnector 614—although the first connectors 126 are not visible in FIG. 10). When the lumen wall anchor 100 is in the expanded-secured-configuration, it has a diameter of about 24 mm and a length of about 6 cm.

Referring to FIG. 35, when the lumen wall anchor 100 is in an expanded-released-configuration, the wire network 102 is dimensioned and shaped to exert a force on the wall 902 of the lumen 904 of the conduit 900. This force is sufficient to anchor the assembly 1100 in place at the implantation site 908. Further, as can be seen in FIG. 35, when the anchor 100 is in the expanded-released-configuration, the first connector positioning wires 106 are in their released position, as the first connectors 126 have been released from their connection with the first interconnector 614. In the released position, the ends of the first connector positioning wires 106 (and the first connectors 126 disposed thereat) are proximate the wall 902 of the lumen 904 of the conduit 900, generally parallel to the longitudinal axis 906 of body conduit 900 and generally in line with the periphery of the wire network 102. In this configuration, the first connector positioning wires 106 and the first connectors 126 do not obstruct fluid flow axially through the conduit 902 while the anchor 100 is anchored in place at the implantation site 908 with the device 600 having been retrieved and removed from the body conduit 900 (as can be best seen in FIG. 23, albeit in which another embodiment of the anchor, anchor 400, is shown). In FIGS. 10, 33, and 35 (for example), the native fluid flow axially through the conduit 900 can be either from left to right or from right to left in the figures, depending on the location of the implantation site 908 within the mammalian body and in which the orientation the assembly 1100 has been implanted. When the lumen wall anchor 100 is in the expanded-released-configuration, it has a diameter of about 24 mm and a length of about 6 cm.

The lumen wall anchor 100 is based towards its expanded-released-configuration. In this embodiment, this bias is the case as the anchor 100 is made of nitinol (a shape-memory alloy) with the expanded-released-configuration being the "remembered shape" thereof. (The anchor 400 is manufacturable according to any conventional techniques appropriate to the material of which it is made, e.g., laser cutting.) As was described hereinabove, this bias can be overcome during normal usage of the assembly 1100. In particular, referring to FIG. 15, when the assembly 1100 is within the delivery sheath 950, the bias of the wire network 102 has been overcome (via its insertion into the delivery sheath 950, e.g., during manufacturing and assembling). As long as the assembly 1100 remains within the delivery sheath 950, the anchor 100 will remain in this compact configuration. In this embodiment, there is no other structure retaining the wire network 102 itself in a compact configuration. (Which is not the case in all embodiments, as will be described in further detail hereinbelow.) Thus, as the anchor 100 is caused to exit the delivery sheath 950 (through the distal end 952 thereof), at the delivery site (which, in this embodiment, is the implantation site 908) the wire network 102 will expand owing to its bias. The first connector positioning wires 106 will remain in their secured position, however, as the first connectors 126 remain releasably connected to the first interconnector 614 of the device 600. Thus, when the anchor 100 has fully exited the delivery sheath 950, it will be in its expanded-secured-configuration, anchoring the assembly 1100 at the implantation site 908.

Assembly First Embodiment—Implantation

Referring to FIGS. 16-19, the delivery and anchoring process of the assembly 1200 is shown via models, albeit with different embodiments of the present technology. For purposes of illustration of this process the differences between assembly 1100 described hereinabove and assembly 1200 shown in FIGS. 16-19 (and described hereinbelow) are not relevant. Thus, the process with respect to assembly 1200 is described immediately below and it is to be understood that the description applies to process 1100.

As shown in the Figs., the delivery sheath 950 is modeled using a dark plastic tubing 960 (hereinafter the "delivery sheath model"). The delivery sheath model 960 has a distal end 962. The mammalian body conduit 900 is modeled using clear plastic tubing 910 (hereinafter the "conduit model"). The conduit model 910 has a lumen 914, with lumen walls 912.

Figure 16:
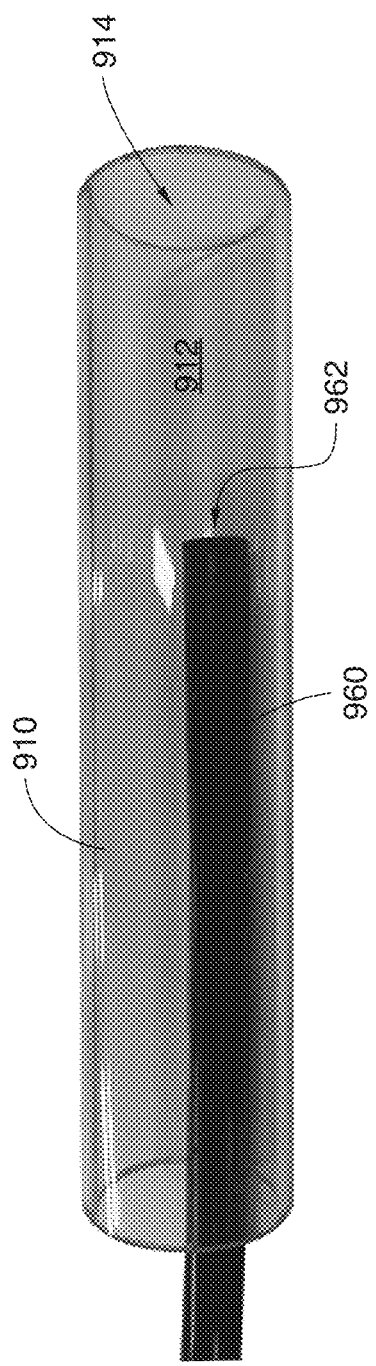
FIG. 16 shows a model of a delivery sheath and a body conduit. The assembly of FIG. 11, although not shown in FIG. 16, is within the delivery sheath model with the anchor in the compact-secured-configuration.

In FIG. 16, the assembly 1200 is completely within the delivery sheath model 960 with the lumen wall anchor 400 being in the compact-secured configuration (e.g., FIG. 15) in proximity to the distal end 962 of the delivery sheath model 960. The distal end 962 of the delivery sheath model 960 is itself located at a delivery site within the lumen 914 of the conduit 910. (In this embodiment, the delivery site is the implantation site 918; but, as is described hereinbelow, in other embodiments this is not the case.) (A description of a transcatheter technique to bring the assembly implantation to this point is described in detail in the WO '765 Publication; it is not repeated herein for the sake of brevity.)

Figure 17:
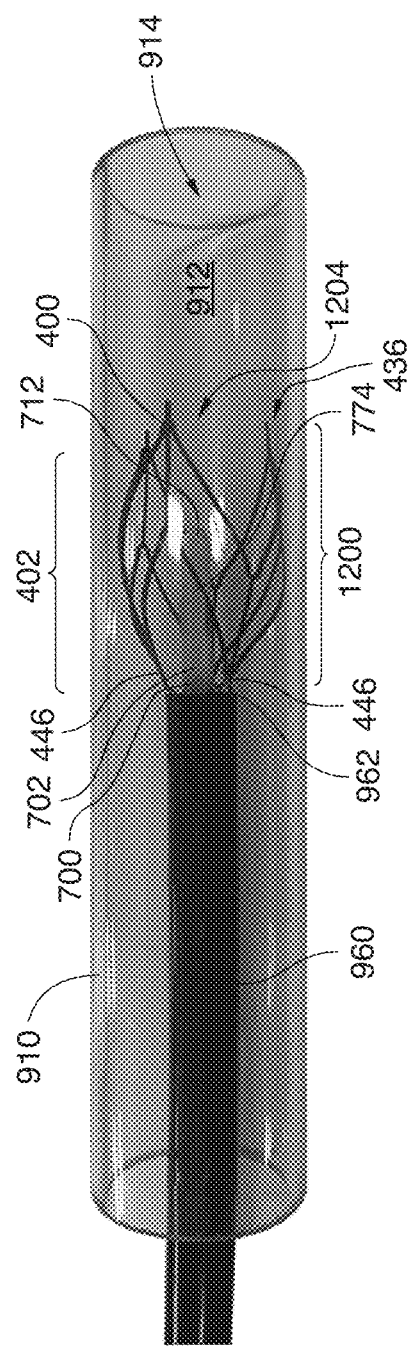
FIG. 17 shows the model of a delivery sheath and a body conduit of FIG. 16, similar to FIG. 16, with the exceptions that the distal end of the assembly (including the distal end of the anchor and the distal end of the docking unit of the device) have exited the delivery sheath model, and the wire network of the anchor has begun to expand.

In FIG. 17, the interventionist has pushed on the proximal end of the control cable (not shown in FIG. 17—See, for example, 2768 FIG. 25A, which shows the proximal end albeit in a different embodiment) of the docking unit 702 causing the assembly 1200 to start to exit the distal end 962 of the delivery sheath model 960 distal end 1204 first. Thus, first to exit delivery sheath model 960 is the distal end 436 of the anchor 400. As the anchor progressively exits the delivery sheath model 960, the delivery sheath model 960 is no longer present to overcome the bias of the anchor 400 towards its expanded configuration. Thus, the wire network 402 begins to expand as is shown in FIG. 17. Eventually the distal end 712 of the docking unit 702 will exit the delivery sheath model 960. (In this model of the process, the pumping units (e.g., 704) are not present in the device 700 for ease in understanding the change in configuration of the anchor 400. As would be understood by the skilled addressee, and as is described briefly hereinbelow and in detail in the WO '765 Publication, had the pumping units been present, they would have exited the delivery sheath model 960 first, one at a time.)

Figure 18:
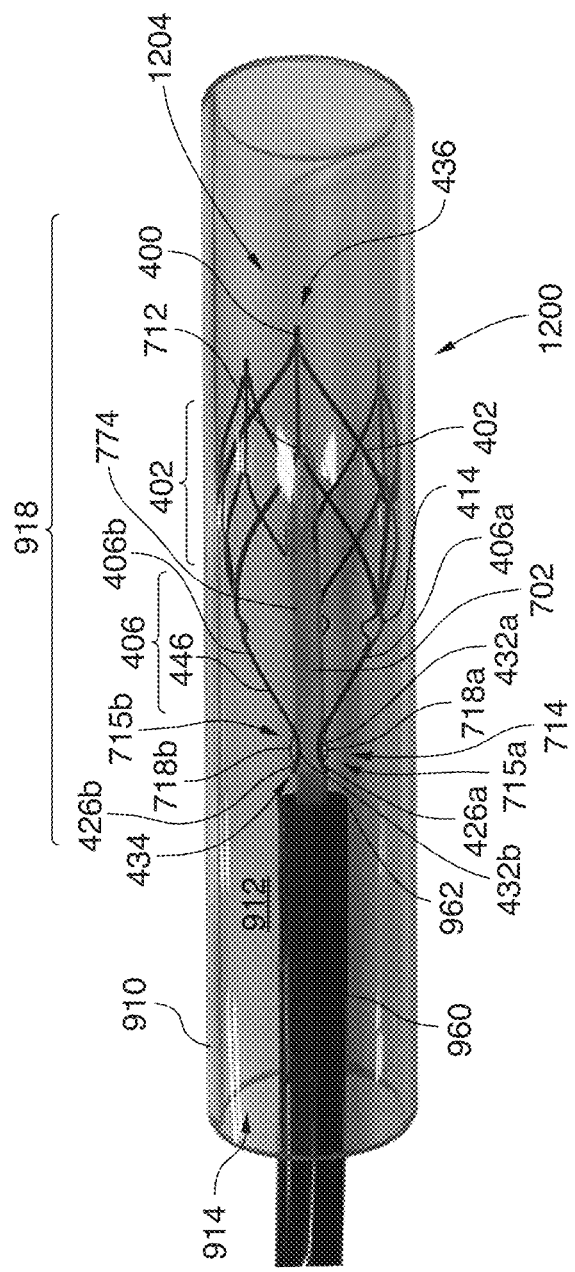
FIG. 18 shows the model of a delivery sheath and a body conduit of FIG. 16, similar to FIG. 17, with the exceptions that the anchor has entirely exited the delivery sheath model and the anchor has adopted its expanded-secured-configuration.

In FIG. 18, the assembly 1200 has almost completely exited the delivery sheath model 960. Only the proximal end 434 of the docking unit 702 of the device 700 remains within the delivery sheath model 960. At this point in time, the entirety of the anchor 400 has exited the delivery sheath model 960 freeing the anchor 400 from the restraint thereby. Under its own bias, the anchor 400 has converted from its compact-secured-configuration to its expanded-secured-configuration (shown in FIG. 18). (The anchor 400 has not converted to its expanded-released-configuration as the first connectors 426 are releasably connected to the first interconnector 714.) As can been seen in FIG. 18, in the expanded-secured-configuration, most of the wire network 402 of the anchor 400 abuts up against the wall 912 of the lumen of the body conduit model 910. As a result of this abutment, the lumen wall anchor 400 exerts a force conduit lumen wall 912 sufficient to anchor the assembly in place at the implantation site 918. (Further, in this embodiment, disposed on the first nodes 422 of the wire network 402 of the anchor 400 are anchor cleats 424, which assisting in preventing movement of the anchor 400 within the conduit 900 when anchored. Similarly, anchor cleats 124 are disposed on the first nodes 122 of the wire network 102 of anchor 100 for a similar purpose; as are anchor cleats 224 of anchor 200 and anchor cleats 324 of anchor 300.)

Figure 19:
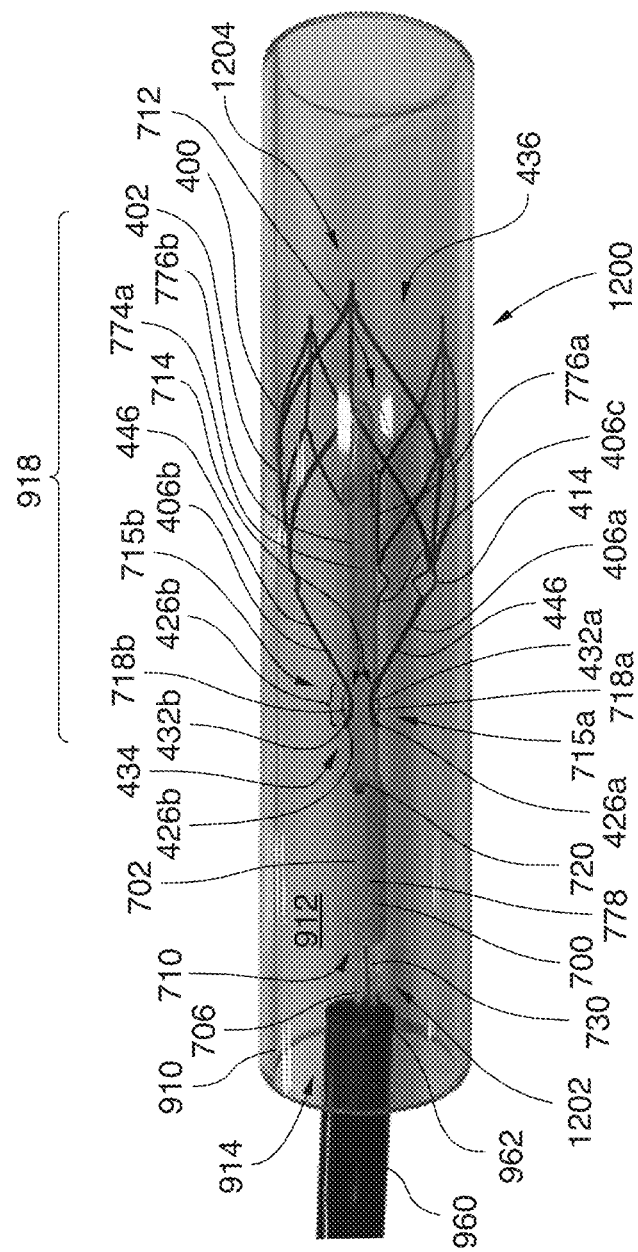
FIG. 19 shows the model of a delivery sheath and a body conduit of FIG. 16, similar to FIG. 18, with the exception that the entire assembly has exited the delivery sheath model.

In FIG. 19, the interventionist beings to the withdraw the delivery sheath model 960 from the body conduit 910, leaving the assembly 1200 anchored in place. (The removal of a delivery sheath (model 960) is conventional and is within the understanding of a skilled addressee. Further description thereof may be found in the WO '765 Publication as well. It is not repeated herein for the sake of brevity.) In FIG. 19, the cable housing 706 is clear, allowing a wire 730 for actuating (e.g., releasing) the first connector 714 to be seen. (The operation of the wire 730 is described in further detail hereinbelow.)

As was stated hereinabove, as a reminder, the differences between assembly 1100 and assembly 1200 shown in FIGS. 16-19 are not relevant to the foregoing implantation process description. Thus, the implantation process described above with respect to assembly 1200 is to be understood as an applicable description of the implantation process with respect to assembly 1100.

Returning now to the embodiment shown in FIGS. 10, 15, 35, et al., once the assembly 1100 is anchored at the implantation site 908, the device 600 may be assembled and operated. As was described hereinabove, in this embodiment the device is a fluid pump as described in the WO '765 Publication. Thus, in this particular embodiment, the device 600 is in an unassembled delivery configuration (not shown in the figures), with each of the three pumping units 604 being linearly disposed within the delivery sheath 950 distal end first, distal to the docking unit 602. Once the delivery sheath 950 is within the conduit system of the body with its distal end 952 being at the delivery site 908 within a particular conduit 900, the interventionist causes the pumping units 604 to exit the distal end 952 of the delivery sheath 950 one at a time, followed by the docking unit 602 (having the anchor 100 releasably connected thereto). As was described hereinabove, as the as the docking unit 602 exits the delivery sheath 950, the anchor 100 will convert from the compact-secured-configuration to the expanded-secured-configuration anchoring the docking unit 602 to the conduit lumen wall 902. Once the docking unit 602 has fully exited the delivery sheath 950 and is fully anchored at the implantation site 908, the interventionist can assembly the assemble the device 600 into an assembled operating configuration, by manipulating the control wires thereof (not shown) causing the pumping units 604 to be received at the receiving surfaces 674 of the docking unit. (This process is described in detail in the WO '765 Publication and is not repeated herein for the sake of brevity.) In FIG. 10, the device 600 is in its assembled configuration and is ready to be operated. The operation of the device 600 is described in detail in the WO '765 Publication and is not repeated herein for the sake of brevity.

The assembly 1100 (including both the device 600 and the anchor 100) may remain implanted within the body conduit 910 for as long as is appropriate (which may depend on many factors, including, inter alia, the type, function, purpose and/or design of the device, the location of the implantation site, the duration of the device's implantation, the prognosis of the patient, etc. This is list is not intended to be limiting.) During this time, as was described hereinabove, there may be tissue overgrowth (not shown) over, in particular, the portions of wire network 102 of the anchor 100 abutting the wall 902 of the lumen 904 of conduit 900.

Assembly First Embodiment—Explantation

At some point after its implantation, the assembly 1100 may be explanted from the conduit 900 of the mammalian body. In this embodiment, the assembly 1100 has been designed and constructed to allow for either (1) the explant of the entire assembly 1100 (i.e., both the device 600 and the anchor 100) from the conduit 900 of the body, or (2) the explant of only the device 600 from the conduit 900 leaving the anchor 100 remaining in the conduit 900 at the implantation site 908. Different methods of explantation exist for each of the aforementioned options.

Referring again to FIGS. 16-19, and the description of the process with respect to assembly 1200, if the entire assembly 1200 is to be explanted (i.e., removed from the conduit 900 of the body), the explantation process is essentially the reverse of the implantation process described hereinabove with respect to those figures, substituting a retrieval sheath for the delivery sheath 950 (modeled in FIGS. 16-19 using delivery sheath model 960). Specifically referring to FIG. 19, once the device 600 is no longer in operation, the explantation process starts by railing the retrieval sheath (model 960) along the cable housing 706 of the docking unit 702 up to the implantation site 918. (The "railing" process is conventional and is within the understanding of a skilled addressee, and is thus not described herein for the sake of brevity.) The device 700 is then converted to its unassembled delivery (now retrieval) configuration by undocking each of the pumping units 704 from the receiving surfaces 774 of the docking unit 702, and positioning the pumping units 704 in line one after another (distal end of one facing the proximal end of the next) within the conduit 910. (This process is described in detail in the WO '765 Publication and is not repeated herein for the sake of brevity.)

Next, referring sequentially to FIGS. 18, 17 and 16 in that order, the assembly 1100 is caused to enter the retrieval sheath (model 960) proximal end 1102 first, beginning with the proximal end 710 of the device 700. As the entry of the assembly 1100 into the retrieval sheath (model 960) progresses, eventually the proximal end 434 of the anchor 400 will enter into the retrieval sheath (model 960). This occurs as the first connectors 426 remain connected to the first interconnector 415 and thus the first connector positioning wires 406 each form a proximally facing slopped surface 446. These proximally facing slopped surfaces 446 act to appropriately position the distal end 962 of the retrieval sheath (model 960) with respect to the proximal end 710 of the anchor 700 to facilitate the entry of the anchor 700 in the retrieval sheath (model 960) (best illustrated in FIG. 17). The proximally facing slopped surfaces 446 also act to facilitate the change in configuration of the anchor 400 from the expanded-secured-configuration to the compact-secured configuration as the distal end 962 of the retrieval sheath (model 960) progressively contacts points of the surfaces 446 further from the proximal end 434 of the anchor 400 as the anchor 400 progressively enters the retrieval sheath (model 960) thus exerting a force progressively at the various contact points, overcoming the bias of the anchor 400 towards its expanded configuration (including the bias of the first connector positioning wires towards their released position). Once the assembly 1200 has completely entered the retrieval sheath (model 960), the anchor 400 will be in its compact-secured-configuration (see FIG. 15). The retrieval sheath (model 960) is then removed from the body conduit 910 as with any transcatheter procedure. (The removal of a retrieval sheath (model 960) is conventional and is within the understanding of a skilled addressee; it is not described herein for the sake of brevity.)

As was stated hereinabove, as a reminder, the differences between assembly 1100 and assembly 1200 shown in FIGS. 16-19 are not relevant to the foregoing explantation process description. Thus, the explantation process described above with respect to assembly 1200 is to be understood as an applicable description of the explantation process with respect to assembly 1100.

Figure 22:
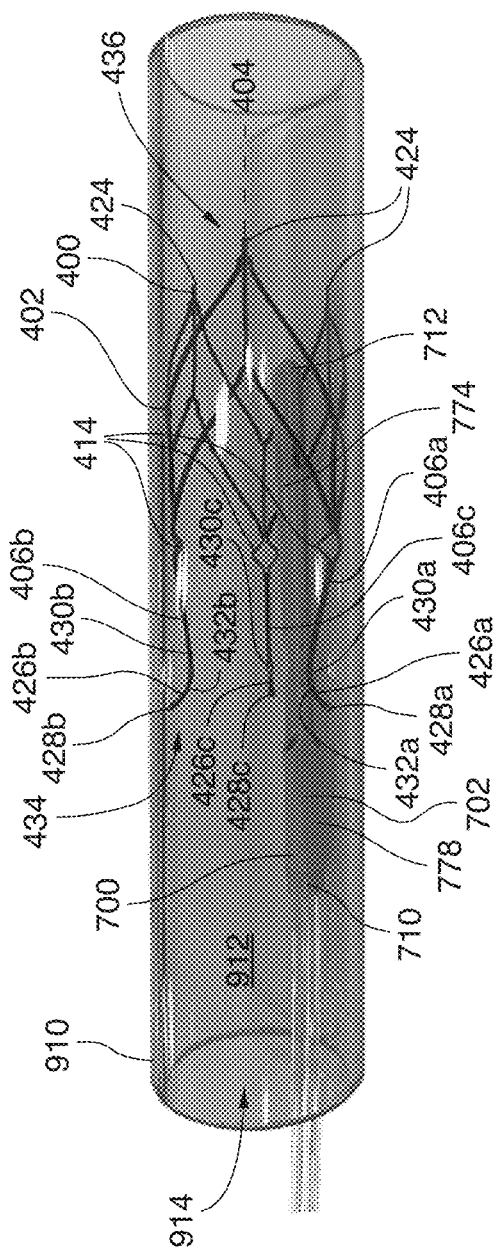
FIG. 22 shows the model of a delivery sheath and a body conduit of FIG. 16, similar to FIG. 19, with the exceptions that the first connectors of the anchor have been released from the first-sub-interconnectors of the first connector of the device and the lumen wall anchor is in the expanded-released-configuration.
Figure 23:
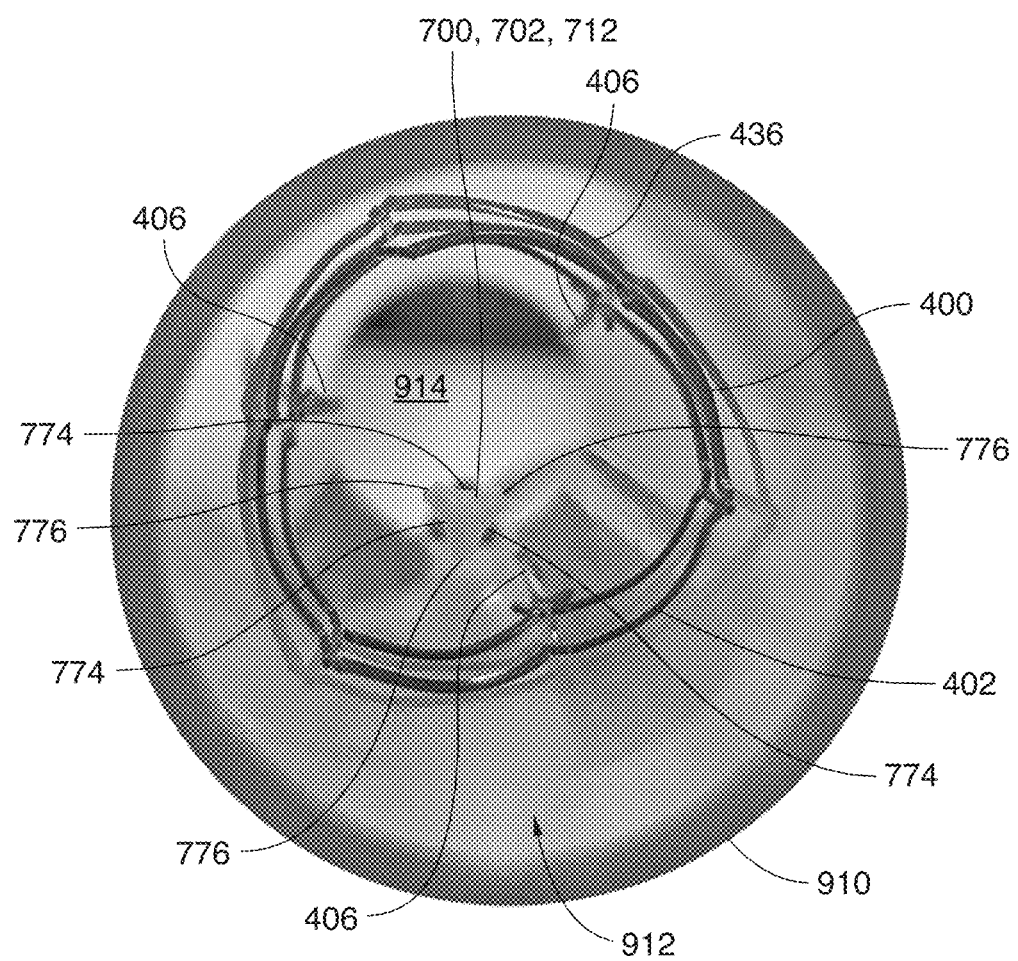
FIG. 23 shows the model of a delivery sheath and body conduit of FIG. 22 from the distal end of the anchor.
Figure 24:
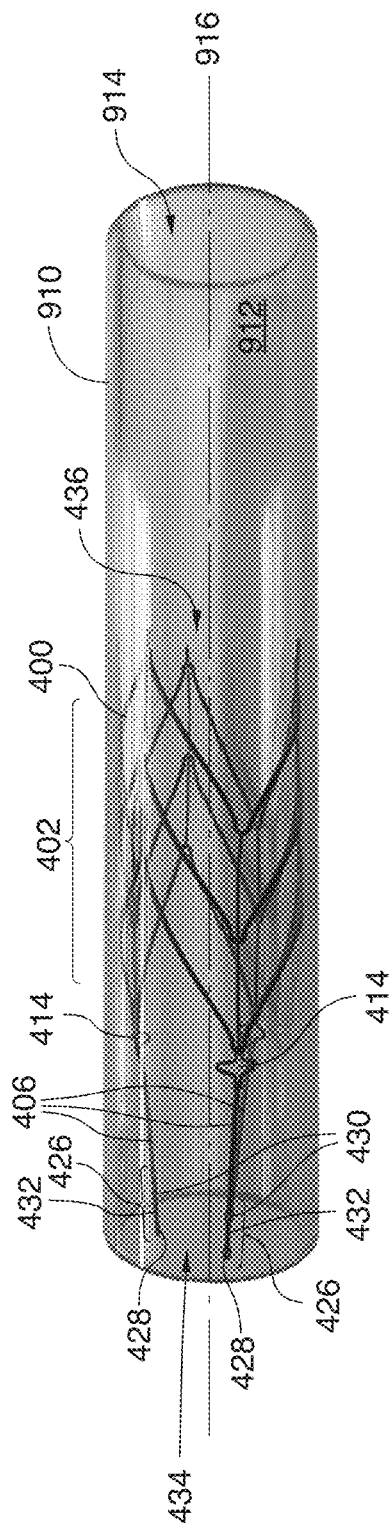
FIG. 24 shows the model of a delivery sheath and body conduit of FIG. 22, with the exceptions that the device has been explanted and the delivery sheath model has been removed. The anchor remains in the expanded-released-condition at the implantation site.

Referring now to FIGS. 19, 22, and 23, if the only the device 600 is to be explanted, and the anchor 100 is to remain at the implantation site 908, the explantation process differs. Again, a retrieval sheath (model 960) is used. Particularly referring to FIG. 19, once the device 700 is no longer in operation, the explantation process starts by railing the retrieval sheath (model 960) along the cable housing 706 of the docking unit 702 up to the implantation site 918 (FIG. 19). The device 700 is then converted to its unassembled delivery (now retrieval) configuration by undocking each of the pumping units 704 from the receiving surfaces 774 of the docking unit 702, and positioning the pumping units 704 in line one after another (distal end of one facing the proximal end of the next) within the conduit 910. (Again, this process is described in detail in the WO '765 Publication and is not repeated herein for the sake of brevity.) Next the first interconnector 714 is actuated by the interventionist to release each of the first connectors 426 from their connection to the first interconnector 714 (in this embodiment, to one of the sub-first-interconnectors 715). (The exact interconnector structure and release actuation is described hereinbelow for some embodiments.) As each first connector 426 is released, the bias of the first connector positioning wire 406 on which that first connector 426 is disposed is no longer overcome. Thus, that first connector positioning wire 406 moves from its secured position (FIG. 19) to its released position (FIG. 22), and the lumen wall anchor 400 (which was previously in its expanded-secured-configuration (FIG. 19)) adopts its expanded-released-configuration (FIG. 22). Further, as the first connectors 426 are no longer connected to the first interconnector 714, the device 700 is no longer connected to the anchor 400, and is ready for retrieval (FIGS. 22-23). The device 700 (in this embodiment in its dissembled configuration) is then caused to enter the retrieval sheath (model 960) (in this embodiment, first the docking unit 702 enters the retrieval sheath, followed sequentially by each of the pumping units (not shown in FIG. 19, 22, or 23)). Once the device 700 has completely entered the retrieval sheath (model 960), the retrieval sheath (model 960) is then removed from the body conduit 910 as is conventional with such a transcatheter procedure. As shown in FIG. 24, the anchor 400, in its expanded-released-configuration remains within the lumen 914 of the body conduit (model 910) with the anchor's wire network 402 abutting the wall 912 of the lumen 914 continuing to anchor the anchor 400 in place. As is shown in FIGS. 23 and 24, the first connector positioning wires 406 of the anchor 400 are in their released position, proximate to the wall 912 of the lumen, generally aligned with the periphery of the wire network 402, and generally parallel to the central longitudinal axis of the anchor 400 and the central longitudinal axis 916 of the lumen 914 (locally, at the implantation site). In embodiments such is this one, where the anchor 400 is made of a non-resorbable material (e.g., nitinol) the anchor will remain anchored at the implantation site 918 indefinitely (although it may be covered by tissue overgrowth). In embodiments where the anchor is made of a resorbable material, the anchor will eventually be resorbed by the mammalian body.

Assembly First Embodiment—Device First Embodiment—First Interconnector

Returning now to the embodiment shown in FIGS. 10, 15, 35, et al., the device 600 has a first interconnector 614 structured to releasably connect the device 600 with the anchor 100 to maintain the device 600 in place within a mammalian body conduit 900 at an implantation site 908. The first interconnector 614 is located at the distal end 612 of the docking unit 602 of the device 600 in this embodiment. The first interconnector 614 includes an end cap 616 that comprises the tip of the distal end 602. The end cap 616 is moveable along the central longitudinal axis 608 of the docking unit 602 between a secured configuration (shown in FIGS. 10, 15, 32) and a released configuration (shown in FIGS. 33, 34, 35) with respect to the body 680 of the docking unit 602. When the end cap 616 is in the secured configuration, it registers with the body 680 of the docking unit 602. When the end cap 616 is in the released configuration, it is longitudinally spaced part from (e.g., is more distal than) the body 380 of the docking unit 602. Disposed within the body 680 of the docking unit 602, along the central longitudinal axis 608 thereof is a channel 632 (FIG. 34). Longitudinally moveably disposed within the channel 632 is a rod 640 used to actuate the end cap 616. The end cap 616 is mounted at the distal end of the actuation rod 640. Attached to the proximal end of the rod 640 is the distal end of an actuation cable (not shown) that extends within the cable housing 606. The proximal end of the cable is manipulable by the interventionist to longitudinally move the rod 640 within the channel 632, and to thereby move the end cap 616 between its secured configuration and its released configuration.

Referring to FIG. 34, disposed at the longitudinal distal end 682 of the body 680 of docking unit 602, the within the raised portions 676 in between the receiving surfaces 674 of the exterior surface 678 of the docking unit 602 are sub-first-interconnectors 615. In this embodiment there are three sub-first-interconnectors 615, each being disposed within a different one of the raised portions 676 of the docking unit 602. In this embodiment, each sub-first-interconnector 615 is a hook that is sized, shaped, positioned, oriented and arranged to be looped by a loop 132 of a first connector 126 (the first connector 126 is described in detail hereinbelow). (The sub-first-interconnector hooks 615 and the loops 132 of the first connectors 126 are shown schematically in the figures.) As can be seen in FIGS. 10 and 32, when the sub-first-interconnectors hooks 615 are looped by the loops 132 of the first connector 126, and the end cap 616 of the docking unit 602 is in the secured configuration, the hooks 615 cannot become unlooped by the loops 132, as there is no space for them to do so. (For ease of understanding, one of the pumping units 604 is not shown in FIG. 10, and none pumping units 604 are shown in FIG. 32.) Thus, the first connectors 126 are connected to the first interconnector 614, connecting the anchor 100 to the device 600; this connection is releasable, but not without manual intervention by an interventionist.

It was described hereinabove, that during an explantation of the device 600 alone leaving the anchor 100 to remain within the lumen 904 of the conduit 900, each of the first connectors 126 are released from their connection to the first interconnector 614. In this embodiment, this occurs in the following manner: The interventionist pushes the control cable that is attached to the proximal end of the actuating rod 604 (or causes to be it to be pushed). This pushing movement causes the rod 604 to move longitudinally distally within the channel 632 of the docking unit. This movement of the rod 604 moves the end cap 616 from its registered position (secured configuration)(FIG. 32) with respect to the body 680 of the docking unit 602 to its spaced-apart position (released configuration) (FIG. 34). This creates space in between the distal end 682 of the body 680 of the docking unit 682 and the end cap 616 (FIGS. 33 and 34) and exposes the sub-first-interconnector 615 hooks of the first connector 614. This, combined with the bias of the first connector positioning wires 106 towards their released positioning, allows the loops 132 to be become free of (e.g., unlooped by) the hooks 615, allowing the first connector positioning wires 106 to move to their released position (FIG. 35). Thus, the anchor 100 adopts its expanded-released-configuration (FIG. 35), allowing for retrieval of the device 600 as was described hereinabove.

Assembly First Embodiment—Anchor First Embodiment—First Connectors

As was stated above, in this embodiment, each first connector 126 includes a loop 132 (shown schematically in the figures) that is formed at the joined ends of two adjacent first connector positioning wires (e.g., 106a and 106g, 106b and 106c, 106d and 106e). There are thus three first connectors 126 and three first loops 132 in total in this embodiment. The first connector positioning wires 106, the first connectors 126, and the loops 132 are all cooperatively shaped, sized, arranged, positioned and oriented such that: When the first connectors positioning wires 106 are in their secured position, the loops 132 are capable of looping the sub-first-interconnector hooks 615 of the first interconnector 614 (FIG. 34). And, when the loops 132 are looping the sub-first-interconnector hooks 615, and the end cap 616 of the docking unit 602 is in its secured configuration, the loops 132 are prevented from becoming unlooped from the sub-first-interconnector hooks 615, retaining the connection between the device 600 and the anchor 100 (until the end cap 616 is moved to its released configuration).

Assembly Second Embodiment—Introduction

Figure 36:
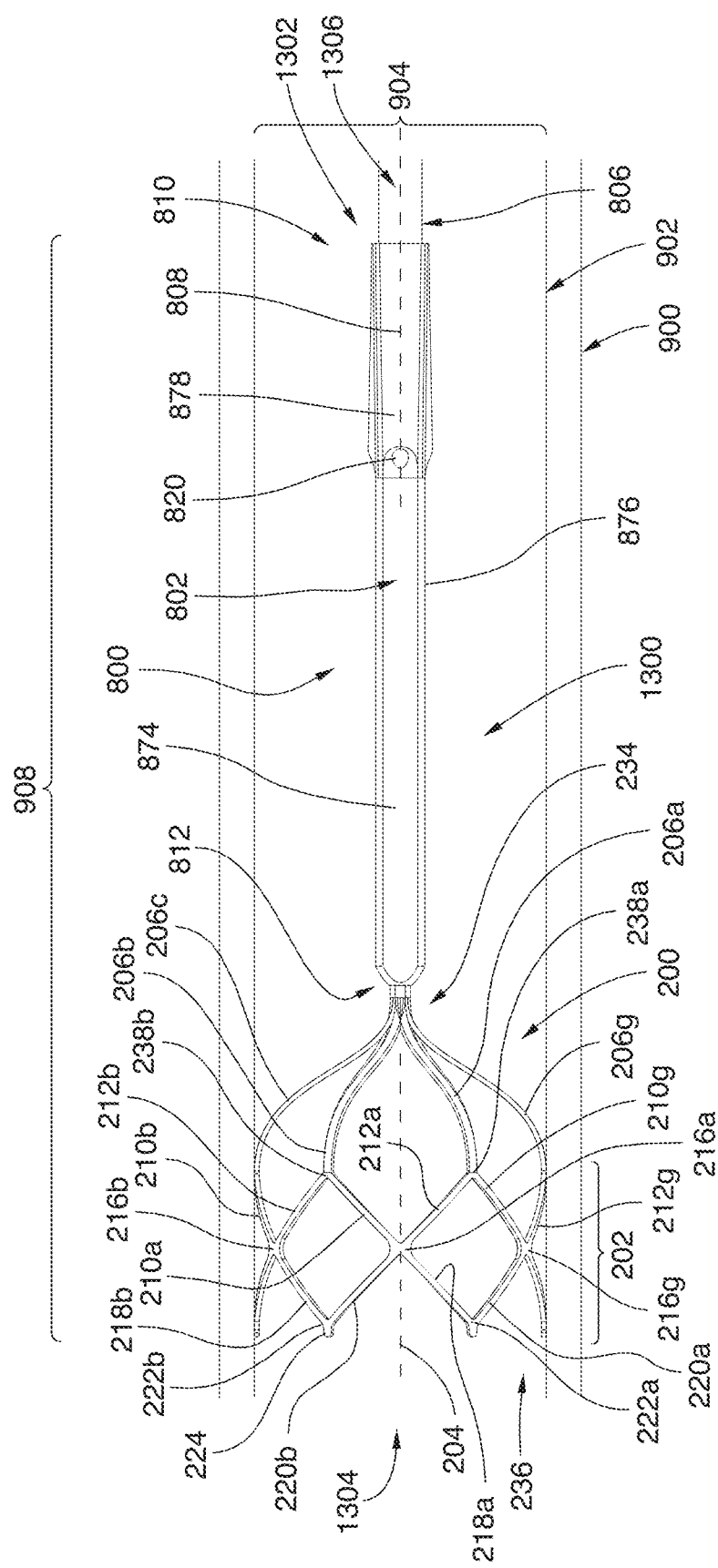
FIG. 36 shows a side view of an intraluminal device and anchor assembly being a second embodiment of the present technology being anchored within the lumen of a body conduit. The assembly includes a second embodiment of a device of the present technology and a second embodiment of an anchor of the present technology. The device is shown with none of its three pumping units having been received in the receiving surfaces of the docking unit. The anchor is shown in its expanded-secured-configuration.

Referring to FIG. 36 to 39, there is shown a mammalian body conduit intralumenal device and lumen wall anchor assembly 1300 being a second embodiment of an assembly of the present technology (FIG. 36). The assembly 1300 has a proximal end 1302 and a distal end 1304 defined consistently with the orientation in which the assembly 1300 is implanted. The assembly 1300 has a central longitudinal axis 1306. The assembly 1306 includes a mammalian body conduit intralumenal device 800 and a lumen wall anchor 200, each of which will be discussed in turn hereinbelow.

Assembly Second Embodiment—Device Second Embodiment

The mammalian body conduit intralumenal device 800 is a second embodiment of a device of the present technology. In this embodiment, the device 800 is also a modular fluid pump as described in the WO '765 Publication. Thus, the device 800 has a docking unit 802 and three pumping units 874 (none of which are shown in FIG. 36, for ease of understanding). The device 800 has a proximal end 810 and a distal end 812. The proximal end 810 and the distal end 812 are defined consistently with the orientation in which the device 800 is implanted. Thus, the proximal end 810 and distal end 812 of the device 800 are defined consistently with the proximal end 1302 and distal end 1304 of the assembly 1300, respectively. The device 800 has a central longitudinal axis 808 which, in this embodiment, is colinear with the central longitudinal axis 1306 of the assembly 1300. A cable housing 806 extends proximally from the proximal end 810 of the device 800. Within the cable housing 806 are the various control wires and electrical wires (not shown) of the pumping units 804 and the docking unit 802 (e.g., the first interconnector actuation wire 830) of the device 800. (The WO '765 Publication provides a detailed description of some of such control wires and electrical wires; that description is not repeated herein for the sake of brevity.)

In this embodiment, the docking unit 802 of the device 800 has three receiving surfaces 874 (FIG. 36), each of which receives therein one of the three pumping units of the device 800. (In this embodiment, the device 800 has three pumping units 804 in total. At the proximal end of each receiving surface 874 is an opening 820 through which control wires, etc. of a pumping unit 804 can pass through the docking unit 802 into the cable housing 806.) In between each of the receiving surfaces 874 of the docking unit 802 is a raised portion 876 of the exterior surface 878 of the docking unit 802. A first interconnector 814 having three sub-first-interconnectors 815 (FIG. 37) located within the docking unit 802 and accessible via the distal end 812 thereof (FIG. 37), is present in the device 800. As will be described hereinbelow, the first interconnector 814 with its sub-first-interconnectors 815 connects the lumen wall anchor 200 to the device 800.

Assembly Second Embodiment—Anchor Second Embodiment—General Structure

Still referring to FIG. 36, the lumen wall anchor 200 is second embodiment of an anchor of the present technology. In this embodiment, the anchor 200 has a 3D-shaped wire network 202, which itself has a central longitudinal axis 204.

In this embodiment, the central longitudinal axis 204 of the wire network 202 is colinear with the central longitudinal axis 1306 of the assembly 1300 and with the central longitudinal axis 808 of the device 800. In other embodiments this need not be the case.

Figure 39:
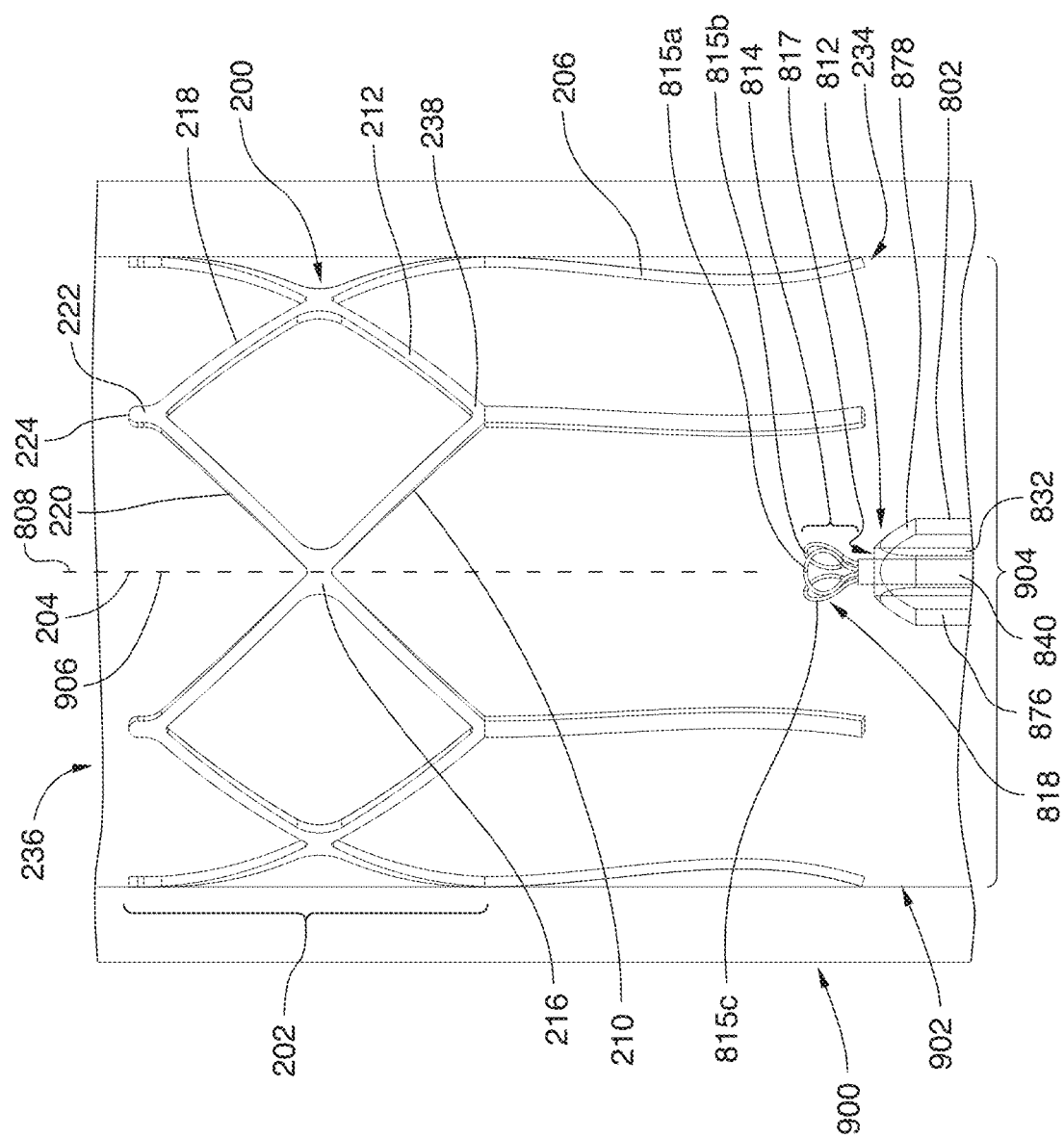
FIG. 39 shows a close-up view of the assembly of FIG. 36, similar to FIG. 37, with the exception that the anchor is shown in the expanded-released-configuration.

Referring now to FIG. 39, the various structures of the anchor 200 are shown. In this embodiment, the wire network 202 of the anchor 200 has various structural members (210, 212, 218, 220) that are joined together at various nodes (216, 222, 238). In this embodiment there are six first nodes 222; with each first node 222 being located at the distal end 236 of the anchor 200. (The anchor 200 has a distal end 236 and a proximal end 234, that are defined consistently with the implantation orientation of the anchor 200, and thus consistently with the distal end 1304 and proximal end 1202 of the assembly.)

Extending from each first node 222 (e.g., 222*a*) is a first structural member 218 (e.g., 218*a*) and a second structural member 220 (e.g., 220*a*). The first structural member 218 and the second structural member 220 of each first node 222 are defined orientationally consistently for each first node 222. The first structural member 218 (e.g., 218*a*) of each first node 222 (e.g., 222*a*) extends proximally to a one of the second nodes 216 (e.g., 216*a*) tangentially in between that first node 222*a* and a tangentially adjacent first node 222 (e.g., 222*b*). The second structural member 220 (e.g., 220*b*) of that adjacent first node 222*b* extends proximally to that one of the second nodes 216*a* as well. In this embodiment, this configuration is consistent for each of the first nodes 222, the second nodes 216, the first structural members 218, and the second structural members 220. In this embodiment there are six first nodes 222 and six second nodes 216.

Extending from each second node 216 (e.g., 216*a*) is a third structural member 210 (e.g., 210*a*) and a fourth structural member 212 (e.g., 212*a*). The third structural member 210 and the fourth structural member 212 of each second node 216 are defined orientationally consistently for each second node 216. The fourth structural member 212 (e.g., 212*a*) of each second node 216 (e.g., 216*a*) extends proximally to a one of the third nodes 238 (e.g., 238*a*) tangentially in between that second node 216*a* and a tangentially adjacent second node 216 (e.g., 216*g*). The first structural member 210 (e.g., 210*g*) of that adjacent second node 216*g* extends proximally to that one of the third nodes 238*a* as well. In this embodiment, this configuration is consistent for each of the second nodes 216, the third nodes 238, the third structural members 210, and the fourth structural members 212. In this embodiment there are six third nodes 238, with each one of the third nodes 238 (e.g., 238*a*) being axially aligned with a one of the first nodes 222 (e.g., 222*a*).

Extending proximally from each of the third nodes 238 are first connector positioning wires 206, one first connector positioning wire 206 (e.g., 206*a*) per third node 238 (e.g., 238*a*). The ends of two adjacent first connector positioning wires 206 (e.g., 206*a* and 206*g*, 206*b* and 206*c*, and 206*d* and 206*e*) are joined together (in this embodiment via a hook element 240, e.g., 240*a*) on which is located a first connector 226 (i.e., 226*a*; which, in this embodiment, includes hook 232, e.g., 232*a*, FIG. 37). There are thus three first connectors 226 (e.g., 226*a*, 226*b*, 226*c*) in total in this embodiment. As will be described in further detail hereinbelow, each first connector 226 (e.g., 226*a*) is structured to be connectable to one of the sub-first-interconnectors 815 (e.g., 815*a*, via loops 818, FIG. 37) of first interconnector 814 of the device 800.

Figure 37:
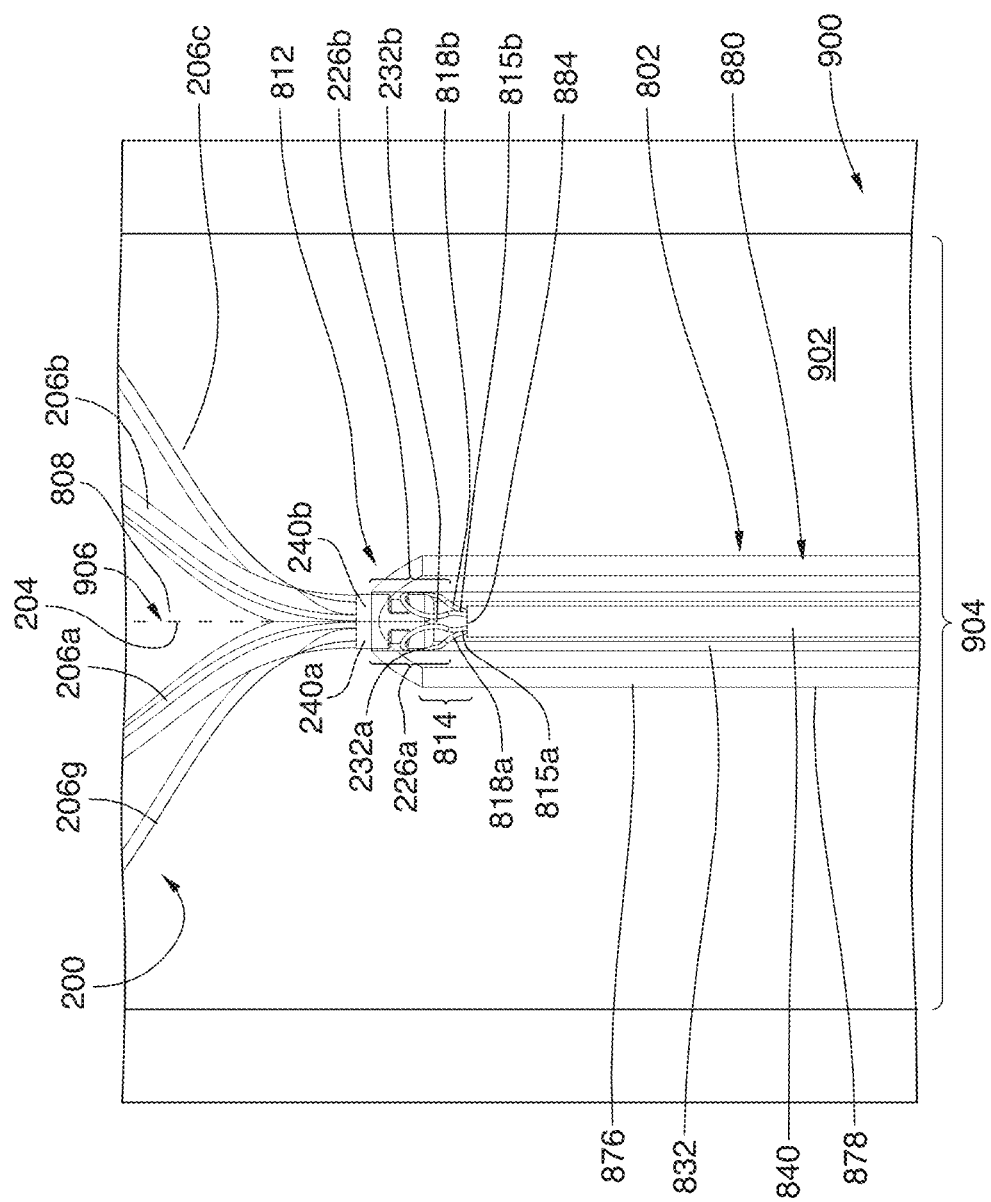
FIG. 37 shows a close-up view of the assembly of FIG. 36 within a body conduit, focusing on the distal end of the docking unit of the device and the proximal end of the anchor. The pumping units of the device are not shown. The central longitudinal portion of the docking unit of the device is shown with transparency. The end cap of the device is shown in its secured configuration. The anchor is shown in the expanded-secured-configuration.

Each of the first connector positioning wires 206 is moveable between a secured position (that which is shown in FIG. 37) and a released position (that which is shown in FIG. 39). In the secured position the first connector positioning wires 206 (e.g., 206a) are positioned in proximity to the central longitudinal axis 204 of the anchor 200), such that a first connector 226 (e.g., 226a) that is disposed on a first connector position wire 206 (e.g., 206a) is positioned with respect to a one of the sub-first-interconnectors 815 (e.g., 815a, loops 818, e.g., 818a) to be releasably connectable thereto. In the released position, the first connector positioning wires 206 are away from the central longitudinal axis 204 of the anchor 200. The first connector wires 206 are overcomably biased towards the released position. The first connector wires 206 e.g., 206a) can be maintained in the secured position by releasable connection of the first connectors 226 (e.g., 226a) to the sub-first-interconnectors 815 (e.g., 815, via loops 818, e.g., 818a) of the first connector 814.

Assembly Second Embodiment—Anchor Second Embodiment—Configurations

The lumen wall anchor 200 has a compact-secured-configuration, an expanded-secured-configuration, and an expanded-released configuration.

Similar to the first embodiment previously described hereinabove (shown in FIG. 15), when the lumen wall anchor 200 is in a compact-secured configuration, the lumen wall anchor 200 is shaped and dimensioned to be deliverable to a delivery site within a lumen 904 of a body conduit 900 via a catheter (e.g., delivery sheath 950 in FIG. 15). Thus, when the lumen wall anchor 200 is in the compact-secured-configuration, the first connector positioning wires 206 are in their secured position (in the embodiment shown in FIG. 15 they are shown as being releasably connected to first interconnector 614). Further, the wire network 202 is in a compact form within the delivery sheath 950. See, for example, the WO '765 Publication for a detailed description of a transcatheter implantation technique.) When the lumen wall anchor 200 is in the compact-secured-configuration, it has a diameter of 22 French.

Referring to FIG. 36, when the lumen wall anchor 200 is in an expanded-secured-configuration, the wire network 202 is dimensioned and shaped to exert a force on the wall 902 of the lumen 904 of the conduit 900. This force is sufficient to anchor the assembly 1300 in place at the implantation site 908 (including during operation of the device 800). Further, as can be seen in FIG. 36, when the anchor 200 is in the expanded-secured-configuration, the first connector positioning wires 206 are in their secured position (and are shown in FIG. 36 with the first connectors 226 disposed thereon being releasably connected to first interconnector 814). When the lumen wall anchor 200 is in the expanded-secured-configuration, it has a diameter of about 24 mm and a length of about 6 cm.

Referring to FIG. 37, when the lumen wall anchor 200 is in an expanded-released-configuration, the wire network 202 is dimensioned and shaped to exert a force on the wall 902 of the lumen 904 of the conduit 900. This force is sufficient to anchor the assembly 1300 in place at the implantation site 908. Further, as can be seen in FIG. 37, when the anchor 200 is in the expanded-released-configuration, the first connector positioning wires 206 are in their released position, as the first connectors 226 disposed thereon have been released from their connection with the first interconnector 814. In the released position, the ends of the first connector positioning wires 206 are proximate the wall 902 of the lumen 904 of the conduit 900, generally in line with the longitudinal axis 906 of body conduit 900. In this configuration, the first connector positioning wires 206 do not obstruct fluid flow axially through the conduit 902 while the anchor 200 is anchored in place at the implantation site 908 with the device 800 having been retrieved and removed from the body conduit 900 (as can be best seen in FIG. 23, albeit in which another embodiment of the anchor, anchor 400, is shown). In FIG. 37 (for example), the native fluid flow axially through the conduit 900 can be either from top to bottom or from bottom to top in the figures, depending on the location of the implantation site 908 within the mammalian body and in which the orientation the assembly 1300 has been implanted. When the lumen wall anchor 200 is in the expanded-released-configuration, it has a diameter of about 24 mm and a length of about 6 cm.

The lumen wall anchor 200 is biased towards its expanded-released-configuration. In this embodiment, this bias is the case as the anchor 200 is made of nitinol (a shape-memory alloy) with the expanded-released-configuration being the "remembered shape" thereof. (The anchor 400 is manufacturable according to any conventional techniques appropriate to the material of which it is made, e.g., laser cutting.) As was described hereinabove, this bias can be overcome during normal usage of the assembly 1300. In particular, when the assembly 1300 is within the delivery sheath (not shown, but see FIG. 15 as an illustration of the principle with respect to a different embodiment, assembly 1200), the bias of the wire network 202 has been overcome (via its insertion into the delivery sheath, e.g., during manufacturing and assembling). As long as the assembly 1300 remains within the delivery sheath, the anchor 200 will remain in this compact configuration. In this embodiment, there is no other structure retaining the wire network 202 itself in a compact configuration. (Which is not the case in all embodiments, as will be described in further detail hereinbelow.) Thus, as the anchor 200 is caused to exit the delivery sheath (through the distal end thereof), at the delivery site (which, in this embodiment, is the implantation site 908) the wire network 202 will expand owing to its bias. The first connector positioning wires 206 will remain in their secured position, however, as the first connectors 226 remain releasably connected to the first interconnector 814 of the device 800. Thus, when the anchor 200 has fully exited the delivery sheath, it will be in its expanded-secured-configuration, anchoring the assembly 1300 at the implantation site 908 (FIG. 36).

Assembly Second Embodiment—Implantation & Explantation

The implantation and explantation of the assembly, and the explantation of the device only, are materially the same as was previously described hereinabove with respect to the first embodiment, assembly 1100 (including device 600). Thus, they will not be described herein again with respect to the assembly 1300 (including device 800), for the sake of brevity.

Assembly Second Embodiment—Device Second Embodiment—First Interconnector

Figure 38:
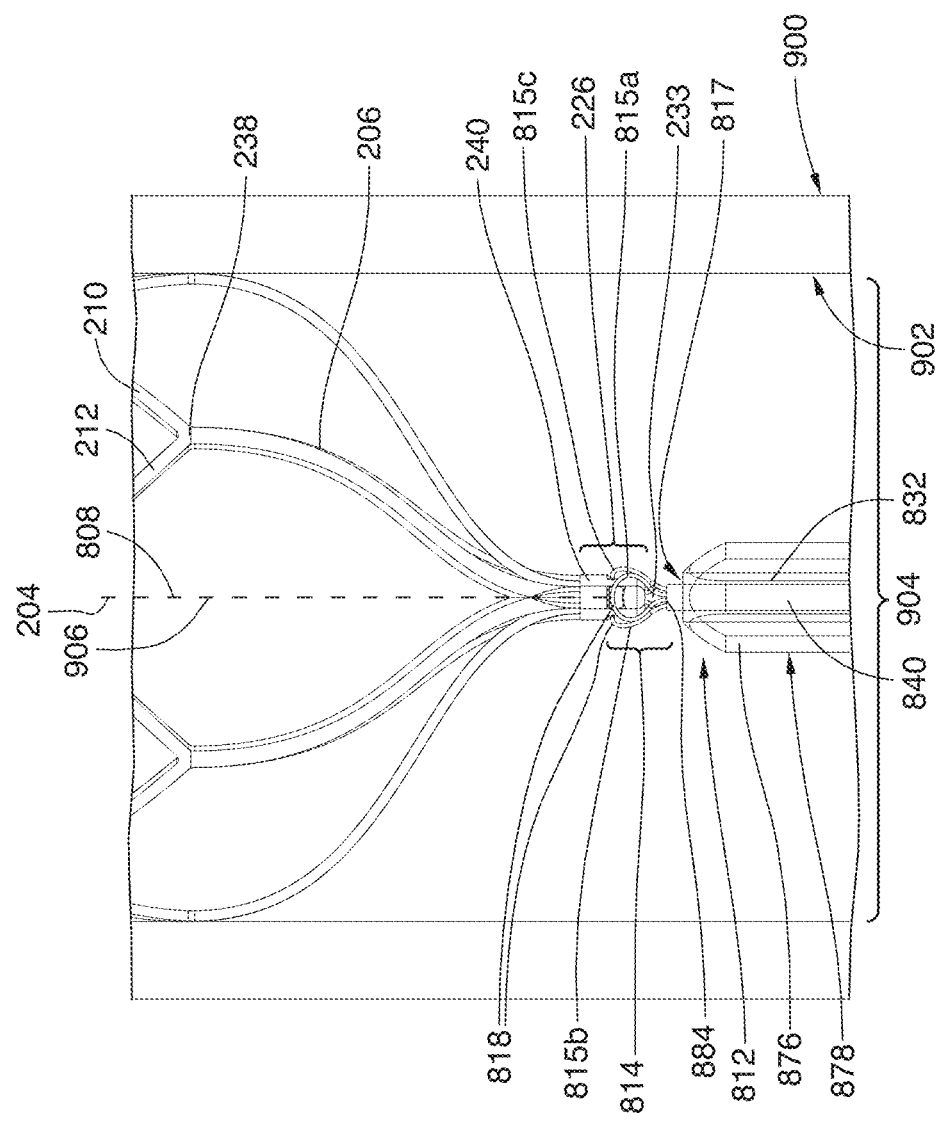
FIG. 38 shows a close-up view of the assembly of FIG. 36, similar to FIG. 37, with the exception that the end cap of the device is shown in its released configuration.

In this embodiment, the device 800 has a first interconnector 814 structured to releasably connect the device 800 with the anchor 200 to maintain the device 800 in place within a mammalian body conduit 900 at an implantation site 908. The first interconnector 814 is located at the distal end 812 of the docking unit 802 of the device 800. Disposed within the docking unit 802, along the central longitudinal axis 808 thereof is a channel 832 (FIG. 37). Longitudinally moveably disposed within the channel 832 is an actuation rod 840. Attached to the proximal end of the rod 840 is the distal end of a cable (not shown) that extends within the cable housing 806 (FIG. 36). The proximal end of the cable is manipulable by the interventionist to longitudinally move the rod 840 within the channel 832 between a secured configuration (in which the distal end 884 of the rod 840 is within the channel 832 (FIG. 37)) and a released configuration (in which the distal end 884 of the rod 840) is outside of the channel 832 (FIG. 38).

Referring to FIG. 37, disposed at the distal end 884 of the rod 840 are sub-first-interconnectors 815. In this embodiment there are three sub-first-interconnectors 815. Each sub-first-interconnector 815 has a loop 818 that is sized, shaped, positioned, oriented and arranged to be hooked by a hook 232 of a first connector 226 (the first connector 226 is described in detail hereinbelow). As can be best seen in FIG. 37, when the sub-first-interconnectors 815 (e.g., 815a) loops 818 (e.g., 818a) are hooked by the hooks 232 (e.g., 232a) of the first connector 226 (e.g., 226a) and the rod 840 is in the secured configuration, the loops 232 cannot become unhooked from the hooks 818, as there is no space for them to do so. (For ease of understanding, none of the pumping units 804 are shown in FIGS. 36 to 39.) Thus, the first connectors 226 (e.g., 226a) are connected to the first interconnector 815 (e.g., 815a), connecting the anchor 200 to the device 800. This connection is releasable, but not without manual intervention by the interventionist.

During an explantation of the device 800 alone leaving the anchor 200 to remain within the lumen 904 of the conduit 900, each of the first connectors 226 (e.g., 226a) are released from their connection to the sub-first-interconnectors 815 (e.g., 815a) of the first interconnector 814. In this embodiment, this occurs in the following manner: The interventionist pushes the control cable that is attached to the proximal end of the actuating rod 804 (or causes to be it to be pushed). This pushing movement causes the rod 804 to move longitudinally distally within the channel 832 of the docking unit, to its released configuration. This movement of the rod 804 moves the loops 818 from inside of the channel 832 (FIG. 37) to outside of the channel 832 (FIG. 38). This exposes the sub-first-interconnector 815 loops 818 of the first connector 814 and creates space around the loops 818. This, combined with the bias of the first connector positioning wires 206 towards their released positioning, allows the loops 818 to be become free of (e.g., unhooked to) the hooks 232, allowing the first connector positioning wires 206 to move to their released position (FIG. 39). Thus, the anchor 200 adopts its expanded-released-configuration (FIG. 39), allowing for retrieval of the device 800 in a manner similar to that which was described hereinabove.

Assembly Second Embodiment—Anchor Second Embodiment—First Connectors

As was stated above, in this embodiment, each first connector 226 (e.g., 226a) includes a hook 232 (e.g., 232a) that is formed at the joined ends of two adjacent first connector positioning wires 206 (e.g., 206a and 206g). There are thus three first connectors 226 and three first loops 232 in total in this embodiment. The first connector positioning wires 206, the first connectors 226, and the hooks 232 are all cooperatively shaped, sized, arranged, positioned and oriented such that: When the first connectors positioning wires 206 (e.g., 206a and 206g) are in their secured position, the hooks 232 (e.g., 232a) are capable of hooking the sub-first-interconnector 815 (e.g., 815a) hooks 818 (e.g., 818a) of the first interconnector 814 (FIG. 34). And, when the hooks 232 are hooking the sub-first-interconnector 815 loops 818, and the rod 840 is in its secured configuration, the hooks 232 are prevented from becoming unhooked from the sub-first-interconnector 814 loops 818, retaining the connection between the device 800 and the anchor 200 (until the rod 840 is moved to its released configuration, as was described in the previous paragraph).

Assembly Third Embodiment—Introduction

Figure 7:
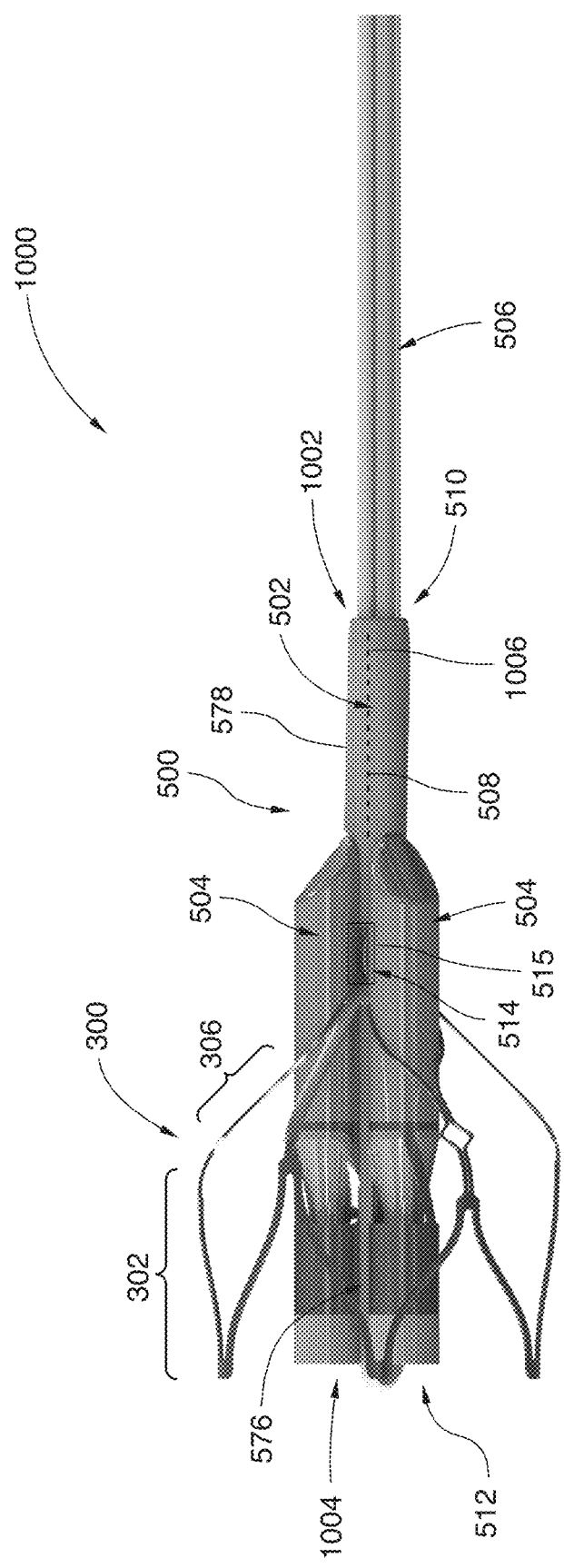
FIG. 7 shows a side view of an intraluminal device and anchor assembly being a third embodiment of the present technology. The assembly includes a third embodiment of a device of the present technology and a third embodiment of an anchor of the present technology. The device is shown with two of the three pumping units having been received in their receiving surfaces of the docking unit. The anchor is shown in its expanded-secured-configuration.

Referring to FIG. 7, there is shown a mammalian body conduit intralumenal device and lumen wall anchor assembly 1000 being a third embodiment of an assembly of the present technology. The assembly 1000 has a proximal end 1002 and a distal end 1004 defined consistently with the orientation in which the assembly 1000 is implanted. The assembly 1000 has a central longitudinal axis 1006. The assembly 1000 includes a mammalian body conduit intralumenal device 500 and a lumen wall anchor 300, each of which will be discussed in turn hereinbelow.

Assembly Third Embodiment—Device Third Embodiment

The mammalian body conduit intralumenal device 500 is a third embodiment of a device of the present technology. In this embodiment, the device 500 is also a modular fluid pump as described in the WO '765 Publication. Thus, the device 500 has a docking unit 502 and three pumping units 504 (only two of which are shown in FIG. 7). The device 500 is shown in FIG. 7 in its assembled configuration with the pumping units 504 having been received in the receiving surfaces 574 (not shown in FIG. 7) of the docking unit 500. The device 500, when in its assembled configuration, has a proximal end 510 and a distal end 512. The proximal end 510 and the distal end 512 are defined consistently with the orientation in which the device 500 is implanted. Thus, the proximal end 510 and distal end 512 of the device 500 are defined consistently with the proximal end 1002 and distal end 1004 of the assembly 1000, respectively. The device 500 has a central longitudinal axis 508 which, in this embodiment, is colinear with the central longitudinal axis 1006 of the assembly 1000. A cable housing 506 extends proximally from the proximal end 510 of the device 500. Within the cable housing 506 are the various control and electrical wires of the pumping units 504 and the docking unit 502 (e.g., the first interconnector actuation wire 530) of the device 500. (The WO '765 Publication provides a detailed description of some of such control wires and electrical wires, which is not repeated herein for the sake of brevity.)

In this embodiment, the docking unit 502 of the device 500 has three receiving surfaces 574 (not shown in FIG. 7), each of which has received therein (in FIG. 7) one of the three pumping units 504 of the device 500. (In this embodiment, the device 500 has three pumping units 504 total. At the proximal end of each receiving surface 574 is an opening 520 through which control wires, etc. of a pumping unit 504 can pass through the docking unit 502 into the cable housing 506.) In between each of the receiving surfaces 574 (FIG. 9) of the docking unit 502 is a raised portion 576 of the exterior surface 578 of the docking unit 502. A first interconnector 514 having three sub-first-interconnectors 515 (e.g., 515a, 515b, 515c, although not individually labelled in FIG. 7), one located on each of the three raised portions 576 of docking unit 506, is present in the device 500. As will be described herein below, the first interconnector 514 with its sub-first-interconnectors 515 connects the lumen wall anchor 300 to the device 500.

Assembly Third Embodiment—Anchor Third Embodiment—General Structure

Still referring to FIG. 7, the lumen wall anchor 300 is third embodiment of an anchor of the present technology. In this embodiment, the anchor 300 has a 3D-shaped wire network 302, which itself has a central longitudinal axis 304. In this embodiment, the central longitudinal axis 304 of the wire network 302 is colinear with the central longitudinal axis 1006 of the assembly 1000 and with the central longitudinal axis 508 of the device 500. In other embodiments this need not be the case.

Figure 8:
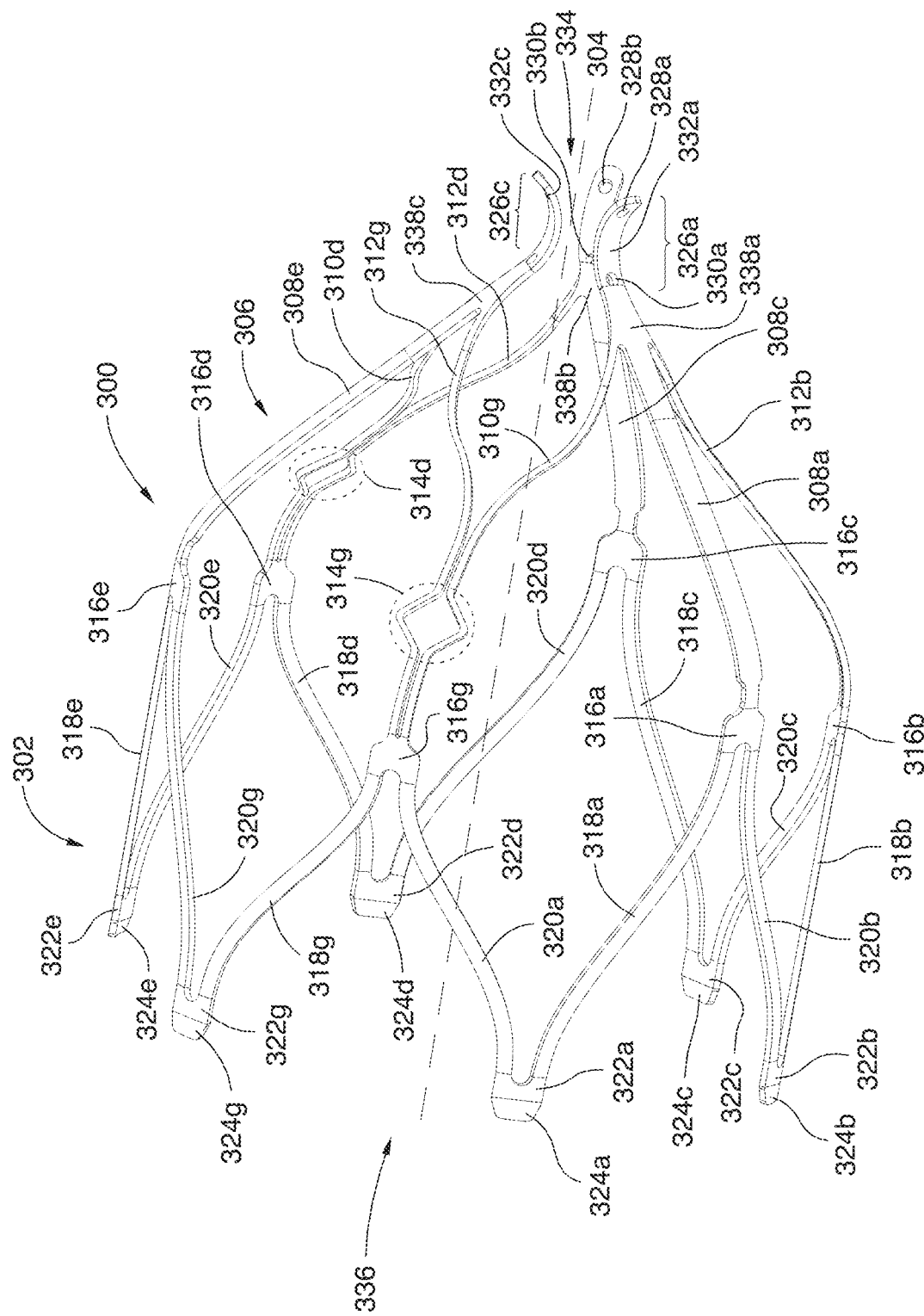
FIG. 8 shows a close up view of the anchor of the assembly of FIG. 7. The anchor is in the expanded-secured-configuration (although the device is not shown in FIG. 8).

Referring now to FIG. 8, the various structures of the anchor 300 are shown. In the embodiment, the wire network 302 of the anchor 300 has various structural members (318, 320) that are joined together at various nodes (316, 322). In this embodiment there are six first nodes 322; with each first node 322 being located at the distal end 336 of the anchor 300. (The anchor 300 has a distal end 336 and a proximal end 334, that are defined consistently with the implantation orientation of the anchor 300, and thus consistently with the distal end 1004 and proximal end 1002 of the assembly.)

Extending from each first node 322 (e.g., 322a) is a first structural member 318 (e.g., 318a) and a second structural member 320 (e.g., 320a). The first structural member 318 and the second structural member 320 of each first node 322 are defined orientationally consistently for each first node 322. The first structural member 318 (e.g., 318a) of each first node 322 (e.g., 322a) extends proximally to a one of the second nodes 316 (e.g., 316a) tangentially in between that first node 322a and an adjacent first node 322 (e.g., 322b). The second structural member 320 (e.g., 320b) of that adjacent first node 322b extends proximally to that one of the second nodes 316 (e.g., 316a) as well. In this embodiment, this configuration is consistent for each of the first nodes 322, the second nodes 316, the first structural members 318, and the second structural members 320. In this embodiment there are six second nodes 316.

Extending proximally from the second nodes 316 are first connector positioning wires 306. The first connector positioning wires 306 extending from a first set of three of the six second nodes 316 (e.g., 316a, 316c, 316e) are single, relatively broad, connector positioning wires 308 (e.g., 308a, 308c, 308e). The first connector positioning wires 306 extending from a second set of the other three of the six second nodes 316 (e.g., 316b, 316d, 316g) are a pair of relatively narrow connector positioning wires 310, 312 (e.g., 310b, 312b; 310d, 312d; 310g, 312g—each one of the pair being separately referenced). Progressing tangentially around the wire network, second nodes 316 of the first set and second nodes 316 of the second set alternate.

In this embodiment, each of the broad connector positioning wires 308 (e.g., 308a) extends to a third node 338a (which forms the end of that broad connector positioning wire 308 (e.g., 308a)). A one 310 (e.g., 310g) of the pair of the narrow connector positioning wires 310, 312 (e.g., 310g, 312g) of the second node 316 (e.g., 316g) adjacent the second node 316a from which that broad connector positioning wire 308a extends also extends to that third node 338a. A one 312 (e.g., 312b) of the pair of the narrow connector positioning wires 310, 312 (e.g., 310b, 312b) of the second node 316 (e.g., 316b) adjacent the second node 316a from which that broad connector positioning wire 308a, on the opposite "side" (in the opposite tangential direction) extends also extends to that third node 338a. In this embodiment there are thus three third nodes 338 (338a, 338c, 338e).

Disposed at the end of each of the broad connector positioning wires 308 (e.g., 308a; i.e., at each third node 338 (e.g., 338a)) is a first connector 326 (e.g., 326a). As will be described in further detail hereinbelow, each first connector 326 (e.g., 326a) is structured to be connectable to one of the sub-first-interconnectors 515 (e.g., 515a) of first interconnector 514 of the device 500.

Figure 1:
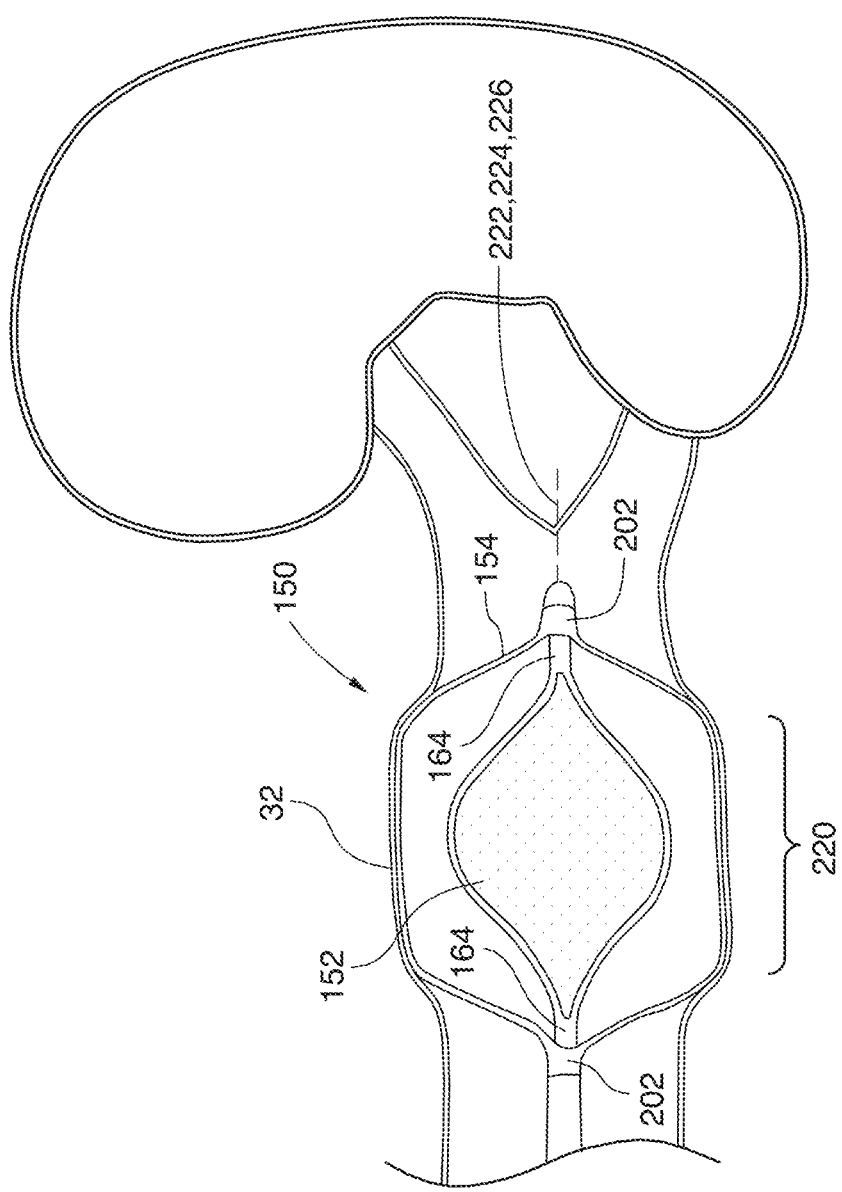
FIG. 1 shows a prior art endovascular device with an anchor, disclosed in Schwammenthal et al., being originally FIG. 19B in Schwammenthal et al.
Figure 2:
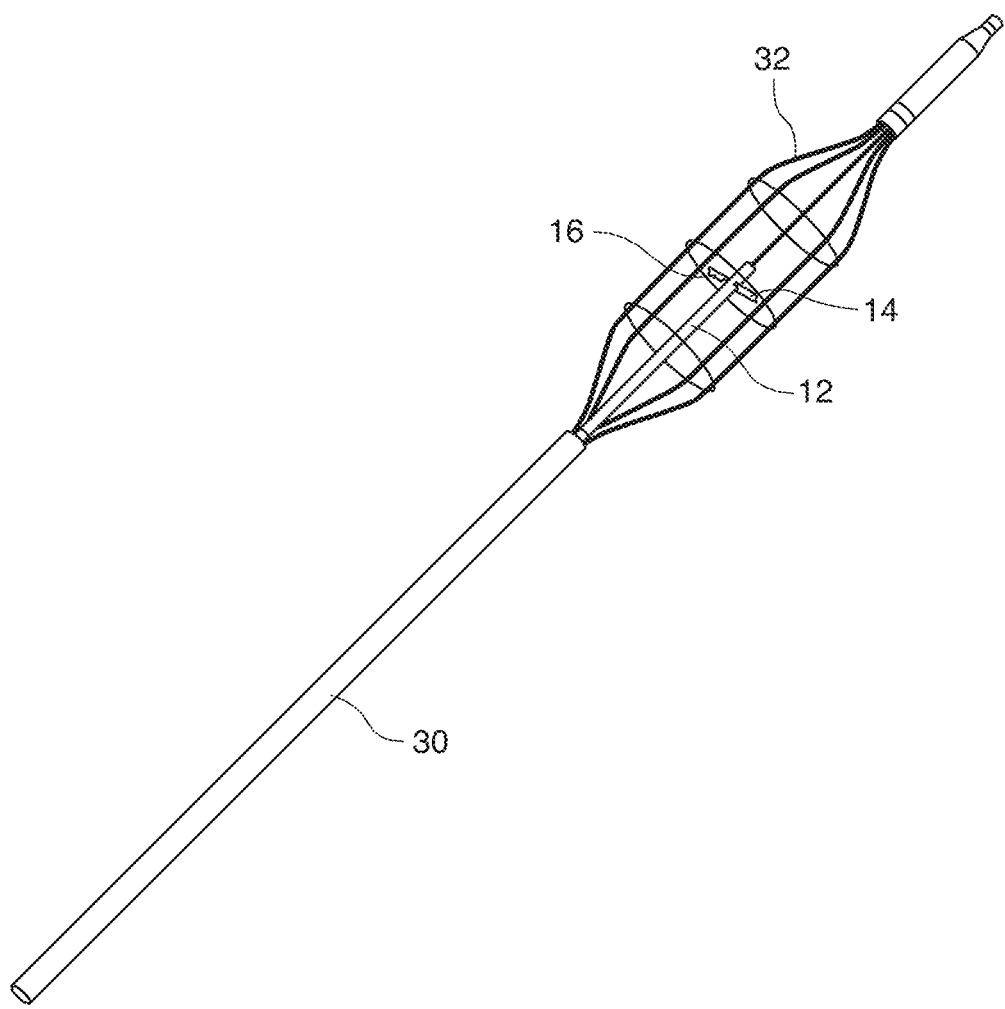
FIG. 2 shows a prior art endovascular device with an anchor, disclosed in Second Heart Assist, Inc., being originally FIG. 16 of Second Heart Assist, Inc.
Figure 3:
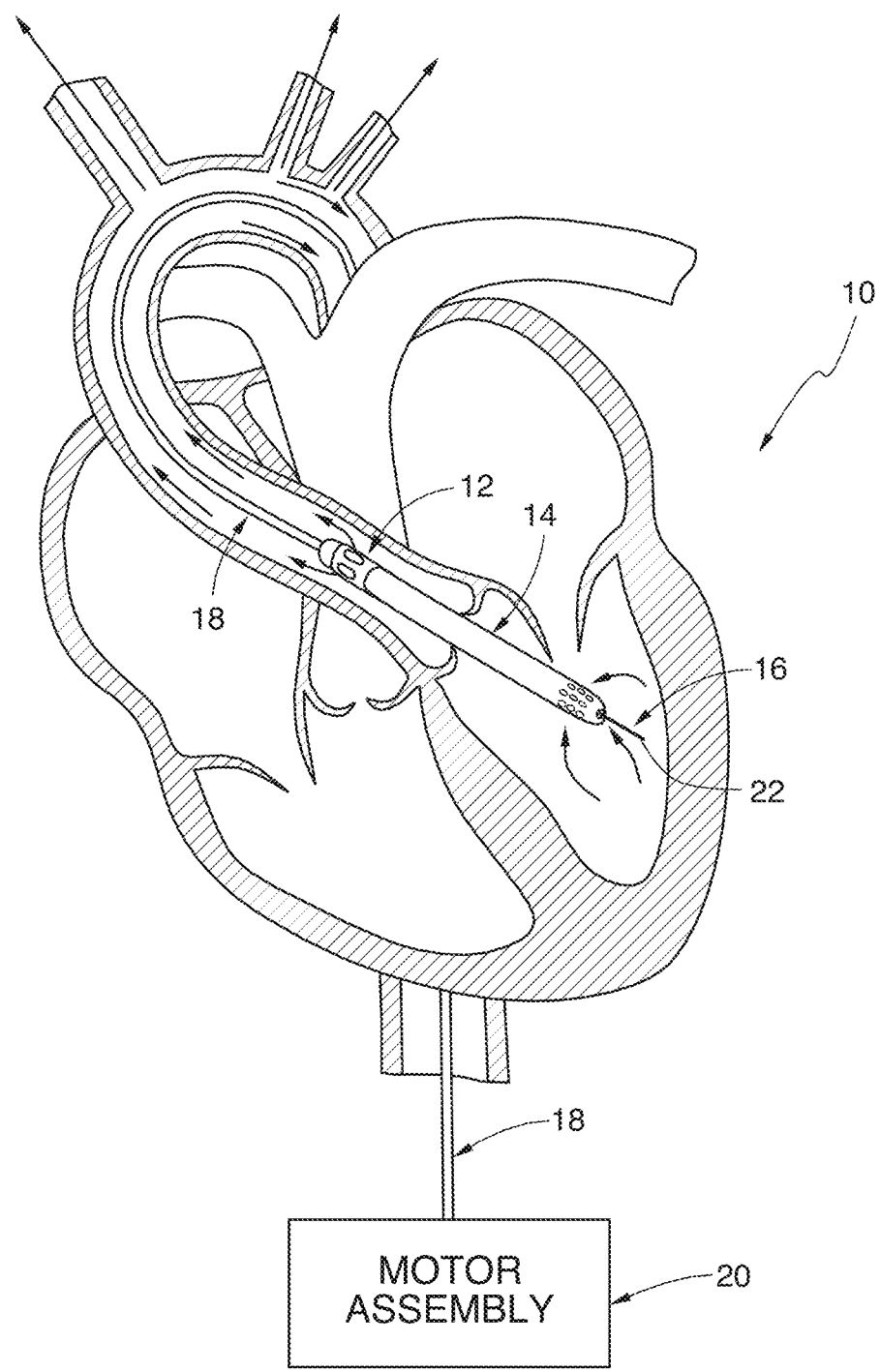
FIG. 3 shows a prior art endovascular device, disclosed in Aboul-Hosn et al., being originally FIG. 1 of Aboul-Hosn et al.
Figure 4:
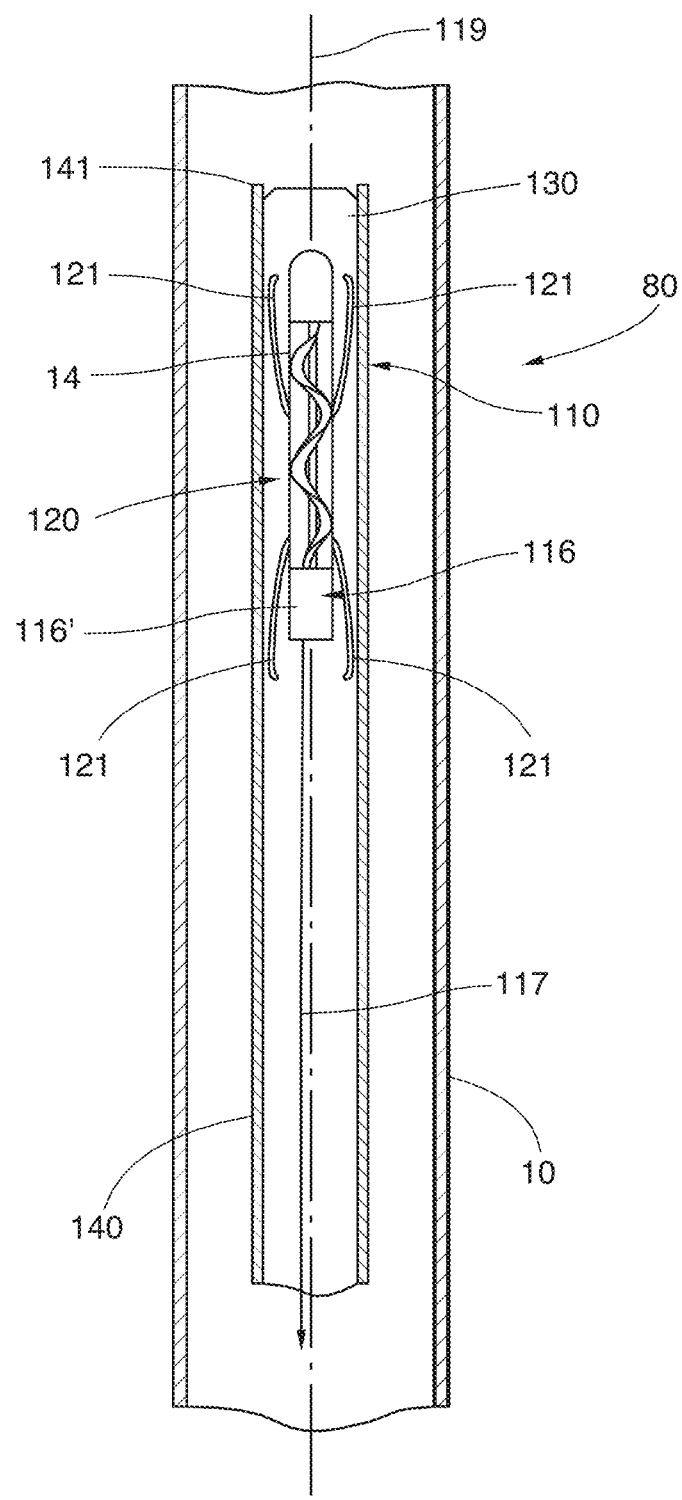
FIG. 4 shows a prior art endovascular device, disclosed in Delgado, III, being originally FIG. 3 of Delgado, III.
Figure 5:
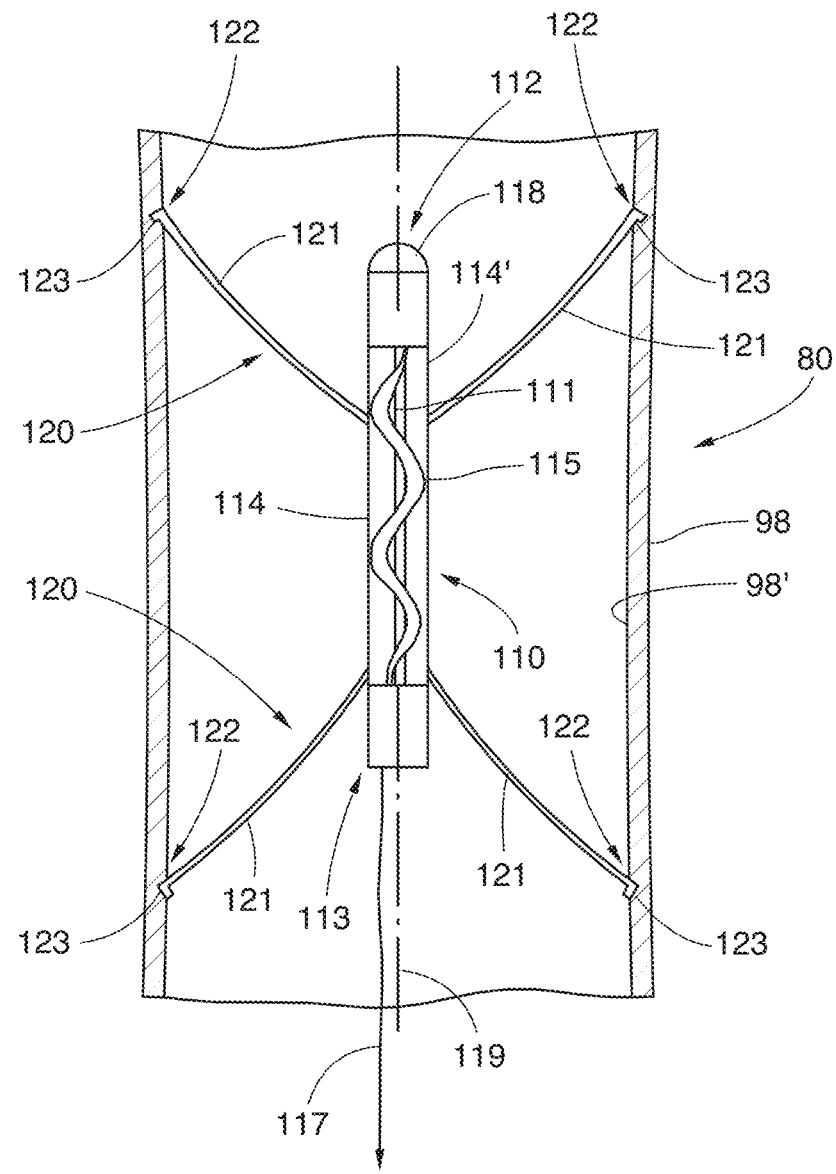
FIG. 5 shows the prior art endovascular device disclosed in Delgado, III shown in FIG. 4 hereof, being originally FIG. 4 of Delgado, III.
Figure 6:
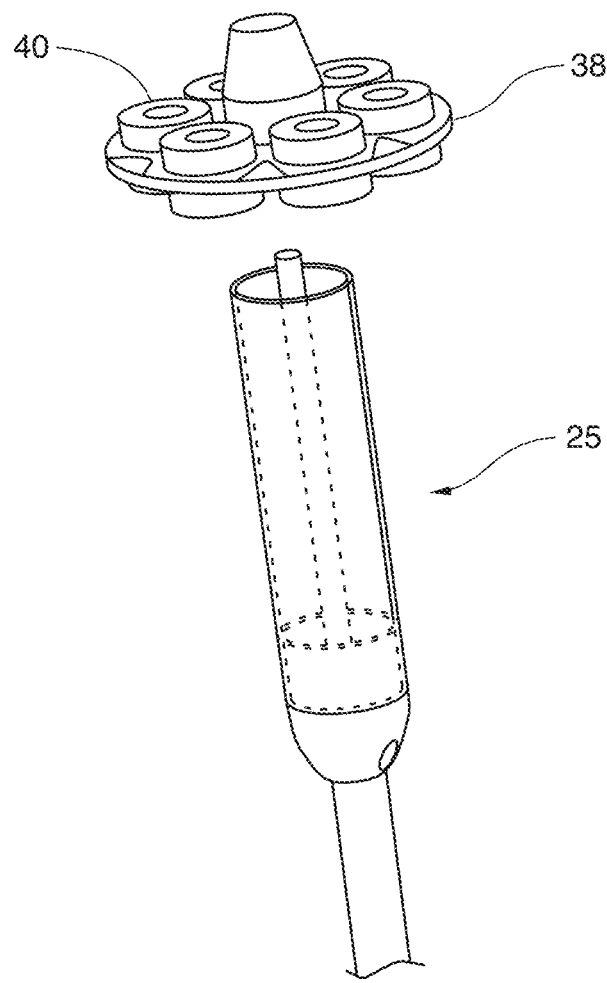
FIG. 6 shows a prior art endovascular device disclosed in Anderson et al., being originally FIG. 5D of Anderson et al.

Each of the first connector positioning wires 306 (e.g., 308, 310, 312) is moveable between a secured position (that which is shown in FIG. 3) and a released position (which is shown in FIG. 35, albeit with a different embodiment, assembly 1100, described hereinabove). In the secured position the first connector positioning wires 306 (308, 310, 312)—in groups of those connected to the same third node 338 (e.g., 308a, 310g, 312b are all connected to third node 338a)—are positioned in proximity to the central longitudinal axis 304 of the anchor 300, such that the first connector 326 (e.g., 326a) which is disposed on those first connector position wires 308, 310, 312 (e.g., 308a, 310g, 312b) is positioned with respect to a one of the sub-first-interconnectors 515 (e.g., 515a) to be releasably connectable thereto. The released position, the first connector positioning wires 306 (e.g., 308, 310, 312) are positioned generally in alignment with the periphery of the wire network 302 (away from the central longitudinal axis 304 of the anchor 300). The first connector positioning wires 306 (e.g., 308, 310, 312) are overcomably biased towards the released position. (The first positioning connector wires 306 (e.g., 308a, 310g, 312b) can be maintained in the secured position by releasable connection of the first connectors 326 (i.e., 326a) to the sub-first-interconnectors 515 (e.g., 515a) of the first interconnector 514, as is described hereinbelow).

Each of the narrow first connector positioning wires 310, 312 (e.g., 310g, 312g) has a stress relieving portion 314 (e.g., 314g) in order to accommodate the bending of that first connector positioning wire 310, 312 (e.g., 310g, 312g—as the case may be) that occurs when that first connector positioning wire 310, 212 moves from the released position to the secured position. In this embodiment, each stress relieving portion 314 is chevron-shaped. In other embodiments, where present, the stress relieving portions may be of any other appropriate shape or configuration. In this embodiment, no stress relieving portion is present in association with the broad connector positioning wires 308 as none is necessary. In other embodiments, stress relieving portions may be present, where necessary or desirable.

Assembly Third Embodiment—Anchor Third Embodiment—Configurations

The lumen wall anchor 300 has a compact-secured-configuration, an expanded-secured-configuration, and an expanded-released configuration.

Similar to the embodiments previously described hereinabove (e.g., in FIG. 15), when the lumen wall anchor 300 is in a compact-secured configuration, the lumen wall anchor 300 is shaped and dimensioned to be deliverable to a delivery site within a lumen 904 of a body conduit 900 via a catheter (e.g., delivery sheath 950 in FIG. 15). Thus, when the lumen wall anchor 300 is in the compact-secured-configuration, the first connector positioning wires 306 (e.g., 308, 310, 312) are in their secured position (in the embodiment shown in FIG. 15 they are shown with the first connectors 326 at the third nodes 338 at the ends thereof) being releasably connected to sub-first-interconnectors 615 of the first interconnector 614). Further, the wire network 302 is in a compact form within the delivery sheath 950. (See, for example, the WO '765 Publication for a detailed description of a transcatheter implantation technique.) When the lumen wall anchor 300 is in the compact-secured-configuration, it has a diameter of 22 French.

Referring to FIGS. 7 and 8 and FIG. 19 (which shows a different embodiment, lumen wall anchor 400 described hereinbelow, but for present purposes similar to lumen wall anchor 300), when the lumen wall anchor 300 is in an expanded-secured-configuration, the wire network 302 is dimensioned and shaped to exert a force on the wall 902 (FIG. 19) of the lumen 904 of the conduit 900. This force is sufficient to anchor the assembly 1000 in place at the implantation site 908 (including during operation of the device 500). Further, as can be seen in FIG. 19, when the anchor 300 is in the expanded-secured-configuration, the first connector positioning wires 306 (e.g., 308, 310, 312) are in their secured position, and are shown in FIGS. 7 and 19 having the first connectors 326 disposed at the ends thereof (e.g., on the third node 338) being releasably connected to the sub-first-interconnectors 515 of the first interconnector 514. When the lumen wall anchor 300 is in the expanded-secured-configuration, it has a diameter of about 24 mm and a length of about 6 cm.

When the lumen wall anchor 300 is in an expanded-released-configuration (see FIGS. 22 and 24, which show a different embodiment, anchor 400, but which is similar for present purposes.) For this embodiment, but similar to that described hereinabove with respect to other embodiments, the wire network 302 is dimensioned and shaped to exert a force on the wall 902 of the lumen 904 of the conduit 900. This force is sufficient to anchor the assembly 1000 in place at the implantation site 908. When the anchor 300 is in the expanded-released-configuration, the first connector positioning wires 306 (e.g., 308, 310, 312) are in their released position, as the first connectors 326 have been released from their connection with the sub-first-interconnectors 515 of first interconnector 514. In the released position, the ends of the first connector positioning wires 306 (e.g., 308, 310, 312) (and third nodes 338) are proximate the wall 902 of the lumen 904 of the conduit 900, generally in line with the longitudinal axis 906 of body conduit 900. In this configuration, the first connector positioning wires 306, the third nodes 338, and the first connectors 326 do not obstruct fluid flow axially through the conduit 902 while the anchor 300 is anchored in place at the implantation site 908 with the device 500 having been retrieved and removed (e.g., explanted) from the body conduit 900. When the lumen wall anchor 300 is in the expanded-released-configuration, it has a diameter of about 24 mm and a length of about 6 cm.

The lumen wall anchor 300 is based towards its expanded-released-configuration. In this embodiment, this bias is the case as the anchor 300 is made of nitinol (a shape-memory alloy) with the expanded-released-configuration being the "remembered shape" thereof. (The anchor 300 is manufacturable according to any conventional techniques appropriate to the material of which it is made, e.g., laser cutting.) As was described hereinabove, this bias can be overcome during normal usage of the assembly 1000. In particular, when the assembly 1000 is within the delivery sheath (not shown, but see FIG. 15 as an illustration of the principle with respect to a different embodiment, assembly 1100), the bias of the wire network 302 has been overcome (via its insertion into the delivery sheath, e.g., during manufacturing and assembling). As long as the assembly 1000 remains within the delivery sheath, the anchor 300 will remain in this compact configuration. In this embodiment, there is no other structure retaining the wire network 302 itself in a compact configuration. (Which is not the case in all embodiments, as will be described in further detail hereinbelow.) Thus, as the anchor 300 is caused to exit the delivery sheath (through the distal end thereof), at the delivery site (which, in this embodiment, is the implantation site 908) the wire network 302 will expand owing to its bias. The first connector positioning wires 306 (e.g., 308, 310, 312) will remain in their secured position, however, as the first connectors 326 remain releasably connected to the sub-first-interconnectors 515 of the first interconnector 514 of the device 500. Thus, when the anchor 300 has fully exited the delivery sheath, it will be in its expanded-secured-configuration, anchoring the assembly 1000 at the implantation site 908.

Assembly Third Embodiment—Implantation & Explantation

The implantation and explantation of the assembly 1000 and the explantation of the device 500 only, are materially the same as was previously described hereinabove with respect to the first embodiment, assembly 1100 (including device 600). Thus, they will not be described herein again with respect to the assembly 1000 (including device 500), for the sake of brevity.

Assembly Third Embodiment—Anchor Third Embodiment—First Connectors

Figure 9:
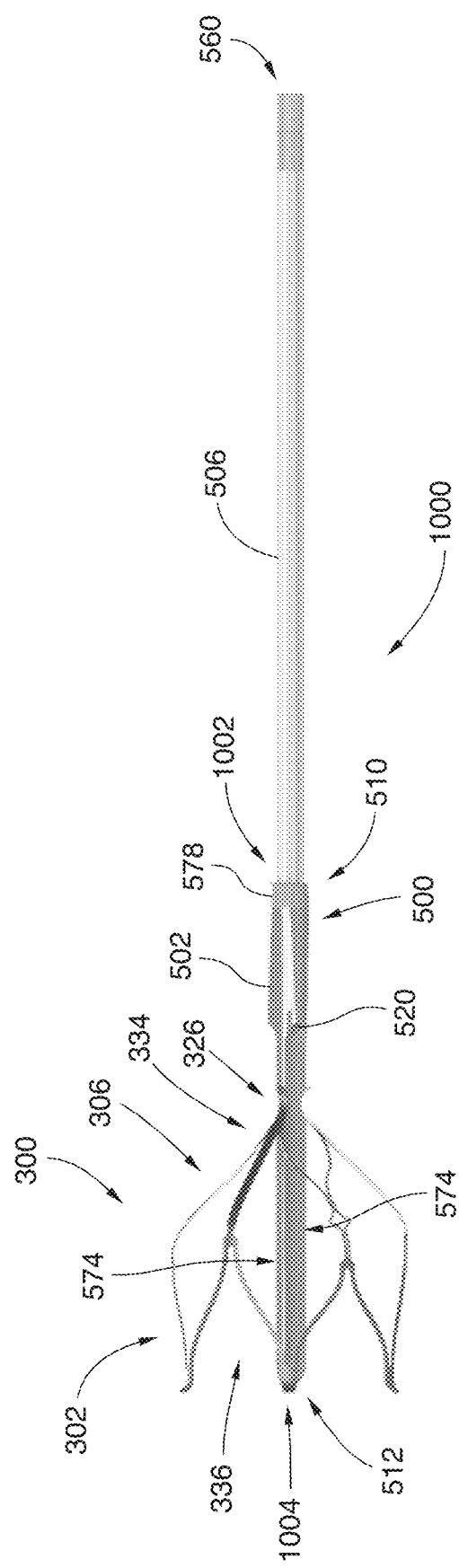
FIG. 9 shows a side view of the assembly of FIG. 7, similar to FIG. 7, with the exceptions that the pumping units of the device are not shown, and the docking unit of the device is shown with a partial cut-away to show the channels within.

Referring to FIG. 8, in this embodiment, each first connector 326 (e.g., 326a) has an elongated element 332 (e.g., 332a) that is convexly curved (inward, towards the central longitudinal axis 304 of the anchor 300). Each element 332 (e.g., 332a) has two longitudinally spaced apart holes, a proximal hole 328 (e.g., 328a) and a distal hole 330 (e.g., 330a). Referring to FIGS. 8 and 9, when the first connector positioning wires 306 (e.g., 308a, 310g, 312b) are in the secured position, the first connectors 326 (e.g., 326a), including their elements 332 (e.g., 332a) and holes 328, 330 (e.g., 328a, 330a) are shaped, sized, arranged, positioned and oriented to releasably connect to the sub-first-interconnectors 515 (e.g., 515a), as will be further described hereinbelow. In this embodiment, the aforementioned orientation of the first connectors 326 is such that they are oriented generally parallel to the central longitudinal axis 304 of the anchor 300 (which itself is parallel to the central longitudinal axis 508 of the device 500 and the central longitudinal axis 1106 the assembly 1000).

Assembly Third Embodiment—Anchor Third Embodiment—First Interconnector

Referring to FIGS. 7 and 9, in this embodiment, the device 500 has a first interconnector 514 structured to releasably connect the device 500 with the anchor 300 to maintain the device 500 in place within a mammalian body conduit 900 at an implantation site 908. In this embodiment, the first interconnector 514 is located midway between the proximal end 510 and the distal end 512 of the docking unit 502 of the device 500. The first interconnector 514 has three sub-first-interconnectors 515, with each one of the sub-first-interconnectors 515 being located on one of the three raised portions 576 in between the receiving surfaces 574 of the exterior surface 578 of the docking unit 502.

The sub-first interconnectors 515 of the first interconnector 514 of the device 500 of assembly 1000 are identical to the sub-first-interconnectors 715 of the first interconnector 714 of the device 700 of the assembly 1200. Sub-first-interconnectors 715 are described immediately below and it is to be understood that the description applies to sub-first-interconnectors 515.

Figure 11:
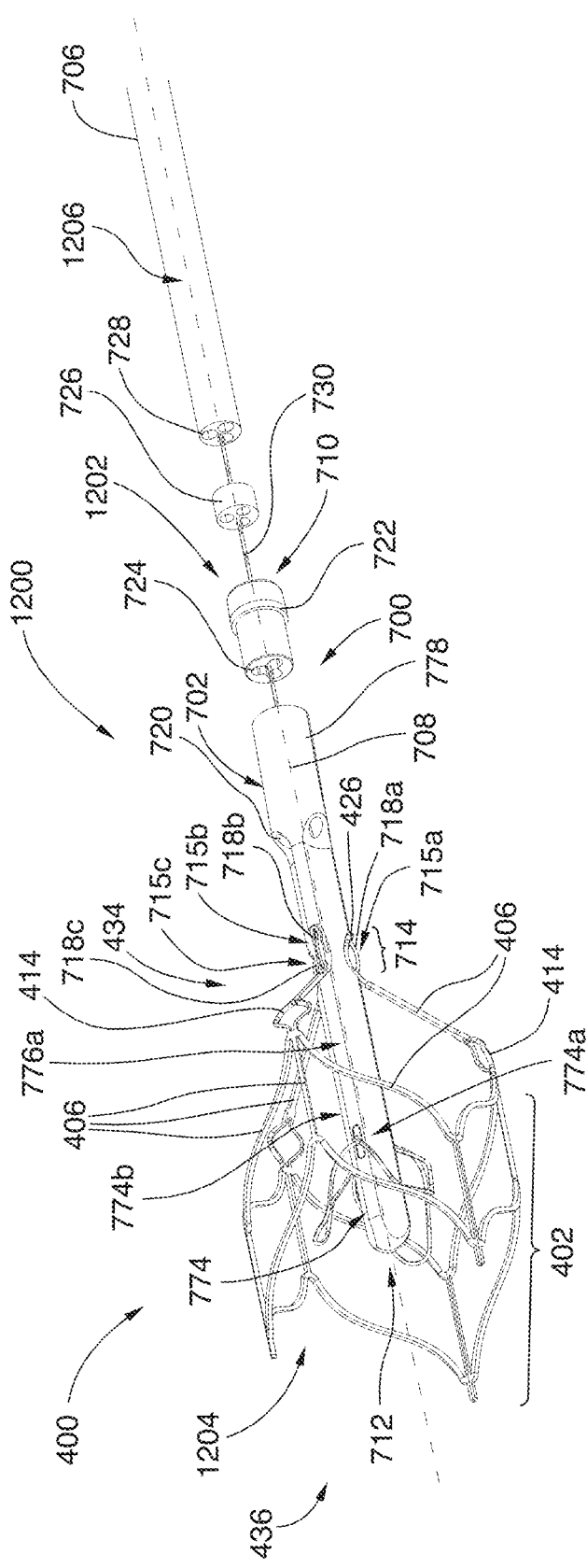
FIG. 11 shows an isometric view of an intraluminal device and anchor assembly being a fourth embodiment of the present technology. The assembly includes a fourth embodiment of a device of the present technology and a fourth embodiment of an anchor of the present technology. The device is shown with none of its three pumping units having been received in their receiving surfaces of the docking unit. The distal end of the device, and the control cable housing, and the connection therebetween are shown in an exploded view. The anchor is shown in its expanded-secured-configuration.
Figure 20:
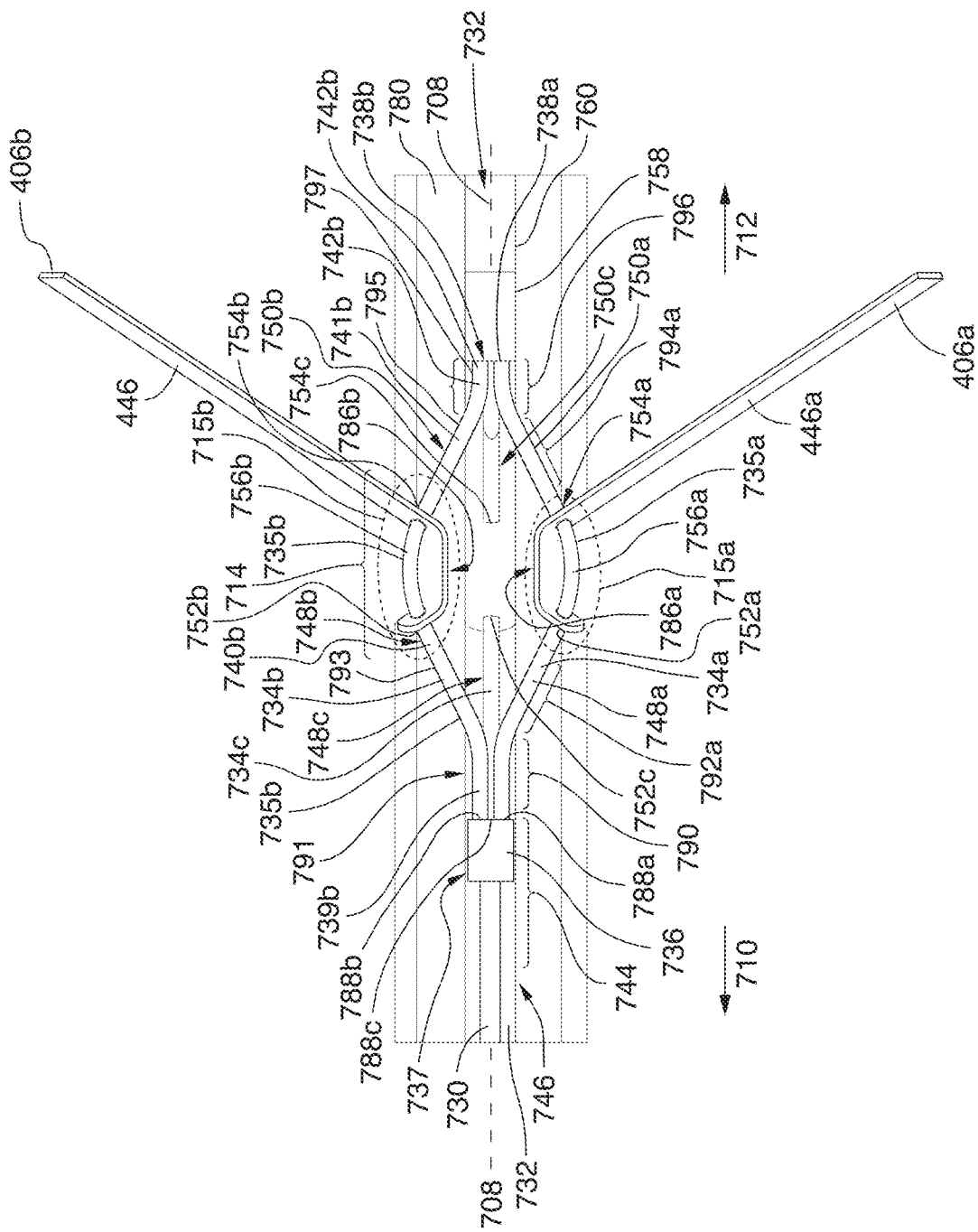
FIG. 20 shows schematic of first connectors of anchor of the assemblies in FIGS. 7 and 11 being connected to a first interconnector of the device of the assemblies of FIGS. 7 and 11.
Figure 21:
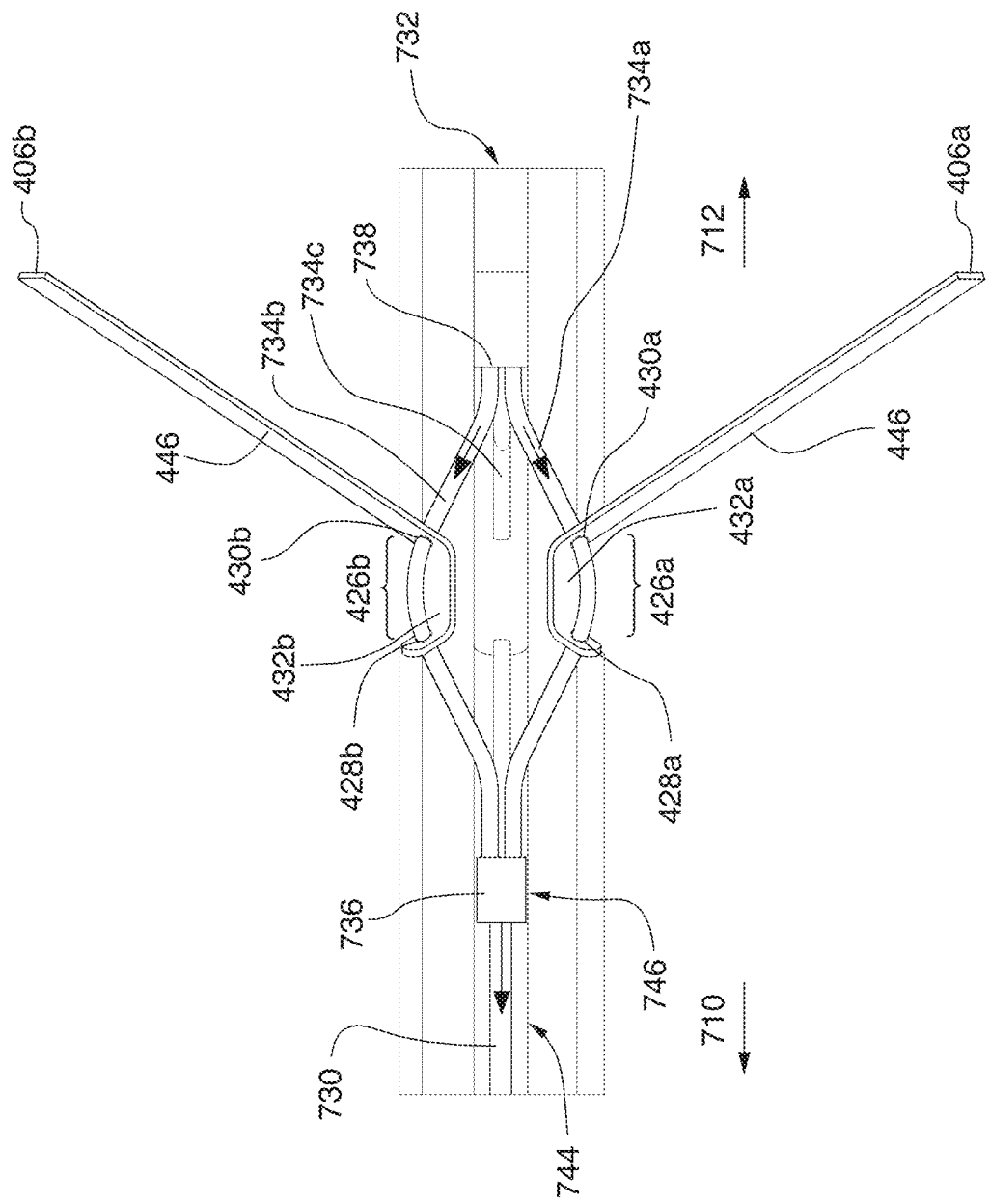
FIG. 21 shows a schematic similar to FIG. 20 with the exception that the direction of movement of the wires during the release of the connection is shown.

Referring to FIGS. 11, 20 and 21, each sub-first-interconnector 715 (e.g., 715b) is a concavity 786 (e.g., 786b) in one of the raised portions 776 (e.g., 776b) between the receiving surfaces 774 (e.g., 774b, 774c (not shown)) of the docking unit 702. Each concavity 786 extends from the exterior surface 778 inward towards the central longitudinal axis 708 of the device 700.

Referring now to the schematic shown in FIG. 20, two sub-first-interconnectors 715 (e.g., 715a, 715b) are shown schematically. Solely for ease of understanding, each concavity 786 (e.g., 786a, 786b) is shown in FIGS. 20 and 21 as having three planar portions, instead of being shown as curved. (Although in other embodiments cavities 786 can actually have three planar portions instead of a curve.) Each concavity 786 (e.g., 786b) has two openings therein, a proximal opening 752 (e.g., 752b) and a distal opening 754 (e.g., 754b). A central longitudinal channel 732 extends from the proximal end 710 of the docking unit 702 longitudinally along the central longitudinal axis 708 and terminates within the body 780 of the docking unit 702 at a point distal to the first-sub-interconnectors 715. A first branch channel 748 (e.g., 748b) connects the central longitudinal channel 732 with the proximal opening 752 (e.g., 752b) of the concavity 786 (e.g., 786b). A second branch channel 750 (e.g., 750b) connects the distal opening 754 (e.g., 754b) with the channel 732. Each sub-first-interconnector 715 (e.g., 715b) has a sub-first interconnector wire 734 (e.g., 734b). In this embodiment, each sub-first-interconnector wire 734 (e.g., 734b) has a proximal end 788 (e.g., 788b) attached to a common channel element 736 disposed within a proximal portion 744 of the channel 732. A first portion 739 (e.g., 739b) of the sub-first-interconnector wire 734 (e.g., 734b) extends within the proximal portion 744 of the channel 732 from the common channel element 736 to the first branch channel 748 (e.g., 748b). A second portion 740 of the sub-first-interconnector wire 734 (e.g., 734b) extends within the first branch channel 748 (e.g., 748b) from the channel 732 to the proximal opening 752 (e.g., 752b) of the concavity 786 (e.g., 786b) of the sub-first-interconnector 715 (e.g., 715b) and exits the body 780 of the docking unit 702 through that proximal opening 752 (e.g., 752b).

The first connector positioning wires 406 (e.g., 406b) are in their secured position (see also FIG. 21) and thus the connector elements 432 (e.g., 432b) of the first connectors 426 (e.g., 426b) register with the concavities 786 (e.g., 786b) of the sub-first-interconnectors 715 (e.g., 715b) of the first interconnector 714. The proximal hole 428 (e.g., 428b) of the connector element 432 (e.g., 432b) is aligned with the proximal opening 752 (e.g., 752b) of the concavity 786 (e.g., 786b), and the distal hole 430 (e.g., 430b) of the connector element 432 (e.g., 432b) is aligned with the distal opening 754 (e.g., 754b) of the concavity 786 (e.g., 786b). Thus, sub-first-interconnector wire 734 (e.g., 734b) immediately after exiting the body 780 of the docking unit 702 passes through the proximal hole 428 (e.g., 428b) in the connector element 432 (e.g., 432b). Next, a third portion 756 (e.g., 756b) of the sub-first-interconnector wire 734 (e.g., 734b) passes outside the body 780 of the docking unit 702 from the proximal hole 728 (e.g., 728b) in the connector element 432 (e.g., 432b) to the distal hole 430 (e.g., 430b) in the connector element 732 (e.g., 732b). The sub-first-connector wire 734 (e.g., 734b) then passes through the distal hole 430 (e.g., 430b) and immediately re-enters the body 780 of the docking unit 702 through the distal opening 754 (e.g., 754b) of the concavity 786 (e.g., 786b). A fourth portion 741 (e.g., 741b) of the sub-first-interconnector wire 734 (e.g., 734b) extends within the second branch channel 750 (e.g., 750b) from the distal opening 754 (e.g., 754b) to the channel 732. Finally, a fifth portion 742 (e.g., 742b) extends from the second branch channel 750 (e.g., 750b) distally within the channel 732.

The bias of the first connector positioning wires 406 towards their released position is overcome and the first connector positioning wires 406 are maintained in their secured position, by frictional forces between the walls of the various channels 732, 748, 750 and their abutment by the various sub-first-interconnector wires 734, the common channel element 736, and first connector actuation wire 730 (as the case may be). For example, the exterior surface 737 of the common channel element 736 abuts the interior wall 746 of the portion 744 of the channel 732. The exterior surfaces 735 (e.g., 735b) of the sub-first-connector wires 734 (e.g., 734b) abut the interior wall 791 of the portion 790 of the channel 732 (shown with a gap in the schematics of FIGS. 20 and 21 for ease of understanding.) The exterior surfaces 735 (e.g., 735b) of the sub-first-connector wires 734 (e.g., 734b) abut the interior wall 793 (e.g., 793b) of the portion 792 (e.g., 792b) of first branch channel 748 (e.g., 748b). The exterior surfaces 735 (e.g., 735b) of the sub-first-connector wires 734 (e.g., 734b) abut the interior wall 795 (e.g., 795b) of the portion 794 (e.g., 794b) of second branch channel 750 (e.g., 750b). The exterior surfaces 735 (e.g., 735b) of the sub-first-connector wires 734 (e.g., 734b) abut the interior wall 797 of the portion 796 of the channel 732 until the distal ends 738 (e.g., 738b) of the sub-first-interconnector wire (shown with a gap in the schematics of FIGS. 20 and 21 for ease of understanding.)

It was described hereinabove that during an explantation of the device (e.g., 700) alone leaving the anchor (e.g., 400) to remain within the lumen 904 of the conduit 900, each of the first connectors 426 are released from their connection to the first interconnector 714. In this embodiment, referring to FIG. 21, this occurs in the following manner: The interventionist pulls the first connector actuation wire 730 that is attached to the proximal end of the common channel element 736 (or causes to be it to be pulled). This pulling movement (with a sufficient force) overcomes frictional forces (described hereinabove) between the walls (e.g., 746, 791, 793, 795, 797) of the various channels described above (e.g., 732, 748, 750) and their abutment by the various sub-first-interconnector wires 734, the common channel element 736, and first connector actuation wire 730; thus moving the sub-first-interconnector wires 734, the common channel element 736, and the first connector actuation wire 730 proximally (direction of movement shown by the arrows in FIG. 21). After the first connector actuation wire 730 has been pulled a sufficient length, the distal ends 738 (e.g., 738b) of the sub-first-interconnector wires 734 (e.g., 734b) pass first through the distal opening 754 (e.g., 754b) in the concavity 786 (e.g., 786b), then through the distal hole 430 (e.g., 430b) in the connector element 432 (e.g., 432b), then through the proximal hole 428 (e.g., 428b) in the connector element 432 (e.g., 432b), then through the proximal opening 752 (e.g., 752b) in the concavity 786 (e.g., 786b) of the sub-first-connector 715 (e.g., 715b), and finally into the first branch channel 748 (e.g., 748b).

Removing the sub-first-interconnector wire 734 (e.g., 734b) from the passing through the two holes 428, 430 (e.g., 428b, 430b) in the first connector element 432 (e.g., 732b), releases the connection between the first connector 426 (e.g., 426b) and the sub-first-interconnector wire 734 (e.g., 734b). Thus, the bias of the first connector positioning wire 406 (e.g., 406b) is no longer overcome, and the first connector positioning wire 406 (e.g., 406b) moves to its released position. In this embodiment, as all of the sub-first-interconnector wires 734 are connected to the common channel element 736, the sub-first-interconnector wires 734 all move in synchronicity. Thus, each of the first connectors 426 are simultaneously released, and the first connector positioning wires 406 all simultaneously move toward their released positions. The anchor 400 thus adopts its expanded-released-configuration, allowing for retrieval of the device 700 as was described hereinabove.

As was stated hereinabove, as the sub-first interconnectors 515 of the first interconnector 514 of the device 500 of assembly 1000 are identical to the sub-first-interconnectors 715 of the first interconnector 714 of the device 700 of the assembly 1200, the foregoing description the sub-first-interconnectors 715 is equally applicable to the sub-first-interconnectors 515.

Assembly Fourth Embodiment—Introduction

Referring to FIG. 11, there is shown a mammalian body conduit intralumenal device and lumen wall anchor assembly 1200 being a fourth embodiment of an assembly of the present technology. The assembly 1200 has a proximal end 1202 and a distal end 1204 defined consistently with the orientation in which the assembly 1200 is implanted. The assembly 1200 has a central longitudinal axis 1206. The assembly 1200 includes a mammalian body conduit intralumenal device 700 and a lumen wall anchor 400, each of which will be discussed in turn hereinbelow.

Assembly Fourth Embodiment—Device Fourth Embodiment

The mammalian body conduit intralumenal device 700 is a fourth embodiment of a device of the present technology. In this embodiment, the device 700 is a modular fluid pump as described in the WO '765 Publication. Thus, the device 700 has a docking unit 702 and three pumping units 704 (none of which are shown in FIG. 11). The device 700, when in its assembled configuration, has a proximal end 710 and a distal end 712. The proximal end 710 and the distal end 712 are defined consistently with the orientation in which the device 700 is implanted. Thus, the proximal end 710 and distal end 712 of the device 700 are defined consistently with the proximal end 1202 and distal end 1204 of the assembly 1200, respectively. The device 700 has a central longitudinal axis 708 which, in this embodiment, is colinear with the central longitudinal axis 1206 of the assembly 1200. A cable housing 706 extends proximally from the proximal end 710 of the device 700. Within the cable housing 706 are the various control and electrical wires (not shown) of the pumping units 704 and the docking unit 702 (e.g., the first interconnector actuation wire 730) of the device 700. (The WO '765 Publication provides a detailed description of some of such control wires and electrical wires; that description is not repeated herein for brevity.)

In this embodiment, the docking unit 702 of the device 700 has three receiving surfaces 774 (two of which are shown in FIG. 11), each of which receives therein one of the three pumping units 704 (not shown) of the device 700. (In this embodiment, the device 700 has three pumping units 704 total. At the proximal end of each receiving surface 774 is an opening 720 through which control wires, etc. of a pumping unit 704 can pass through the docking unit 702 into the cable housing 706) In between each of the receiving surfaces 774 of the docking unit 702 is a raised portion 776 of the exterior surface 778 of the docking unit 702. A first interconnector 714 having three sub-first-interconnectors 715 (e.g., 715a, 715b, 715c), one located on each of the three raised portions 776 of docking unit 702, is present in the device 700. As will be described herein below, the first interconnector 714 with its sub-first-interconnectors 715 connects the lumen wall anchor 400 to the device 700.

Assembly Fourth Embodiment—Anchor Fourth Embodiment—General Structure

Figure 12:
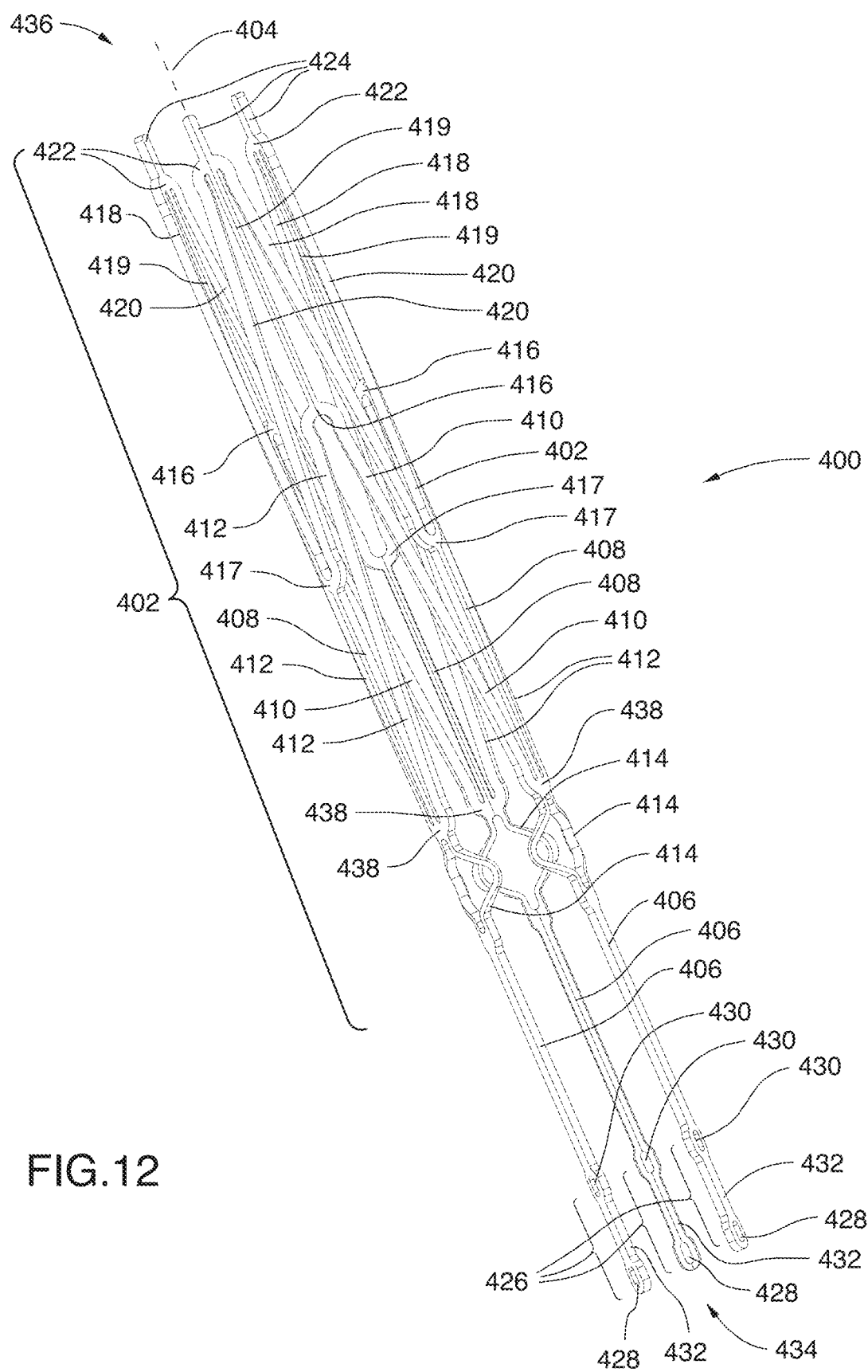
FIG. 12 shows a side view of the anchor of the assembly of FIG. 11 in its compact-secured-configuration (although the device is not shown in FIG. 12).
Figure 13:
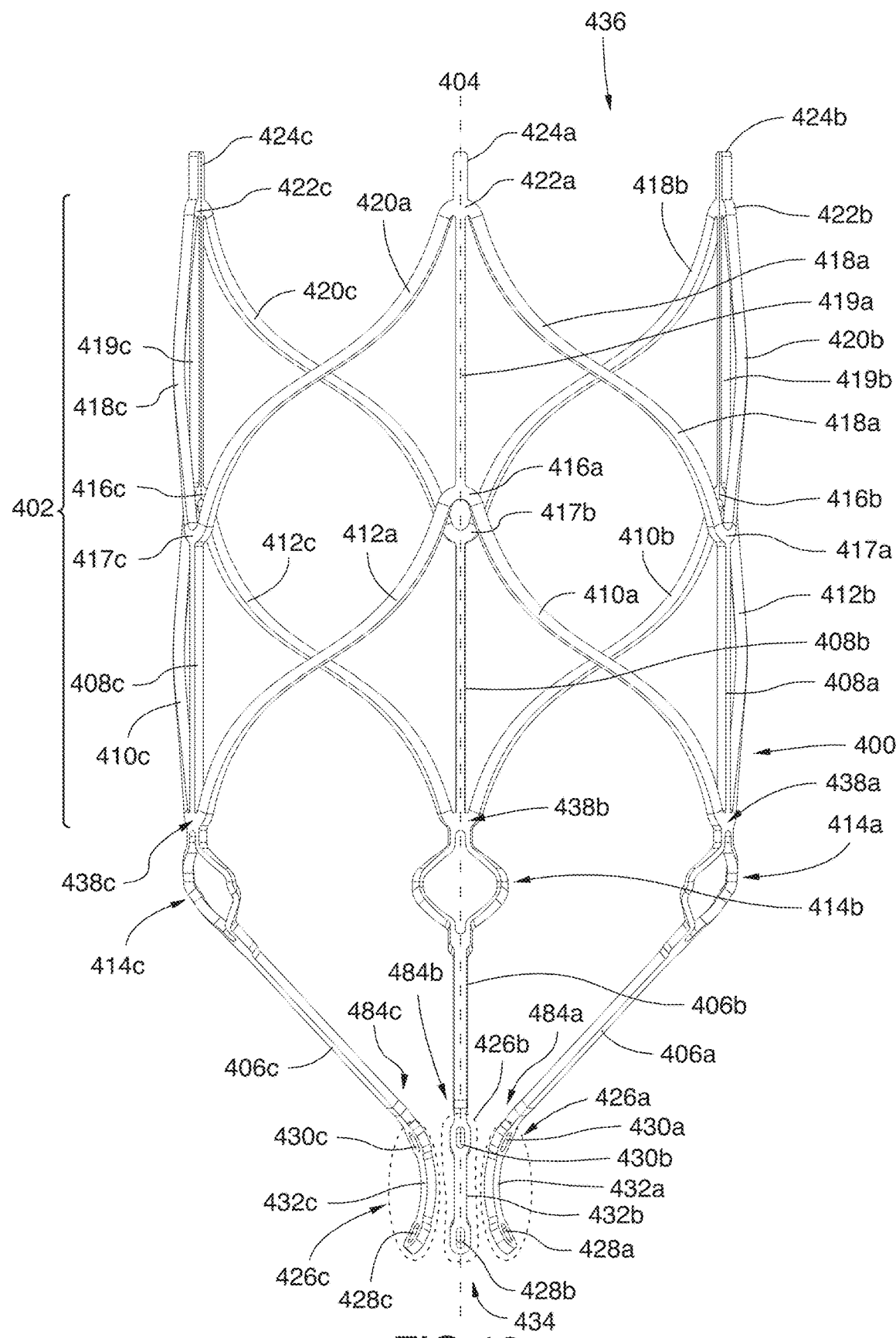
FIG. 13 shows a side view of the anchor of the assembly of FIG. 11 in its expanded-secured-configuration (although the device is not shown in FIG. 13).
Figure 14:
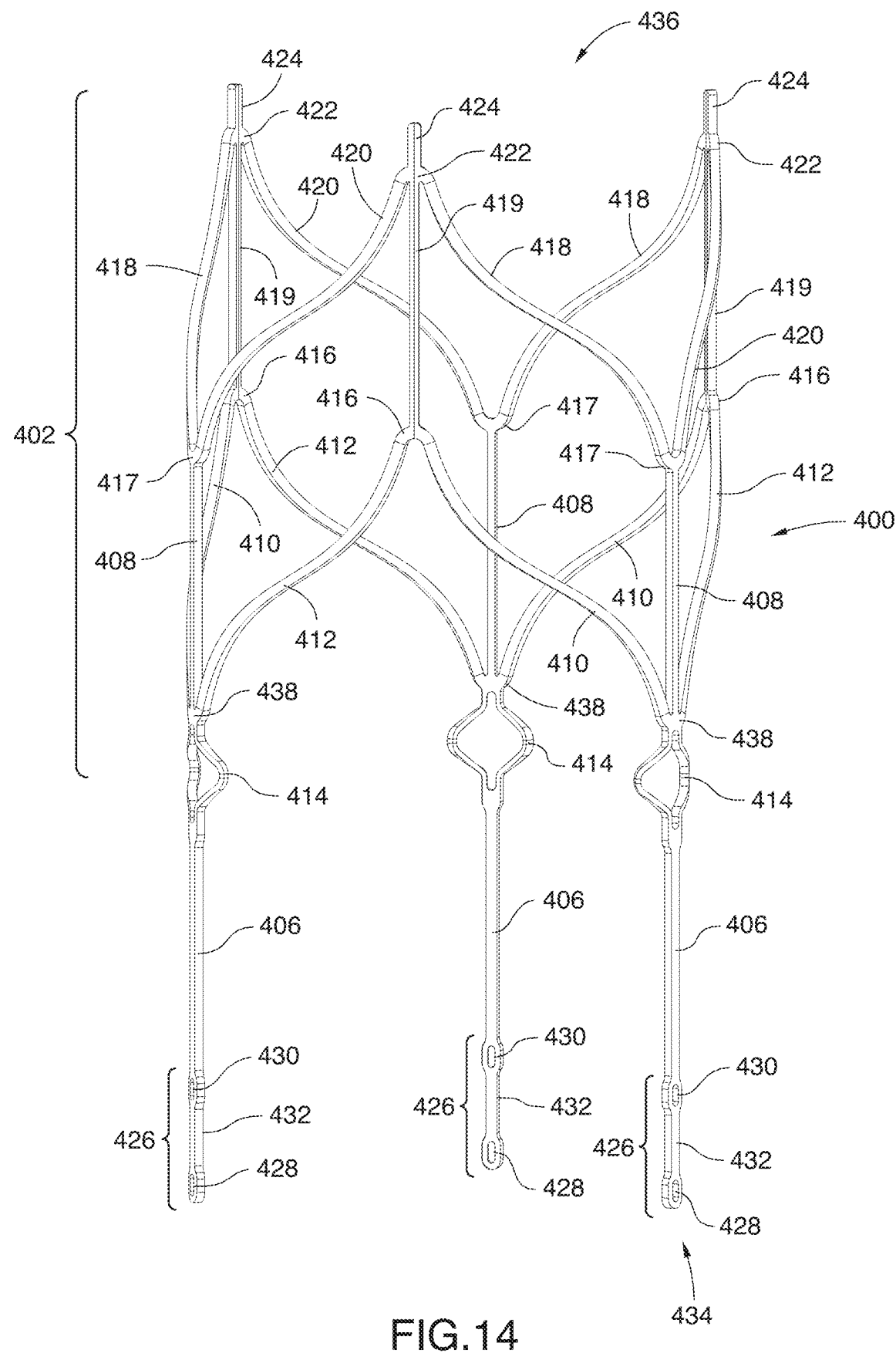
FIG. 14 shows a side view of the anchor of the assembly of FIG. 11 in its expanded-released-configuration (although the device is not shown in FIG. 14).

Referring now to FIGS. 12 to 14, the lumen wall anchor 400 is fourth embodiment of an anchor of the present technology. In this embodiment, the anchor 400 has a 3D-shaped wire network 402, which itself has a central longitudinal axis 404. In this embodiment, the central longitudinal axis 404 of the wire network 402 is colinear with the central longitudinal axis 1206 of the assembly 1200 and with the central longitudinal axis 708 of the device 700. In other embodiments this need not be the case.

In this embodiment, the wire network 402 of the anchor 400 has various structural members (e.g., 408, 410, 412, 418, 419, 420) that are joined together at various nodes (e.g., 416, 417, 422, 438). In this embodiment there are three first nodes 422; with each first node 422 being located at the distal end 436 of the anchor 400. (The anchor 400 has a distal end 436 and a proximal end 434, that are defined consistently with the implantation orientation of the anchor 400, and thus consistently with the distal end 1204 and proximal end 1202 of the assembly 1200.)

Extending from each first node 422 (e.g., 422a) are a first structural member 418 (e.g., 418a), a second structural member 420 (e.g., 420a), and a third structural member 419 (e.g., 419a). The first structural member 418, the second structural member 420, and the third structural member 419 of each first node 422 are defined orientationally consistently for each first node 422. The first structural member 418 (e.g., 418a) of each first node 422 (e.g., 422a) extends proximally to a one of the second nodes (of a second type) 417 (e.g., 417a) tangentially in between that first node 422 (e.g., 422a) and an adjacent first node 422 (e.g., 422b). The second structural member 420 (e.g., 420b) of that adjacent first node 422 (e.g., 422b) extends proximally to that one of the second nodes 417 (e.g., 417a) as well. The third structural member 419 (e.g., 419a) of that first node 422 (e.g., 422a) extends proximally to a second node (of a first type) 416 (e.g., 416a) that is axially aligned with that first node 422 (e.g., 422a). In this embodiment there are six second nodes, three of the first type 416 (e.g., 416a, 416b, 416c) and three of the second type 417 (e.g., 417a, 417b, 417c). The second nodes of the first type 416 alternate tangentially with the second nodes of the second type 417 (e.g., 416a, 417a, 416b, 417b, 416c, 417c).

Extending from each the second nodes (of the first type) 416 (e.g., 416a) are a fourth structural member 410 (e.g., 410a) and a fifth structural member 412 (e.g., 412a). The fourth structural member 410 (e.g., 410a) of each second node (of the first type) 416 (e.g., 416a) extends proximally to a one of the third nodes 438 (e.g., 438a) tangentially in between that second node (of the first type) 416 (e.g., 416a) and the next second node (of the first type) 416 (e.g., 416b). That third node 438 (e.g., 438a) is in axial alignment with the second node (of the second type) 417 (e.g., 417a) in between that second node (of the first type) 416 (e.g., 416a) and the next second node (of the first type) 416 (e.g., 416b). The second structural member 420 (e.g., 420b) of that adjacent first node 422 (e.g., 422b) extends proximally to that one of the second nodes 417 (e.g., 417a) as well. The fifth structural member 412 (e.g., 412a) of each second node (of the first type) 416 (e.g., 416a) extends proximally to a one of the third nodes 438 (e.g., 438c) tangentially in between that second node (of the first type) 416 (e.g., 416a) and the next second node (of the first type) 416 (e.g., 416c) in the "opposite" tangential direction. That third node 438 (e.g., 438c) is in axial alignment with the second node (of the second type) 417 (e.g., 417c) in between that second node (of the first type) 416 (e.g., 416a) and the next second node (of the first type) 416 (e.g., 416c).

Extending from each of the second nodes (of the second type) 417 (e.g., 417a) is a sixth structural member 308 (e.g., 308a). Each sixth structural member 308 (e.g., 308a) extends proximally from a second node (of the second type) 417 (e.g., 417a) to the third node 438 (e.g., 438a) in axial alignment with that second node (of the second type) 417 (e.g., 417a). In this embodiment, there are three third nodes 438 total.

In this embodiment, the configuration described above is consistent for each of the first nodes 422, the second nodes 416, 417, the third nodes 438 the first structural members 418, the second structural members 420, the third structural members 319, the fourth structural members 410, the fifth structural members 412, and the sixth structural members 408.

Extending proximally from the third nodes 438 (e.g., 438a) are first connector positioning wires 406 (e.g., 406a). There is one first connector positioning wire 406 per third node 438, and thus there are three first connector positioning wires 406 total in this embodiment. Each first connector positioning wire 406 (e.g., 406a) has a stress relieving portion 414 (e.g., 414a) immediately proximal to the third node 438 (e.g., 438a) from which it extends. Each stress relieving portion 414 has two outwardly tangentially bowed elements (not separately referenced) that are similar but not exactly the same in shape to stress relieving portions 314 of anchor 300 (described hereinabove). In other embodiments, where present, the stress relieving portions 414 may be of any other appropriate shape or configuration, or may not be present at all.

Disposed at the proximal end of each of the broad connector positioning wires 408 (e.g., 408a) is a first connector 426 (e.g., 426). As will be described in further detail hereinbelow, each first connector 426 (e.g., 426a) is structured to be connectable to one of the sub-first-interconnectors 715 (e.g., 715a) of the device 700.

Each of the first connector positioning wires 406 is moveable between a secured position (that which is shown in FIG. 13) and a released position (that which is shown in FIG. 14). In the secured position the first connector positioning wires 406 are positioned in proximity to the central longitudinal axis 404 of the anchor 400, such that the first connector 426 (e.g., 426a) which is disposed on that first connector position wire 406 (e.g., 406a) is positioned with respect to a one of the sub-first-interconnectors 715 (e.g., 715a) to be releasably connectable thereto. The released position, the first connector positioning wires 406 are positioned generally in alignment with the periphery of the wire network 402 (away from the central longitudinal axis 404 of the anchor 400). The first connector wires 406 are overcomably biased towards the released position. The first connector wires can be maintained in the secured position by releasable connection of the first connectors 426 to the sub-first-interconnectors 715, as is described hereinbelow.

Assembly Fourth Embodiment—Anchor Fourth Embodiment—Configurations

The lumen wall anchor 400 has a compact-secured-configuration (FIG. 12), an expanded-secured-configuration (FIGS. 11 and 13), and an expanded-released configuration (FIG. 14).

Similar to the embodiments previously described hereinabove (see FIG. 15), when the lumen wall anchor 400 is in a compact-secured-configuration, the lumen wall anchor 400 is shaped and dimensioned to be deliverable to a delivery site within a lumen 904 of a body conduit 900 via a catheter (e.g., delivery sheath 950 in FIG. 15). Thus, when the lumen wall anchor 400 is in the compact-secured-configuration, the first connector positioning wires 406 are in their secured position (in the embodiment shown in FIG. 15 they are shown as being releasably connected to first interconnector 614). Further, the wire network 402 is in a compact form within the delivery sheath 950. See, for example, the WO '765 Publication for a detailed description of a transcatheter implantation technique.) When the lumen wall anchor 400 is in the compact-secured-configuration, it has a diameter of 22 French.

Referring to FIGS. 11, 13 and 19 when the lumen wall anchor 400 is in an expanded-secured-configuration, the wire network 402 is dimensioned and shaped to exert a force on the wall 902 of the lumen 904 of the conduit 900 (in FIG. 19, this is the wall 912 of the lumen 914 of the conduit model 910). This force is sufficient to anchor the assembly 1200 in place at the implantation site 908 (including during operation of the device 700) (in FIG. 19, implantation site 918). Further, as can be seen in FIG. 19, when the anchor 400 is in the expanded-secured-configuration, the first connector positioning wires 406 are in their secured position (and are shown in FIGS. 11 and 19) with the first connectors 426 being releasably connected to the first interconnector 714). When the lumen wall anchor 400 is in the expanded-secured-configuration, it has a diameter of about 24 mm and a length of about 6 cm.

The lumen wall anchor 400 is shown in an expanded-released-configuration in FIGS. 14 and 22 to 24. The wire network 402 remains dimensioned and shaped to exert a force on the wall 902 of the lumen 904 of the conduit 900 (in FIGS. 22 to 24, this is the wall 912 of the lumen 914 of the conduit model 910). This force is sufficient to anchor the anchor 400 in place at the implantation site 908 (in FIGS. 22 to 24, implantation site 918). When the anchor 400 is in the expanded-released-configuration, the first connector positioning wires 406 are in their released position, as their connectors 426 have been released from their connection with the first interconnector 714. In the released position, the ends of the first connector positioning wires 406 are proximate the wall 902 of the lumen 904 of the conduit 900, in line with the longitudinal axis 906 of body conduit 900 (in FIGS. 22 to 24, proximate the wall 912 of the lumen 914 of the conduit model 910, generally in line with the longitudinal axis 916 of the conduit model 910). In this configuration, the first connector positioning wires 406 do not obstruct fluid flow axially through the conduit 900 while the anchor 400 is anchored in place at the implantation site 908 with the device 700 having been retrieved and removed (e.g., explanted) from the body conduit 900 (See FIG. 23, wherein this principle is illustrated using conduit model 910.) When the lumen wall anchor 400 is in the expanded-released-configuration, it has a diameter of about 24 mm and a length of about 6 cm.

The lumen wall anchor 400 is based towards its expanded-released-configuration. In this embodiment, this bias is the case as the anchor 400 is made of nitinol (a shape-memory alloy) with the expanded-released-configuration being the "remembered shape" thereof. (The anchor 400 is manufacturable according to any conventional techniques appropriate to the material of which it is made, e.g., laser cutting.) As was described hereinabove, this bias can be overcome during normal usage of the assembly 1200. In particular, when the assembly 1200 is within the delivery sheath (not shown, but see FIG. 15 as an illustration of the principle with respect to a different embodiment, assembly 1100), the bias of the wire network 402 has been overcome (via its insertion into the delivery sheath, e.g., during manufacturing and assembling). As long as the assembly 1200 remains within the delivery sheath, the anchor 400 will remain in this compact configuration. In this embodiment, there is no other structure retaining the wire network 402 itself in a compact configuration. (Which is not the case in all embodiments, as will be described in further detail hereinbelow.) Thus, as the anchor 400 is caused to exit the delivery sheath (through the distal end thereof), at the delivery site (which, in this embodiment, is the implantation site 908) the wire network 402 will expand owing to its bias. The first connector positioning wires 406 will remain in their secured position, however, as the first connectors 426 remain releasably connected to sub-first-connectors of the first interconnector 714 of the device 700. Thus, when the anchor 400 has fully exited the delivery sheath, it will be in its expanded-secured-configuration, anchoring the assembly 1200 at the implantation site 908.

Assembly Fourth Embodiment—Implantation & Explantation

The implantation and explantation of the assembly 1200, and the explantation of the device 700 only, are the same as was previously described hereinabove with respect to the first embodiment, assembly 1100 (including device 600); as the present embodiment, assembly 1200 (including device 700 and anchor 400), was actually used in the description with respect to the first embodiment, assembly 1100. Thus, that description will not be repeated here again, for the sake of brevity.

Assembly Fourth Embodiment—Anchor Fourth Embodiment—First Connectors

Referring to FIGS. 12 to 14, in this embodiment, each first connector 426 (e.g., 426*a*) has an elongated element 432 (e.g., 432*a*) that is convexly curved (inward, towards the central longitudinal axis 404 of the anchor 400). Each element 432 (e.g., 432*a*) has two longitudinally spaced apart holes, a proximal hole 428 (e.g., 428*a*) and a distal hole 430 (e.g., 430*b*). Referring to FIG. 19, when the first connector positioning wires 406 (e.g., 406*a*) are in the secured position, the first connectors 426 (e.g., 426*a*), including their elements 432 (e.g., 432*a*) and holes 428, 430 (e.g., 428*a*, 430*a*) are shaped, sized, arranged, positioned and oriented to releasably connect to the sub-first-interconnectors 715 (e.g., 715*a*) of the first interconnector 714, as will be further described hereinbelow. In this embodiment, the aforementioned orientation of the first connectors 426 is such that they are oriented generally in line to the central longitudinal axis 404 of the anchor 400 (which itself is parallel to the central longitudinal axis 708 of the device 700 and the central longitudinal axis 1206 the assembly 1200).

Assembly Fourth Embodiment—Anchor Fourth Embodiment—First Interconnector

Referring to FIGS. 11 and 17 to 23, in this embodiment, the device 700 has a first interconnector 714 structured to releasably connect the device 700 with the anchor 400 to maintain the device 700 in place within a mammalian body conduit 900 at an implantation site 908 (including during operation of the device 700). The first interconnector 714 is located midway between the proximal end 710 and the distal end 712 of the docking unit 702 of the device 700. The first interconnector 714 has three sub-first-interconnectors 715 (e.g., 715*a*, 715*b*, 715*c*), with each one of the sub-first-interconnectors 715 being located on one of the three raised portions 776 (e.g., 776*a*) in between the receiving surfaces 774 (e.g., 774*a* and 774*b*) of the exterior surface 778 of the docking unit 702.

As the sub-first interconnectors 515 of the first interconnector 514 of the device 500 of assembly 1000 are identical to the sub-first-interconnectors 715 of the first interconnector 714 of the device 700 of the assembly 1200, the description of the sub-first-interconnectors 715 and the first interconnector 714 was set forth hereinabove in relation to device 500 (third embodiment). This description will not be repeated here again, for the sake of brevity.

Device Fifth Embodiment

Figure 25A:
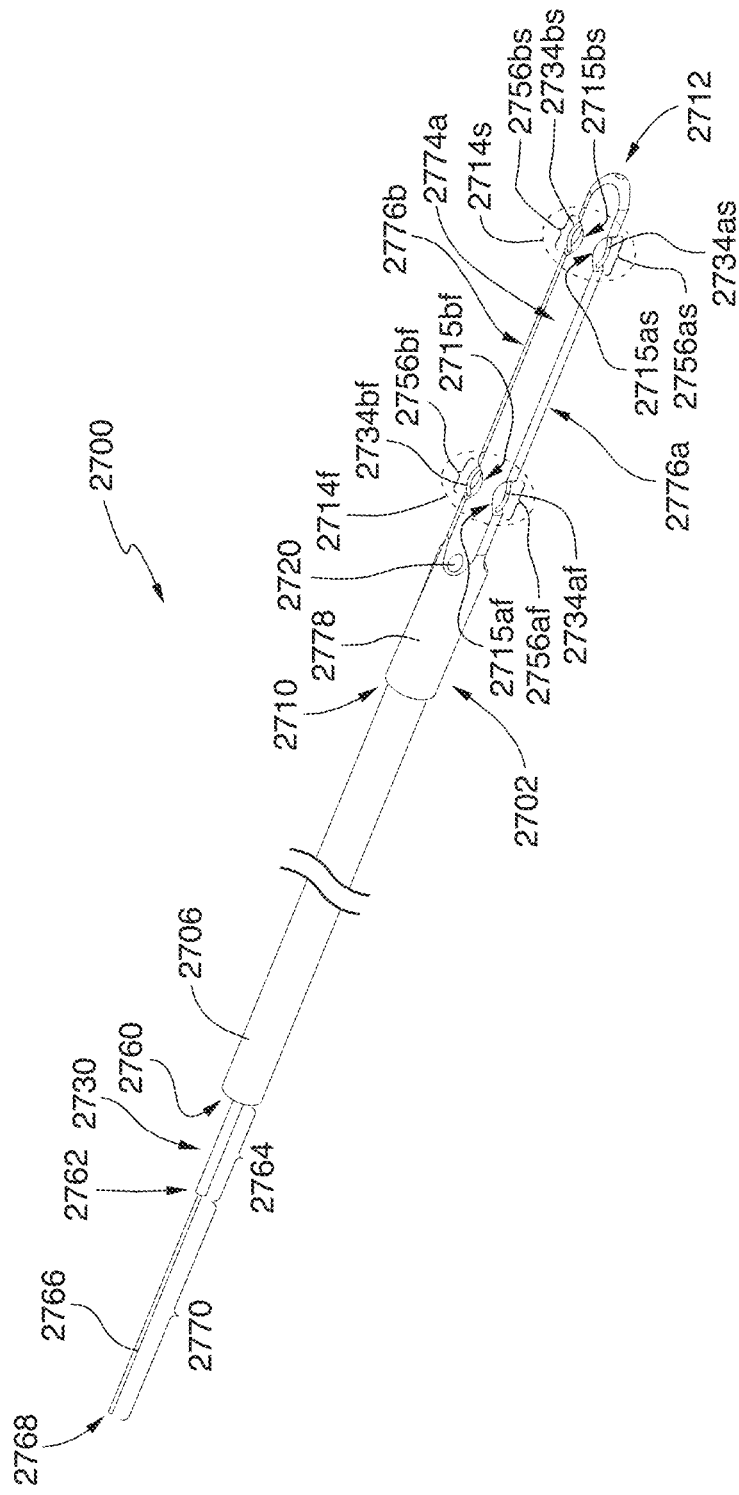
FIG. 25A shows a schematic of a fifth embodiment of a device of the present technology, shown without the pumping units of the device and with a cable housing attached to the proximal end of the device and wires exiting the proximal end of the cable housing. The device has a first interconnector and a second interconnector.
Figure 25B:
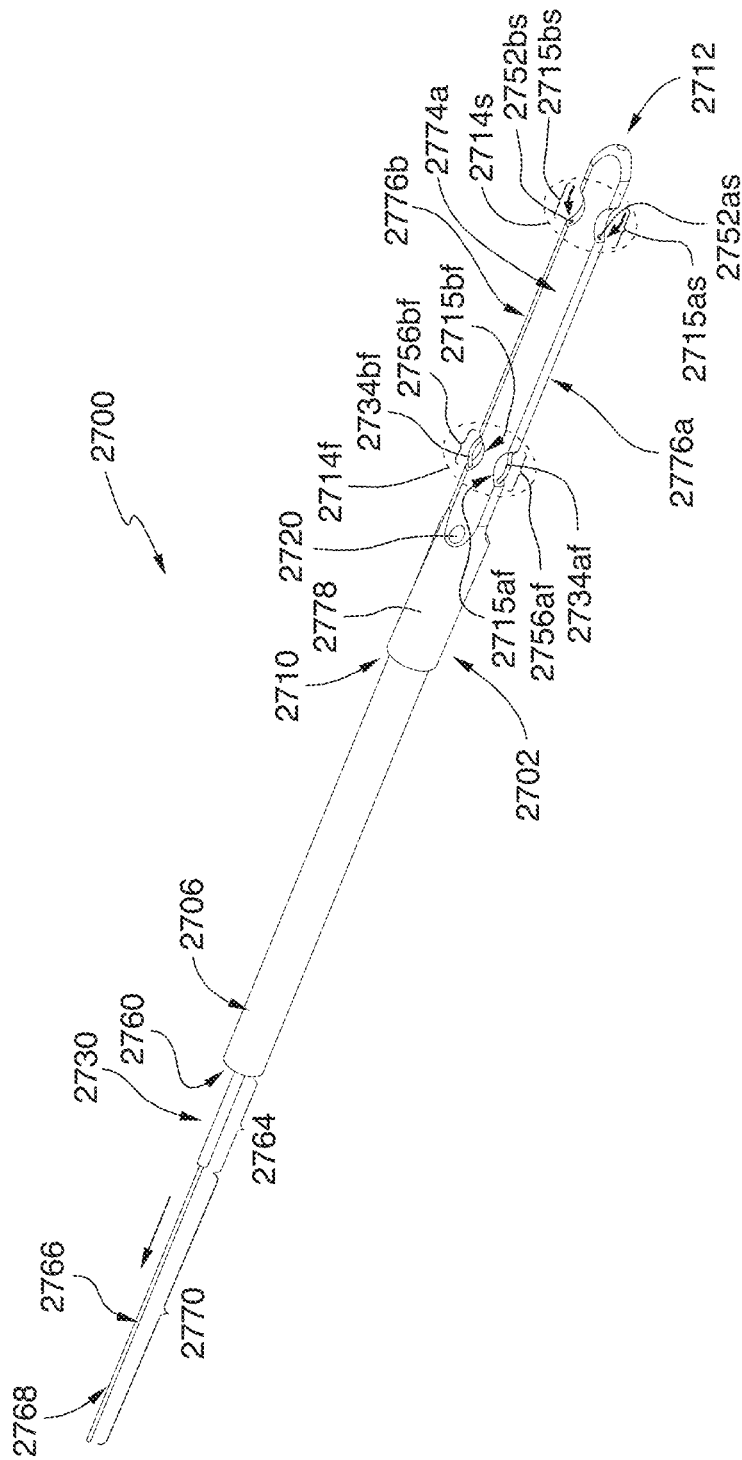
FIG. 25B shows the schematic of the device of FIG. 25A, with the second interconnector having been released.
Figure 25C:
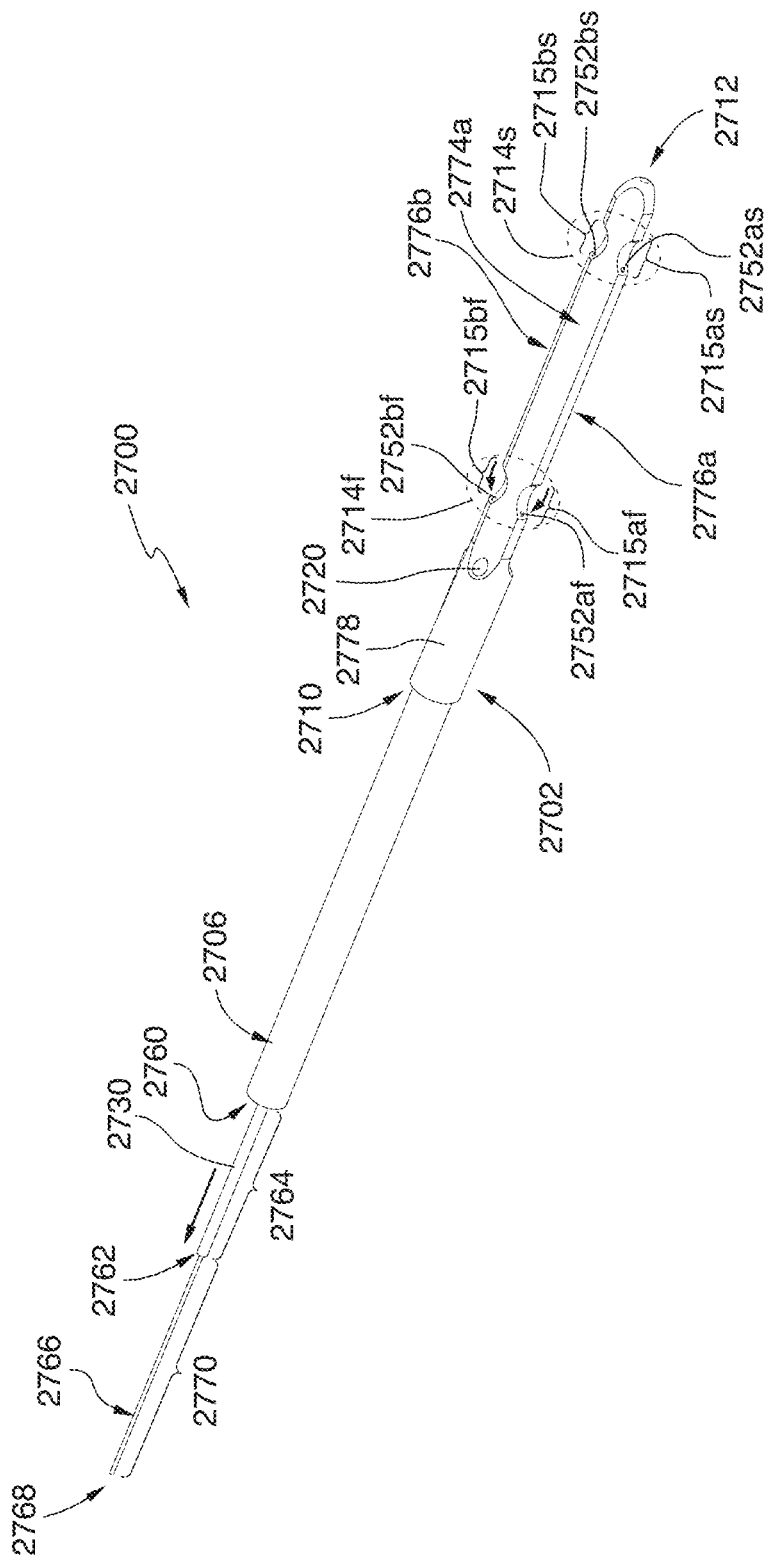
FIG. 25C shows the schematic of the device of FIG. 25A, with the first interconnector and the second interconnector having been released.

Referring to FIGS. 25A, 25B, and 25C, there is shown schematically a docking unit 2702 of a modular fluid pump as described in the WO '765 Publication, being a fifth embodiment of a device 2700 of the present technology. This device 2700 is similar to device 700 (fourth embodiment) described hereinabove, with the exception that the device 2700 has two interconnectors, a first (proximal) interconnector 2714*f* and a second (distal) interconnector 2714*s*. As will be described hereinbelow, each of these interconnectors 2714*f*, 2714*s* are similar to the interconnectors 714 of the device 700.

The device 2700 has a docking unit 2702 and three pumping units 2704 (none of which are shown in FIGS. 25A-C). The device 2700 has a proximal end 2710 and a distal end 2712. The proximal end 2710 and the distal end 2712 are defined consistently with the orientation in which the device 2700 is implanted. The device 2700 has a central longitudinal axis 2708 (not shown). A cable housing 2706 extends proximally from the proximal end 2710 of the device 2700. Within the cable housing 2706 are the various control and electrical wires (not shown) of the pumping units 2704 and the docking unit 2702 of the device 2700. (The WO '765 Publication provides a detailed description of some of such control wires and electrical wires, which is not repeated herein for the safe of brevity.) The proximal end 2760 of the cable housing 2706 is also shown in the Figs., the function of which will be described hereinbelow.

In this embodiment, the docking unit 2702 of the device 2700 has three receiving surfaces 2774 (one of which is shown in FIGS. 25A-25B, 2774*a*), each of which can receive therein one of the three pumping units 2704 of the device 2700. In between each of the receiving surfaces 2774 of the docking unit 2702 is a raised portion 2776 of the exterior surface 2778 of the docking unit 2702 (two of which, 2776a and 2776b, are shown in the Figs.). A first interconnector 2714f having three sub-first-interconnectors 2715xf (e.g., 2715af, 2715bf, etc.), one sub-first-interconnector 2715xf (e.g., 2715af, 2715bf, etc.) located on each of the three raised portions 2776 (e.g., 2776a, 2776b, etc.) of docking unit 2702, is present near the proximal end 2710 of the device 2700. A second interconnector 2714s having three sub-first-interconnectors 2715xs (2715as, 2715bs, etc.), one sub-first-interconnectors 2715xs (2715as, 2715bs, etc.) located on each of the three raised portions 2776 (e.g., 2776a, 2776b, etc.) of docking unit 2702, is present near the distal end 2712 of the device 2700.

Both the first interconnector 2714f and the second interconnector 2714s are similar (although not identical) in structure, function, and operation to interconnector 714 (fourth embodiment), as will be described in more detail hereinbelow. (The skilled address is also referred to the description of interconnector 714 hereinabove, the extent that any additional details are believed to be necessary.)

Referring to FIG. 25A, with respect to the second interconnector 2714s, each sub-second-interconnector 2715xs (e.g., 2715as) has a sub-second-interconnector wire 2734xs (e.g., 2734as), a portion 2756xs (e.g., 2756as) of which extends outside of the exterior 2778 of the docking unit 2702. Similarly, with respect to the first interconnector 2714f, each sub-first-interconnector 2715xf (e.g., 2715af) has a sub-first-interconnector wire 2734xf (e.g., 2734af) a portion of which 2756xf (e.g., 2756af) of which extends outside of the exterior 2778 of the docking unit 2702.

In this embodiment, the first interconnector actuation wire 2730 is hollow. As can be seen in FIG. 25A, a portion 2764 of the first interconnector actuation wire 2730 extends proximally past the proximal end 2760 of the cable housing 2706 of the docking unit 2702. A second interconnector actuation wire 2766 is moveably disposed within lumen of the hollow first interconnector actuation wire 2730. A portion 2770 of the second interconnector actuation wire 2766 extends proximally from the proximal end 2762 of the first interconnector actuation wire 2730 to the wire 2766's proximal end 2768.

Referring to FIG. 25B, in first instance, in order to release the sub-second-interconnectors 2715s of the second interconnector 2714s, the interventionist pulls the portion 2770 of the proximal end of the second interconnector actuation wire 2766 proximally (the direction shown in the arrow in FIG. 25B), while not pulling the first interconnector actuation wire 2730. Once the interventionist has pulled the proximal end portion 2770 of the second interconnector actuation wire 2766 by a sufficient length to cause the distal end of each of the sub-second-interconnector wires 2734s to enter the proximal opening 2752s of their sub-second-interconnector 2715s, release occurs (as was described hereinabove with respect to the first interconnector 714 (fourth embodiment)).

Referring to FIG. 25C, in a second instance, once the second interconnector 2714s has been released, in order to release the sub-first-interconnectors 2175f of the first interconnector 2714f, the interventionist pulls the portion 2764 of the proximal end of the first interconnector actuation wire 2730 proximally (the direction shown in the arrow in FIG. 25C). Once the interventionist has pulled the proximal end portion 2764 of the first interconnector actuation wire 2730 by a sufficient length to cause the distal end of each of the sub-first-interconnector wires 2734f to enter the proximal opening 2752f of their sub-first-interconnector 2715f, release occurs (as was described hereinabove with respect to the first interconnector 714 (fourth embodiment)).

Device Other Embodiments

While not shown in the figures, certain other embodiments described in the "Summary" hereinabove are similar to device 2700. In particular, the presence of and disposition of the various sub-first-interconnector wires, sub-second interconnector wires, and other wires operationally connected thereto are different in various embodiments, some of which may easily be described with reference to the device 2700.

As was noted above, in device 2700 the second interconnector actuation wire 2766 is disposed within a hollow cavity of the first interconnector actuation wire 2730. And, the first interconnector actuation wire 2730 is disposed within a longitudinally extending channel 2732.

In other embodiments, there may be two separate and distinct channels within the device, one for the first interconnector actuation wire and another for the second interconnector actuator wire.

In other embodiments, there may only be a single interconnector actuation wire that actuates both the first interconnector and the second interconnector. For example, that single actuation wire may first be pulled a first length to actuate the second interconnector, and may then be pulled a second length to actuate the first interconnector.

In other embodiments, each sub-first-interconnector and each sub-second-interconnector may have their own actuation wires. Those wires may be disposed with a single channel or multiple channels. The sub-second-interconnector wires may be disposed within hollow channels within the sub-first-interconnector actuation wires, may be separate.

In other embodiments, there may be one single actuation wire for a sub-first-interconnector/sub-second-interconnector wire pair; with as many actuation wires as there are pairs of sub-first-interconnectors and sub-second interconnectors. Those wires may be disposed within a single channel or multiple channels.

The list of possible embodiments set forth above is intended to be illustrative and exemplary, not exhaustive; other embodiments not listed hereinabove are possible.

Assembly Fifth Embodiment

Figure 26:
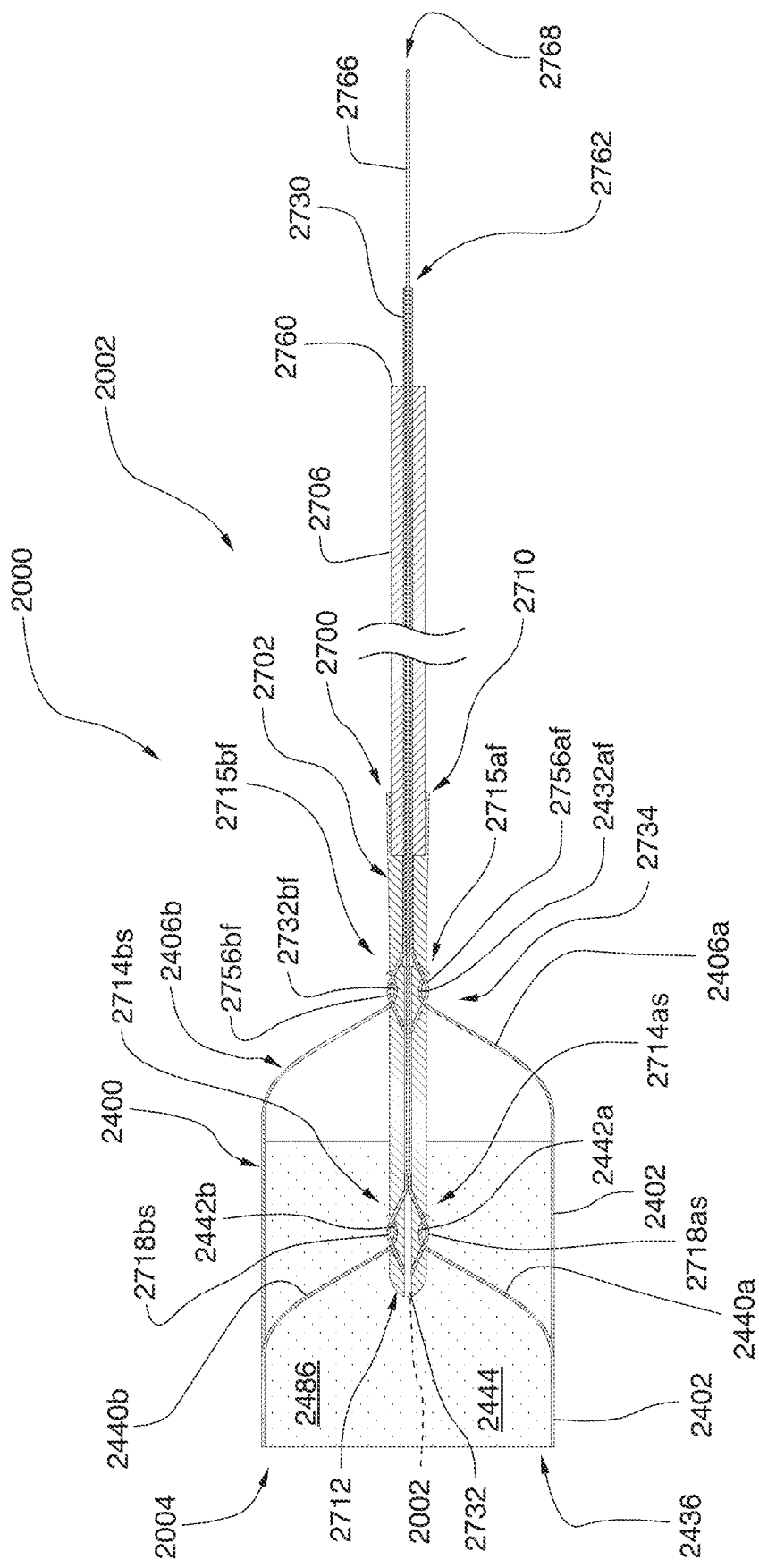
FIG. 26 shows a schematic of the device of FIG. 25A, in conjunction with a fifth embodiment of an anchor of the present invention. The anchor has a set of first connectors connected to the first interconnector of the device and a set of second connectors connected to the second interconnector of the device. The anchor is in its expanded-secured-configuration.
Figure 27:
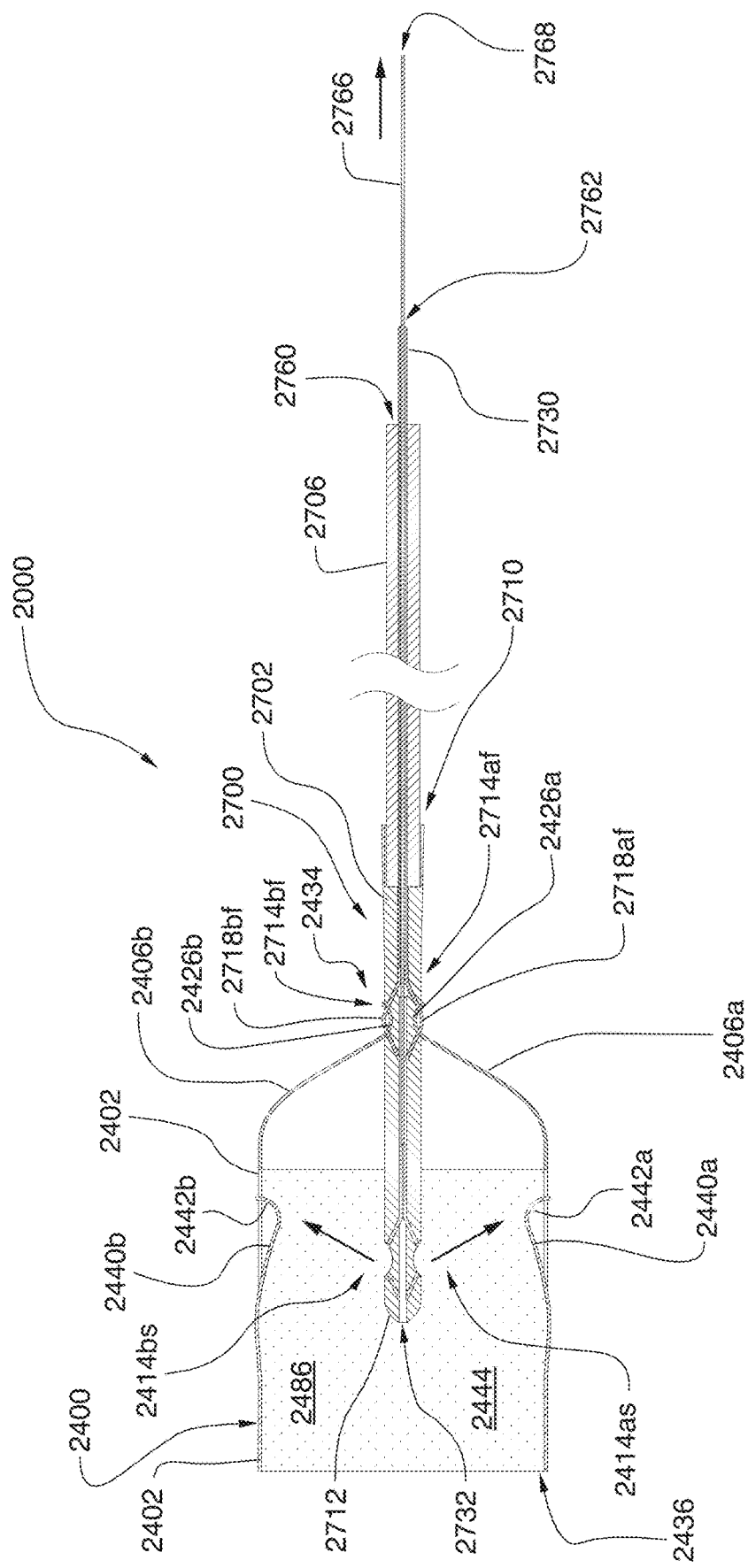
FIG. 27 shows a schematic of the device and anchor of FIG. 26, with the second set of connectors having been released from the second interconnector of the device. The first set of connectors are connected to the first interconnector of the device. The anchor is an unnamed configuration between the expanded-secured-configuration and the expanded-released-configuration.
Figure 28:
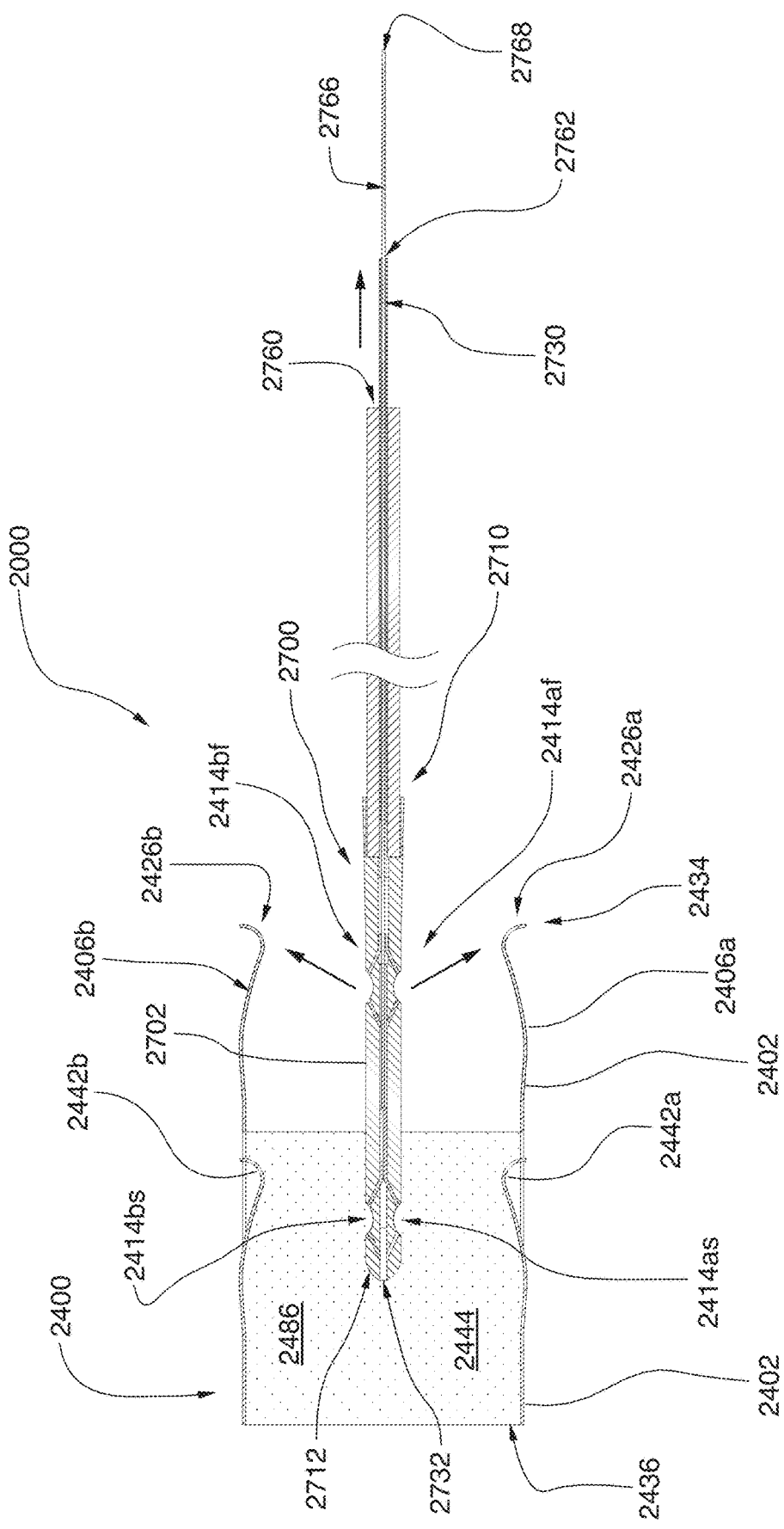
FIG. 28 shows a schematic of the device and anchor of FIG. 26, with both the first set of connectors having been released from the first interconnector of the device, and the second set of connectors having been released from the second interconnector of the device. The anchor is in its expanded-released-configuration.

Referring to FIGS. 26 to 28, there is shown a mammalian body conduit intralumenal device and lumen wall anchor assembly 2000 being a fifth embodiment of an assembly of the present technology. The assembly 2000 has a proximal end 2002 and a distal end 2004 defined consistently with the orientation in which the assembly 2000 is implanted. The assembly 2000 has a central longitudinal axis 2006. The assembly 2000 includes a mammalian body conduit intralumenal device 2700, described hereinabove, and a lumen wall anchor 2400, which is discussed in turn hereinbelow.

Assembly Fifth Embodiment—Anchor Fifth Embodiment

Referring to FIGS. 26 to 28, there is shown schematics of an anchor 2400 being a fifth embodiment of the present technology. The anchor 2400 and the implantation, explantation and use thereof is similar to anchor 400 except as described hereinbelow. The anchor 2400 is suitable for use with the device 2700 described above.

Referring to FIG. 26, the anchor 2400 has a set of first (proximal) connector positioning wires 2406xf (e.g., 2406af) each of which has a first connector 2426xf (e.g., 2426af) disposed at the end thereof. Each of the first connector positioning wires 2406xf (e.g., 2406af) is in its secured position, with the first connector 2426xf (e.g., 2426af) thereof being releasably connected to one of the sub-first-interconnectors 2715xf of the first interconnector 2714f. The anchor 2400 also a set of second (distal) positioning wires 2406xs (e.g., 2406as) extending from the wire network 2402 thereof. Each second connector positioning wire 2406xs (e.g., 2406as) has a second connector 2426xs (e.g., 2426as) disposed at the end of thereof. Each of the second connector positioning wires 2406xs (e.g., 2406as) is in its secured position, with the second connector 2426xs (e.g., 2426as) thereof being releasably connected to one of the sub-second-interconnectors 2715xs of the second interconnector 2714s. The anchor 2400 is in its expanded-secured-configuration.

Figure 26A:
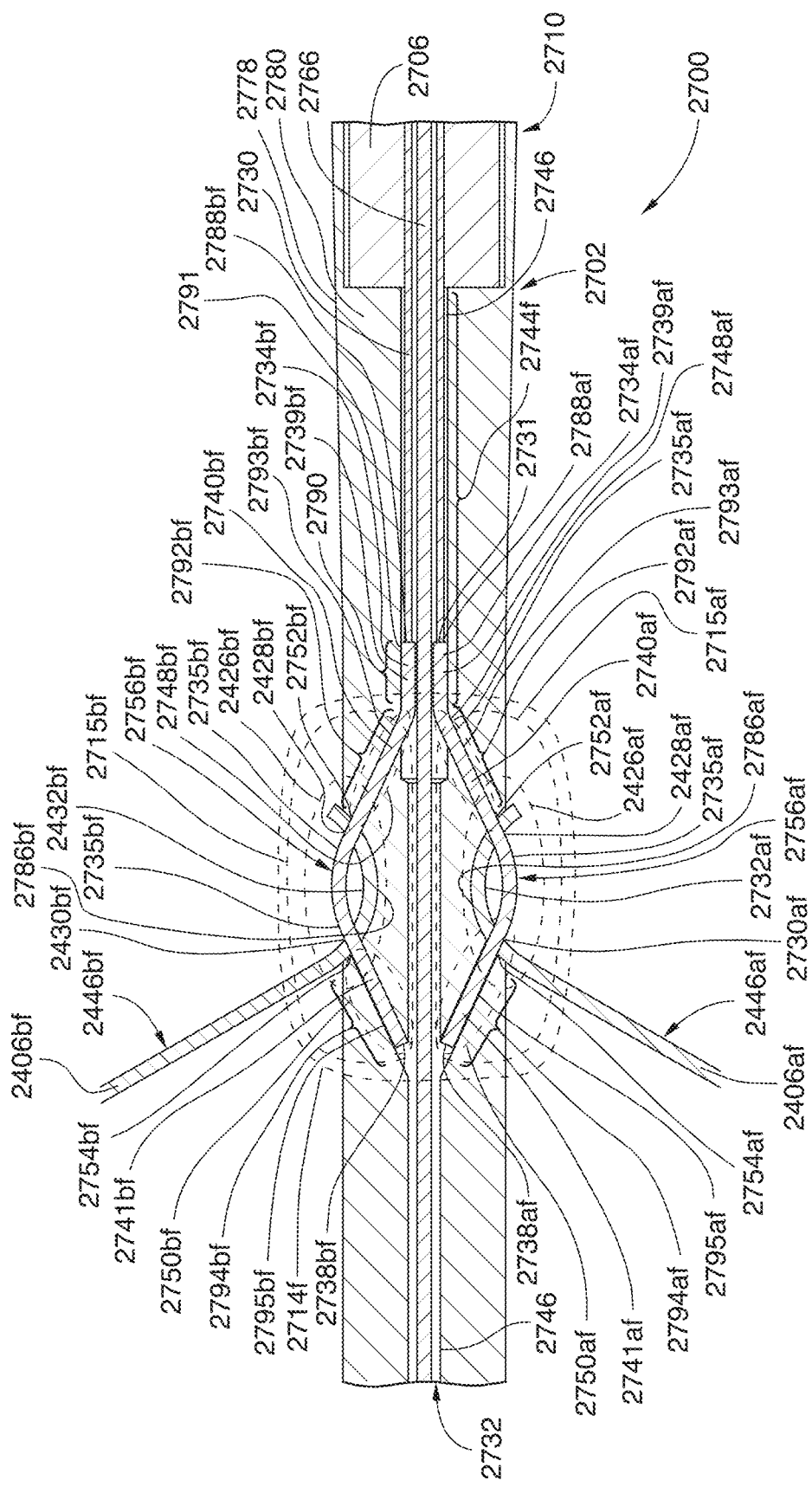
FIG. 26A shows a close-up of the first interconnector of the device and the first connector positioning wires of FIG. 26.

Referring now to FIGS. 26 and 26A, each sub-first-interconnector 2715xf (e.g., 2715bf) is a concavity 2786rf (e.g., 2786bf) in one of the raised portions 2776xf (e.g., 2776bf) between the receiving surfaces 2774 (e.g., 2774b) of the docking unit 2702. Each concavity 2786xf extends from the exterior surface 2778 inward within the body 2780 of the device 2700 towards the central longitudinal axis 2708 of the device 2700.

Two sub-first-interconnectors 2715xf (e.g., 2715af, 2715bf) are shown schematically. Each concavity 2786xf (e.g., 2786bf) has two openings therein, a proximal opening 2752xf (e.g., 2752bf) and a distal opening 2754xf (e.g., 2754bf). A central longitudinal channel 2732 extends from the proximal end 2710 of the docking unit 2702 longitudinally along the central longitudinal axis 2708 within the body 2780 of the docking unit 2702. A first branch channel 2748xf(e.g., 2748bf) connects the central longitudinal channel 2732 with the proximal opening 2752rf (e.g., 2752bf) of the concavity 2786xf (e.g., 2786bf). A second branch channel 2750xf (e.g., 2750bf) connects the distal opening 2754xf (e.g., 2754bf) with the central longitudinal channel 2732. Each sub-first-interconnector 2715xf (e.g., 2715bf) has a sub-first-interconnector wire 2734xf (e.g., 2734bf). In this embodiment, each sub-first-interconnector wire 2734xf(e.g., 2734bf) has a proximal end 2788xf (e.g., 2788bf) attached to the distal end 2731 of the first interconnector actuation wire 2730. A first portion 2739xf (e.g., 2739bf) of the sub-first-interconnector wire 2734xf (e.g., 2734bf) extends within the proximal portion 2744f of the channel 732 to the first branch channel 2748xf (e.g., 2748bf). A second portion 2740xf of the sub-first-interconnector wire 2734xf(e.g., 2734bs) extends within the first branch channel 2748xf (e.g., 2748bf) from the channel 2732 to the proximal opening 2752xf (e.g., 2752bf) of the concavity 2786xf (e.g., 2786bf) of the sub-first-interconnector 2715xf (e.g., 2715bf) and exits the body 2780 of the docking unit 2702 through that proximal opening 2752xf (e.g., 2752bf).

The first connector positioning wires 2406 (e.g., 2406b) are in their secured position (FIG. 27A, 27B, 27D) and thus the connector elements 2432xf (e.g., 2432bf) of the first connectors 2426xf (e.g., 2426bf) register with the concavities 2786xf (e.g., 2786bf) of the sub-first-interconnectors 2715xf (e.g., 2715bf) of the first interconnector 2714f. The proximal hole 2428xf (e.g., 2428bf) of the connector element 2432xf (e.g., 2432bf) is aligned with the proximal opening 2752rf (e.g., 2752bf) of the concavity 2786xf (e.g., 2786bf), and the distal hole 2430xf (e.g., 2430bf) of the connector element 2432rf (e.g., 2432b) is aligned with the distal opening 2754xf (e.g., 2754bf) of the concavity 2786xf (e.g., 2786bf). Thus, sub-first-interconnector wire 2734xf(e.g., 734b) immediately after exiting the body 2780 of the docking unit 2702 passes through the proximal hole 2428xf (e.g., 2428bf) in the connector element 2432xf (e.g., 2432bf). Next, a third portion 2756xf(e.g., 2756bf) of the sub-first-interconnector wire 2734xf (e.g., 2734bf) passes outside the body 2780 of the docking unit 2702 from the proximal hole 2728xf (e.g., 2728bf) in the connector element 2432rf (e.g., 432bf) to the distal hole 2430xf (e.g., 2430bf) in the connector element 2732rf (e.g., 2732bf). The sub-first-connector wire 2734xf (e.g., 2734bf) then passes through the distal hole 2430xf (e.g., 2430bf) and immediately re-enters the body 2780 of the docking unit 2702 through the distal opening 7254xf (e.g., 2754b) of the concavity 2786xf (e.g., 2786bf). Finally, a fourth portion 2741xf (e.g., 2741bf) of the sub-first-interconnector wire 2734xf (e.g., 2734bf) extends within the second branch channel 2750xf (e.g., 2750bf) from the distal opening 2754xf (e.g., 2754bf) to the channel 2732.

The bias of the first connector positioning wires 2406xf towards their released position is overcome and the first connector positioning wires 2406xf are maintained in their secured position, by frictional forces between the walls of the various channels 2732, 2748xf, 2750xf and their abutment by the various sub-first-interconnector wires 2734xf and first connector actuation wire 2730. In particular, the exterior surfaces 2735xf (e.g., 2735bf) of the sub-first-connector wires 2734xf (e.g., 2734bf) abut the interior wall 2791 of the portion 2790 of the channel 2732. The exterior surfaces 2735xf (e.g., 2735bf) of the sub-first-connector wires 2734xf (e.g., 2734bf) abut the interior wall 2793xf (e.g., 2793bf) of the portion 2792rf (e.g., 2792bf) of first branch channel 2748xf (e.g., 2748bf). The exterior surfaces 2735xf (e.g., 2735bf) of the sub-first-connector wires 2734xf (e.g., 2734bf) abut the interior wall 2795xf (e.g., 2795bf) of the portion 2794xf (e.g., 2794bf) of second branch channel 2750xf (e.g., 2750bf).

Figure 26B:
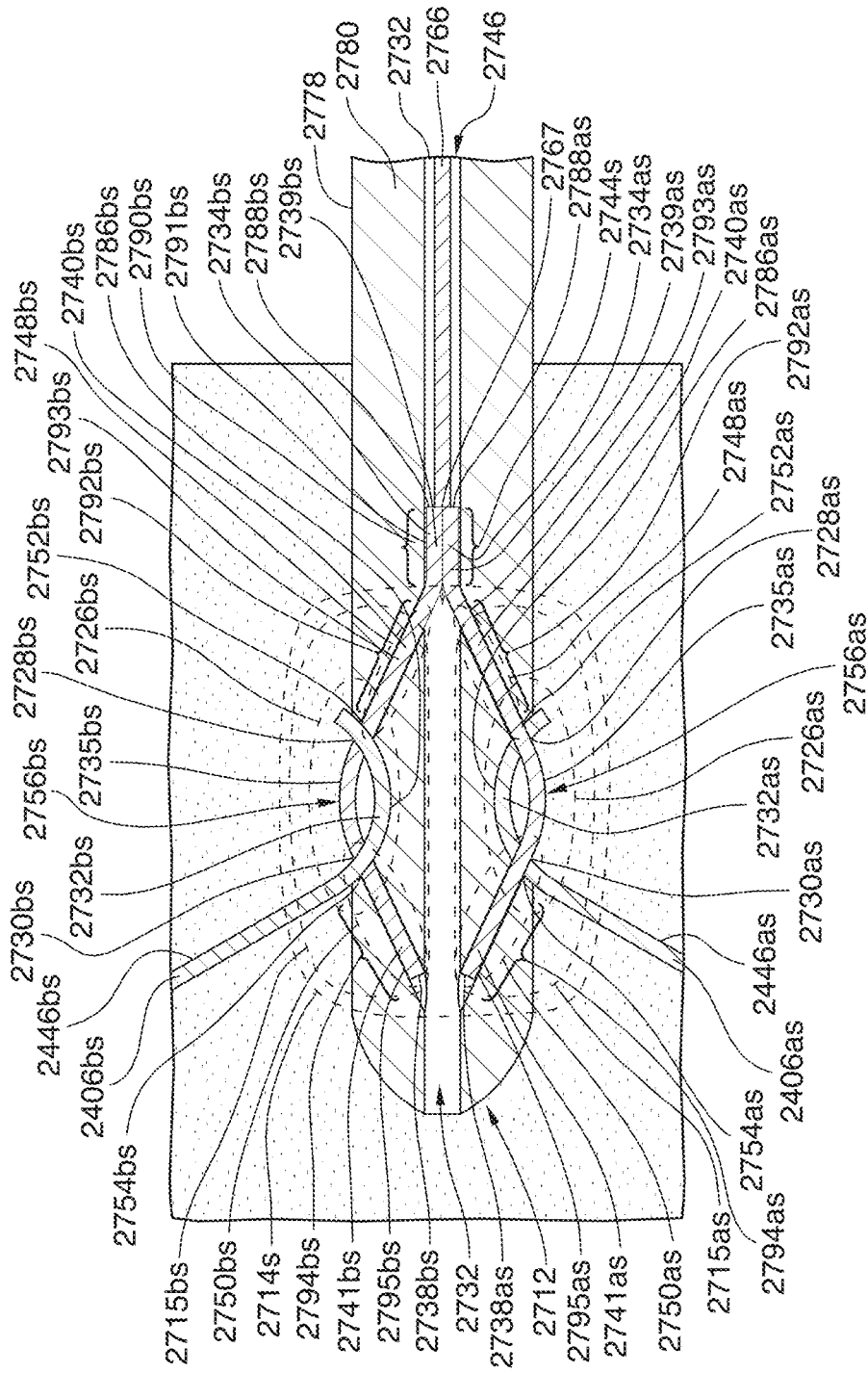
FIG. 26B shows a close-up of the second interconnector of the device and the second connector positioning wires of FIG. 26.

Referring to FIGS. 26 and 26B, each sub-first-interconnector 2715xf (e.g., 2715bf) is a concavity 2786xf (e.g., 2786bf) in one of the raised portions 2776xf (e.g., 2776bf) between the receiving surfaces 2774 (e.g., 2774b) of the docking unit 2702. Each concavity 2786xf extends from the exterior surface 2778 inward within the body 2780 of the device 2700 towards the central longitudinal axis 2708 of the device 2700.

Two sub-first-interconnectors 2715xf (e.g., 2715af, 2715bf) are shown schematically. Each concavity 2786xf (e.g., 2786bf) has two openings therein, a proximal opening 2752xf (e.g., 2752bf) and a distal opening 2754xf (e.g., 2754bf). A central longitudinal channel 2732 extends from the proximal end 2710 of the docking unit 2702 longitudinally along the central longitudinal axis 2708 within the body 2780 of the docking unit 2702. A first branch channel 2748xf(e.g., 2748bf) connects the central longitudinal channel 2732 with the proximal opening 2752xf (e.g., 2752bf) of the concavity 2786xf (e.g., 2786bf). A second branch channel 2750xf (e.g., 2750bf) connects the distal opening 2754xf (e.g., 2754bf) with the central longitudinal channel 2732. Each sub-first-interconnector 2715xf (e.g., 2715bf) has a sub-first-interconnector wire 2734xf (e.g., 2734bf). In this embodiment, each sub-first-interconnector wire 2734xf(e.g., 2734bf) has a proximal end 2788xf (e.g., 2788bf) attached to the distal end 2731 of the first interconnector actuation wire 2730. A first portion 2739xf (e.g., 2739bf) of the sub-first-interconnector wire 2734xf (e.g., 2734bf) extends within the proximal portion 2744f of the channel 2732 from to the first branch channel 2748xf (e.g., 2748bf). A second portion 2740xf of the sub-first-interconnector wire 2734xf (e.g., 2734bs) extends within the first branch channel 2748xf (e.g., 2748bf) from the channel 2732 to the proximal opening 2752xf (e.g., 2752bf) of the concavity 2786xf (e.g., 2786bf) of the sub-first-interconnector 2715xf (e.g., 2715bf) and exits the body 2780 of the docking unit 2702 through that proximal opening 2752 (e.g., 2752bf).

The first connector positioning wires 2406 (e.g., 406b) are in their secured position (FIG. 27A, 27B, 27D) and thus the connector elements 2432xf (e.g., 2432bf) of the first connectors 2426xf (e.g., 2426bf) register with the concavities 2786xf (e.g., 2786bf) of the sub-first-interconnectors 2715xf (e.g., 2715bf) of the first interconnector 2714f. The proximal hole 2428xf (e.g., 2428bf) of the connector element 2432xf (e.g., 2432bf) is aligned with the proximal opening 2752xf (e.g., 2752bf) of the concavity 2786xf (e.g., 2786bf), and the distal hole 2430xf (e.g., 2430bf) of the connector element 2432xf (e.g., 2432b) is aligned with the distal opening 2754xf (e.g., 2754bf) of the concavity 2786xf (e.g., 2786bf). Thus, sub-first-interconnector wire 2734xf (e.g., 734b) immediately after exiting the body 2780 of the docking unit 2702 passes through the proximal hole 2428xf (e.g., 2428bf) in the connector element 2432xf (e.g., 2432bf). Next, a third portion 2756xf (e.g., 2756bf) of the sub-first-interconnector wire 2734xf (e.g., 2734bf) passes outside the body 2780 of the docking unit 2702 from the proximal hole 2728xf (e.g., 2728bf) in the connector element 2432xf (e.g., 2432bf) to the distal hole 2430xf (e.g., 2430bf) in the connector element 2732xf (e.g., 2732bf). The sub-first-connector wire 2734xf (e.g., 2734bf) then passes through the distal hole 2430xf (e.g., 2430bf) and immediately re-enters the body 2780 of the docking unit 2702 through the distal opening 2754xf (e.g., 2754bf) of the concavity 2786xf (e.g., 2786bf). Finally, a fourth portion 2741xf (e.g., 2741bf) of the sub-first-interconnector wire 2734xf (e.g., 2734bf) extends within the second branch channel 2750xf (e.g., 2750bf) from the distal opening 2754xf (e.g., 2754bf) to the channel 2732.

The bias of the first connector positioning wires 2406xf towards their released position is overcome and the first connector positioning wires 2406xf are maintained in their secured position, by frictional forces between the walls of the various channels 2732, 2748xf, 2750xf and their abutment by the various sub-first-interconnector wires 2734xf and first connector actuation wire 2730. In particular, the exterior surfaces 2735xf (e.g., 2735bf) of the sub-first-connector wires 2734xf (e.g., 2734bf) abut the interior wall 2791 of the portion 2790 of the channel 2732. The exterior surfaces 2735xf (e.g., 2735bf) of the sub-first-connector wires 2734xf (e.g., 2734bf) abut the interior wall 2793xf (e.g., 2793bf) of the portion 2792xf (e.g., 2792bf) of first branch channel 2748xf (e.g., 2748bf). The exterior surfaces 2735xf (e.g., 2735bf) of the sub-first-connector wires 2734xf (e.g., 2734bf) abut the interior wall 2795xf (e.g., 2795bf) of the portion 2794xf (e.g., 2794bf) of second branch channel 2750xf (e.g., 2750bf).

Referring now to FIG. 26B, each sub-second-interconnector 2715xs (e.g., 2715bs) is a concavity 2786xs (e.g., 2786bs) in one of the raised portions 2776xs (e.g., 2776bs) between the receiving surfaces 2774 (e.g., 2774b) of the docking unit 2702. Each concavity 2786xs extends from the exterior surface 2778 inward within the body 2780 of the device 2700 towards the central longitudinal axis 2708 of the device 2700.

Two sub-second-interconnectors 2715xs (e.g., 2715as, 2715bs) are shown schematically. Each concavity 2786xs (e.g., 2786bs) has two openings therein, a proximal opening 2752xs (e.g., 2752bs) and a distal opening 2754xs (e.g., 2754bs). A central longitudinal channel 2732 extends from the proximal end 2710 of the docking unit 2702 longitudinally along the central longitudinal axis 2708 within the body 2780 of the docking unit 2702. A first branch channel 2748xs (e.g., 2748bs) connects the central longitudinal channel 2732 with the proximal opening 2752xs (e.g., 2752bs) of the concavity 2786xs (e.g., 2786bs). A second branch channel 2750xs (e.g., 2750bs) connects the distal opening 2754xs (e.g., 2754bs) with the central longitudinal channel 2732. Each sub-second-interconnector 2715xs (e.g., 2715bs) has a sub-second-interconnector wire 2734xs (e.g., 2734bs). In this embodiment, each sub-second-interconnector wire 2734xs (e.g., 2734bs) has a proximal end 2788xs (e.g., 2788bs) attached to the distal end 2731 of the second interconnector actuation wire 2730. A first portion 2739xs (e.g., 2739bs) of the sub-second-interconnector wire 2734xs (e.g., 2734bs) extends within the proximal portion 2744s of the channel 732s to the first branch channel 2748xs (e.g., 2748bs). A second portion 2740xs of the sub-second-interconnector wire 2734xs (e.g., 2734bs) extends within the first branch channel 2748xs (e.g., 2748bs) from the channel 2732 to the proximal opening 2752xs (e.g., 2752bs) of the concavity 2786xs (e.g., 2786bs) of the sub-second-interconnector 2715xs (e.g., 2715bs) and exits the body 2780 of the docking unit 2702 through that proximal opening 2752rs (e.g., 2752bs).

The second connector positioning wires 2406xs (e.g., 2406bs) are in their secured position (FIG. 27E) and thus the connector elements 2432rs (e.g., 2432bs) of the second connectors 2426xs (e.g., 2426bs) register with the concavities 2786xs (e.g., 2786bs) of the sub-second-interconnectors 2715xs (e.g., 2715bs) of the second interconnector 2714s. The proximal hole 2428xs (e.g., 2428bs) of the connector element 2432rs (e.g., 2432bs) is aligned with the proximal opening 2752rs (e.g., 2752bs) of the concavity 2786xs (e.g., 2786bs), and the distal hole 2430xs (e.g., 2430bs) of the connector element 2432rs (e.g., 2432b) is aligned with the distal opening 2754xs (e.g., 2754bs) of the concavity 2786xs (e.g., 2786bs). Thus, sub-second-interconnector wire 2734xs (e.g., 2734bs) immediately after exiting the body 2780 of the docking unit 2702 passes through the proximal hole 2428xs (e.g., 2428bs) in the connector element 2432xs (e.g., 2432bs). Next, a third portion 2756xs (e.g., 2756bs) of the sub-second-interconnector wire 2734xs (e.g., 2734bs) passes outside the body 2780 of the docking unit 2702 from the proximal hole 2728xs (e.g., 2728bs) in the connector element 2432rs (e.g., 2432bs) to the distal hole 2430xs (e.g., 2430bs) in the connector element 2732rs (e.g., 2732bs). The sub-second-connector wire 2734xs (e.g., 2734bs) then passes through the distal hole 2430xs (e.g., 2430bs) and immediately re-enters the body 2780 of the docking unit 2702 through the distal opening 2754xs (e.g., 2754bs) of the concavity 2786xs (e.g., 2786bs). Finally, a fourth portion 2741xs (e.g., 2741bs) of the sub-second-interconnector wire 2734xs (e.g., 2734bs) extends within the second branch channel 2750xs (e.g., 2750bs) from the distal opening 2754xs (e.g., 2754bs) to the channel 2732.

The bias of the second connector positioning wires 2406xs towards their released position is overcome and the second connector positioning wires 2406xs are maintained in their secured position, by frictional forces between the walls of the various channels 2732, 2748xs, 2750xs and their abutment by the various sub-second-interconnector wires 2734xs and second connector actuation wire 2730. In particular, the exterior surfaces 2735xs (e.g., 2735bs) of the sub-second-connector wires 2734xs (e.g., 2734bs) abut the interior wall 2791 of the portion 2790 of the channel 2732. The exterior surfaces 2735xs (e.g., 2735bs) of the sub-second-connector wires 2734xs (e.g., 2734bs) abut the interior wall 2793xs (e.g., 2793bs) of the portion 2792rs (e.g., 2792bs) of second branch channel 2748xs (e.g., 2748bs). The exterior surfaces 2735xs (e.g., 2735bs) of the sub-second-connector wires 2734xs (e.g., 2734bs) abut the interior wall 2795xs (e.g., 2795bs) of the portion 2794xs (e.g., 2794bs) of second branch channel 2750xs (e.g., 2750bs).

During an explantation of the device 2700 alone leaving the anchor 2400 to remain within the lumen of the conduit, each of the first connectors 2426xf are released from their connection to the first interconnector 2714f and each of the second connectors 2426xs are released from their connection to the first interconnector 2714s, as was generally described hereinabove with reference to FIGS. 25B and 25C.

In more detail, in this embodiment, referring to FIG. 27 this occurs in the following manner: The interventionist pulls the second connector actuation wire 2766 that is attached to the proximal end 2788xs of the sub-second-interconnectors 2734xs (e.g., 2734bs) (or causes to be it to be pulled). This pulling movement (with a sufficient force) overcomes frictional forces (described hereinabove) between the walls (e.g., 2746xs, 2791xs, 2793xs, 2795xs) of the various channels described above (e.g., 2732, 2748xs, 2750xs) and their abutment by the various sub-second-interconnector wires 2734xs (e.g., 2734bs) and second connector actuation wire 2766; thus moving the sub-second-interconnector wires 2734xs and the second connector actuation wire 2766 proximally (direction of movement shown by the arrows in FIG. 27). After the second connector actuation wire 2766 has been pulled a sufficient length, the distal ends 2738xs (e.g., 2738bs) of the sub-second-interconnector wires 2734xs (e.g., 2734bs) pass first through the distal opening 2754xs (e.g., 2754bs) in the concavity 2786xs (e.g., 2786bs), then through the distal hole 2430xs (e.g., 2430bs) in the connector element 2432xs (e.g., 2432bs), then through the proximal hole 2428xs (e.g., 2428bs) in the connector element 2432xs (e.g., 2432bs), then through the proximal opening 2752xs (e.g., 2752bs) in the concavity 2786xs (e.g., 2786bs) of the sub-second-connector 2715xs (e.g., 2715bs), and finally into the first branch channel 2748xs (e.g., 2748bs).

Removing the sub-second-interconnector wire 2734xs (e.g., 2734bs) from the passing through the two holes 2428xs, 2430xs (e.g., 2428bs, 2430bs) in the second connector element 2432xs (e.g., 2732bs), releases the connection between the second connector 2426xs (e.g., 2426bs) and the sub-second-interconnector wire 2734xs (e.g., 2734bs). Thus, the bias of the second connector positioning wire 2406xs (e.g., 2406bs) is no longer overcome, and the second connector positioning wire 2406xs (e.g., 2406bs) moves to its released position. In this embodiment, as all of the sub-second-interconnector wires 2734xs are connected to the distal end 2767 of the second connector actuation wire 2766, the sub-second-interconnector wires 2734xs all move in synchronicity. Thus, each of the second connectors 2426xs are simultaneously released, and the second connector positioning wires 2406xs all simultaneously move toward their released positions.

Referring now to FIG. 28, the interventionist next pulls the first connector actuation wire 2730 that is attached to the proximal end 2788xf of the sub-first-interconnectors 2734xf (e.g., 2734bf) (or causes to be it to be pulled). This pulling movement (with a sufficient force) overcomes frictional forces (described hereinabove) between the walls (e.g., 2746xf, 2791xf, 2793xf, 2795xf) of the various channels described above (e.g., 2732, 2748xf, 2750xf) and their abutment by the various sub-first-interconnector wires 2734xf (e.g., 2734bf) and first connector actuation wire 2730; thus moving the sub-first-interconnector wires 2734xf and the first connector actuation wire 2730 proximally (direction of movement shown by the arrows in FIG. 28). After the first connector actuation wire 2730 has been pulled a sufficient length, the distal ends 2738xf (e.g., 2738bf) of the sub-first-interconnector wires 2734xf (e.g., 2734bf) pass first through the distal opening 2754xf (e.g., 2754bf) in the concavity 2786xf (e.g., 2786bf), then through the distal hole 2430xf (e.g., 2430bf) in the connector element 2432xf (e.g., 2432bf), then through the proximal hole 2428xf (e.g., 2428bf) in the connector element 2432xf (e.g., 2432bf), then through the proximal opening 2752xf (e.g., 2752bf) in the concavity 2786xf (e.g., 2786bf) of the sub-first-connector 2715xf (e.g., 2715bf), and finally into the first branch channel 2748xf (e.g., 2748bf).

Removing the sub-first-interconnector wire 2734xf (e.g., 2734bf) from the passing through the two holes 2428xf, 2430xf (e.g., 2428bf, 2430bf) in the first connector element 2432xf (e.g., 2732bf), releases the connection between the first connector 2426xf (e.g., 2426bf) and the sub-first-interconnector wire 2734xf (e.g., 2734bf). Thus, the bias of the first connector positioning wire 2406xf (e.g., 2406bf) is no longer overcome, and the first connector positioning wire 2406xf (e.g., 2406bf) moves to its released position. In this embodiment, as all of the sub-first-interconnector wires 2734xf are connected to the distal end 2731 of the first connector actuation wire 2730, the sub-first-interconnector wires 2734xf all move in synchronicity. Thus, each of the first connectors 2426xf are simultaneously released, and the first connector positioning wires 2406xf all simultaneously move toward their released positions. The anchor 2400 thus adopts its expanded-released-configuration, allowing for retrieval of the device 2700 as was described hereinabove.

In this embodiment, the anchor 2400 is made of Nitinol, with a portion 2486 of the wire network 2402 being covered in polytetrafluoroethylene (PTFE) sheet. In other embodiments, the covering may be formed from any appropriate compatible material, e.g., knitted polyester. When the lumen wall anchor 2400 is in the compact-secured-configuration, it has a diameter of 22 French. When the lumen wall anchor 2400 is in the expanded-secured-configuration and in the expanded-released-configuration, it has a diameter of about 24 mm and a length of up to about 20 cm.

Assembly Sixth Embodiment

Figure 29:
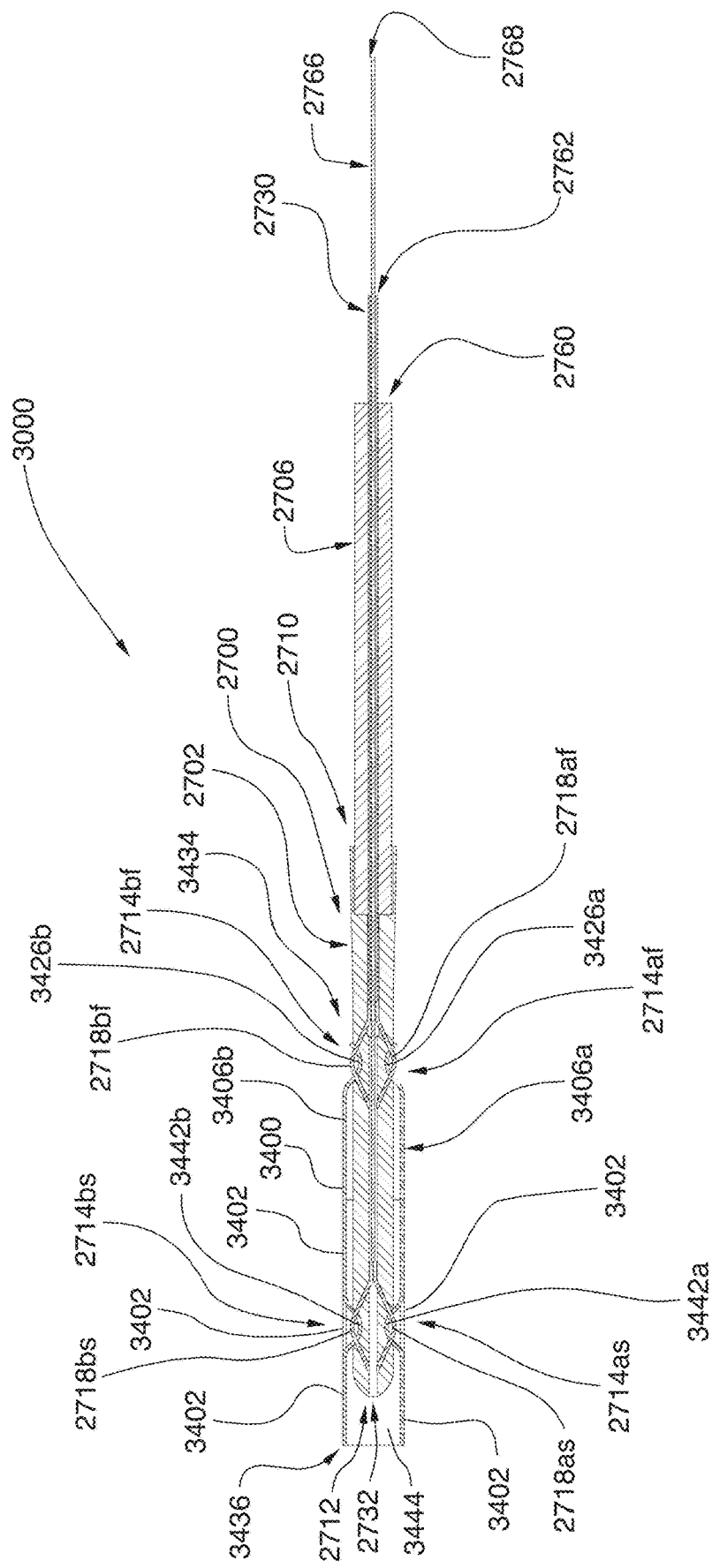
FIG. 29 shows a schematic of the device of FIG. 25A, in conjunction with a sixth embodiment of an anchor of the present invention. The anchor has a set of first connectors connected to the first interconnector of the device and a set of second connectors connected to the second interconnector of the device. The anchor is in its compact-secured-configuration.
Figure 30:
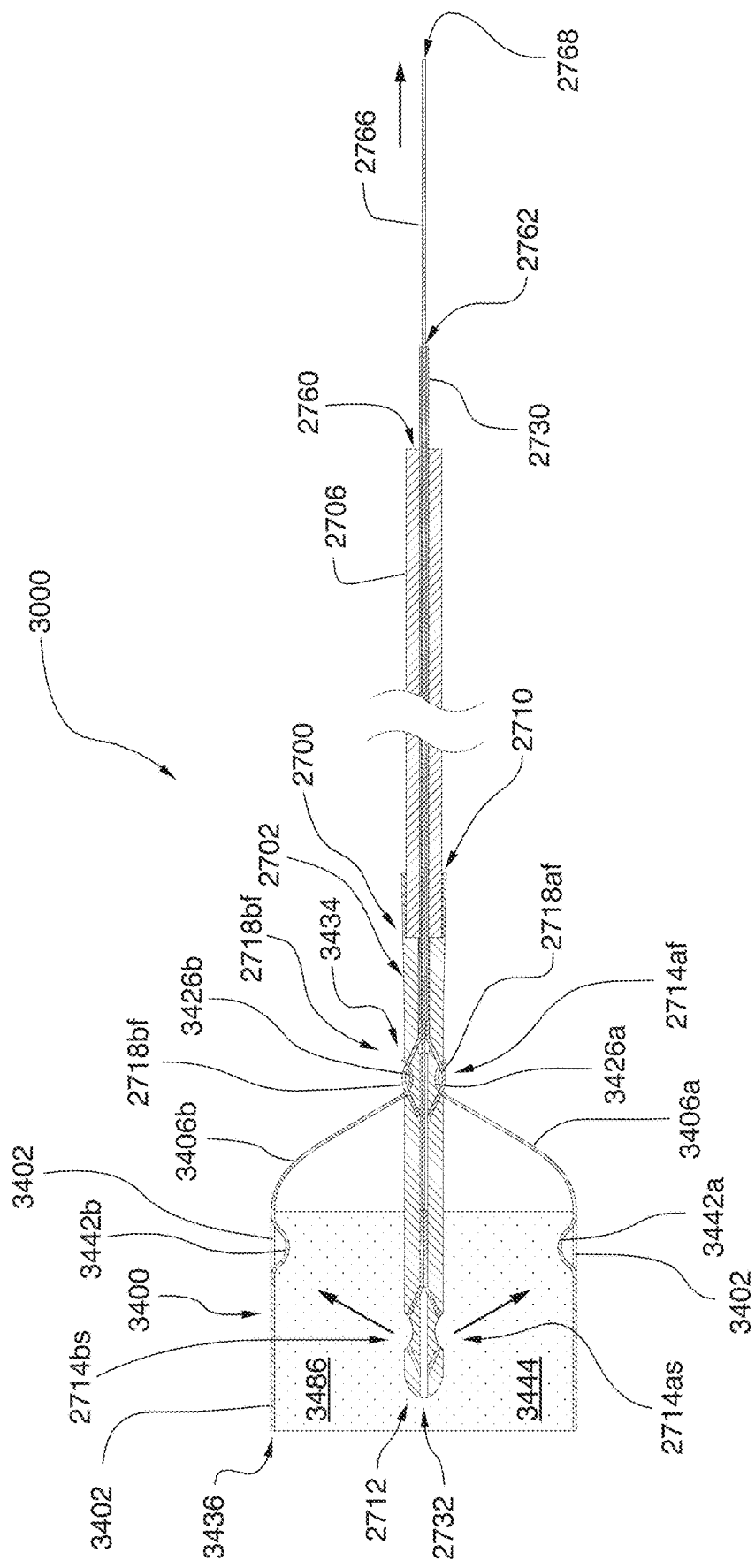
FIG. 30 shows a schematic of the device and anchor of FIG. 29, with the second set of connectors having been released from the second interconnector of the device. The first set of connectors are connected to the first interconnector of the device. The anchor is its expanded-secured-configuration.
Figure 31:
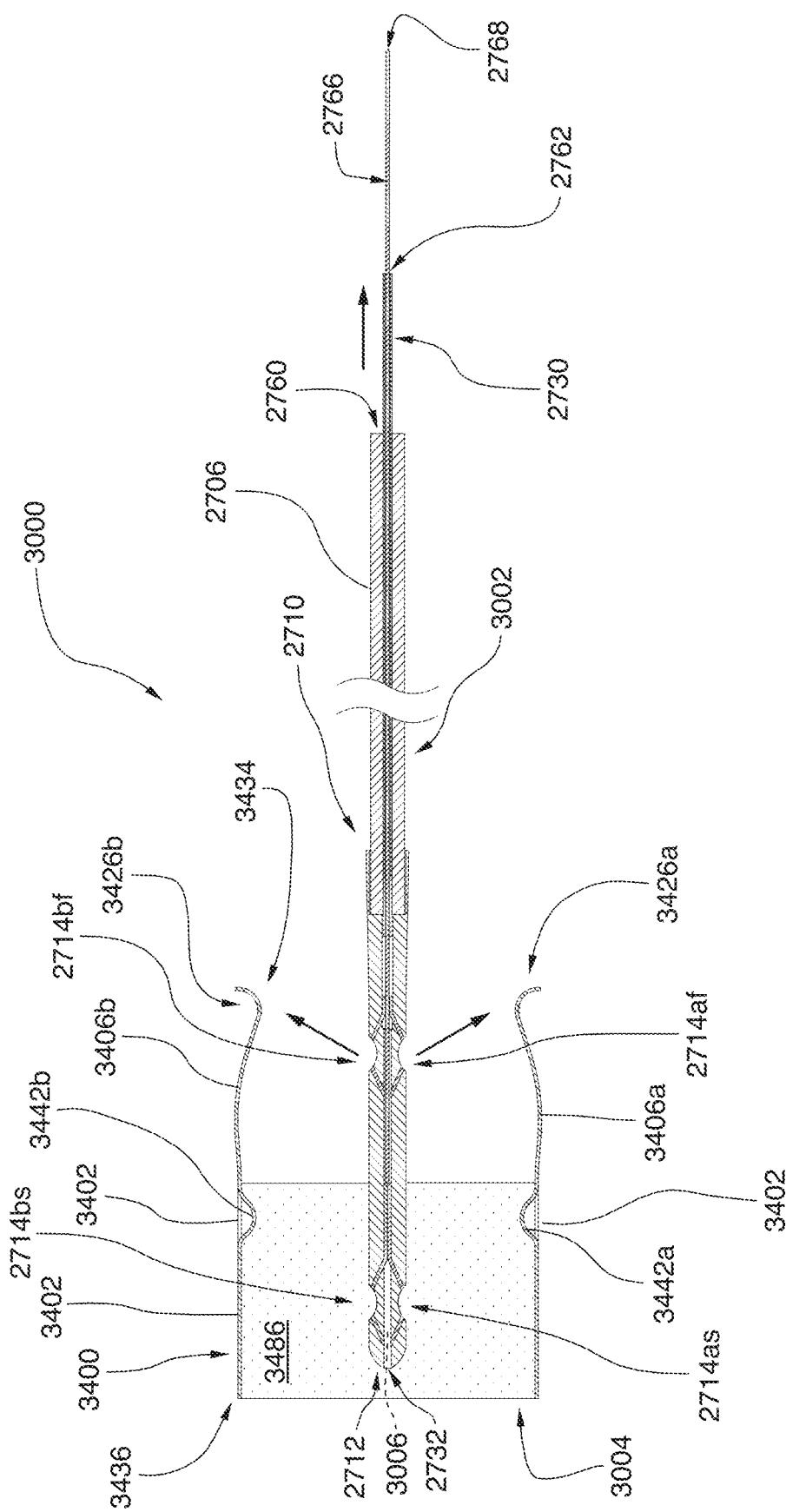
FIG. 31 shows a schematic of the device and anchor of FIG. 29, with the first set of connectors having been released from the first interconnector of the device and the second set of connectors having been released from the second interconnector of the device. The anchor is in its expanded-released-configuration.

Referring to FIGS. 29 to 31, there is shown a mammalian body conduit intralumenal device and lumen wall anchor assembly 3000 being a sixth embodiment of an assembly of the present technology. The assembly 3000 has a proximal end 3002 and a distal end 3004 defined consistently with the orientation in which the assembly 3000 is implanted. The assembly 3000 has a central longitudinal axis 3006. The assembly 3000 includes a mammalian body conduit intralumenal device 2700, described hereinabove, and a lumen wall anchor 3400, which is discussed in turn hereinbelow.

Assembly Sixth Embodiment—Anchor Sixth Embodiment

Referring to FIGS. 29 to 31, there is shown schematics of an anchor 3400 being a sixth embodiment of the present technology. The anchor 3400 and the implantation, explantation and use thereof is similar to anchor 400 except as described hereinbelow. The anchor 3400 is suitable for use with the device 2700 described above.

Referring to FIG. 29, the anchor 3400 has a set of first (proximal) connector positioning wires 3406xf (e.g., 3406af) each of which has a first connector 3426xf (e.g., 3426af) disposed at the end thereof. Each of the first connector positioning wires 3406xf (e.g., 3406af) is in its secured position, with the first connector 3426xf (e.g., 3426af) thereof being releasably connected to one of the sub-first-interconnectors 2715xf of the first interconnector 2714f. The anchor 3400 also has a set of second connectors 3406xs (e.g., 3406as) disposed on the wire network 3402 of the anchor 3400 (and not at the end of a connector positioning wire, in this embodiment). Each of the second connectors 3406xs (e.g., 3406as) is releasably connected to one of the sub-second-interconnectors 2715xs of the second interconnector 2714s.

In this manner, the anchor 3400 remains in its compact-secured-configuration when it exits the delivery sheath at a delivery site (as in shown in FIG. 29). This allows for the assembly 3000 to be delivered to a delivery site that is not the implantation site. Typically, in such cases, the delivery site is proximal to the implantation site, as there is not enough space at the implantation site to deliver the assembly 3000 with the device 2700 being in a delivery (unassembled) configuration. Thus, the assembly 3000 is delivered to the delivery site, organized so as to require less volume for the device and its various units, and then moved to the implantation site where the device is assembled into its operative configuration. The anchor 3400 is structured (and cooperates with the device 2700) so that the anchor 3400 exits the delivery sheath in its compact-secured-configuration (FIG. 29) and remains in that configuration. In this embodiment, the wire network 3402 of the anchor 3400 does not expand upon exiting the delivery sheath as the connection of the second connectors 3426xs to the sub-second-interconnectors 3415xs of the second interconnector 3414s prevents that expansion from occurring. Thus, the anchor does not adopt its expanded-secured-configuration at that time, allowing for movement of the assembly with the conduit system of the body.

Referring now to FIGS. 30 and 31, as the device 2700 and the operation of its interconnectors 2714 were described in detail hereinabove this description is not repeated here for the sake of brevity. Only the differences are noted hereinabove.

Referring to FIG. 30, at the implantation site, the second connectors 3426xs are released from their connection to the sub-second-interconnectors 2715xs of the second interconnector 2714s in the manner described hereinabove. The wire network 3402 thus expands, and the anchor 3400 adopts its expanded-secured position at the implantation site, anchoring the assembly 3000 in place.

Finally, referring to FIG. 31, if the device 2700 is to be explanted leaving the anchor 3400 in place, the first connectors 3426xf are released from their connection to the sub-first-interconnectors 2715xf of the first interconnector 2714f in the manner described hereinabove. The anchor 3400 is then in its expanded-released-configuration. The device 2700 is then explantable by the method described hereinabove.

In this embodiment, the anchor 3400 is made of Nitinol, with a portion 3486 of the wire network 3402 being covered in polytetrafluoroethylene (PTFE) sheet. In other embodiments, the covering may be formed from any appropriate compatible material, e.g., knitted polyester. When the lumen wall anchor 3400 is in the compact-secured-configuration, it has a diameter of 22 French. When the lumen wall anchor 3400 is in the expanded-secured-configuration and in the expanded-released-configuration, it has a diameter of about 24 mm and a length of up to about 20 cm.

Stent

Figure 40:
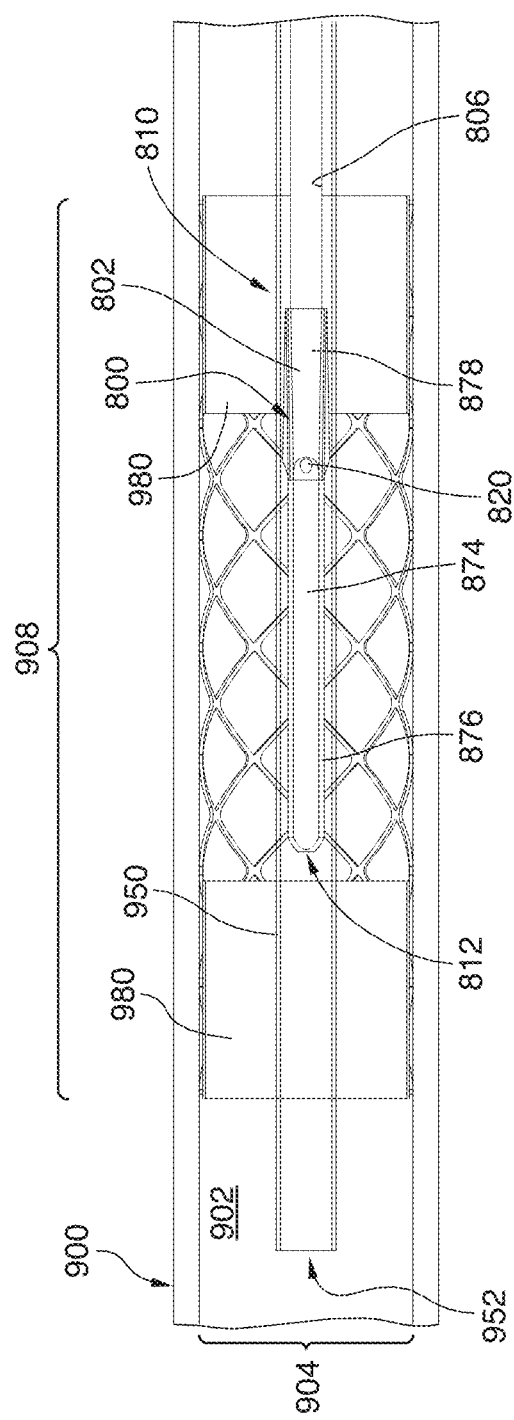
FIG. 40 shows a side of the device of the assembly of FIG. 36, similar to FIG. 36, with the exception that no anchor is shown, and a stent lining portions of the conduit lumen wall is shown.

As is shown in schematic in FIG. 40, in some embodiments, a conventional (or modified conventional) stent 980 may be implanted at an implantation site 908 prior to implantation of an assembly or an anchor of the present technology. Thus, the stent will abut the wall 902 of the lumen 904 of the conduit 900 at the implantation site 908. The anchor will be implanted after the stent has been implanted and will exert its anchoring force indirectly on the wall 902 via exertion of its anchoring force directly on the stent 980. The anchor is not shown in FIG. 40 for ease of understanding (the device 800 of the assembly 1300 is shown).

Miscellaneous

The present technology is not limited in its application to the details of construction and the arrangement of components set forth in the preceding description or illustrated in the drawings. The present technology is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the description the same numerical references refer to similar elements.

It must be noted that, as used in this specification and the appended claims, the singular form "a", "an" and "the" include plural referents unless the context clearly dictates otherwise.

As used herein, the term "about" or "generally" or the like in the context of a given value or range (whether direct or indirect, e.g., "generally in line", "generally aligned", "generally parallel", etc.) refers to a value or range that is within 20%, preferably within 10%, and more preferably within 5% of the given value or range.

As used herein, the term "and/or" is to be taken as specific disclosure of each of the two 10 specified features or components with or without the other. For example, "A and/or B" is to be taken as specific disclosure of each of (i) A, (ii) B and (iii) A and B, just as if each is set out individually herein.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

Clauses for Use in National Phase Entries
Clauses 1 to 5
1. A mammalian body conduit intralumenal device and lumen wall anchor assembly comprising:
   a mammalian body conduit intralumenal device, the device being shaped and dimensioned to be deliverable to a delivery site within a lumen of a mammalian body conduit via a catheter, the device having a first interconnector structured to releasably connect the device with a lumen wall anchor for use in maintaining the device in place within the mammalian body conduit; and the lumen wall anchor, the lumen wall anchor including:
a 3D-shaped wire network, the wire network having a central longitudinal axis,
a plurality of first connector positioning wires extending from the wire network, each wire of the plurality of first connector positioning wires being moveable between a secured position and a released position and being overcomeably biased towards the released position;
at least one first connector disposed at an end of at least one wire of the plurality of first connector positioning wires;
the lumen wall anchor having a compact-secured-configuration, an expanded-secured-configuration, and an expanded-released-configuration,
when the lumen wall anchor is in the compact-secured-configuration,
the lumen wall anchor is shaped and dimensioned to be deliverable to the delivery site within the lumen of the mammalian body conduit via the catheter,
each wire of the first plurality of connector positioning wires is in the secured position, the secured position being the end of that wire of the first plurality of connector positioning wires being positioned in proximity to the first interconnector of the device such that the at least one first connector disposed at the end of that wire is positioned to be releasably connectable to the first interconnector of the device, and
each of the at least one first connector is releasably connected to the first interconnector of the device;
when the lumen wall anchor is in the expanded-secured-configuration,
the wire network is dimensioned and shaped to exert a force on a wall of the lumen of the conduit, the force being sufficient to anchor the mammalian body conduit intralumenal device and lumen wall anchor assembly in place at an implantation site,
each wire of the first plurality of connector positioning wires is in the secured position, and
each of the at least one first connector is releasably connected to the first interconnector of the device; and
when the lumen wall anchor is in the expanded-released-configuration,
the wire network is dimensioned and shaped to exert a force on the wall of the lumen of the conduit, the force being sufficient to anchor the lumen wall anchor assembly in place at the implantation site, and
each wire of the plurality of first connector positioning wires is in the released position, the released position being each of the at least one first connector being released from and unconnected to the first interconnector of the device, and the end of each wire of the first plurality of connector positioning wires being proximate the wall of the lumen of the conduit, and
the plurality of first connector positioning wires and all of the at least one first connector do not obstruct fluid flow axially through the mammalian body conduit while the lumen wall anchor is anchored in place at the implantation site.

2. The assembly of clause 1, wherein, when in the expanded-secured-configuration and in the expanded-released-configuration, the wire network is dimensioned and shaped to exert a force on the wall of the lumen of the conduit indirectly by exerting a force directly on the wall of a stent having been implanted within the conduit.

3. The assembly of any one of clauses 1 to 2, wherein the device has a proximal end and a distal end.

4. The assembly of any one of clauses 1 to 3, wherein the device further has
an elongate body having a central longitudinal axis, and
an exterior surface; and
the first interconnector is disposed, at least in part, on the exterior surface of the device.

5. The assembly of any one of clauses 1 to 4, wherein the at least one first connector disposed at the end of at least one wire of the plurality of first connector positioning wires is a plurality of first connectors.

Clause 6

6. The assembly of clause 5, wherein a single one of the plurality of first connectors is disposed at the end of each wire of the plurality of first connector positioning wires.

Clause 7

7. The assembly of clause 5, wherein the ends of the plurality of first connector positioning wires are joined together in multiples, a single one of plurality of first connectors being disposed at the joined ends of each of the multiples.

Clauses 8 to 34

8. The assembly of any one of clauses 6 and 7, wherein the first interconnector includes two openings in the exterior surface of the device and a first interconnector wire, the first interconnector wire
traversing from an interior of the device to an exterior of the device through a first one of the two openings,
extending outside the exterior of the device, and then
traversing from the exterior of the device to the interior of the device through a second one of the two openings.

9. The assembly of clause 8, wherein
the device has a first cavity extending within the body, the first cavity having a first portion extending within the interior of the device to the first opening and a second portion extending from the second opening within the interior of the device; and
the first interconnector wire further extends within at least a part of the first portion of the first cavity to the first opening and from the second opening within at least a part of the second portion of the first cavity.

10. The assembly of any one of clauses 6 and 7, wherein the first interconnector has multiple sub-first-interconnectors, the sub-first-interconnectors being spaced apart from one another, each sub-first-interconnector including two openings in the exterior surface of the device and a sub-first-interconnector wire, the sub-first-interconnector wire
traversing from an interior of the device to an exterior of the device through a first one of the two openings of that sub-first-interconnector,
extending outside the exterior of the device, and then
traversing from the exterior of the device to the interior of the device through a second one of the two openings of that sub-first-interconnector.

11. The assembly of clause 10, wherein
the device has a first cavity extending within the body, the first cavity having a first portion extending within the interior of the device to the first opening of each sub-first-interconnector and a second portion extending from the second opening of each sub-first-interconnector within the interior of the device; and
the sub-first-interconnector wire of each sub-first-interconnector extends within at least part of the first portion of the first cavity to the first opening of that sub-first-interconnector and from the second opening of that sub-first-interconnector within at least part of the second portion of the first cavity.

12. The assembly of clause 11, wherein a majority of the first cavity extends within the body of the device generally parallel to the central longitudinal axis of the body of the device.

13. The assembly of clause 10, wherein
the device further has multiple first cavities extending within the body, each first cavity being associated with a one of the sub-first-interconnectors, each first cavity having a first portion extending within the interior of the device to the first opening of the sub-first-interconnector associated with that first cavity and a second portion extending from the second opening of the sub-first-interconnector associated with that first cavity within the interior of the device; and
the sub-first-interconnector wire of each sub-first-interconnector further extends within the interior of the device within at least a part of the first portion of the first cavity associated with that sub-first-interconnector to the first opening associated with that sub-first-interconnector and from the second opening associated with that sub-first-interconnector within at least part of the second portion of the first cavity associated with that sub-first-interconnector.

14. The assembly of clause 13, wherein the multiple first cavities overlap in part.

15. The assembly of any one of clauses 13 to 14, wherein a majority of each first cavity extends within the body of the device generally parallel to the central longitudinal axis of the body of the device.

16. The assembly of any one of clauses 10 to 15, wherein the sub-first-interconnectors are equally tangentially spaced apart along the exterior surface of the device in a plane perpendicular to the central longitudinal axis of the body of the device.

17. The assembly of any one of clauses 10 to 16 as they depend indirectly from clause 5, wherein a number of the plurality of first connectors is equal to a number of the sub-first-interconnectors, and each one of the plurality of first connectors is associated with a single one of the multiple sub-first-interconnectors.

18. The assembly of clause 17, wherein each one of the plurality of first connectors includes an element having a hole therein, the hole being shaped and dimensioned to allow the sub-first-interconnector wire of the sub-first-interconnector associated with that one of the first connectors to pass therethrough.

19. The assembly of clause 18, wherein each one of the plurality of first connectors includes an element having two holes therein, the holes being shaped and dimensioned, and positioned on the element with respect to each other, to allow the sub-first-interconnector wire of the sub-first-interconnector associated with that one of the first connectors to pass therethrough.

20. The assembly of clause 19, wherein each element is positioned, shaped and dimensioned such that, when the first connector positioning wire on which the one of the plurality of first connectors of which that element is included is disposed is in its securing position, each of the two holes in that element is disposed between a first plane perpendicular to the central longitudinal axis of the body of the device that includes at least a part of the first opening of the sub-first-interconnector associated with the one of the plurality of first connectors of which that element is included and a second plane perpendicular to the central longitudinal axis of the body of the device that includes at least part of the second opening of that sub-first-interconnector.

21. The assembly of clause 19, wherein each element is positioned, shaped and dimensioned such that, when the first connector positioning wire on which the one of the plurality of first connectors of which that element is disposed is in its securing position, a first hole of the two holes in that element is positioned adjacent the first opening of the sub-first-interconnector associated with the one of the plurality of first connectors of which that element is included, and a second hole of the two holes in that element is positioned adjacent the second opening of that sub-first-interconnector.

22. The assembly of any one of clauses 9 and 10, wherein each element is shaped to mate with a portion of the exterior surface of the device between the first opening of the sub-first interconnector associated with the one of the plurality of first connectors of which that element is included and the second opening of that sub-first interconnector.

23. The assembly of any one of clauses 19 to 22 as they depend indirectly from clause 11, wherein when the lumen wall anchor is in the expanded-secured configuration, for each sub-first-interconnector, the sub-first-interconnector wire of that sub-first-interconnector,
extends within at least a part of the first portion of the first cavity for a first length towards the first opening of that sub-first-interconnector;
traverses to the exterior of the device through the first opening of that sub-first-interconnector;
passes through the first hole of the two holes of the element of the one of the plurality of first connectors associated with that sub-first-interconnector;
extends outside the exterior of the device to the second hole of the two holes of that element;
passes through the second hole of the two holes of that element;
traverses through the second opening of that sub-first-interconnector; and
extends with the second portion of the first cavity for a second length.

24. The assembly of clause 23, wherein for each sub-first-interconnector,
an exterior surface of the sub-first-interconnector wire of that sub-first-interconnector frictionally engages an interior surface of the first cavity, and
a force generated by the bias towards the released position of the first connector positioning wire on which the one of the plurality of first connectors associated with that sub-first-interconnector is disposed exerts a force on the sub-first-interconnector wire of that sub-first-interconnector, that force exerted on the sub-first-interconnector wire of that sub-first-interconnector being insufficient to overcome a force generated by frictional engagement of the exterior surface of that sub-first-interconnector wire with the interior surface of the first cavity and with exterior surfaces of other sub-first-interconnector wires within the first cavity,
whereby, the bias of that first connector positioning wire toward the released position is overcome and that first connector positioning wire remains in the secured position.

25. The assembly of clause 24, wherein for each sub-first-interconnector, the sub-first-interconnector wire of that sub-first-interconnector is at least indirectly pullable from the exterior of the device with a sufficient amount of force to overcome the force generated by frictional engagement of the exterior surface of the sub-first-interconnector wire of that sub-first-interconnector with the interior surface of the first cavity and with exterior surfaces of the other sub-first-interconnector wires within the first cavity, to remove the sub-first-interconnector wire of that sub-first-interconnector from passing through the two holes of the element of the one of the plurality of first connectors associated with that sub-first-interconnector, thereby disconnecting that one of the plurality of first connectors from that sub-first-interconnector and allowing the first connector positioning wire on which that one of the plurality of first connectors is disposed to move to the released position.

26. The assembly of any one of clauses 19 to 22 as they depend indirectly from clause 13, wherein when the lumen wall anchor is in the expanded-secured configuration, for each sub-first-interconnector, the sub-first-interconnector wire of that sub-first-interconnector,
- extends from within at least a part of the first portion of the first cavity associated with that sub-first-interconnector for a first length towards the first opening of that sub-first-interconnector;
- traverses to the exterior of the device through the first opening of that sub-first-interconnector;
- passes through the first hole of the two holes of the element of the one of the plurality of first connectors associated with that sub-first-interconnector;
- extends outside the exterior of the device to the second hole of the two holes of that element;
- passes through the second hole of the two holes of that element;
- traverses through the second opening of that sub-first-interconnector; and
- extends within the second portion of the first cavity associated with that sub-first-interconnector for a second length.

27. The assembly of clause 26, wherein for each sub-first-interconnector,
- an exterior surface of the sub-first-interconnector wire of that sub-first-interconnector frictionally engages an interior surface of the first cavity associated with that sub-first-interconnector, and
- a force generated by the bias towards the released position of the first connector positioning wire on which the one of the plurality of first connectors associated with that sub-first-interconnector is disposed exerts a force on the sub-first-interconnector wire of that sub-first-interconnector, that force exerted on the sub-first-interconnector wire of that sub-first-interconnector being insufficient to overcome a force generated by frictional engagement of the exterior surface of that sub-first-interconnector wire with the interior surface of the first cavity associated with that sub-first-interconnector,
- whereby, the bias of that first connector positioning wire toward the released position is overcome and that first connector positioning wire remains in the secured position.

28. The assembly of clause 29, wherein for each sub-first-interconnector, the sub-first-interconnector wire of that sub-first-interconnector is at least indirectly pullable from the exterior of the device with a sufficient amount of force to overcome the force generated by frictional engagement of the exterior surface of the sub-first-interconnector wire of that sub-first-interconnector with the interior surface of the first cavity associated with that sub-first-interconnector to remove the sub-first-interconnector wire of that sub-first-interconnector from passing through the two holes of the element of the one of the plurality of first connectors associated with that sub-first-interconnector, thereby disconnecting that one of the plurality of first connectors from that sub-first-interconnector and allowing the first connector positioning wire on which that one of the plurality of first connectors is disposed to move to the released position.

29. The assembly of any one of clauses 25 and 26, wherein the sub-first-interconnector wires of all of the sub-first-interconnectors of the first interconnector are simultaneously at least indirectly pullable from the exterior of the device.

30. The assembly of clause 29, wherein the sub-first-interconnector wires of all of the sub-first-interconnectors of the first interconnector are at least indirectly connected to a single first connector actuation wire at least indirectly pullable from the exterior of the device.

31. The assembly of any one of clauses 25 and 28 to 30, wherein the device is disconnected from the lumen wall anchor when all of the sub-first-interconnectors of the first interconnector are disconnected from each one of the plurality of first connectors associated with each sub-first-interconnector.

32. The assembly of any one of clauses 3 and 4 to 31 as they depend directly or indirectly from clause 3, wherein at least one of
- the sub-first-interconnector wires of each of the sub-first-interconnectors of the first connector extend proximally away from the proximal end of the device, and
- the single first connector actuation wire extends proximally away from the proximal end of the device.

33. The assembly of any one of clauses 3 and 4 to 32 as they depend directly or indirectly from clause 3, wherein the lumen wall anchor, when in the expanded-secured-configuration, extends from the first interconnector toward the distal end of the device.

34. The assembly of clause 33, wherein, each of the first connector positioning wires in the secured position forms a proximally-facing sloped surface such that a retrieval sheath being manoeuvered from the proximal end of the device towards the distal end of the device, via contact with the sloped surfaces of the first connector positioning wires, causes, at least in part, the lumen wall anchor to adopt the compact-secured-configuration as it enters a lumen of the retrieval sheath.

Clauses 35 to 55

35. The assembly of any one of clauses 10 to 34 as they depend indirectly from clause 3, wherein
- the device further has a second interconnector spaced-apart from and distal to the first interconnector, the second interconnector being structured to releasably connect the device with the lumen wall anchor for use in maintaining the device in place within the mammalian body conduit;
- the lumen wall anchor further includes
  - a plurality of second connector positioning wires extending from the wire network, each wire of the plurality of second connector positioning wires being moveable between a secured position and a released position and being overcomeably biased towards the released position;
  - a plurality of second connectors, a single one of the plurality of second connectors being disposed at an end of each wire of the plurality of second connector positioning wires;
- when the lumen wall anchor is in the expanded-secured-configuration,
  - each wire of the plurality of second connector positioning wires is in the secured position, the secured position being the end of that wire of the second plurality of connector wires being positioned in proximity to the second interconnector of the device such that each of the plurality of second connectors is positioned to be releasably connectable to the second interconnector of the device, and each of the plurality of second connectors is releasably connected to the second interconnector of the device;

when the lumen wall anchor is in the expanded-released-configuration, each wire of the plurality of second connector positioning wires is in the released position, the released position being the end of that wire of the plurality of second connector positioning wires being proximate the wall of the lumen of the conduit, and the plurality of second connector positioning wires and the plurality of second connectors do not obstruct fluid flow axially through the wire network while the lumen wall anchor is anchored in place.

36. The assembly of clause 35, wherein each wire of the plurality of second connector positioning wires extends from a point intermediate between each end of the wire network.

37. The assembly of clause 35, wherein the plurality of first connector positioning wires and the plurality of second connector positioning wires extend from opposite ends of the wire network.

38. The assembly of clause 35, wherein the plurality of second connector positioning wires extend from the wire network at points more distal than points from which the plurality of first connector positioning wires extend.

39. The assembly of any one of clauses 35 to 38, wherein, when the lumen wall anchor is in the expanded-released-configuration, each of the second connectors is generally aligned with a periphery of the wire network.

40. The assembly of any one of clauses 35 to 39, wherein the second interconnector has multiple sub-second-interconnectors, the sub-second-interconnectors being spaced-apart from one another, each sub-second-interconnector including two openings in the exterior surface of the device and a sub-second-interconnector wire, the sub-second-interconnector wire traversing from the interior of the device to the exterior of the device through a first one of the two openings, extending outside the exterior of the device, and then traversing from the exterior of the device to the interior of the device through a second one of the two openings.

41. The assembly of clause 40 as it depends indirectly from clause 11, wherein the second portion of the first cavity extends to the first opening of each sub-second-interconnector and a third portion extends from the second opening of each sub-second-interconnector within the interior of the device; and the sub-second-interconnector wire of each sub-second-interconnector extends within the interior of the device within at least part of the first portion of the first cavity and the second portion of the first cavity to the first opening of that sub-second-interconnector and from the second opening of that sub-second-interconnector within at least part of the third portion of the first cavity.

42. The assembly of clause 41 as it depends indirectly from clause 13, wherein the device has multiple second cavities extending within the body, the second cavities being distinct from the first cavities, each second cavity being associated with one of the sub-second-interconnectors, each second cavity having a first portion extending within the interior of the device to the first opening of the sub-second-interconnector associated with that cavity and a second portion extending from the second opening of that sub-second-interconnector within the interior of the device; and the sub-second-interconnector wire of each sub-second-interconnector further extends from within the interior of the device within at least a part of the first portion of the cavity associated with that sub-second-interconnector to the first opening associated with that sub-second-interconnector and from the second opening associated with that sub-second-interconnector within at least a part of the second portion of the cavity associated with that sub-second-interconnector.

43. The assembly of clause 42, wherein a majority of each second cavity extends within the body generally parallel to the central longitudinal axis of the body of the device.

44. The assembly of any one of clauses 41 to 43, wherein the sub-second-interconnectors are equally tangentially spaced-apart along the exterior surface of the device in a plane perpendicular to the central longitudinal axis of the body of the device; and each of the sub-second-interconnectors is tangentially is aligned with a one of the sub-first-interconnectors along a line parallel to the central longitudinal axis of the body of the device.

45. The assembly of any one of clauses 41 to 44, wherein a number of the plurality of second connectors is equal to a number of the sub-second-interconnectors, and each one of the plurality of second connectors is associated with a single one of the multiple sub-second-interconnectors.

46. The assembly of any one of clauses 41 to 45, wherein each one of the second connectors includes an element having two holes therein, the holes being shaped and dimensioned, and positioned on the element with respect to each other, to allow the sub-second-interconnector wire of the sub-second-interconnector associated with that one of the second connectors to pass therethrough;

each element is positioned, shaped and dimensioned such that, when the second connector positioning wire on which the one of the plurality of second connectors of which that element is included is disposed in its securing position, a first hole of the two holes in that element is positioned adjacent the first opening of the sub-second-interconnector associated with that one of the plurality of second connectors and a second hole of the two holes in the element is positioned adjacent the second opening of that one of the plurality of sub-second-interconnectors.

47. The assembly of clause 46 as it depends indirectly from clause 41, wherein when the lumen wall anchor is in the expanded-secured configuration, for each sub-first-interconnector, the sub-first-interconnector wire of that sub-first-interconnector, extends within the interior of the device within at least part of the first portion of the first cavity for a first length towards the first opening of that sub-first-interconnector;

traverses to the exterior of the device through the first opening of that sub-first-interconnector;

passes through the first hole of the two holes of the element of the one of the plurality of first connectors associated with that sub-first-interconnector;

extends outside the exterior of the device to the second hole of the two holes of that element;

passes through the second hole of the two holes of that element;

traverses through the second opening of that sub-first-interconnector; and extends within at least part of the second portion of the first cavity for a second length; and for each sub-second-interconnector, the sub-second-interconnector wire of that sub-second-interconnector, extends within the interior of the device within at least part of the first portion of the first cavity and the second portion of the first cavity for a first length towards the first opening of that sub-second-interconnector;

traverses to the exterior of the device through the first opening of that sub-second-interconnector;

passes through the first hole of the two holes of the element of the one of the plurality of second connectors associated with that sub-second-interconnector;

extends outside the exterior of the device to the second hole of the two holes of that element;

passes through the second hole of the two holes of that element;

traverses through the second opening of that sub-second-interconnector; and extends within at least a part of the third portion of the first cavity for a second length.

48. The assembly of clause 47, wherein for each sub-first-interconnector, an exterior surface of the sub-first-interconnector wire of that sub-first-interconnector frictionally engages an interior surface of the first cavity, and a force generated by the bias towards the released position of the first connector positioning wire on which the one of the plurality of first connectors associated with that sub-first-interconnector is disposed exerts a force on the sub-first-interconnector wire of that sub-first-interconnector, that force exerted on the sub-first-interconnector wire of that sub-first-interconnector being insufficient to overcome a force generated by frictional engagement of the exterior surface of that sub-first-interconnector wire with the interior surface of the first cavity and with exterior surfaces of other interconnector wires within the first cavity, whereby, the bias of that first connector positioning wire toward the released position is overcome and that first connector positioning wire remains in the secured position; and for each sub-second-interconnector, an exterior surface of the sub-second interconnector wire of that sub-second-interconnector frictionally engages an interior surface of the first cavity, and a force generated by the bias towards the released position of the second connector positioning wire on which the one of the plurality of second connectors associated with that sub-second-interconnector is disposed exerts a force on the sub-second-interconnector wire of that sub-second-interconnector, that force exerted on the sub-second-interconnector wire of that sub-second-interconnector being insufficient to overcome a force generated by frictional engagement of the exterior surface of that sub-second-interconnector wire with the interior surface of the first cavity and with exterior surfaces of other interconnector wires within the first cavity, whereby, the bias of that second connector positioning wire toward the released position is overcome and that second connector positioning wire remains in the secured position.

49. The assembly of clause 48, wherein for each sub-first-interconnector, the sub-first-interconnector wire of that sub-first-interconnector is at least indirectly pullable from the exterior of the device with a sufficient amount of force to overcome the force generated by frictional engagement of the exterior surface of the sub-first-interconnector wire of that sub-first-interconnector with the interior surface of the first cavity and with exterior surfaces of the other interconnector wires within the first cavity, to remove the sub-first-interconnector wire of that sub-first-interconnector from passing through the two holes of the element of the one of the plurality of first connectors associated with that sub-first-interconnector, thereby disconnecting that one of the plurality of first connectors from that sub-first-interconnector and allowing the first connector positioning wire on which that one of the plurality of first connectors is disposed to move to the released position; and for each sub-second-interconnector, the sub-second-interconnector wire of that sub-second-interconnector is at least indirectly pullable from the exterior of the device with a sufficient amount of force to overcome the force generated by frictional engagement of the exterior surface of the sub-second-interconnector wire of that sub-second-interconnector with the interior surface of the first cavity and with exterior surfaces of the other interconnector wires within the first cavity, to remove the sub-second-interconnector wire of that sub-second-interconnector from passing through the two holes of the element of the one of the plurality of second connectors associated with that sub-second-interconnector, thereby disconnecting that one of the plurality of second connectors from that sub-second-interconnector and allowing the second connector positioning wire on which that one of the plurality of second connectors is disposed to move to the released position.

50. The assembly of clause 46 as it depends directly or indirectly from clause 41, wherein, when the lumen wall anchor is in the expanded-secured configuration, for each sub-first-interconnector, the sub-first-interconnector wire of that sub-first-interconnector, extends within the interior of the device within at least a part of the first portion of the first cavity associated with that sub-first-interconnector for a first length towards the first opening of that sub-first-interconnector;

traverses to the exterior of the device through the first opening of that sub-first-interconnector;

passes through the first hole of the two holes of the element of the one of the plurality of first connectors associated with that sub-first-interconnector;

extends outside the exterior of the device to the second hole of the two holes of that element;

passes through the second hole of the two holes of that element;

traverses through the second opening of that sub-first-interconnector; and extends within at least a part of the second portion of the first cavity associated with that sub-first-interconnector for a second length; and for each sub-second-interconnector, the sub-second-interconnector wire of that sub-second-interconnector, extends within the interior of the device within at least a part of the first portion of the second cavity associated with that sub-second-interconnector for a first length to the first opening of that sub-second-interconnector;

traverses to the exterior of the device through the first opening of that sub-second-interconnector;

passes through the first hole of the two holes of the element of the one of the plurality of second connectors associated with that sub-second-interconnector;

extends outside the exterior of the device to the second hole of the two holes of that element;

passes through the second hole of the two holes of that element;

traverses through the second opening of that sub-second-interconnector; and extends within at least a part of the second portion of the first cavity associated with that sub-second-interconnector for a second length.

51. The assembly of clause 51, wherein for each sub-first-interconnector,
an exterior surface of the sub-first-interconnector wire of that sub-first-interconnector frictionally engages an interior surface of the first cavity associated with that sub-first-interconnector, and
a force generated by the bias towards the released position of the first connector positioning wire on which the one of the plurality of first connectors associated with that sub-first-interconnector is disposed exerts a force on the sub-first-interconnector wire of that sub-first-interconnector, that force exerted on the sub-first-interconnector wire of that sub-first-interconnector being insufficient to overcome a force generated by frictional engagement of the exterior surface of that sub-first-interconnector wire with the interior surface of the first cavity associated with that sub-first-interconnector,
whereby, the bias of that first connector positioning wire toward the released position is overcome and that first connector positioning wire remains in the secured position;

for each sub-second-interconnector,
an exterior surface of the sub-second-interconnector wire of that sub-second-interconnector frictionally engages an interior surface of the second cavity associated with that sub-second-interconnector, and
a force generated by the bias towards the released position of the second connector positioning wire on which the one of the plurality of second connectors associated with that sub-second-interconnector is disposed exerts a force on the sub-second-interconnector wire of that sub-second-interconnector, that force exerted on the sub-second-interconnector wire of that sub-second-interconnector being insufficient to overcome a force generated by frictional engagement of the exterior surface of the sub-second-interconnector wire of that sub-second-interconnector with the interior surface of the first cavity associated with that sub-second-interconnector,
whereby, the bias of that wire of the second connector positioning wires toward the released position is overcome and that second connector positioning wire remains in the secured position.

52. The assembly of clause 51, wherein,
for each sub-first-interconnector, the sub-first-interconnector wire of that sub-first-interconnector is at least indirectly pullable from the exterior of the device with a sufficient amount of force to overcome the force generated by frictional engagement of the exterior surface of the sub-first-interconnector wire of that sub-first-interconnector with the interior surface of the first cavity associated with that sub-first-interconnector to remove the sub-first-interconnector wire of that sub-first-interconnector from passing through the two holes of the element of the one of the plurality of first connectors associated with that sub-first-interconnector, thereby disconnecting that one of the plurality of first connectors from that sub-first-interconnector and allowing the first connector positioning wire on which that one of the plurality of first connectors is disposed to move to the released position; and for each sub-second-interconnector, the sub-second-interconnector wire of that sub-second-interconnector is at least indirectly pullable from the exterior of the device with a sufficient amount of force to overcome the force generated by frictional engagement of the exterior surface of the sub-second-interconnector wire of that sub-second-interconnector with the interior surface of the second cavity associated with that sub-second-interconnector, to remove that sub-second-interconnector wire from passing through the two holes of the element of the one of the plurality of second connectors associated with that sub-second-interconnector, thereby disconnecting that one of the plurality of second connectors from that sub-second-interconnector and allowing the one of the plurality of second connector wires on which that one of the second connectors is disposed to move to the released position.

53. The assembly of any one of clauses 49 and 52, wherein the sub-second-interconnector wires of all of the sub-second interconnectors of the second interconnector are simultaneously at least indirectly pullable from the exterior of the device.

54. The assembly of any one of clauses 49, 52, and 53, wherein the device is disconnected from the lumen wall anchor when
each of the sub-first-interconnectors of the first interconnector is disconnected from the one of the plurality of first connectors associated with that sub-first-interconnector; and
each of the sub-second-interconnectors of the second interconnector is disconnected from the one of the plurality of second connectors associated with that sub-second-interconnector.

55. The assembly of clause 41 to 54, wherein the sub-second-interconnector wires of the each of the plurality of sub-second-interconnectors of the second connector exteriorly extend away from the proximal end of the device.

Clauses 56 to 64

56. The assembly of any one of clauses 35 to 39, wherein
the second interconnector has multiple sub-second-interconnectors, the sub-second-interconnectors being tangentially spaced-apart from one another, and axially spaced-apart from the sub-first-connectors;
each of the second-sub-connectors is tangentially aligned in a one-to-one relationship a single one of the sub-first-connectors; and
each sub-second-interconnector includes two openings in the exterior surface of the device.

57. The assembly of clause 56 as it depends indirectly from clause 11, wherein the second portion of the first cavity extends from the second opening of each sub-first-interconnector to the first opening of each sub-second-interconnector, and the first cavity has a third portion extending from the second opening of each sub-second-interconnectors within the interior of the device.

58. The assembly of clause 56 as it depends indirectly from clause 13, wherein each first cavity is further associated with the one of the sub-second-interconnectors that is in a one-to-one relationship with the one of the sub-first interconnectors that that first cavity is associated with, the second portion of each first cavity extending from the second opening of its associated sub-first-interconnector to the first opening of its associated sub-second-interconnector, and each first cavity has a third portion extending from the second opening of its associated sub-second-interconnector within the interior of the device.

59. The assembly of any one of clauses 56 to 58, wherein
a number of the plurality of second connectors is equal to a number of the sub-second-interconnectors, and each one of the plurality of second connectors is associated with a single one of the sub-second-interconnectors;
each one of the plurality of second connectors includes an element having two holes therein, the holes being shaped and dimensioned, and positioned on the element with respect to each other, to allow the sub-first-interconnector wire of the sub-first-interconnector associated with the sub-second-interconnector associated with that one of the plurality of second connectors to pass therethrough;
each element is positioned, shaped and dimensioned such that, when the second connector positioning wire on which the one of the plurality of second connectors of which that element is included is disposed is in its securing position, a first hole of the two holes in that element is positioned adjacent the first opening of the sub-second-interconnector associated with the one of the plurality of second connectors of which that element is included, and a second hole of the two holes in that element is positioned adjacent the second opening of that sub-second-interconnector.

60. The assembly of clause 59 as it depends from clause 58, wherein, when the lumen wall anchor is in the expanded-secured-configuration, for each sub-first interconnector and its associated sub-second-interconnector, the sub-first-interconnector wire of that sub-first-interconnector,
extends within the interior of the device within at least part of the first portion of the first cavity for a first length towards the first opening of that sub-first-interconnector;
traverses to the exterior of the device through the first opening of that sub-first-interconnector;
passes through the first hole of the two holes of the element of the one of the plurality of first connectors associated with that sub-first-interconnector;
extends outside the exterior of the device to the second hole of the two holes of that element;
passes through the second hole of the two holes of that element;
traverses through the second opening of that sub-first-interconnector;
extends with the second portion of the first cavity for a second length to the first opening of the sub-second-connector associated with that sub-first interconnector;
traverses to the exterior of the device through the first opening of that sub-second-interconnector;
passes through the first hole of the two holes of the element of the one of the plurality of second connectors associated with that sub-second-interconnector;
extends outside the exterior of the device to the second hole of the two holes of that element;
passes through the second hole of the two holes of that element;
traverses through the second opening of that sub-second-interconnector; and
extends within at least part of the third portion of the first cavity for a third length.

61. The assembly of clause 60, wherein
for each sub-first-interconnector,
an exterior surface of the sub-first-interconnector wire of that sub-first-interconnector frictionally engages an interior surface of the first cavity, and
a force generated by the bias towards the released position of the first connector positioning wire on which the one of the plurality of first connectors associated with that sub-first-interconnector is disposed exerts a force on the sub-first-interconnector wire of that sub-first-interconnector, that force exerted on the sub-first-interconnector wire of that sub-first-interconnector being insufficient to overcome a force generated by frictional engagement of the exterior surface of that sub-first-interconnector wire with the interior surface of the first cavity and with exterior surfaces of other interconnector wires within the first cavity,
whereby, the bias of that first connector positioning wire toward the released position is overcome and that first connector positioning wire remains in the secured position; and
for each sub-second-interconnector,
a force generated by the bias towards the released position of the second connector positioning wire on which the one of the plurality of second connectors associated with that sub-second-interconnector is disposed exerts a force on the sub-first-interconnector wire of the sub-first-interconnector wire associated with that sub-second-interconnector, that force exerted on that sub-first-interconnector wire being insufficient to overcome the force generated by frictional engagement of the exterior surface of that sub-first-interconnector wire with the interior surface of the first cavity,
whereby, the bias of that wire of the second connector positioning wires toward the released position is overcome and that second connector positioning wire remains in the secured position.

62. The assembly of clause 59 as it depends from clause 58, wherein, when the lumen wall anchor is in the expanded-secured configuration, for each sub-first-interconnector and its associated sub-second-interconnector, the sub-first-interconnector wire of that sub-first-interconnector,
extends within the interior of the device within at least part of the first portion of the first cavity associated with that sub-first-interconnector for a first length towards the first opening of that sub-first-interconnector;
traverses to the exterior of the device through the first opening of that sub-first-interconnector;
passes through the first hole of the two holes of the element of the one of the plurality of first connectors associated with that sub-first-interconnector;
extends outside the exterior of the device to the second hole of the two holes of that element;
passes through the second hole of the two holes of that element;
traverses through the second opening of that sub-first-interconnector;

extends with the second portion of the first cavity associated with that sub-first-interconnector for a second length to the first opening of the sub-second-connector associated with that sub-first interconnector;
   traverses to the exterior of the device through the first opening of that sub-second-interconnector;
   passes through the first hole of the two holes of the element of the one of the plurality of second connectors associated with that sub-second-interconnector;
   extends outside the exterior of the device to the second hole of the two holes of that element;
   passes through the second hole of the two holes of that element;
   traverses through the second opening of that sub-second-interconnector; and
   extends within at least part of the third portion of the first cavity associated with that sub-second-interconnector for a third length.
63. The assembly of clause 62, wherein
   for each sub-first-interconnector,
      an exterior surface of the sub-first-interconnector wire of that sub-first-interconnector frictionally engages an interior surface of the first cavity associated with that sub-first-interconnector, and
      a force generated by the bias towards the released position of the first connector positioning wire on which the one of the plurality of first connectors associated with that sub-first-interconnector is disposed exerts a force on the sub-first-interconnector wire of that sub-first-interconnector, that force exerted on the sub-first-interconnector wire of that sub-first-interconnector being insufficient to overcome a force generated by frictional engagement of the exterior surface of that sub-first-interconnector wire with the interior surface of the first cavity associated with that sub-first-interconnector,
   whereby, the bias of that first connector positioning wire toward the released position is overcome and that first connector positioning wire remains in the secured position; and
   for each sub-second-interconnector,
      a force generated by the bias towards the released position of the second connector positioning wire on which the one of the plurality of second connectors associated with that sub-second-interconnector is disposed exerts a force on the sub-first-interconnector wire of the sub-first-interconnector wire associated with that sub-second-interconnector, that force exerted on that sub-first-interconnector wire being insufficient to overcome the force generated by frictional engagement of the exterior surface of that sub-first-interconnector wire with the interior surface of the first cavity associated with that sub-second-interconnector,
   whereby, the bias of that wire of the second connector positioning wires toward the released position is overcome and that second connector positioning wire remains in the secured position.
64. The assembly of any one of clauses 61 and 63 wherein
   for each sub-second-interconnector, the sub-first-interconnector wire of the sub-first-interconnector associated with that sub-second-interconnector is at least indirectly pullable from the exterior of the device by a first length to remove that sub-first-interconnector wire from passing through the two holes of the element of the one of the plurality of second connectors associated with that sub-second-interconnector, thereby disconnecting the one of the plurality of second connectors associated with that sub-second-interconnector from that sub-second-interconnector and allowing the one of the second connector wires on which the one of the plurality of second connectors associated with that sub-second-interconnector is disposed to move to the released position, the first length being insufficient to remove that sub-first-interconnector wire from passing through the two holes of the element of the one of the plurality of first connectors associated the sub-first-interconnector associated with that sub-second-interconnector; and
   for each sub-first-interconnector, that sub-first-interconnector wire is thereafter is least indirectly pullable from the exterior of the device by a second length to remove that interconnector wire from passing through the two holes of the element of the one of the plurality of first connectors associated with that sub-first-interconnector, thereby disconnecting the one of the plurality of first connectors associated with that sub-first-interconnector from that sub-first-interconnector and allowing the one of the first connector positioning wires on which the one of the plurality of first connectors associated with that sub-first-interconnector is disposed to move to the released position.
65. The assembly of clause 64, wherein the device is disconnected from the lumen wall anchor when
   each of the sub-first-interconnectors of the first interconnector is disconnected from the one of the plurality of first connectors associated with that sub-first-interconnector; and
   each of the sub-second-interconnectors of the second interconnector is disconnected from the one of the second connectors associated with that sub-second-interconnector.
Clauses 66 to 72
66. The assembly of clause 56, wherein
   a number of the plurality of second connectors is equal to a number of the sub-second-interconnectors, and each one of the plurality of second connectors is associated with a single one of the sub-second-interconnectors;
   each one of the plurality of second connectors includes an element having two holes therein, the holes being shaped and dimensioned, and positioned on the element with respect to each other, to allow the sub-second-interconnector wire of the sub-second-interconnector associated with that one of the plurality of second connectors to pass therethrough;
   each element is positioned, shaped and dimensioned such that, when the second connector positioning wire on which the one of the plurality of second connectors of which that element is included is disposed is in its securing position, a first hole of the two holes in that element is positioned adjacent the first opening of the sub-second-interconnector associated with the one of the plurality of second connectors of which that element is included, and a second hole of the two holes in that element is positioned adjacent the second opening of that sub-second-interconnector.
67. The assembly of clause 66, wherein
   the sub-first-interconnector wire of each of the sub-first-interconnectors has a hollow core; and
   the sub-second-interconnector wire of each of the sub-second-interconnectors is disposed within the hollow core of the sub-first-interconnector wire of the one of the sub-first-interconnectors associated with that sub-second-interconnector.

68. The assembly of clause 67 as it depends indirectly from clause 24, wherein
   the second portion of the first cavity extends to the first opening of each sub-second-interconnector and a third portion extends from the second opening of each sub-second-interconnector within the interior of the device; and
   when the lumen wall anchor is in the expanded-secured configuration, for each sub-first-interconnector and its associated sub-second-interconnector,
      the sub-first-interconnector wire of that sub-first-interconnector,
         has a proximal end, and
         has a distal end that extends within the second portion of the first cavity for a second length and ends before reaching the first opening of the sub-second-connector associated with that sub-first interconnector; and
      the sub-second-interconnector wire of that sub-second-connector,
         has a proximal end that extends proximally beyond the proximal end of the sub-first-interconnector wire of the sub-first-interconnector associated with that sub-second-interconnector;
         has a distal end that
            exits the hollow core of the sub-first-interconnector wire of that sub-first-connector within the second portion of the first cavity;
            extends within the second portion of the first cavity to the first opening of that sub-second-interconnector;
            traverses to the exterior of the device through the first opening of that sub-second-interconnector;
            passes through the first hole of the two holes of the element of the one of the plurality second connectors associated with that sub-second-interconnector;
            extends outside the exterior of the device to the second hole of the two holes of that element;
            passes through the second hole of the two holes of that element;
            traverses through the second opening of that sub-second-interconnector;
            extends within at least part of the third portion of the first cavity for a third length;
      an exterior surface of the sub-second-interconnector wire of that sub-second-interconnector frictionally engages an interior surface of the hollow core of the sub-first-interconnector wire of the sub-first-interconnector within which that sub-second-interconnector wire is disposed prior to exiting the hollow core of that sub-first-interconnector wire;
      the exterior surface of the sub-second-interconnector wire of that sub-second-interconnector further frictionally engages an interior surface of the first cavity after exiting the hollow core of the sub-first-interconnector wire of that sub-first-connector associated with that sub-second-connector; and
      a force generated by the bias towards the released position of the second connector positioning wire on which the one of the plurality of second connectors associated with that sub-second-interconnector is disposed exerts a force on the sub-second-interconnector wire of that sub-second-interconnector, that force exerted on that sub-second-interconnector wire being insufficient to overcome a force generated by frictional engagement of the exterior surface of that sub-second-interconnector wire with the interior surface of the first cavity and of the exterior surface of that sub-second-interconnector with the interior surface of the hollow core of the sub-first-interconnector wire of the sub-first-interconnector within which that sub-second-interconnector wire is disposed; whereby, the bias of that wire of the second connector positioning wire towards the released position is overcome and that second connector positioning wire remains in the secured position.

69. The assembly of clause 68, wherein
   for each sub-second-interconnector, the sub-second-interconnector wire of that sub-second-interconnector is at least indirectly pullable from the exterior of the device with a sufficient amount of force to overcome the force generated by frictional engagement of the exterior surface of that sub-second-interconnector wire with the interior surface of the first cavity and of the exterior surface of that sub-second-interconnector wire and the interior surface of the hollow core of the sub-first-interconnector wire of the sub-first-interconnector within which that sub-second-interconnector wire is disposed, to remove that sub-second-interconnector wire from passing through the two holes of the element of the one of the plurality of second connectors associated with that sub-second-interconnector, thereby disconnecting the one of the plurality of second connectors associated with that sub-second-interconnector from that sub-second-interconnector and allowing the one of the second connector positioning wires on which the one of the plurality of second connectors associated with that sub-second-interconnector is disposed to move to the released position, while leaving that sub-first-interconnector wire in place; and
   for each sub-first-interconnector, the sub-first-interconnector wire of that sub-first-interconnector is thereafter at least indirectly pullable from the exterior of the device with a sufficient amount of force to overcome the force generated by frictional engagement of the exterior surface of the sub-first-interconnector wire of that sub-first-interconnector with the interior surface of the first cavity and with exterior surfaces of the other interconnector wires within the first cavity, to remove the sub-first-interconnector wire of that sub-first-interconnector from passing through the two holes of the element of the one of the plurality of first connectors associated with that sub-first-interconnector, thereby disconnecting that one of the plurality of first connectors from that sub-first-interconnector and allowing the first connector positioning wire on which that one of the plurality of first connectors is disposed to move to the released position.

70. The assembly of clause 67 as it depends indirectly from clause 27, wherein,
   each first cavity is further associated with the one of the sub-second-interconnectors that is in a one-to-one relationship with the one of the sub-first interconnectors that that first cavity is associated with, the second portion of each first cavity extending from the second opening of its associated sub-first-interconnector to the first opening of its associated sub-second-interconnector, and each first cavity has a third portion extending from the second opening of its associated sub-second-interconnector within the interior of the device; and
   when the lumen wall anchor is in the expanded-secured configuration, for each sub-first-interconnector and its associated sub-second-interconnector, the sub-first-interconnector wire of that sub-first-interconnector,
has a proximal end, and
has a distal end that extends within the second portion of the first cavity associated with that sub-first-interconnector for a second length and ends before reaching the first opening of the sub-second-connector associated with that sub-first interconnector; and the sub-second-interconnector wire of that sub-second-connector,
has a proximal end that extends proximally beyond the proximal end of the interconnector wire of the sub-first-interconnector associated with that sub-second-interconnector;
has a distal end that
exits the hollow core of the interconnector wire of that sub-first-connector within the second portion of the first cavity associated with that sub-second-connector;
extends within the second portion of the first cavity to the first opening of that sub-second-interconnector associated with that sub-second-connector;
traverses to the exterior of the device through the first opening of that sub-second-interconnector;
passes through the first hole of the two holes of the element of the one of the plurality second connectors associated with that sub-second-interconnector;
extends outside the exterior of the device to the second hole of the two holes of that element;
passes through the second hole of the two holes of that element;
traverses through the second opening of that sub-second-interconnector;
extends within at least part of the third portion of the first cavity associated with that sub-second-interconnector for a third length;
an exterior surface of the sub-second-interconnector wire of that sub-second-interconnector frictionally engages an interior surface of the hollow core of the sub-first-interconnector wire of the sub-first-interconnector within which that sub-second-interconnector wire is disposed prior to exiting the hollow core of that sub-first-interconnector wire;
the exterior surface of the sub-second-interconnector wire of that sub-second-interconnector further frictionally engages an interior surface of the first cavity within which that sub-second-interconnector wire is disposed after exiting the hollow core of the sub-first-interconnector wire of that sub-first-connector associated with that sub-second-connector; and
a force generated by the bias towards the released position of the second connector positioning wire on which the one of the plurality of second connectors associated with that sub-second-interconnector is disposed exerts a force on the sub-second-interconnector wire of that sub-second-interconnector, that force exerted on that sub-second-interconnector wire being insufficient to overcome a force generated by frictional engagement of the exterior surface of that sub-second-interconnector wire with the interior surface of the first cavity associated with that sub-second-interconnector and of the exterior surface of that sub-second-interconnector with the interior surface of the hollow core of the sub-first-interconnector wire of the sub-first-interconnector within which that sub-second-interconnector wire is disposed; whereby, the bias of that wire of the second connector positioning wire towards the released position is overcome and that second connector positioning wire remains in the secured position.

71. The assembly of clause 70, wherein
for each sub-second-interconnector, the sub-second-interconnector wire of that sub-second-interconnector is at least indirectly pullable from the exterior of the device with a sufficient amount of force to overcome the force generated by frictional engagement of the exterior surface of that sub-second-interconnector wire with the interior surface of the first cavity associated with that sub-second-interconnector and of the exterior surface of that sub-second-interconnector and the interior surface of the hollow core of the sub-first-interconnector wire of the sub-first-interconnector within which that sub-second-interconnector wire is disposed, to remove that sub-second-interconnector wire from passing through the two holes of the element of the one of the plurality of second connectors associated with that sub-second-interconnector, thereby disconnecting the one of the plurality of second connectors associated with that sub-second-interconnector from that sub-second-interconnector and allowing the one of the second connector positioning wires on which the one of the plurality of second connectors associated with that sub-second-interconnector is disposed to move to the released position, while leaving that sub-first-interconnector wire in place; and
for each sub-first-interconnector, the sub-first-interconnector wire of that sub-first-interconnector is thereafter at least indirectly pullable from the exterior of the device with a sufficient amount of force to overcome the force generated by frictional engagement of the exterior surface of that sub-first-interconnector wire and the interior surface of the first cavity associated with that sub-first-interconnector, to remove that sub-first-interconnector wire from passing through the two holes of the element of the one of the plurality of first connectors associated with that sub-first-interconnector, thereby disconnecting the one of the plurality of first connectors associated with that sub-first-interconnector from that sub-first-interconnector and allowing the one of the first connector positioning wires on which the one of the first connectors associated with that sub-first-interconnector is disposed to move to the released position.

72. The assembly of clause 71, wherein the device is disconnected from the lumen wall anchor when
each of the sub-first-interconnectors of the first interconnector is disconnected from the one of the plurality of first connectors associated with that sub-first-interconnector; and
each of the sub-second-interconnectors of the second interconnector is disconnected from the one of the second connectors associated with that sub-second-interconnector.

Clauses 73 to 85

73. The assembly of any one of clauses 10 to 34 as they depend indirectly from clause 3, wherein
the device further has a second interconnector spaced-apart from and distal to the first interconnector, the second interconnector being structured to releasably connect the device with the lumen wall anchor for use in maintaining the lumen anchor in the compact-secured-configuration;

the lumen wall anchor further includes a plurality of second connectors disposed on the wire network;

when the lumen wall anchor is in the compact-secured-position, each of the plurality of second connectors is connected to the second interconnector;

when the lumen wall anchor is in the expanded-secured-configuration, each of the second connectors is disconnected from the second interconnector;

when the lumen wall anchor is in the expanded-released-configuration, each of the second connectors is disconnected from the second interconnector and does not obstruct fluid flow axially through the wire network while the lumen wall anchor is anchored in place.

74. The assembly of clause 73, wherein the second connectors are disposed distally of the first connectors.

75. The assembly of any one of clauses 73 and 74, wherein the second interconnector has multiple sub-second-interconnectors, the sub-second-interconnectors being spaced-apart from one another, each sub-second-interconnector including two openings in the exterior surface of the device and a sub-second-interconnector wire, the sub-second-interconnector wire
traversing from the interior of the device to the exterior of the device through a first one of the two openings, extending outside the exterior of the device, and then traversing from the exterior of the device to the interior of the device through a second one of the two openings.

76. The assembly of clause 75 as it depends indirectly from clause 11, wherein
the second portion of the first cavity extends to the first opening of each sub-second-interconnector and a third portion extends from the second opening of each sub-second-interconnector within the interior of the device; and
the sub-second-interconnector wire of each sub-second-interconnector extends within the interior of the device within at least part of the first portion of the first cavity and the second portion of the first cavity to the first opening of that sub-second-interconnector and from the second opening of that sub-second-interconnector within at least part of the third portion of the first cavity.

77. The assembly of clause 75 as it dependents indirectly from clause 13, wherein
the device has multiple second cavities extending within the body, the second cavities being distinct from the first cavities, each second cavity being associated with one of the sub-second-interconnectors, each second cavity having a first portion extending within the interior of the device to the first opening of the sub-second-interconnector associated with that cavity and a second portion extending from the second opening of that sub-second-interconnector within the interior of the device; and
the sub-second-interconnector wire of each sub-second-interconnector further extends from within the interior of the device within at least part of the first portion of the cavity associated with that sub-second-interconnector to the first opening associated with that sub-second-interconnector and from the second opening associated with that sub-second-interconnector within at least part of the second portion of the cavity associated with that sub-second-interconnector.

78. The assembly of any one of clauses 75 to 77, wherein
the sub-second-interconnectors are equally tangentially spaced-apart along the exterior surface of the device in a plane perpendicular to the central longitudinal axis of the body of the device; and
each of the sub-second-interconnectors is tangentially is aligned with a one of the sub-first-interconnectors along a line parallel to the central longitudinal axis of the body of the device.

79. The assembly of any one of clauses 75 to 78, wherein a number of the plurality of second connectors is equal to a number of the sub-second-interconnectors, and each one of the plurality of second connectors is associated with a single one of the multiple sub-second-interconnectors.

80. The assembly of any one of clauses 75 to 79, wherein
each one of the second connectors includes an element having two holes therein, the holes being shaped and dimensioned, and positioned on the element with respect to each other, to allow the sub-second-interconnector wire of the sub-second-interconnector associated with that one of the second connectors to pass therethrough;
each element is positioned, shaped and dimensioned such that, when the lumen wall anchor is in the compact-secured-configuration, a first hole of the two holes in that element is positioned adjacent the first opening of the sub-second-interconnector associated with the one of the second connectors of which that element is included, and a second hole of the two holes in the element is positioned adjacent the second opening of the sub-second-interconnector associated with the one of the second connectors of which that element is included.

81. The assembly of clause 80 as it depends indirectly from clause 76, wherein when the lumen wall anchor is in the compact-secured configuration,
for each sub-first-interconnector, the sub-first-interconnector wire of that sub-first-interconnector,
extends within the interior of the device within at least part of the first portion of the first cavity for a first length towards the first opening of that sub-first-interconnector;
traverses to the exterior of the device through the first opening of that sub-first-interconnector;
passes through the first hole of the two holes of the element of the one of the plurality of first connectors associated with that sub-first-interconnector;
extends outside the exterior of the device to the second hole of the two holes of that element;
passes through the second hole of the two holes of that element;
traverses through the second opening of that sub-first-interconnector; and
extends within at least part of the second portion of the first cavity for a second length; and
for each sub-second-interconnector, the sub-second-interconnector wire of that sub-second-interconnector,
extends within the interior of the device within at least part of the first portion of the first cavity and the second portion of the first cavity for a first length towards the first opening of that sub-second-interconnector;
traverses to the exterior of the device through the first opening of that sub-second-interconnector;
passes through the first hole of the two holes of the element of the one of the plurality of second connectors associated with that sub-second-interconnector;

extends outside the exterior of the device to the second hole of the two holes of that element;
passes through the second hole of the two holes of that element;
traverses through the second opening of that sub-second-interconnector; and
extends within at least part of the third portion of the first cavity for a second length.

82. The assembly of clause 81, wherein
for each sub-first-interconnector,
an exterior surface of the sub-first-interconnector wire of that sub-first-interconnector frictionally engages an interior surface of the first cavity, and
a force generated by the bias towards the released position of the first connector positioning wire on which the one of the plurality of first connectors associated with that sub-first-interconnector is disposed exerts a force on the sub-first-interconnector wire of that sub-first-interconnector, that force exerted on the sub-first-interconnector wire of that sub-first-interconnector being insufficient to overcome a force generated by frictional engagement of the exterior surface of that sub-first-interconnector wire with the interior surface of the first cavity and with exterior surfaces of other interconnector wires within the first cavity,
whereby, the bias of that first connector positioning wire toward the released position is overcome and that first connector positioning wire remains in the secured position; and
for each sub-second-interconnector,
an exterior surface of the sub-second-interconnector wire of that sub-second-interconnector frictionally engages an interior surface of the first cavity, and
a force generated by a bias of the lumen wall anchor away from its compact-secured-configuration exerts a force on the sub-second-interconnector wire of that sub-second-interconnector, that force exerted on the sub-second-interconnector wire of that sub-second-interconnector being insufficient to overcome a force generated by frictional engagement of the exterior surface of that sub-second-interconnector wire with the interior surface of the first cavity and with exterior surfaces of other interconnector wires within the first cavity,
whereby, the bias of the lumen wall anchor away from its compact-secured-configuration is overcome, and the lumen wall anchor remains in the compact-secured-configuration.

83. The assembly of clause 82, wherein
for each sub-first-interconnector, the sub-first-interconnector wire of that sub-first-interconnector is at least indirectly pullable from the exterior of the device with a sufficient amount of force to overcome the force generated by frictional engagement of the exterior surface of the sub-first-interconnector wire of that sub-first-interconnector with the interior surface of the first cavity and with exterior surfaces of the other interconnector wires within the first cavity, to remove the sub-first-interconnector wire of that sub-first-interconnector from passing through the two holes of the element of the one of the plurality of first connectors associated with that sub-first-interconnector, thereby disconnecting that one of the plurality of first connectors from that sub-first-interconnector and allowing the first connector positioning wire on which that one of the plurality of first connectors is disposed to move to the released position; and
for each sub-second-interconnector, the sub-second-interconnector wire of that sub-second-interconnector is at least indirectly pullable from the exterior of the device with a sufficient amount of force to overcome the force generated by frictional engagement of the exterior surface of the sub-second-interconnector wire of that sub-second-interconnector with the interior surface of the first cavity and with exterior surfaces of the other interconnector wires within the first cavity, to remove the sub-second-interconnector wire of that sub-second-interconnector from passing through the two holes of the element of the one of the plurality of second connectors associated with that sub-second-interconnector, thereby disconnecting that one of the plurality of second connectors from that sub-second-interconnector and allowing the lumen wall anchor to adopt, at least in part, the expanded-secured-configuration.

84. The assembly of clause 80, wherein when the lumen wall anchor is in the compact-secured configuration, for each sub-second-interconnector,
the sub-second-interconnector wire of that sub-second-interconnector,
extends within the interior of the device within at least part of the first portion of the second cavity associated with that sub-second-interconnector for a first length to the first opening of that sub-second-interconnector;
traverses to the exterior of the device through the first opening of that sub-second-interconnector;
passes through the first hole of the two holes of the element of the one of the plurality of second connectors associated with that sub-second-interconnector;
extends outside the exterior of the device to the second hole of the two holes of the element of the one of the plurality of second connectors associated with that sub-second-interconnector;
passes through the second hole of the two holes of that element;
traverses through the second opening of that sub-second-interconnector;
extends with at least a part of the second portion of the first cavity associated with that sub-second-interconnector for a second length; and
an exterior surface of the sub-second-interconnector wire of that sub-second-interconnector frictionally engages an interior surface of the second cavity associated with that sub-second-interconnector, and
a force generated by a bias of the lumen wall anchor away from its compact-secured-configuration exerts a force on the sub-second-interconnector wire of that sub-second-interconnector, the force exerted on the sub-second-interconnector wire of that sub-second-interconnector being insufficient to overcome a force generated by frictional engagement of the exterior surface of the sub-second-interconnector wire of that sub-second-interconnector with the interior surface of the first cavity associated with that sub-second-interconnector,
whereby, the bias of the lumen wall anchor away from its compact-secured-configuration is overcome, and the lumen wall anchor remains in the compact-secured-configuration.

85. The assembly of clause 84, wherein, for each sub-second-interconnector, the sub-second-interconnector wire of that sub-second-interconnector is at least indirectly pullable from the exterior of the device with a sufficient amount of force to overcome the force generated by frictional engagement of the exterior surface of the sub-second-interconnector wire of that sub-second-interconnector with the interior surface of the second cavity associated with that sub-second-interconnector, to remove that sub-section-interconnector wire from passing through the two holes of the element of the one of the plurality of second connectors associated with that sub-second-interconnector, thereby disconnecting that one of the plurality of second connectors associated from that sub-second-interconnector and allowing the lumen wall anchor to adopt, at least in part, the expanded-secured-configuration.

Clauses 86 to 93

86. The assembly of any one of clauses 73 to 74, wherein
the second interconnector has multiple sub-second-interconnectors, the sub-second-interconnectors being the sub-second-interconnectors being tangentially spaced-apart from one another, and axially spaced-apart from the sub-first-connectors;
each of the second-sub-connectors is tangentially aligned in a one-to-one relationship a single one of the sub-first-connectors; and
each sub-second-interconnector includes two openings in the exterior surface of the device.

87. The assembly of clause 86 as it depends indirectly from clause 11, wherein the second portion of the first cavity extends from the second opening of each sub-first-interconnector to the first opening of each sub-second-interconnector, and the first cavity has a third portion extending from the second opening of each sub-second-interconnectors within the interior of the device.

88. The assembly of clause 86 as it depends indirectly from clause 13, wherein each first cavity is further associated with one of the sub-second-interconnectors that is in a one-to-one relationship with the one of the sub-first interconnector that that first cavity is associated with, the second portion of each first cavity extending from the second opening of its associated sub-first-interconnector to a first opening of its associated sub-second-interconnector, and each first cavity having a third portion extending from a second opening of its associated sub-second-interconnector within the interior of the device.

89. The assembly of any one of clauses 87 to 88, wherein
a number of the plurality of second connectors is equal to a number of the sub-second-interconnectors, and each one of the plurality of second connectors is associated with a single one of the sub-second-interconnectors.
each one of the plurality of second connectors includes an element having two holes therein, the holes being shaped and dimensioned, and positioned on the element with respect to each other, to allow the sub-first-interconnector wire of the sub-first-interconnector associated with the sub-second-interconnector associated with that one of the second connectors to pass therethrough;
each element is positioned, shaped and dimensioned such that, when the lumen wall anchor is in the compact-securing-configuration, a first hole of the two holes in that element is positioned adjacent the first opening of the sub-second-interconnector associated with the one of the plurality of second connectors of which that element is included, and a second hole of the two holes in that element is positioned adjacent the second opening of that sub-second-interconnector.

90. The assembly of clause 89 as it depends from clause 87, wherein, when the lumen wall anchor is in the compact-secured-configuration, for each sub-first interconnector and its associated sub-second-interconnector, the sub-first-interconnector wire of that sub-first-interconnector,
extends within the interior of the device within at least part of the first portion of the first cavity for a first length towards the first opening of that sub-first-interconnector;
traverses to the exterior of the device through the first opening of that sub-first-interconnector;
passes through the first hole of the two holes of the element of the one of the plurality of first connectors associated with that sub-first-interconnector;
extends outside the exterior of the device to the second hole of the two holes of that element;
passes through the second hole of the two holes of that element;
traverses through the second opening of that sub-first-interconnector;
extends with the second portion of the first cavity for a second length to the first opening of the sub-second-connector associated with that sub-first interconnector;
traverses to the exterior of the device through the first opening of that sub-second-interconnector;
passes through the first hole of the two holes of the element of the one of the plurality of second connectors associated with that sub-second-interconnector;
extends outside the exterior of the device to the second hole of the two holes of that element;
passes through the second hole of the two holes of that element;
traverses through the second opening of that sub-second-interconnector;
extends within at least part of the third portion of the first cavity for a third length.

91. The assembly of clause 90, wherein
for each sub-first-interconnector,
an exterior surface of the sub-first-interconnector wire of that sub-first-interconnector frictionally engages an interior surface of the first cavity, and
a force generated by the bias towards the released position of the first connector positioning wire on which the one of the plurality of first connectors associated with that sub-first-interconnector is disposed exerts a force on the sub-first-interconnector wire of that sub-first-interconnector, that force exerted on the sub-first-interconnector wire of that sub-first-interconnector being insufficient to overcome a force generated by frictional engagement of the exterior surface of that sub-first-interconnector wire with the interior surface of the first cavity and with exterior surfaces of other interconnector wires within the first cavity,
whereby, the bias of that first connector positioning wire toward the released position is overcome and that first connector positioning wire remains in the secured position; and
for each sub-second-interconnector,
an exterior surface of the sub-first-interconnector wire of the sub-first-interconnector associated with that sub-second-interconnector frictionally engages an interior surface of the first cavity, and
a force generated by a bias of the lumen wall anchor away from its compact-secured-configuration exerts a force on the sub-first-interconnector wire of the sub-first-interconnector wire associated with that sub-second-interconnector, that force exerted on that sub-first-interconnector wire being insufficient to overcome the force generated by frictional engagement of the exterior surface of that sub-first-interconnector wire with the interior surface of the first cavity, whereby, the bias of the lumen wall anchor away from its compact-secured-configuration is overcome, and the lumen wall anchor remains in the compact-secured-configuration.

92. The assembly of clause 89 as it depends from clause 88, wherein when the lumen wall anchor is in the compact-secured configuration, for each sub-first-interconnector and its associated sub-second-interconnector, the sub-first-interconnector wire of that sub-first-interconnector,
extends within the second portion of the first cavity associated with that sub-first-interconnector for a second length to the first opening of the sub-second-connector associated with that sub-first interconnector;
traverses to the exterior of the device through the first opening of that sub-second-interconnector;
passes through the first hole of the two holes of the element of the one of the plurality of second connectors associated with that sub-second-interconnector;
extends outside the exterior of the device to the second hole of the two holes of that element;
passes through the second hole of the two holes of that element;
traverses through the second opening of that sub-second-interconnector;
extends within at least a part of the third portion of the first cavity associated with that sub-second-interconnector for a third length;
a force generated by a bias of the lumen wall anchor away from its compact-secured-configuration exerts a force on the sub-first-interconnector wire of the sub-first-interconnector associated with that sub-second-interconnector, that force exerted on that sub-first-interconnector wire being insufficient to overcome the force generated by frictional engagement of the exterior surface of that sub-first-interconnector wire and the interior surface of the first cavity associated with that sub-second-interconnector;
whereby, the bias of the lumen wall anchor towards its expanded-secured-configuration is overcome, and the lumen wall anchor remains in the compact-secured-configuration.

93. The assembly of any one of clauses 91 and 92, wherein
for each sub-second-interconnector, the sub-first-interconnector wire of the sub-first-interconnector associated with that sub-second-interconnector is at least indirectly pullable from the exterior of the device by a first length to remove that sub-first-interconnector wire from passing through the two holes of the element of the one of the plurality of second connectors associated with that sub-second-interconnector, thereby disconnecting the one of the plurality of second connectors associated with that sub-second-interconnector from that sub-second-interconnector and allowing the lumen wall anchor to adopt, at least in part, the expanded-secured-configuration, the first length being insufficient to remove that sub-first-interconnector wire from passing through the two holes of the element of the one of the plurality of first connectors associated the sub-first-interconnector associated with that sub-second-interconnector; and
for each sub-first-interconnector, that sub-first-interconnector wire is thereafter at least indirectly pullable from the exterior of the device by a second length to remove that sub-first-interconnector wire from passing through the two holes of the element of the one of the plurality of first connectors associated with that sub-first-interconnector, thereby disconnecting the one of the plurality of first connectors associated with that sub-first-interconnector from that sub-first-interconnector and allowing the one of the first connector wires on which the one of the plurality of first connectors associated with that sub-first-interconnector is disposed to move to the released position.

Clauses 94 to 99

94. The assembly of clause 86, wherein
a number of the plurality of second connectors is equal to a number of the sub-second-interconnectors, and each one of the plurality of second connectors is associated with a single one of the sub-second-interconnectors;
each one of the plurality of second connectors includes an element having two holes therein, the holes being shaped and dimensioned, and positioned on the element with respect to each other, to allow the sub-second-interconnector wire of the sub-second-interconnector associated with that one of the plurality of second connectors to pass therethrough;
each element is positioned, shaped and dimensioned such that, when the lumen wall anchor is in the compact-securing-configuration, a first hole of the two holes in that element is positioned adjacent the first opening of the sub-second-interconnector associated with the one of the plurality of second connectors of which that element is included, and a second hole of the two holes in that element is positioned adjacent the second opening of that sub-second.

95. The assembly of clause 94, wherein
the sub-first-interconnector wire of each of the sub-first-interconnectors has a hollow core; and
the sub-second-interconnector wire of each of the sub-second-interconnectors is disposed within the hollow core of the sub-first-interconnector wire of the one of the sub-first-interconnectors associated with that sub-second-interconnector.

96. The assembly of clause 95 as it depends indirectly from clause 24, wherein
the second portion of the first cavity extends to the first opening of each sub-second-interconnector and a third portion extends from the second opening of each sub-second-interconnector within the interior of the device; and
when the lumen wall anchor is in the compact-secured configuration, for each sub-first-interconnector and its associated sub-second-interconnector,
the sub-first-interconnector wire of that sub-first-interconnector,
has a proximal end, and
has a distal end that extends within the second portion of the first cavity for a second length and ends before reaching the first opening of the sub-second-connector associated with that sub-first interconnector; and
the sub-second-interconnector wire of that sub-second-connector, has a proximal end that extends proximally beyond the proximal end of the sub-first-interconnector wire of the sub-first-interconnector associated with that sub-second-interconnector;

has a distal end that
  exits the hollow core of the sub-first-interconnector wire of that sub-first-connector within the second portion of the first cavity;
  extends within the second portion of the first cavity to the first opening of that sub-second-interconnector;
  traverses to the exterior of the device through the first opening of that sub-second-interconnector;
  passes through the first hole of the two holes of the element of the one of the plurality second connectors associated with that sub-second-interconnector;
  extends outside the exterior of the device to the second hole of the two holes of that element;
  passes through the second hole of the two holes of that element;
  traverses through the second opening of that sub-second-interconnector;
  extends at least in part with the third portion associated with that sub-second-interconnector for a third length;

an exterior surface of the sub-second-interconnector wire of that sub-second-interconnector frictionally engages an interior surface of the hollow core of the sub-first-interconnector wire of the sub-first-interconnector within which that sub-second-interconnector wire is disposed prior to exiting the hollow core of that sub-first-interconnector wire;

the exterior surface of the sub-second-interconnector wire of that sub-second-interconnector further frictionally engages an interior surface of the first cavity after exiting the hollow core of the sub-first-interconnector wire of that sub-first-connector associated with that sub-second-connector; and a force generated by a bias of the lumen wall anchor away from its compact-secured-configuration exerts a force on the sub-second-interconnector wire of that sub-second-interconnector, that force exerted on that sub-second-interconnector wire being insufficient to overcome a force generated by frictional engagement of the exterior surface of that sub-second-interconnector wire with the interior surface of the first cavity and of the exterior surface of that sub-second-interconnector with the interior surface of the hollow core of the sub-first-interconnector wire of the sub-first-interconnector within which that second-sub-interconnector wire is disposed; whereby, the bias of the lumen wall anchor away from its compact-secured-configuration is overcome, and the lumen wall anchor remains in the compact-secured-configuration.

97. The assembly of clause 96, wherein
for each sub-second-interconnector, the sub-second-interconnector wire of that sub-second-interconnector is at least indirectly pullable from the exterior of the device with a sufficient amount of force to overcome the force generated by frictional engagement of the exterior surface of that sub-second-interconnector wire with the interior surface of the first cavity and of the exterior surface of that sub-second-interconnector and the interior surface of the hollow core of the sub-first-interconnector wire of the sub-first-interconnector within which that sub-second-interconnector wire is disposed, to remove that sub-second-interconnector wire from passing through the two holes of the element of the one of the plurality of second connectors associated with that sub-second-interconnector, thereby disconnecting the one of the plurality of second connectors associated with that sub-second-interconnector from that sub-second-interconnector and allowing the lumen wall anchor to adopt, at least in part, the expanded-secured-configuration; and for each sub-first-interconnector, the sub-first-interconnector wire of that sub-first-interconnector is thereafter at least indirectly pullable from the exterior of the device with a sufficient amount of force to overcome the force generated by frictional engagement of the exterior surface of the sub-first-interconnector wire of that sub-first-interconnector with the interior surface of the first cavity and with exterior surfaces of the other interconnector wires within the first cavity, to remove the sub-first-interconnector wire of that sub-first-interconnector from passing through the two holes of the element of the one of the plurality of first connectors associated with that sub-first-interconnector, thereby disconnecting that one of the plurality of first connectors from that sub-first-interconnector and allowing the first connector positioning wire on which that one of the plurality of first connectors is disposed to move to the released position.

98. The assembly of clause 95 as it depends indirectly from clause 27,
each first cavity is further associated with the one of the sub-second-interconnectors that is in a one-to-one relationship with the one of the sub-first interconnectors that that first cavity is associated with, the second portion of each first cavity extending from the second opening of its associated sub-first-interconnector to the first opening of its associated sub-second-interconnector, and each first cavity has a third portion extending from the second opening of its associated sub-second-interconnector within the interior of the device; and wherein when the lumen wall anchor is in the compact-secured-configuration, for each sub-first-interconnector and its associated sub-second-interconnector,
the sub-first-interconnector wire of that sub-first-interconnector,
  has a proximal end,
  has a distal end that extends within the second portion of the first cavity associated with that sub-first-interconnector for a second length and ends before reaching the first opening of the sub-second-connector associated with that sub-first interconnector; and
the sub-second-interconnector wire of that sub-second-connector,
  has a proximal end that extends proximally beyond the proximal end of the interconnector wire of the sub-first-interconnector associated with that sub-second-interconnector;
  has a distal end that
    exits the hollow core of the sub-first-interconnector wire of that sub-first-connector within the second portion of the first cavity associated with that sub-second-connector;
    extends within the second portion of the first cavity to the first opening of that sub-second-interconnector;

traverses to the exterior of the device through the first opening of that sub-second-interconnector;

passes through the first hole of the two holes of the element of the one of the second connectors associated with that sub-second-interconnector;

extends outside the exterior of the device to the second hole of the two holes of that element;

passes through the second hole of the two holes of that element;

traverses through the second opening of that sub-second-interconnector;

extends with at least in part the third portion of the first cavity associated with that sub-second-interconnector for a third length;

an exterior surface of the sub-second-interconnector wire of that sub-second-interconnector frictionally engages an interior surface of the hollow core of the sub-first-interconnector wire of the sub-first-interconnector within which that sub-second-interconnector wire is disposed prior to exiting the hollow core of that sub-first-interconnector wire;

the exterior surface of the sub-second-interconnector wire of that sub-second-interconnector further frictionally engages an interior surface of the first cavity within which that sub-second-interconnector wire is disposed after exiting the hollow core of the sub-first-interconnector wire of that sub-first-connector associated with that sub-second-connector; and a force generated by a bias of the lumen wall anchor away from its compact-secured-configuration exerts a force on the sub-second-interconnector wire of that sub-second-interconnector, that force exerted on that sub-second-interconnector wire being insufficient to overcome a force generated by frictional engagement of the exterior surface of that sub-second-interconnector wire with the interior surface of the first cavity associated with that sub-second-interconnector and of the exterior surface of that sub-second-interconnector wire with the interior surface of the hollow core of the sub-first-interconnector wire of the sub-first-interconnector within which that sub-second-interconnector wire is disposed; whereby, the bias of the lumen wall anchor away from its compact-secured-configuration is overcome and the lumen wall anchor remains in the compact-secured-configuration.

99. The assembly of clause 98, wherein for each sub-second-interconnector, the sub-second-interconnector wire of that sub-second-interconnector is at least indirectly pullable from the exterior of the device with a sufficient amount of force to overcome the force generated by frictional engagement of the exterior surface of that sub-second-interconnector wire with the interior surface of the first cavity associated with that sub-second-interconnector and of the exterior surface of that sub-second-interconnector with the interior surface of the hollow core of the sub-first-interconnector wire of the sub-first-interconnector within which that sub-second interconnector wire is disposed, to remove that sub-second-interconnector wire from passing through the two holes of the element of the one of the plurality of second connectors associated with that sub-second-interconnector, thereby disconnecting the one of the plurality of second connectors associated with that sub-second-interconnector from that sub-second-interconnector and allowing the lumen wall anchor to adopt, at least in part, the expanded-secured-configuration; and for each sub-first-interconnector, that sub-first-interconnector wire is thereafter at least indirectly pullable from the exterior of the device with a sufficient amount of force to overcome the force generated by frictional engagement of the exterior surface of that sub-first-interconnector wire and the interior surface of the first cavity associated with that sub-first-interconnector, to remove that sub-first-interconnector wire from passing through the two holes of the element of the one of the plurality of first connectors associated with that sub-first-interconnector, thereby disconnecting the one of the plurality of first connectors associated with that sub-first-interconnector from that sub-first-interconnector and allowing the one of the first connector positioning wires on which the one of the first connectors associated with that sub-first-interconnector is disposed to move to the released position.

Clauses 100 to 107

100. The assembly of any one of clauses 4 and 5 to 99 as they depend directly or indirectly from clause 4, wherein the device is a modular fluid flow influencing device having a central docking unit and a plurality of functional units, the docking unit being non-expandable and being the elongate body of the device;

the docking unit having:

a plurality of concave receiving surfaces for receiving the functional units, the receiving surfaces extending parallel to the central longitudinal axis of the docking units and being positioned equidistantly radially along the exterior surface thereof;

a plurality of inter-receiving-surface portions, an inter-receiving-surface portion extending longitudinally, parallel to the central longitudinal axis of the docking unit, between each two adjacent receiving surfaces.

101. The assembly of clause 102, wherein each of the sub-first-interconnectors is located on a one of the inter-receiving-surface portions.

102. The assembly of clause 103, wherein each of the sub-first-interconnectors includes a first concavity of the one of the inter-receiving surface portions on which that sub-first interconnector is located, with the two openings of that sub-first-interconnector being disposed through a surface of that first concavity.

103. The assembly of clause 102 as it depends indirectly from clause 19, wherein the element of each one of the plurality of first connectors is convex and confirms to a curvature of the first concavity of the sub-first-interconnector associated with the one of the plurality of first connectors of which that element is included.

104. The assembly of any one of clauses 101 to 103 as they depend indirectly from any one of clauses 35, 56, 73 and 86, wherein each of the sub-second-interconnectors is located on a one of the inter-receiving-surface portions.

105. The assembly of clause 104, wherein each of the sub-second-interconnectors includes a second concavity of the one of the inter-receiving-surface portions on which that sub-second-interconnector is located, with the two openings of that sub-second-interconnector being disposed through a surface of that second concavity.

106. The assembly of clause 105, wherein the element of each one of the second connectors is convex and confirms to a curvature of the second concavity of the sub-secondinterconnector associated with the one of the second connectors of which that element is included.

107. The assembly of clause 103, wherein the element of each one of the second connectors is convex and confirms to a curvature of the second concavity of the sub-second-interconnector Clauses 108 to 123

108. The assembly of any one of clauses 7 and 8 to 34 as they depend directly or indirectly from clause 7, wherein each of the plurality of first connectors is located at the joined ends of pairs of the plurality of first connector positioning wires.

109. The assembly of clause 108, wherein the pairs of the plurality of first connector positioning wires are unitarily formed as a single structure.

110. The assembly of any one of clauses 108 to 109, wherein each of the plurality of first connectors is a loop formed at the joined ends of the pairs of the plurality of first connector positioning wires.

111. The assembly of clause 110, wherein each loop is formed, at least in part, by a clasp.

112. The assembly of any one of clauses 110 and 111, wherein the first interconnector includes a plurality of hooks positioned, dimensioned and shaped to hook the loops of the lumen wall anchor when the first connector positioning wires on which the loops located are in the secured position.

113. The assembly of clause 114, wherein the first interconnector includes a secured configuration in which the hooked loops are held captive by the first interconnector and a released configuration in which the loops are allowed to be become unhooked from the hooks of the first interconnector.

114. The assembly of clause 113, wherein the first interconnector of the device includes a distal end portion of the body of the device longitudinally movable along the central longitudinal axis of the body of the device.

115. The assembly of clause 114, wherein the end portion is moveable between a secured position and a released position with respect to a body of the device.

116. The assembly of clause 115, wherein the end portion is an end cap that registers with the body of the device.

117. The assembly of clause 116, wherein the end cap registers with the body of the device when in the end cap is in the secured position.

118. The assembly of clause 117, wherein the end cap is longitudinally spaced apart from the body when of the device when the end cap is in the released position.

119. The assembly of clause 120, wherein the end cap is disposed on rod moveably disposed within a channel within the body of the device, the channel extending along the central longitudinal axis of the body of the device.

120. The assembly of clause 119, wherein actuation of the rod moves the end cap from the secured position to the released position.

121. The assembly of clause 120, wherein the rod is attachable to an interconnector actuation wire for actuating the rod.

122. The assembly of any one of clauses 114 to 121, wherein,
when the end portion is in the secured position the first interconnector is in the secured configuration, whereby the hooked loops are held captive, and
when the end portion is in the released position the first interconnector is in the released configuration, whereby the hooked loops are allowed to become unhooked from the hooks of the first interconnector.

123. The assembly of any one of clauses 114 to 122, wherein,
when the end portion is in the secured position,
the first interconnector is in the secured configuration, whereby the hooked loops are held captive,
a bias of the first connector positioning wires on which the hooked loops are located towards the released position is overcome, and
the first connector positioning wires on which the hooked loops are located are maintained in the secured position,
whereby the first interconnector releasably connects the lumen wall anchor to the device; and
when the end portion is in the released position,
the first interconnector is in the released configuration, whereby the hooked loops are allowed to become unhooked from the hooks of the first interconnector,
the first connector positioning wires on which the hooked loops are located move towards the released position as a result of the bias, unhooking the hooked loops,
whereby the first interconnector disconnects the lumen wall anchor from the device.

Clauses 124 to 138

124. The assembly of any one of clauses 7 and 8 to 34 as they depend directly or indirectly from clause 7, wherein each first connector is a hook.

125. The assembly of clause 124, wherein the first interconnector includes a plurality of loops positioned, dimensioned and shaped to loop the hooks of the lumen wall anchor when the first connector positioning wires on which the hooks are located are in the secured position.

126. The assembly of clause 125, wherein the first interconnector includes a secured configuration in which the looped hooks are held captive by the first interconnector and a released configuration in which the hooks are allowed to be become unlooped from the loops of the first interconnector.

127. The assembly of clause 126, the body of the device has a channel extending along the central longitudinal axis thereof.

128. The assembly of clause 127, wherein the loops extend through the channel of the body of the device.

129. The assembly of any one of clauses 127 or 128, wherein the loops are moveable within the channel parallel to the central longitudinal axis of the body of the device.

130. The assembly of clause 129, wherein the loops are moveable between a secured position and a released position with respect to the body of the device.

131. The assembly of clause 130, wherein the loops are within the channel of the body of the device when in the secured position.

132. The assembly of clause 131, wherein the loops are outside of the body of the device when in the released position.

133. The assembly of any one of clauses 129 to 132, wherein the loops are disposed at an end of a rod disposed within the channel and moveable along one of the central longitudinal axis of the device and a line parallel to the central longitudinal axis of the body of the device.

134. The assembly of clause 133, wherein at least portion of the rod is hollow, and the loops are secured within the hollow portion of the rod.

135. The assembly of any one of clauses 133 to 134, wherein actuation of the rod moves the loops from the secured position to the released position.

136. The assembly of clause 135, wherein the rod is attached to an actuation wire for actuating the rod.

137. The assembly of any one of clauses 131 to 136, wherein the loops, the hooks, the ends of each of the first connector positioning wires on which the hooks are located, and the channel of the body of the device, are all positioned, dimensioned and shaped, each with respect to the others, such that when the hooks are looped by the loops, and the loops are in the secured position, the first interconnector is in the secured configuration, whereby the looped hooks are held captive within the channel of the body of the device, and when the hooks are looped by the loops, and the loops are in the released position, the first interconnector is in the released configuration, whereby the looped hooks are allowed to become unlooped from the loops of the first interconnector.

138. The assembly of any one of clauses 131 to 138, wherein the loops, the hooks, the ends of each of the first connector positioning wires on which the hooks are located, and the channel of the body of the device, are all positioned, dimensioned and shaped, each with respect to the others, such that when the hooks are looped by the loops, and the loops are in the secured position, the first interconnector is in the secured configuration, whereby the looped hooks are held captive within the channel of the body of the device, a bias of the first connector positioning wires on which the looped hooks towards the released position is overcome, and the first connector positioning wires on which the looped hooks are located are maintained in the secured position, whereby the first interconnector releasably connects the lumen wall anchor to the device; and when the hooks are looped by the loops, and the loops are in the released position, the first interconnector is in the secured configuration, whereby the looped hooks are allowed to become unlooped from the loops, the first connector positioning wires on which the looped hooks are located move towards the released position as a result of the bias, unlooping the looped hooks, whereby the first interconnector disconnects the lumen wall anchor from the device.

Clauses 139 to 162

139. The assembly of any one of clauses 1 to 138, wherein each wire of the plurality of first connector positioning wires extends from a proximal end of the wire network.

140. The assembly of any one of clauses 1 to 139, wherein, when in the lumen wall anchor is in at least one of the expanded-secured-configuration and the expanded-released-configuration, the wire network is generally cylindrical in peripheral shape.

141. The assembly of any one of clauses 1 to 139, wherein, when in the lumen wall anchor is in at least one of the expanded-securing-configuration and the expanded-released-configuration, the wire network is generally a truncated cone in peripheral shape.

142. The assembly of any one of clauses 1 to 141, wherein when the lumen wall anchor is in the expanded-released-configuration, each of the plurality of first connectors is generally in line with a periphery of the wire network.

143. The assembly of any one of clauses 1 to 142, wherein at least some of the wires of the wire network are one of square and rectangular in cross-section.

144. The assembly of any one of clauses 1 to 143, wherein the lumen wall anchor is overcomably biased toward the expanded-released-configuration.

145. The assembly of clause 144, wherein the bias is overcomable, at least in part, via insertion of the lumen wall anchor into the catheter.

146. The assembly of any one of clauses 1 to 145, wherein the lumen wall anchor consists essentially of a shape-memory alloy.

147. The assembly of clause 146, wherein the wire network consists essentially of nitinol.

148. The assembly of any one of clauses 1 to 145, wherein the lumen wall anchor consists essentially of resorbable material.

149. The assembly of clause 148, wherein the lumen wall anchor consists essentially of at least one from a group consisting of poly(L-lactide), poly(D,L-lactide) and platinum.

150. The assembly of any one of clauses 1 to 143, wherein the lumen wall anchor is not self-expandable.

151. The assembly of clause 150, where in the lumen wall anchor is structured to be expanded from the compact-secured-configuration to the expanded-secured-configuration via inflation of a balloon within the wire network.

152. The assembly of any one of clauses 1 to 151, wherein the mammalian body conduit is a human body conduit.

153. The assembly of clause 152, wherein the human body conduit is a vascular system conduit.

154. The assembly of clause 153, wherein the vascular system conduit is one of an aorta and an inferior vena cava.

155. The assembly of clause 153, wherein the intralumenal device is a ventricular assist device and the vascular system conduit of one of a group consisting of an aorta, a left ventricle, a vena cava, a pulmonary artery, and a right ventricle.

156. The assembly of any one of clauses 1 to 155, wherein the wire network has a plurality of tangentially-spaced-apart projections connected to a distal end thereof.

157. The assembly of clause 156, wherein the tangentially-spaced-apart projections are anchor elements.

158. The assembly of any one of clauses 1 to 157, wherein at least a portion of the wire network is covered with at least one sheet of material.

159. The assembly of clause 158 wherein the material is at least one of knitted polyester, expanded polytetrafluoroethylene and polyurethane.

160. The assembly of any one of clauses 1 to 159, wherein the wire network is open and uncovered.

161. The assembly of any one clauses 1 to 160, wherein the catheter is a delivery sheath.

162. A loader connectable to the delivery sheath of clause 161, the loader having a cavity in which the mammalian body conduit intralumenal device and lumen wall anchor assembly are disposed in the compact-secured configuration.

Clauses to 163-181

163. The assembly of any one of clauses 7 and 8 to 34 as the depend directly or indirectly from clause 7, wherein the wire network of the lumen wall anchor includes a first plurality of nodes, a second plurality of nodes, and a plurality of internodal wires (being structural elements) r, each node of the second plurality of nodes being interconnected with at least one node of the first plurality of nodes by at least one internodal wire.

164. The assembly of clause 163, wherein the first plurality of nodes is located at an axial end of the wire network.

165. The assembly of clause 164, wherein the second plurality of nodes is axially spaced-apart from the first plurality of nodes.
166. The assembly of any one of clauses 163 to 165, wherein nodes of the first plurality of nodes and nodes of the second plurality of nodes tangentially alternate.
167. The assembly of any one of clauses 163 to 166, wherein each node of the first plurality of nodes is connected to two internodal wires.
168. The assembly of any one of clauses 163 to 167, wherein each one of the first plurality of nodes is connected to a first internodal wire and a second internodal wire, the first internodal wire interconnecting the that one of the first plurality of nodes with a first one of the second plurality of nodes tangentially adjacent to that one of the first plurality of nodes in a first tangential direction, the second internal wire interconnecting that one of the first plurality of nodes with a second one of the second plurality of nodes tangentially adjacent to that one of the first plurality of nodes in a second tangential direction opposite to the first tangential direction.
169. The assembly of any one of clauses 163 to 168, wherein, when the lumen wall anchor is in the expanded-securing-configuration, each internodal wire is curved in an axial direction.
170. The assembly of any one of clauses 163 to 169, wherein each one of the second plurality of nodes is connected to a first internodal wire and a second internodal wire, the first internodal wire interconnecting the that one of the second plurality of nodes with a first one of the first plurality of nodes tangentially adjacent to that one of the second plurality of nodes in a first tangential direction, the second internal wire interconnecting that one of the second plurality of nodes with a second one of the first plurality of nodes tangentially adjacent to that one of the second plurality of nodes in a second tangential direction opposite to the first tangential direction.
171. The assembly of any one of clauses 163 to 170, wherein each wire of the plurality of first connector positioning wires extends from a node of the second plurality of nodes.
172. The assembly of any one of clauses 163 to 171, wherein the ends of at least two of the plurality of first connector positioning wires are joined together to form at least one third node, the at least one first connector being connected to the third node.
173. The assembly of clause 172, wherein the ends of the plurality of first connector positioning wires are joined together in multiples to form a plurality of third nodes, a one of the at least one first connector being disposed on each node of the plurality of third nodes.
174. The assembly of clause 173, wherein the ends of the plurality of first connector positioning wires are joined together in twos to form a plurality of third nodes, a one of the at least one first connector being disposed on each node of the plurality of third nodes.
175. The assembly of clause 174, wherein the ends of the plurality of first connector positioning wires are joined together in threes to form a plurality of third nodes, a one of the at least one first connector being disposed on each node of the plurality of third nodes.
176. The assembly of any one of clauses 163 to 174, wherein the plurality of first connector positioning wires includes unpaired connector positioning wires and paired connector positioning wires.
177. The assembly of any one of clauses 172 and 173 to 176 as they depend directly or indirectly from clause 172, wherein the plurality of first connector positioning wires includes unpaired first connector positioning wires and paired first connector positioning wires extending from tangentially alternating nodes of the plurality of second nodes.
178. The assembly of clause 177, wherein the wires of each pair of the paired first connector positioning wires are tangentially spaced apart from one another.
179. The assembly of any one of clauses 176 to 178, wherein each wire of the paired first connector positioning wires has a portion that is shaped to relieve stress when the wire is in the securing position.
180. The assembly of any one of clauses 176 to 179, wherein each wire of the paired first connector positioning wires has a chevron-shaped portion for relieving stress when the wire is in the securing position.
181. The assembly of any one of clauses 177 to 180 as they depend directly or indirectly from clause 175, wherein, joined together in threes to form each third node are:
- a one of the unpaired first connector positioning wires;
- a one of the wires of the paired first connector positioning wires that is immediately tangentially adjacent to the one of the unpaired first connector positioning wires in a first tangential direction; and
- a one of the wires of the paired first connector positioning wires that is immediately tangentially adjacent to the one of the unpaired first connector positioning wires in a second tangential direction opposite to the first tangential direction.

Clauses 201 to 203

201. A lumen wall anchor for use in maintaining an intralumenal device in place within a mammalian body conduit, the lumen wall anchor comprising:
- a 3D-shaped wire network, the wire network having a central longitudinal axis,
- a plurality of first connector positioning wires extending from the wire network, each wire of the plurality of first connector positioning wires being moveable between a secured position and a released position and being overcomeably biased towards the released position;
- at least one first connector disposed at an end of at least one wire of the plurality of first connector positioning wires;

the lumen wall anchor having distal end, a proximal end, a compact-secured-configuration, an expanded-secured-configuration, and an expanded-released-configuration,
- when the lumen wall anchor is in the compact-secured-configuration,
  - the lumen wall anchor is shaped and dimensioned to be deliverable to the delivery site within the lumen of the mammalian body conduit via the catheter, and
  - each wire of the first plurality of connector positioning wires is in the secured position, the secured position being the end of that wire of the first plurality of connector positioning wires being positioned in proximity to the central longitudinal axis;
- when the lumen wall anchor is in the expanded-secured-configuration,
  - the wire network is dimensioned and shaped to exert a force on a wall of the lumen of the conduit, the force being sufficient to anchor the lumen wall anchor assembly in place, and
  - each wire of the first plurality of connector positioning wires is in the secured position; and
- when the lumen wall anchor is in the expanded-released-configuration, the wire network is dimensioned and shaped to exert a force on a wall of the lumen of the conduit, the force being sufficient to anchor the lumen wall anchor assembly in place, each wire of the plurality of first connector positioning wires is in the released position, the released position being the end of each wire of the first plurality of connector positioning wires being generally in line with the periphery of the wire network, and the plurality of first connector positioning wires and all of the at least one first connector do not obstruct fluid flow axially through the wire network while the lumen wall anchor is anchored in place.

202. The assembly of clause 201, wherein, when in the expanded-secured-configuration and in the expanded-released-configuration, the wire network is dimensioned and shaped to exert a force on the wall of the lumen of the conduit indirectly by exerting a force directly on the wall of a stent having been implanted within the conduit.

203. The lumen wall anchor of any one of clauses 201 to 202, wherein the at least one first connector disposed at the end of at least one wire of the plurality of first connector positioning wires is a plurality of first connectors.

Clause 204

204. The lumen wall anchor of clause 203, wherein a single one of the plurality of first connectors is disposed at the end each of wire of the plurality of first connector positioning wires.

Clause 205

205. The lumen wall anchor of clause 203, wherein the ends of the plurality of first connector positioning wires are joined together in multiples, a single one of plurality of first connectors being disposed at the joined ends of each of the multiples.

Clauses 206 to 209

206. The lumen wall anchor of any one of clauses 204 to 205, wherein each one of the plurality of first connectors includes an element having a hole therein.

207. The lumen wall anchor of any one of clauses 204 to 205, wherein each one of the plurality of first connectors includes an element having two holes therein.

208. The lumen wall anchor of any one of clauses 206 to 207, wherein each element is convex.

209. The lumen wall anchor of any one of clauses 204 to 208, wherein, each of the first connector positioning wires when in the secured position, forms a proximally-facing sloped surface such that a retrieval sheath being manoeuvered from the proximal end of the lumen wall anchor towards the distal end of the lumen wall anchor, via contact with the sloped surfaces of the first connector positioning wires, causes, at least in part, the lumen wall anchor to adopt the compact-secured-configuration as it enters a lumen of the retrieval sheath.

Clauses 210 to 216

210. The lumen wall anchor of any one of clauses 202 to 209, further comprising:
 a plurality of second connector positioning wires extending from the wire network, each wire of the plurality of second connector positioning wires being moveable between a secured position and a released position and being overcomeably biased towards the released position;
 a plurality of second connectors, a single one of the plurality of second connectors being disposed at an end of each wire of the plurality of second connector positioning wires;

when the lumen wall anchor is in the expanded-securing-configuration, each wire of the plurality of second connector positioning wires is in the secured position;

when the lumen wall anchor is in the expanded-released-configuration,
 each wire of the plurality of second connector positioning wires is in the released position, the released position being the end of that wire of the plurality of second connector positioning wires being generally in line with the periphery of wire network,
 the plurality of second connector positioning wires and the plurality of second connectors do not obstruct fluid flow axially through the wire network while the lumen wall anchor is anchored in place.

211. The lumen wall anchor of clause 210, wherein each wire of the plurality of second connector positioning wires extends from a point intermediate ends of the wire network.

212. The lumen wall anchor of any one of clauses 210 to 211, wherein, when the lumen wall anchor is in the expanded-released-configuration, each of the second connectors is generally aligned with a periphery of the wire network.

213. The lumen wall anchor of any one of clauses 210 to 212, wherein each one of the plurality of second connectors includes an element having a hole therein.

214. The lumen wall anchor of any one of clauses 210 to 213, wherein each one of the plurality of second connectors includes an element having two holes therein.

215. The lumen wall anchor of any one of clauses 213 to 214, wherein each element of the plurality of second connectors is convex.

216. The lumen wall anchor of any one of clauses 210 to 215, wherein, each of the second connector positioning wires when in the secured position, forms a proximally-facing sloped surface such that a retrieval sheath being manoeuvered from the proximal end of the lumen wall anchor towards the distal end of the lumen wall anchor, via contact with the sloped surfaces of the second connector positioning wires, causes, at least in part, the lumen wall anchor to adopt the compact-secured-configuration as it enters a lumen of the retrieval sheath.

Clauses 217 to 222

217. The lumen wall anchor of any one of clauses 201 to 209, wherein
 the lumen wall anchor further includes a plurality of second connectors disposed on the wire network;
 when the lumen wall anchor is the compact-secured-position each of the plurality of second connectors is in a secured position;
 when the lumen wall anchor is in a one of the expanded-secured-configuration and the expanded-released-configuration, each of the plurality of second connectors is in a released position being proximate the wall of the lumen of the conduit such that the plurality of second connectors do not obstruct fluid flow axially through the wire network while the lumen wall anchor is anchored in place.

218. The lumen wall anchor of clause 217, wherein the second connectors are disposed distally of the first connectors.

219. The lumen wall anchor of any one of clauses 217 to 218, wherein, when the lumen wall anchor is in the one of the expanded-secured-configuration and the expanded-released-configuration, each of the second connectors is generally aligned with a periphery of the wire network.

220. The lumen wall anchor of any one of clauses 217 to 219, wherein each one of the plurality of second connectors includes an element having a hole therein.
221. The lumen wall anchor of any one of clauses 217 to 219, wherein each one of the plurality of second connectors includes an element having two holes therein.
222. The lumen wall anchor of any one of clauses 220 to 221, wherein each element of the second plurality of connectors is convex.

Clauses 223 to 226

223. The lumen wall anchor of any one of clauses 201 to 203 and 205, wherein each of the plurality of first connectors is located at the joined ends of pairs of the plurality of first connector positioning wires.
224. The lumen wall anchor of clause 223, wherein the pairs of the plurality of first connector positioning wires are unitarily formed as a single structure.
225. The lumen wall anchor of any one of clauses 223 to 224, wherein each of the plurality of first connectors is a loop formed at the joined ends of the pairs of the plurality of first connector positioning wires.
226. The lumen wall anchor of clause 225, wherein each loop is formed, at least in part, by a clasp.

Clause 227

227. The lumen wall anchor of any one of clauses 201 to 204, wherein each first connector is a hook.

Clauses 228 to 247

228. The lumen wall anchor of any one of clauses 201 to 227, wherein each wire of the plurality of first connector positioning wires extends from a proximal end of the wire network.
229. The lumen wall anchor of any one of clauses 201 to 228, wherein, when in the lumen wall anchor is in at least one of the expanded-secured-configuration and the expanded-released-configuration, the wire network is generally cylindrical in peripheral shape.
230. The lumen wall anchor of any one of clauses 201 to 228, wherein, when in the lumen wall anchor is in at least one of the expanded-securing-configuration and the expanded-released-configuration, the wire network is generally a truncated cone in peripheral shape.
231. The lumen wall anchor of any one of clauses 201 to 230, wherein when the lumen wall anchor is in the expanded-released-configuration, each of the plurality of first connectors is generally aligned with a periphery of the wire network.
232. The lumen wall anchor of any one of clauses 201 to 231, wherein at least some of the wires of the wire network are one of square and rectangular in cross-section.
233. The lumen wall anchor of any one of clauses 201 to 232, wherein the lumen wall anchor is overcomably biased toward the expanded-released-configuration.
234. The lumen wall anchor of clause 233, wherein the bias is overcomable, at least in part, via insertion of the lumen wall anchor into the catheter.
235. The lumen wall anchor of any one of clauses 201 to 234, wherein the lumen wall anchor consists essentially of a shape-memory alloy.
236. The lumen wall anchor of clause 235, wherein the wire network consists essentially of nitinol.
237. The lumen wall anchor of any one of clauses 201 to 236, wherein the lumen wall anchor consists essentially of resorbable material.
238. The lumen wall anchor of clause 237, wherein the lumen wall anchor consists essentially of at least one from a group consisting of poly(L-lactide), poly(D,L-lactide) and platinum.
239. The lumen wall anchor of any one of clauses 201 to 232, wherein the lumen wall anchor is not self-expandable.
240. The lumen wall anchor of clause 239, wherein the lumen wall anchor is structured to be expanded from the compact-secured-configuration to the expanded-secured-configuration via inflation of a balloon within the wire network.
241. The lumen wall anchor of any one of clauses 201 to 240, wherein the mammalian body conduit is a human body conduit.
242. The lumen wall anchor of clause 241, wherein the human body conduit is a vascular system conduit.
243. The lumen wall anchor of clause 242, wherein the vascular system conduit is one of an aorta a left ventricle, a vena cava, a pulmonary artery, and a right ventricle.
244. The lumen wall anchor of any one of clauses 201 to 243, wherein the wire network has a plurality of tangentially-spaced-apart projections connected to a distal end thereof.
245. The lumen wall anchor of clause 244, wherein the tangentially-spaced-apart projections are anchor elements.
246. The lumen wall anchor of any one of clauses 201 to 245, wherein at least a portion of the wire network is covered with at least one sheet of material.
247. The lumen wall anchor of any one of clauses 201 to 245, wherein the wire network is open and uncovered.
248. The lumen wall anchor of any one clauses 201 to 248, wherein the catheter is a delivery sheath.

Clauses 301 to 314

301. A mammalian body conduit intralumenal device,
    the device being shaped and dimensioned to be deliverable to a delivery site within a lumen of a mammalian body conduit via a catheter;
    the device having
        a first interconnector for releasably connecting the device with a lumen wall anchor for maintaining the device in place within the mammalian body conduit;
        an elongate body having a central longitudinal axis;
        a proximal end and a distal end; and
        an exterior surface.
302. The device of clause 301, wherein the first interconnector includes two openings in the exterior surface of the device.
303. The device of clause 302, wherein the first interconnector further includes an interconnector wire, the interconnector wire
    traversing from an interior of the device to an exterior of the device through a first one of the two openings,
    extending outside the exterior of the device, and then
    traversing from the exterior of the device to the interior of the device through a second one of the two openings.
304. The device of clause 303, wherein
    the device has a first cavity extending within the body, the first cavity having a first portion extending from the exterior of the device to the first opening and a second portion extending from the second opening within the interior of the device; and
    the interconnector wire further extends from the exterior of the device within the first portion of the first cavity to the first opening and from the second opening within the second portion of the first cavity.
305. The device of clause 301, wherein the first interconnector has multiple sub-first-interconnectors, the sub-first-interconnectors being spaced apart from one another, each sub-first-interconnector including two openings in the exterior surface of the device.

306. The device of clause 305, wherein each sub-first-interconnector further includes a sub-first-interconnector wire, the sub-first-interconnector wire
- traversing from an interior of the device to an exterior of the device through a first one of the two openings of that sub-first-interconnector,
- extending outside the exterior of the device, and then
- traversing from the exterior of the device to the interior of the device through a second one of the two openings of that sub-first-interconnector.

307. The device of clause 306, wherein
- the device has a first cavity extending within the body, the first cavity having a first portion extending within the interior of the device to the first opening of each sub-first-interconnector and a second portion extending from the second opening of each sub-first interconnector within the interior of the device; and
- the sub-first-interconnector wire of each sub-first-interconnector extends within at least a part of the first portion of the first cavity to the first opening of that sub-first-interconnector and from the second opening of that sub-first-interconnector within at least a part of the second portion of the first cavity.

308. The assembly of clause 307, wherein a majority of the first cavity extends within the body of the device generally parallel to the central longitudinal axis of the body of the device.

309. The device of clause 306, wherein
- the device further has multiple first cavities extending within the body, each first cavity being associated with a one of the sub-first-interconnectors, each first cavity having a first portion extending within the interior of the device to the first opening of the sub-first-interconnector associated with that first cavity and a second portion extending from the second opening of the sub-first-interconnector associated with that first cavity within the interior of the device; and
- the sub-first-interconnector wire of each sub-first-interconnector further extends at least in part of within the first portion of the first cavity associated with that sub-first-interconnector to the first opening associated with that sub-first-interconnector and from the second opening associated with that sub-first-interconnector within at least a part of the second portion of the first cavity associated with that sub-first-interconnector.

310. The device of clause 309, wherein a majority of each first cavity extends within the body of the device generally parallel to the central longitudinal axis of the body of the device.

311. The device of any one of clauses 305 to 310, wherein the sub-first-interconnectors are equally tangentially spaced apart along the exterior surface of the device in a plane perpendicular to the central longitudinal axis of the body of the device.

312. The device of clause of any one of clauses 305 to 311, wherein for each sub-first-interconnector, the sub-first-interconnector wire of that sub-first-interconnector is at least indirectly pullable from the exterior of the device.

313. The device of clause 312, wherein the interconnector wires of all of the sub-first interconnectors of the first interconnector are simultaneously at least indirectly pullable from the exterior of the device.

314. The device of any one of clauses 305 to 313, wherein the interconnector wires of each of the sub-first-interconnectors of the first connector exteriorly extend away from the proximal end of the device.

Clauses 315 to 326

315. The device of any one of clauses 305 to 314, further having a second interconnector spaced-apart from and distal to the first interconnector, the second interconnector for releasably connecting the device with the lumen wall anchor for maintaining the device in place within the mammalian body conduit.

316. The device of any one of clauses 305 to 314, further having a second interconnector spaced-apart from and distal to the first interconnector, the second interconnector for releasably connecting the device with the lumen wall anchor for maintaining the lumen anchor in the compact-secured-configuration.

317. The device of any one of clauses 315 to 316, wherein the second interconnector has multiple sub-second-interconnectors, the sub-second-interconnectors being spaced-apart from one another, each sub-second-interconnector including two openings in the exterior surface of the device.

318. The device of clause 317, wherein each sub-second-connector further includes a sub-second-interconnector wire, the sub-second-interconnector wire
- traversing from the interior of the device to the exterior of the device through a first one of the two openings,
- extending outside the exterior of the device, and then
- traversing from the exterior of the device to the interior of the device through a second one of the two openings.

319. The device of clause 318 as it depends indirectly from clause 307, wherein
- wherein the second portion of the first cavity extends to the first opening of each sub-second-interconnector and a third portion extends from the second opening of each sub-second-interconnector within the interior of the device; and
- the sub-second-interconnector wire of each sub-second-interconnector extends within at least a part of the first portion of the first cavity and at least a part of the second portion of the first cavity to the first opening of that sub-second-interconnector and from the second opening of that sub-second-interconnector within at least in part the third portion of the first cavity.

320. The device of clause 318 as it depends indirectly from clause 309, wherein
- the device has a second cavity extending within the body, the second cavity having a first portion extending within the interior of the device to the first opening of each sub-second-interconnector and a second portion extending from the second opening of each sub-second interconnector within the interior of the device; and
- the sub-second-interconnector wire of each sub-second-interconnector extends from the within at least a part of the first portion of the second cavity to the first opening of that sub-second-interconnector and from the second opening of that sub-second-interconnector within at least a part of the second portion of the second cavity.

321. The device of clause 318 as it depends indirectly from clause 309, wherein
- the device has multiple second cavities extending within the body, the second cavities being distinct from the first cavities, each second cavity being associated with one of the sub-second-interconnectors, each second cavity having a first portion extending within the interior of the device to the first opening of the sub-second-interconnector associated with that cavity and a second portion extending from the second opening of that sub-second-interconnector within the interior of the device; and
- the sub-second-interconnector wire of each sub-second-interconnector further extends from within the interior of the device within at least a part of the first portion of the cavity associated with that sub-second-interconnector to the first opening associated with that sub-second-interconnector and from the second opening associated with that sub-second-interconnector within at least a part of the second portion of the cavity associated with that sub-second-interconnector.

322. The device of clause 321, wherein a majority of each second cavity extends within the body generally parallel to the central longitudinal axis of the body of the device.

323. The device of any one of clauses 317 to 322, wherein
the sub-second-interconnectors are equally tangentially spaced-apart along the exterior surface of the device in a plane perpendicular to the central longitudinal axis of the body of the device; and
each of the sub-second-interconnectors is tangentially is aligned with a one of the sub-first-interconnectors along a line parallel to the central longitudinal axis of the body of the device.

324. The device of any one of clauses 318 to 323, wherein, for each sub-second-interconnector, the sub-second-interconnector wire of that sub-second-interconnector is at least indirectly pullable from the exterior of the device.

325. The device of clause 324, wherein the sub-second-interconnector wires of all of the sub-second interconnectors of the second interconnector are simultaneously at least indirectly pullable from the exterior of the device.

326. The device any one of clauses 318 to 325, wherein the sub-second-interconnector wires of the each of the plurality of sub-second-interconnectors of the second connector exteriorly extend away from the proximal end of the device.

Clauses 327 to 331

327. The device of any one of clauses 315 to 326, wherein
the second interconnector has multiple sub-second-interconnectors, the sub-second-interconnectors being tangentially spaced-apart from one another, and axially spaced-apart from the sub-first-connectors;
each of the second-sub-connectors is tangentially aligned in a one-to-one relationship a single one of the sub-first-connectors; and
each sub-second-interconnector includes two openings in the exterior surface of the device.

328. The device of clause 327 as it depends indirectly from clause 307, wherein
the second portion of the first cavity extends to the first opening of each sub-second-interconnector and a third portion extending from the second opening of each sub-second-interconnector within the interior of the device; and
the sub-second-interconnector wire of each sub-first-interconnector further extends within the second portion of the first cavity to the first opening of the sub-second-interconnector associated with that sub-first interconnector and from the second opening of that sub-second-interconnector within at least a part of the third portion of the first cavity.

329. The device of clause 327 as it depends indirectly from clause 309, wherein each first cavity is further associated with the one of the sub-second-interconnectors that is in a one-to-one relationship with the one of the sub-first interconnectors that that first cavity is associated with, the second portion of each first cavity extending from the second opening of its associated sub-first-interconnector to a first opening of its associated sub-second-interconnector, and each first cavity having a third portion extending from a second opening of its associated sub-second-interconnector within the interior of the device.

330. The device of clause 329, wherein each one of the plurality of second connectors includes an element having two holes therein, the holes being shaped and dimensioned, and positioned on the element with respect to each other, to allow the interconnector wire of the sub-first-interconnector associated with the sub-second-interconnector associated with that one of the plurality of second connectors to pass therethrough.

331. The device of clause 330, wherein for each sub-second-interconnector, the interconnector wire of the sub-first-interconnector associated with that sub-second-interconnector is at least indirectly pullable from the exterior of the device.

Clauses 332 to 333

332. The device of clause 328, wherein the first portion and a first part of the second portion of the first cavity have a first cross-sectional diameter, and a second part of the second portion and the third portion of the first cavity have a second cross-sectional diameter, the second cross-sectional diameter being less than the first cross-sectional diameter.

333. The device of clause 329, wherein for each first cavity, the first portion and a first part of the second portion of that first cavity have a first cross-sectional diameter, and a second part of the second portion and the third portion of that first cavity have a second cross-sectional diameter, the second cross-sectional diameter being less than the first cross-sectional diameter.

Clauses 334 to 338

334. The device of clause 301 to 333, wherein the device is a modular fluid flow influencing device having a central docking unit and a plurality of functional units,
the docking unit being non-expandable and being the elongate body of the device;
the docking unit having:
a plurality of concave receiving surfaces for receiving the functional units, the receiving surfaces extending parallel to the central longitudinal axis of the docking units and being positioned equidistantly radially along the exterior surface thereof;
a plurality of inter-receiving-surface portions, an inter-receiving-surface portion extending longitudinally, parallel to the central longitudinal axis of the docking unit, between each two adjacent receiving surfaces.

335. The device of clause 334, wherein each of the sub-first-interconnectors is located on a one of the inter-receiving surface portions.

336. The device of clause 325, wherein each of the sub-first-interconnectors includes a first concavity of the one of the inter-receiving surface portions on which that sub-first interconnector is located, with the two openings of that sub-first-interconnector being disposed through a surface of that first concavity.

337. The device of any one of clauses 334 to 336 as they depend indirectly from any one of clauses 317 and 327, wherein each of the sub-second-interconnectors is located on a one of the inter-receiving surface portions.

338. The device of clause 337, wherein each of the sub-second-includes a second concavity of the one of the inter-receiving surface portions on which that sub-second interconnector is located, with the two openings of that sub-second-interconnector being disposed through a surface of that second concavity.

Clauses 339 to 349

339. The device of clauses 301, wherein the first interconnector includes a plurality of hooks for hooking loops of a lumen wall anchor.

340. The device of clause 339, wherein the first interconnector includes a secured configuration in which hooked loops of the lumen wall anchor are held captive by the first interconnector and a released configuration in which the hooks of the first interconnector are allowed to become unhooked by the loops of the lumen wall anchor.

341. The device of any one of clauses 339 to 340, wherein the first interconnector of the device includes a distal end portion of the body of the device longitudinally movable along the central longitudinal axis of the body of the device.

342. The device of clause 341, wherein the end portion is moveable between a secured position and a released position with respect to the body of the device.

343. The device of clause 342, wherein the end portion is an end cap that registers with the body of the device.

344. The device of clause 343, wherein the end cap registers with the body of the device when in the end cap is in the secured position.

345. The device of clause 344, wherein the end cap is longitudinally spaced apart from the body when of the device when the end cap in the released position.

346. The device of clause 345, wherein the end cap is disposed on rod moveably disposed within a channel within the body of the device, the channel extending along the central longitudinal axis of the body of the device.

347. The device of clause 340, wherein actuation of the rod moves the end cap from the secured position to the released position.

348. The device of clause 347, wherein the rod is attachable to an interconnector actuation wire for actuating the rod.

349. The device of any one of clauses 342 to 348, wherein,
when the end portion is in the secured position the first interconnector is in the secured configuration, whereby the hooked loops are held captive, and
when the end portion is in the released position the first interconnector is in the released configuration, whereby the hooked loops are allowed to become unhooked from the hooks of the first interconnector.

Clauses 350 to 362

350. The device of clause 301, wherein the first interconnector includes a plurality of loops for looping hooks of a lumen wall anchor.

351. The device of clause 350, wherein the first interconnector includes a secured configuration in which looped hooks are held captive by the first interconnector and a released configuration in which the loops of the first interconnector are allowed to become unlooped from the hooks of the lumen wall anchor.

352. The device of clause 351, the body of the device has a channel extending along the central longitudinal axis thereof.

353. The device of clause 352, wherein the loops extend through the channel of the body of the device.

354. The device of any one of clauses 351 to 352, wherein the loops are moveable within the channel parallel to the central longitudinal axis of the body of the device.

355. The device of clause 354, wherein the loops are moveable between a secured position and a released position with respect to the body of the device.

356. The device of clause 355, wherein the loops are within the channel of the body of the device when in the secured position.

357. The device of clause 356, wherein the loops are outside of the body of the device when in the released position.

358. The device of any one of clauses 354 to 357, wherein the loops are disposed at an end of a rod disposed within a channel and moveable along one of the central longitudinal axis of the device and a line parallel to the central longitudinal axis of the body of the device.

359. The device of clause 358, wherein at least portion of the rod is hollow, and the loops are secured within the hollow portion of the rod.

360. The device of any one of clauses 358 to 359, wherein actuation of the rod moves the loops from the secured position to the released position.

361. The device of clause 360, wherein the rod is attached to an actuation wire for actuating the rod.

362. The device of any one of clauses 358 to 361, wherein
when the hooks are looped by the loops, and the loops are in the secured position, the first interconnector is in the secured configuration, whereby the looped hooks are held captive within the channel of the body of the device, and
when the hooks are looped by the loops, and the loops are in the released position, the first interconnector is in the released configuration, whereby the looped hooks are allowed to become unlooped from the loops of the first interconnector.

Clauses 363 to 367

363. The device of any one of clauses 301 to 362, wherein the mammalian body conduit is a human body conduit.

364. The device of clause 363, wherein the human body conduit is a vascular system conduit.

365. The device of clause 364, wherein the vascular system conduit is one of an aorta and an inferior vena cava.

366. The device of clause 365, wherein the intralumenal device is a ventricular assist device and the vascular system conduit of one of a group consisting of an aorta, a left ventricle, a vena cava, a pulmonary artery, and a right ventricle.

367. The device of any one clauses 301 to 366, wherein the catheter is a delivery sheath.

Clauses 401-405

401. A method of implanting a mammalian body conduit intralumenal device and lumen wall anchor assembly into a mammalian body, the assembly having,
a mammalian body conduit intralumenal device, the device being shaped and dimensioned to be deliverable to an implantation site within a lumen of a mammalian body conduit via a delivery sheath, the device having an elongate body, a central longitudinal axis, and a first interconnector structured to releasably connect the device with a lumen wall anchor for use in maintaining the device in place within the mammalian body conduit, the first interconnector having multiple sub-first-interconnectors, and
the lumen wall anchor, the lumen wall anchor including,
a 3D-shaped wire network, the wire network having a central longitudinal axis,
a plurality of first connector positioning wires extending from the wire network, each wire of the plurality of first connector positioning wires being moveable between a secured position and a released position and being overcomeably biased towards the released position,
a plurality of first connectors, a single one of the plurality of first connectors being disposed at an end of each of wire of the plurality of first connector positioning wires, a number of the plurality of first connectors being equal to a number of the sub-first-interconnectors, and each one of the plurality of first connectors being associated with a single one of the multiple sub-first-interconnectors, the lumen wall anchor having a compact-secured-configuration, an expanded-secured-configuration, and an expanded-released-configuration, when the lumen wall anchor is in the compact-secured-configuration, the lumen wall anchor is shaped and dimensioned to be deliverable to the delivery site within the lumen of the mammalian body conduit via the delivery sheath, and each wire of the first plurality of connector positioning wires is in the secured position, the secured position being the end of that wire of the first plurality of connector positioning wires being positioned in proximity to the first interconnector of the device such that each of the plurality of first connectors is positioned to be releasably connectable to its associated sub-first interconnector of the first interconnector of the device, and each of the first connectors is releasably connected to its associated sub-first-interconnector;

when the lumen wall anchor is in the expanded-secured-configuration, the wire network is dimensioned and shaped to exert a force on a wall of the lumen of the conduit, the force being sufficient to anchor the mammalian body conduit intralumenal device and lumen wall anchor assembly in place at the implantation site, and each wire of the first plurality of connector positioning wires is in the secured position, and each of the first connectors is releasably connected to its associated sub-first-interconnector; and when the lumen wall anchor is in the expanded-released-configuration, the wire network is dimensioned and shaped to exert a force on the wall of the lumen of the conduit, the force being sufficient to anchor the lumen wall anchor assembly in place at the implantation site, and each wire of the plurality of first connector positioning wires is in the released position, the released position being each of the plurality of first connectors being released from and unconnected to its associated sub-first interconnector, and the end of each wire of the first plurality of connector positioning wires being proximate the wall of the lumen of the conduit, and the plurality of first connector positioning wires and the plurality of first connectors do not obstruct fluid flow axially through the wire network while the lumen wall anchor is anchored in place at the implantation site, the lumen wall anchor being overcomeably biased away from its compact-secured-configuration, the assembly having a distal end and a proximal end, the method comprising:

h) obtaining access to the conduit system of the mammalian body;

i) guiding a delivery sheath through the conduit system to the implantation site;

j) inserting the mammalian body conduit intralumenal device and lumen wall anchor assembly distal end first into the delivery sheath, with the lumen wall anchor being in the compact-secured-configuration;

k) guiding the assembly within the delivery sheath to the implantation site;

l) promoting exit of the assembly from the delivery sheath at the implantation site;

m) allowing the bias of the lumen wall anchor to cause the lumen wall anchor to adopt the expanded-secured-configuration and exert a force on the wall of the lumen of the conduit at the implantation site, anchoring the assembly in place; and n) withdrawing the delivery sheath from the body.

402. The method of clause 401, wherein the device further has a second interconnector spaced-apart from and distal to the first interconnector, the second interconnector being structured to releasably connect the device with the lumen wall anchor for use in maintaining the device in place within the mammalian body conduit, the second interconnector having multiple sub-second-interconnectors, the lumen wall anchor further includes a plurality of second connector positioning wires extending from the wire network, each wire of the plurality of second connector positioning wires being moveable between a secured position and a released position and being overcomeably biased towards the released position;

a plurality of second connectors, a single one of the plurality of second connectors being disposed at an end of each wire of the plurality of second connector positioning wires, a number of the plurality of second connectors being equal to a number of the sub-second-interconnectors, and each one of the plurality of second connectors being associated with a single one of the multiple sub-second-interconnectors;

when the lumen wall anchor is in the expanded-secured-configuration, each wire of the plurality of second connector positioning wires is in the secured position, the secured position being the end of that wire of the second plurality of connector positioning wires being positioned in proximity to the second interconnector of the device such that each of the plurality of second connectors is positioned to be releasably connectable to its associated sub-second-interconnector, and each of the second connectors is releasably connected to its associated sub-second-interconnector of the device;

when the lumen wall anchor is in the expanded-released-configuration, each wire of the plurality of second connector positioning wires is in the released position, the released position being the end of that wire of the plurality of second connector positioning wires being proximate the wall of the lumen of the conduit, and the plurality of second connector positioning wires and the plurality of second connectors do not obstruct fluid flow axially through the wire network while the lumen wall anchor is anchored in place at the implantation site.

403. The method of any one of clauses 401 to 402, the device further having a control cable attached thereto, an outer diameter of the control cable being sized to be able to pass through the delivery sheath to the implantation site, wherein guiding the assembly within the delivery sheath to the implantation site includes pushing the control cable attached to the device.

404. The method of clause 403, wherein promoting exit of the assembly at the implantation site includes pushing the control cable attached to the device.

405. The method of any one of clauses 401 to 404,
  the device being a modular fluid flow influencing device having a central docking unit and a plurality of functional units,
    the docking unit being non-expandable and being the elongate body of the device,
    the docking unit having:
      a plurality of concave receiving surfaces for receiving the functional units, the receiving surfaces extending parallel to the central longitudinal axis of the docking units and being positioned equidistantly radially along the exterior surface thereof,
      a plurality of inter-receiving-surface portions, an inter-receiving-surface portion extending longitudinally, parallel to the central longitudinal axis of the docking unit, between each two adjacent receiving surfaces,
  wherein promoting exit of the assembly at the implantation site includes, promoting exit of the plurality of functional units of the device from the delivery sheath at the implantation site and then promoting exit of the central docking unit from the delivery sheath at the implantation site; and
  the method further comprising, after f), pulling a control wire of each of the functional units to guide each functional unit into being received by one of the receiving surfaces of the docking unit.

Clause 406 to 410

406. A method of explanting a mammalian body conduit intralumenal device and lumen wall anchor assembly having been implanted into a mammalian body and anchored at an implantation site, the assembly having,
  a mammalian body conduit intralumenal device, the device being shaped and dimensioned to be deliverable to a delivery site within a lumen of a mammalian body conduit via a delivery sheath, the device having an elongate body, a central longitudinal axis, and a first interconnector structured to releasably connect the device with a lumen wall anchor for use in maintaining the device in place within the mammalian body conduit, the first interconnector having multiple sub-first-interconnectors, and
  the lumen wall anchor, the lumen wall anchor including,
    a 3D-shaped wire network, the wire network having a central longitudinal axis,
    a plurality of first connector positioning wires extending from the wire network, each wire of the plurality of first connector positioning wires being moveable between a secured position and a released position and being overcomeably biased towards the released position,
    a plurality of first connectors, a single one of the plurality of first connectors being disposed at an end of each of wire of the plurality of first connector positioning wires, a number of the plurality of first connectors being equal to a number of the sub-first-interconnectors, and each one of the plurality of first connectors being associated with a single one of the multiple sub-first-interconnectors,
    the lumen wall anchor having a compact-secured-configuration, an expanded-secured-configuration, and an expanded-released-configuration,
    when the lumen wall anchor is in the compact-secured-configuration,
      the lumen wall anchor is shaped and dimensioned to be deliverable to the delivery site within the lumen of the mammalian body conduit via the catheter, and
      each wire of the first plurality of connector positioning wires is in the secured position, the secured position being the end of that wire of the first plurality of connector positioning wires being positioned in proximity to the first interconnector of the device such that each of the plurality of first connectors is positioned to be releasably connectable to its associated sub-first interconnector of the first interconnector of the device, and
      each of the first connectors is releasably connected to its associated sub-first-interconnector;
    when the lumen wall anchor is in the expanded-secured-configuration,
      the wire network is dimensioned and shaped to exert a force on a wall of the lumen of the conduit, the force being sufficient to anchor the mammalian body conduit intralumenal device and lumen wall anchor assembly in place at the implantation site, and
      each wire of the first plurality of connector positioning wires is in the secured position, and
      each of the first connectors is releasably connected to its associated sub-first-interconnector; and
    when the lumen wall anchor is in the expanded-released-configuration,
      the wire network is dimensioned and shaped to exert a force on the wall of the lumen of the conduit, the force being sufficient to anchor the lumen wall anchor assembly in place at the implantation site, and
      each wire of the plurality of first connector positioning wires is in the released position, the released position being each of the plurality of first connectors being released from and unconnected to its associated sub-first interconnector, and the end of each wire of the first plurality of connector positioning wires being proximate the wall of the lumen of the conduit, and
      the plurality of first connector positioning wires and the plurality of first connectors do not obstruct fluid flow axially through the wire network while the lumen wall anchor is anchored in place at the implantation site,
    the lumen wall anchor being overcomeably biased away from its compact-secured-configuration,
  the assembly having a distal end and a proximal end,
  the method comprising:
    g) obtaining access to the conduit system of the mammalian body;
    h) guiding a retrieval sheath to the implantation site;
    i) promoting entry of the assembly into the retrieval sheath proximal end first at the implantation site;
    j) overcoming the bias of the lumen wall anchor via contact of the retrieval sheath with the proximally-facing sloped surfaces of the first connector positioning wires, causing the lumen wall anchor to adopt the compact-secured-configuration, unanchoring the assembly;
    k) completing entry of the assembly into the retrieval sheath at the implantation site; and
    l) withdrawing the retrieval sheath and the assembly from the body.

407. The method of clause 406, wherein
the device further has a second interconnector spaced-apart from and distal to the first interconnector, the second interconnector being structured to releasably connect the device with the lumen wall anchor for use in maintaining the device in place within the mammalian body conduit, the second interconnector having multiple sub-second-interconnectors,
the lumen wall anchor further includes
a plurality of second connector positioning wires extending from the wire network, each wire of the plurality of second connector positioning wires being moveable between a secured position and a released position and being overcomeably biased towards the released position;
a plurality of second connectors, a single one of the plurality of second connectors being disposed at an end of each wire of the plurality of second connector positioning wires, a number of the plurality of second connectors being equal to a number of the sub-second-interconnectors, and each one of the plurality of second connectors being associated with a single one of the multiple sub-second-interconnectors;
when the lumen wall anchor is in the expanded-secured-configuration,
each wire of the plurality of second connector positioning wires is in the secured position, the secured position being the end of that wire of the second plurality of connector wires being positioned in proximity to the second interconnector of the device such that each of the plurality of second connectors is positioned to be releasably connectable to its associated sub-second-interconnector, and
each of the second connectors is releasably connected to its associated sub-second-interconnector of the device;
when the lumen wall anchor is in the expanded-released-configuration,
each wire of the plurality of second connector positioning wires is in the released position, the released position being the end of that wire of the plurality of second connector positioning wires being proximate the wall of the lumen of the conduit, and
the plurality of second connector positioning wires and the plurality of second connectors do not obstruct fluid flow axially through the wire network while the lumen wall anchor is anchored in place at the implantation site.
408. The method of any one of clauses 406 to 407, the device further having a control cable attached thereto passing from the implantation site through the conduit system of the body, wherein withdrawing the retrieval sheath and the assembly from the body includes pulling the control cable attached to the device
409. The method of any one of clauses 405 to 408, wherein promoting entry of the assembly into the retrieval sheath proximal end first at the implantation site includes pulling the control cable attached to the device.
410. The method of any one of clauses 405 to 409,
the device being a modular fluid flow influencing device having a central docking unit and a plurality of functional units,
the docking unit being non-expandable and being the elongate body of the device,
the docking unit having:
a plurality of concave receiving surfaces for receiving the functional units, the receiving surfaces extending parallel to the central longitudinal axis of the docking units and being positioned equidistantly radially along the exterior surface thereof,
a plurality of inter-receiving-surface portions, an inter-receiving-surface portion extending longitudinally, parallel to the central longitudinal axis of the docking unit, between each two adjacent receiving surfaces,
each of the plurality of functional units having been received by one of the receiving surfaces of the docking unit,
the method further comprising, prior to c) pushing a control wire of each of the functional units to guide each functional unit from being received by one of the receiving surfaces of the docking unit, and
wherein promoting entry of the assembly into the retrieval sheath includes, promoting entry of the central docking unit into the retrieval sheath and then promoting entry of the functional units into the retrieval sheath.
Clauses 411-416
411. A method of explanting a modular fluid flow influencing intralumenal device being part of assembly including a lumen wall anchor, the assembly having been implanted into a mammalian body and an anchored at an implantation site, the assembly having,
a mammalian body conduit intralumenal device, the device being shaped and dimensioned to be deliverable to a delivery site within a lumen of a mammalian body conduit via a catheter, the device having an elongate body, a central longitudinal axis, and a first interconnector structured to releasably connect the device with a lumen wall anchor for use in maintaining the device in place within the mammalian body conduit, the first interconnector having multiple sub-first-interconnectors, and
the lumen wall anchor, the lumen wall anchor including,
a 3D-shaped wire network, the wire network having a central longitudinal axis,
a plurality of first connector positioning wires extending from the wire network, each wire of the plurality of first connector positioning wires being moveable between a secured position and a released position and being overcomeably biased towards the released position,
a plurality of first connectors, a single one of the plurality of first connectors being disposed at an end of each of wire of the plurality of first connector positioning wires, a number of the plurality of first connectors being equal to a number of the sub-first-interconnectors, and each one of the plurality of first connectors being associated with a single one of the multiple sub-first-interconnectors,
the lumen wall anchor having a compact-secured-configuration, an expanded-secured-configuration, and an expanded-released-configuration,
when the lumen wall anchor is in the compact-secured-configuration,
the lumen wall anchor is shaped and dimensioned to be deliverable to the delivery site within the lumen of the mammalian body conduit via the catheter, and
each wire of the first plurality of connector positioning wires is in the secured position, the secured position being the end of that wire of the first plurality of connector positioning wires being positioned in proximity to the first interconnector of the device such that each of the plurality of first connectors is positioned to be releasably connectable to its associated sub-first interconnector of the first interconnector of the device, and each of the first connectors is releasably connected to its associated sub-first-interconnector;

when the lumen wall anchor is in the expanded-secured-configuration, the wire network is dimensioned and shaped to exert a force on a wall of the lumen of the conduit, the force being sufficient to anchor the mammalian body conduit intralumenal device and lumen wall anchor assembly in place at the implantation site, and each wire of the first plurality of connector positioning wires is in the secured position, and each of the first connectors is releasably connected to its associated sub-first-interconnector; and when the lumen wall anchor is in the expanded-released-configuration, the wire network is dimensioned and shaped to exert a force on the wall of the lumen of the conduit, the force being sufficient to anchor the lumen wall anchor assembly in place at the implantation site, and each wire of the plurality of first connector positioning wires is in the released position, the released position being each of the plurality of first connectors being released from and unconnected to its associated sub-first interconnector, and the end of each wire of the first plurality of connector positioning wires being proximate the wall of the lumen of the conduit, and the plurality of first connector positioning wires and the plurality of first connectors do not obstruct fluid flow axially through the wire network while the lumen wall anchor is anchored in place at the implantation site, the lumen wall anchor being biased away from its compact-secured-configuration, the assembly having a distal end and a proximal end, the method comprising:

f) obtaining access to the conduit system of the mammalian body;

g) guiding a retrieval sheath to the implantation site;

h) pulling at least one wire operationally connected to the sub-first-interconnectors, causing the release of each of the first connectors from its connection to its associated first-sub-interconnector, disconnecting the lumen wall anchor from the device and allowing the first connector positioning wires to move to the released position;

i) promoting entry of the device into the retrieval sheath proximal end first at the implantation site;

j) withdrawing the retrieval sheath and the device from the body.

412. The method of clause 411, wherein, the device further has a second interconnector spaced-apart from and distal to the first interconnector, the second interconnector being structured to releasably connect the device with the lumen wall anchor for use in maintaining the device in place within the mammalian body conduit, the second interconnector having multiple sub-second-interconnectors, the lumen wall anchor further includes a plurality of second connector positioning wires extending from the wire network, each wire of the plurality of second connector positioning wires being moveable between a secured position and a released position and being overcomeably biased towards the released position;

a plurality of second connectors, a single one of the plurality of second connectors being disposed at an end of each wire of the plurality of second connector positioning wires, a number of the plurality of second connectors being equal to a number of the sub-second-interconnectors, and each one of the plurality of second connectors being associated with a single one of the multiple sub-second-interconnectors;

when the lumen wall anchor is in the expanded-secured-configuration, each wire of the plurality of second connector positioning wires is in the secured position, the secured position being the end of that wire of the second plurality of connector wires being positioned in proximity to the second interconnector of the device such that each of the plurality of second connectors is positioned to be releasably connectable to its associated sub-second-interconnector, and each of the second connectors is releasably connected to its associated sub-second-interconnector of the device;

when the lumen wall anchor is in the expanded-released-configuration, each wire of the plurality of second connector positioning wires is in the released position, the released position being the end of that wire of the plurality of second connector positioning wires being proximate the wall of the lumen of the conduit, and the plurality of second connector positioning wires and the plurality of second connectors do not obstruct fluid flow axially through the wire network while the lumen wall anchor is anchored in place at the implantation site;

the method further comprising, after b) and prior to c), pulling at least one wire operationally connected to the sub-second-interconnectors, causing the release of each of the second connectors from its connection to its associated sub-second-interconnector, and allowing the second connector positioning wires to move to the released position.

413. The method of any one of clauses 411 to 412, the device further having a control cable attached thereto passing from the implantation site through the conduit system to outside the conduit system of the body, wherein guiding the retrieval sheath to the implantation site includes railing the retrieval sheath over the control cable.

414. The method of clause 413, wherein promoting entry of the device into the retrieval sheath proximal end first at the implantation site includes pulling the control cable attached to the device.

415. The method of clause 414, wherein withdrawing the retrieval sheath and the device from the body includes pulling the control cable attached to the device.

416. The method of any one of clauses 411 to 415, the device being a modular fluid flow influencing device having a central docking unit and a plurality of functional units, the docking unit being non-expandable and being the elongate body of the device, the docking unit having:
- a plurality of concave receiving surfaces for receiving the functional units, the receiving surfaces extending parallel to the central longitudinal axis of the docking units and being positioned equidistantly radially along the exterior surface thereof,
- a plurality of inter-receiving-surface portions, an inter-receiving-surface portion extending longitudinally, parallel to the central longitudinal axis of the docking unit, between each two adjacent receiving surfaces, each of the plurality of functional units having been received by one of the receiving surfaces of the docking unit, the method further comprising, prior to c) pushing a control wire of each of the functional units to guide each unit from being received by one of the receiving surfaces of the docking unit, and wherein promoting entry of the assembly into the retrieval sheath includes, promoting entry of the central docking unit into the retrieval sheath and then promoting entry of the functional units into the retrieval sheath.

Clauses 417-418

417. A method of implanting a modular fluid flow influencing intralumenal device and lumen wall anchor assembly into a mammalian body, the assembly having,
- a mammalian body conduit intralumenal device, the device being shaped and dimensioned to be deliverable to a delivery site within a lumen of a mammalian body conduit via a catheter, the device having an elongate body, a central longitudinal axis, a first interconnector structured to releasably connect the device with a lumen wall anchor for use in maintaining the device in place within the mammalian body conduit, the first interconnector having multiple sub-first-interconnectors, and a second interconnector spaced-apart from and distal to the first interconnector, the second interconnector being structured to releasably connect the device with the lumen wall anchor for use in maintaining the lumen anchor in a compact-secured-configuration, the second interconnector having multiple sub-second-interconnectors, and the lumen wall anchor, the lumen wall anchor including,
- a 3D-shaped wire network, the wire network having a central longitudinal axis,
- a plurality of first connector positioning wires extending from the wire network, each wire of the plurality of first connector positioning wires being moveable between a secured position and a released position and being overcomeably biased towards the released position,
- a plurality of first connectors, a single one of the plurality of first connectors being disposed at an end of each of wire of the plurality of first connector positioning wires, a number of the plurality of first connectors being equal to a number of the sub-first-interconnectors, and each one of the plurality of first connectors being associated with a single one of the multiple sub-first-interconnectors,
- a plurality of second connectors disposed on the wire network, a number of the plurality of second connectors being equal to a number of the sub-second-interconnectors, and each one of the plurality of second connectors being associated with a single one of the multiple sub-second-interconnectors, the lumen wall anchor having the compact-secured-configuration, an expanded-secured-configuration, and an expanded-released-configuration, when the lumen wall anchor is in the compact-secured-configuration,
- the lumen wall anchor is shaped and dimensioned to be deliverable to the delivery site within the lumen of the mammalian body conduit via the catheter, and
- each wire of the first plurality of connector positioning wires is in the secured position, the secured position being the end of that wire of the first plurality of connector positioning wires being positioned in proximity to the first interconnector of the device such that each of the plurality of first connectors is positioned to be releasably connectable to its associated sub-first interconnector of the first interconnector of the device, and
- each of the first connectors is releasably connected to its associated sub-first-interconnector;
- each of the second connectors is releasably connected to its associated sub-second-interconnector;

when the lumen wall anchor is in the expanded-secured-configuration,
- the wire network is dimensioned and shaped to exert a force on a wall of the lumen of the conduit, the force being sufficient to anchor the mammalian body conduit intralumenal device and lumen wall anchor assembly in place at an implantation site, and
- each wire of the first plurality of connector positioning wires is in the secured position, and
- each of the first connectors is releasably connected to its associated sub-first-interconnector,
- each of the second connectors is released from and unconnected to its associated sub-second-interconnector, and when the lumen wall anchor is in the expanded-released-configuration,
- the wire network is dimensioned and shaped to exert a force on the wall of the lumen of the conduit, the force being sufficient to anchor the lumen wall anchor assembly in place at the implantation site, and
- each wire of the plurality of first connector positioning wires is in the released position, the released position being each of the plurality of first connectors being released from and unconnected to its associated sub-first interconnector, and the end of each wire of the first plurality of connector positioning wires being proximate the wall of the lumen of the conduit, and
- the plurality of first connector positioning wires, the plurality of first connectors, and the plurality of second connectors do not obstruct fluid flow axially through the wire network while the lumen wall anchor is anchored in place at the implantation site, the lumen wall anchor being biased away from its compact-secured-configuration, the assembly having a distal end and a proximal end, the method comprising:
i) obtaining access to the conduit system of the mammalian body;
j) guiding a delivery sheath through the conduit system to a delivery site in advance of the implantation site;

k) inserting the assembly with the lumen wall anchor in its compact-secured-configuration into the delivery sheath;
l) guiding the assembly within the delivery sheath to the delivery site;
m) promoting exit of the assembly from the delivery sheath at the delivery site;
n) advancing the assembly to the implantation site;
o) pulling at least one wire operationally connected to the sub-second-interconnectors, causing the release of each of the second connectors from its connection to its associated sub-second-interconnector, thereby allowing the bias of the lumen wall anchor to cause the lumen wall anchor to adopt the expanded-secured-configuration and exert a force on the wall of the lumen of the conduit at the implantation site, anchoring the assembly in place at the implantation site; and
p) withdrawing the delivery sheath from the body.

418. The method of clause 417,
the device being a modular fluid flow influencing device having a central docking unit and a plurality of functional units,
the docking unit being non-expandable and being the elongate body of the device,
the docking unit having:
a plurality of concave receiving surfaces for receiving the functional units, the receiving surfaces extending parallel to the central longitudinal axis of the docking units and being positioned equidistantly radially along the exterior surface thereof,
a plurality of inter-receiving-surface portions, an inter-receiving-surface portion extending longitudinally, parallel to the central longitudinal axis of the docking unit, between each two adjacent receiving surfaces,
wherein:
inserting the assembly with the lumen wall anchor in its compact-secured-configuration into the delivery sheath includes first inserting the plurality of functional units one-after-another into the delivery sheath and then inserting the docking units into the delivery sheath;
promoting exit of the assembly from the delivery sheath at the delivery site includes promoting exit of the functional units, one-by-one, from the delivery sheath at the at the delivery site and after promoting exit of the docking unit and the lumen wall anchor, with the lumen wall anchor remaining in the compact-secured-configuration;
the method further comprises, after e) and prior to f), bringing the device into a configuration with the functional units side-by-side with each other and proximate the distal end of the docking unit;
wherein advancing the assembly to the implantation site is advancing the assembly to the implantation site with the device in the configuration; and
the method further comprises, after g), pulling a control wire of each of the functional units to guide each functional unit into being received by one of the receiving surfaces of the docking unit.

Clauses 419-420
419. A method of explanting a modular fluid flow influencing intralumenal device being part of assembly including a lumen wall anchor, the assembly having been implanted into a mammalian body and an anchored at an implantation site, the assembly having, a mammalian body conduit intralumenal device, the device being shaped and dimensioned to be deliverable to a delivery site within a lumen of a mammalian body conduit via a catheter, the device having an elongate body, a central longitudinal axis, a first interconnector structured to releasably connect the device with a lumen wall anchor for use in maintaining the device in place within the mammalian body conduit, the first interconnector having multiple sub-first-interconnectors, and a second interconnector spaced-apart from and distal to the first interconnector, the second interconnector being structured to releasably connect the device with the lumen wall anchor for use in maintaining the lumen anchor in a compact-secured-configuration, the second interconnector having multiple sub-second-interconnectors, and
the lumen wall anchor, the lumen wall anchor including,
a 3D-shaped wire network, the wire network having a central longitudinal axis,
a plurality of first connector positioning wires extending from the wire network, each wire of the plurality of first connector positioning wires being moveable between a secured position and a released position and being overcomeably biased towards the released position,
a plurality of first connectors, a single one of the plurality of first connectors being disposed at an end of each of wire of the plurality of first connector positioning wires, a number of the plurality of first connectors being equal to a number of the sub-first-interconnectors, and each one of the plurality of first connectors being associated with a single one of the multiple sub-first-interconnectors,
a plurality of second connectors disposed on the wire network, a number of the plurality of second connectors being equal to a number of the sub-second-interconnectors, and each one of the plurality of second connectors being associated with a single one of the multiple sub-second-interconnectors,
the lumen wall anchor having the compact-secured-configuration, an expanded-secured-configuration, and an expanded-released-configuration,
when the lumen wall anchor is in the compact-secured-configuration,
the lumen wall anchor is shaped and dimensioned to be deliverable to the delivery site within the lumen of the mammalian body conduit via the catheter, and
each wire of the first plurality of connector positioning wires is in the secured position, the secured position being the end of that wire of the first plurality of connector positioning wires being positioned in proximity to the first interconnector of the device such that each of the plurality of first connectors is positioned to be releasably connectable to its associated sub-first interconnector of the first interconnector of the device, and
each of the first connectors is releasably connected to its associated sub-first-interconnector;
each of the second connectors is releasably connected to its associated sub-second-interconnector;
when the lumen wall anchor is in the expanded-secured-configuration,
the wire network is dimensioned and shaped to exert a force on a wall of the lumen of the conduit, the force being sufficient to anchor the mammalian body conduit intralumenal device and lumen wall anchor assembly in place at an implantation site, and each wire of the first plurality of connector positioning wires is in the secured position, and each of the first connectors is releasably connected to its associated sub-first-interconnector, each of the second connectors is released from and unconnected to its associated sub-second-interconnector, and when the lumen wall anchor is in the expanded-released-configuration, the wire network is dimensioned and shaped to exert a force on the wall of the lumen of the conduit, the force being sufficient to anchor the lumen wall anchor assembly in place at the implantation site, and each wire of the plurality of first connector positioning wires is in the released position, the released position being each of the plurality of first connectors being released from and unconnected to its associated sub-first interconnector, and the end of each wire of the first plurality of connector positioning wires being proximate the wall of the lumen of the conduit, and the plurality of first connector positioning wires, the plurality of first connectors, and the plurality of second connectors do not obstruct fluid flow axially through the wire network while the lumen wall anchor is anchored in place at the implantation site, the lumen wall anchor being biased away from its compact-secured-configuration, the assembly having a distal end and a proximal end, the method comprising:

g) obtaining access to the conduit system of the mammalian body;

h) guiding a retrieval sheath through the conduit system to a retrieval site in advance of the implantation site;

i) pulling at least one wire operationally connected to the sub-first-interconnectors, causing the release of each of the first connectors from its connection to its associated first-sub-interconnector, disconnecting the lumen wall anchor from the device and allowing the first connector positioning wires to move to the released position;

j) withdrawing the assembly from the implantation site to the retrieval site;

k) promoting entry of the device into the retrieval sheath at the retrieval site;

l) withdrawing the retrieval sheath and the device from the body.

420. The method of clause 419, the device being a modular fluid flow influencing device having a central docking unit and a plurality of functional units, the docking unit being non-expandable and being the elongate body of the device, the docking unit having:

a plurality of concave receiving surfaces for receiving the functional units, the receiving surfaces extending parallel to the central longitudinal axis of the docking units and being positioned equidistantly radially along the exterior surface thereof, a plurality of inter-receiving-surface portions, an inter-receiving-surface portion extending longitudinally, parallel to the central longitudinal axis of the docking unit, between each two adjacent receiving surfaces, each of the plurality of functional units having been received by one of the receiving surfaces of the docking unit, wherein:

the method further comprises, prior to e), pushing a control wire of each of the functional units to guide each functional unit from being received by one of the receiving surfaces of the docking unit;

promoting entry of the device into the retrieval sheath at the delivery site includes promoting entry of the docking unit into the retrieval sheath and after promoting entry of the functional units, one-by-one, into the retrieval sheath.

End of Clauses

The invention claimed is:

1. A method of explanting an anchored blood pump from a body conduit, the method comprising:

with the blood pump removably coupled to an anchor that is anchored to a wall of the body conduit at a delivery site, decoupling the blood pump from the anchor such that the anchor transitions from a partially-expanded, secured configuration, in which a first portion of the anchor contacts the wall of the body conduit and a second portion of the anchor is secured to contacting the blood pump, to an expanded, released configuration in which the second portion of the anchor is unsecured from the blood pump; and with the anchor anchored to the wall of the body conduit at the delivery site, removing the blood pump from the body conduit, thereby leaving the anchor anchored to the wall of the body conduit at the delivery site.

2. The method of claim 1, wherein the anchor is configured to assume a compact, secured configuration when disposed within a catheter, and to transition from the compact, secured configuration to the partially-expanded, secured configuration when released exited from within the catheter, further wherein the method comprises:

transitioning the anchor from the compact, secured configuration to the partially-expanded, secured configuration with a balloon catheter.

3. The method of claim 1, wherein the anchor is formed of shape-memory material and overcomeably biased towards the expanded, released configuration.

4. The method of claim 1, wherein in the partially-expanded, secured configuration, the second portion of the anchor is secured to the blood pump via an actuation wire that is operatively connected to the anchor and extends at least partially through the blood pump, said decoupling comprising causing, from outside the mammalian body conduit, the actuation wire to move along the blood pump to and decouple the anchor from the blood pump.

5. The method of claim 1, wherein the blood pump includes an impeller, the method further comprising:

prior to the decoupling, delivering a docking unit and the blood pump undocked from the docking unit to the delivery site, and then docking the blood pump to the docking unit at the delivery site.

6. The method of claim 1, wherein the anchor is made of a deformable material.

7. The method of claim 1, further comprising: transitioning the anchor from the partially-expanded, secured configuration to the expanded, released configuration with a balloon catheter.

8. The method of claim 1, wherein the second portion of the anchor comprises a connector positioning wire that is moveable between a secured position in which the connector positioning wire is secured to the blood pump, and a released position in which the connector positioning wire is unsecured from the blood pump, the connector positioning wire being overcomeably biased toward the released position, further wherein the removing causes the connector positioning wire to be clear from the lumen of the body conduit when the anchor is in the expanded, released configuration at the delivery site.

9. The method of claim 1, further comprising: obtaining access to the body conduit.

10. The method of claim 9, further comprising: guiding a retrieval sheath to the delivery site.

11. The method of claim 10, further comprising: promoting entry, at least partially, of the blood pump into the retrieval sheath.

12. The method of claim 10, wherein the removing includes withdrawing the retrieval sheath with the blood pump from the body conduit.

13. The method of claim 1, wherein the blood pump includes an impeller, the method further comprising undocking the blood pump from a docking unit located at the delivery site.

14. The method of claim 13, wherein the undocking is performed prior to the removing the blood pump from the body conduit.

15. The method of claim 13, wherein the docking unit is removably coupled to the anchor.

16. The method of claim 8, wherein the delivery site is the aorta.

17. The method of claim 8, wherein the delivery site is the inferior vena cava.

18. The method of claim 8, wherein the delivery site is the pulmonary artery.

19. The method of claim 1, wherein the delivery site is a cardiac chamber.

20. The method of claim 1, wherein the delivery site is the left ventricle.

21. The method of claim 1, wherein the delivery site is the right ventricle.

* * * * *